(12) United States Patent
Burke, Jr. et al.

(10) Patent No.: US 9,175,038 B2
(45) Date of Patent: Nov. 3, 2015

(54) PEPTIDE MIMETIC LIGANDS OF POLO-LIKE KINASE 1 POLO BOX DOMAIN AND METHODS OF USE

(75) Inventors: Terrence R. Burke, Jr., Bethesda, MD (US); Fa Liu, Indianapolis, IN (US); Kyung S. Lee, Gaithersburg, MD (US); Jung-Eun Park, Bethesda, MD (US)

(73) Assignee: The United States of America, as represented by the Secretary, Department of Health & Human Services, Washington, DC (US)

(*) Notice: Subject to any disclaimer, the term of this patent is extended or adjusted under 35 U.S.C. 154(b) by 857 days.

(21) Appl. No.: 13/320,726

(22) PCT Filed: May 17, 2010

(86) PCT No.: PCT/US2010/035069
§ 371 (c)(1),
(2), (4) Date: Nov. 15, 2011

(87) PCT Pub. No.: WO2010/132869
PCT Pub. Date: Nov. 18, 2010

(65) Prior Publication Data
US 2012/0065146 A1    Mar. 15, 2012

Related U.S. Application Data

(60) Provisional application No. 61/300,349, filed on Feb. 1, 2010, provisional application No. 61/178,593, filed on May 15, 2009.

(51) Int. Cl.
A61K 38/08    (2006.01)
A01K 61/00    (2006.01)
C07K 7/06     (2006.01)
A61K 38/00    (2006.01)

(52) U.S. Cl.
CPC .. *C07K 7/06* (2013.01); *A61K 38/00* (2013.01)

(58) Field of Classification Search
None
See application file for complete search history.

(56) References Cited

U.S. PATENT DOCUMENTS

2011/0076693 A1* 3/2011 Lee et al. ............ 435/7.4

FOREIGN PATENT DOCUMENTS

WO    2004046317 A2    6/2004
WO    2009140632 A1    11/2009

OTHER PUBLICATIONS

Cancer Drug Design and Discovery, Neidle, Stephen, ed. (Elsevier/Academic Press, 2008) pp. 427-431.*
Elia et al., "The Molecular Basis for Phosphodependent Substrate Targeting and Regulation of Plks by the Polo-Box Domain", Cell, vol. 115, No. 1, pp. 83-95 (2003).
Ojea et al., "Conjugate Additions of 1-Propenylphosphonates to Metalated Schollkopfs Bis-lactim Ether: Stereocontrolled Access to 2-Amino-3-methyl-4-phosphonobutanoic Acids", J. Org. Chem., vol. 65, No. 7, pp. 1984-1995 (2000).
Otaka et al., "Stereoselective Synthesis of CF2-Substituted Phosphothreonine Mimetics and Their Incorporation into Peptides Using Newly Developed Deprotection Procedures", J. Org. Chem., vol. 65, No. 16, pp. 4888-4899 (2000).
Otaka et al., "Synthesis of Fluorine-Containing Bioisosteres Corresponding to Phosphoamino Acids and Dipeptide Units", Biopolymers, vol. 76, No. 2, pp. 140-149 (2004).
Yun et al., "Structural and functional analyses of minimal phosphopeptides targeting the polo-box domain of polo-like kinase 1", Nature Structural & Molecular Biology, vol. 16, No. 8, pp. 876-882 (2009).
Liu et al., "Preparation of orthogonally protected (2S,3R)-2-amino-3-methyl-4-phosphonobutyric acid (Pmab) as a phosphate-stable phosphothreonine mimetic and its use in the synthesis of polo-box domain-binding peptides", Tetrahedron, vol. 65, No. 47, pp. 9673-9679 (2009).
Park et al., "Polo-box domain: A versatile mediator of polo-like kinase function", Cellular and Molecular Life Sciences, vol. 67, No. 12, pp. 1957-1970 (2010).
Liao et al., "Probing Binding Modes of Small Molecules Inhibitors to the Polo-Box Domain of Human Polo-like Kinase 1", ACS Medicinal Chemistry Letters, vol. 1, pp. 110-114 (2010).
Burke et al., "Potent Inhibition of Insulin Receptor Dephosphorylation by a Hexamer Peptide Containing the Phosphotyrosyl Mimetic F2Pmp", Biochemical and Biophysical Research Communications, vol. 204, No. 1, pp. 129-134 (1994).
Johnson et al., "Pharmacological and Functional Comparison of the Polo-like Kinase Family: Insight into Inhibitor and Substrate Specificity", Biochemistry, vol. 46, No. 33, pp. 9551-9563 (2007).

* cited by examiner

*Primary Examiner* — Karlheinz R Skowronek
*Assistant Examiner* — Joseph Fischer
(74) *Attorney, Agent, or Firm* — Bryan D. Zerhusen; Locke Lord LLP

(57) ABSTRACT

Found in various eukaryotic organisms, polo-like kinases (collectively, Plks) are a conserved subfamily of Ser/Thr protein kinases that play critical roles in cell proliferation. Provided herein are compounds that specifically inhibit the activity of Plks, specifically Plk1. Further provided herein are methods for use of the compounds for the treatment of hyperproliferative disorders, particularly cancer. Also provided are uses of the compounds for the preparation of a medicament.

21 Claims, 47 Drawing Sheets

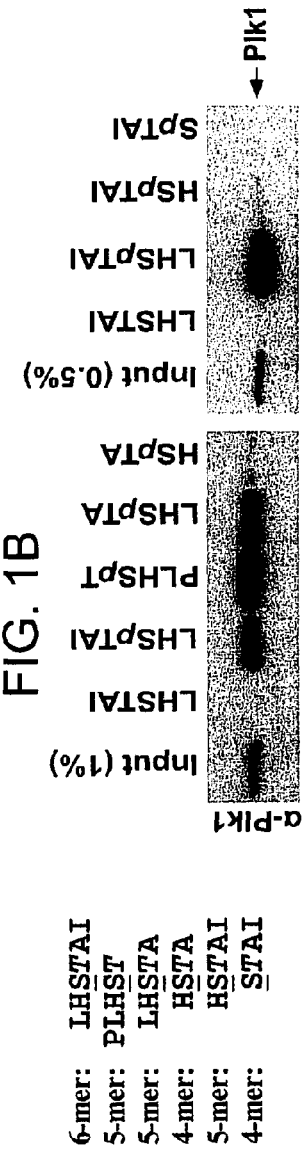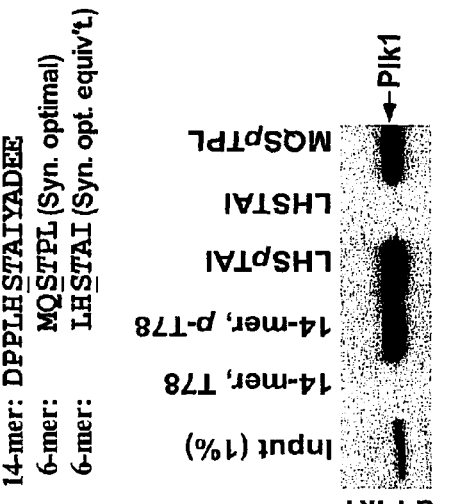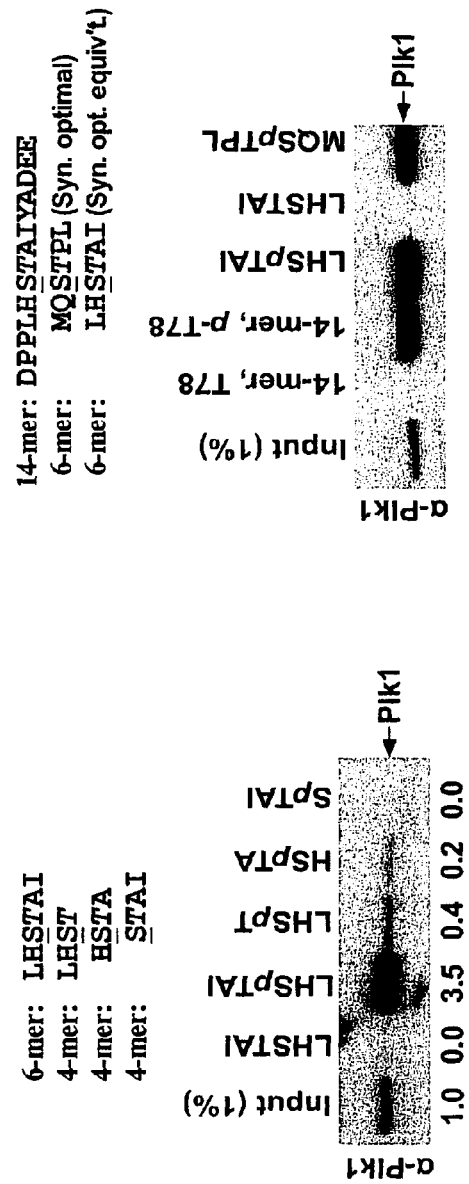

FIG. 4A
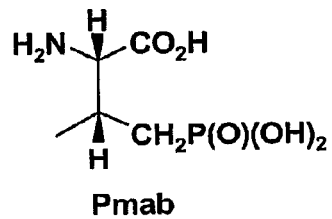
Pmab
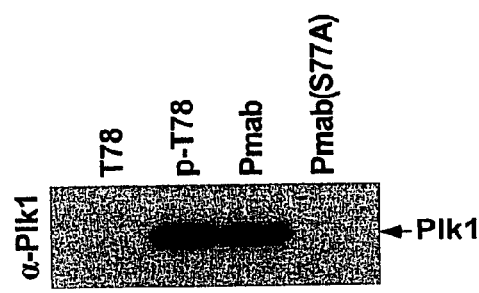
FIG. 4B
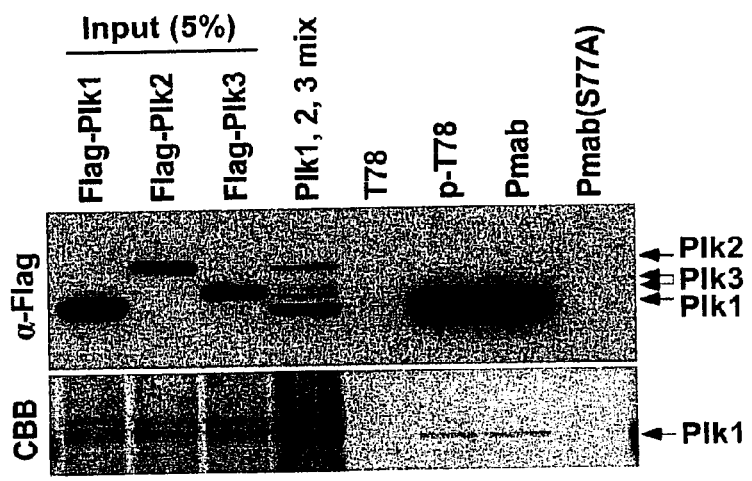

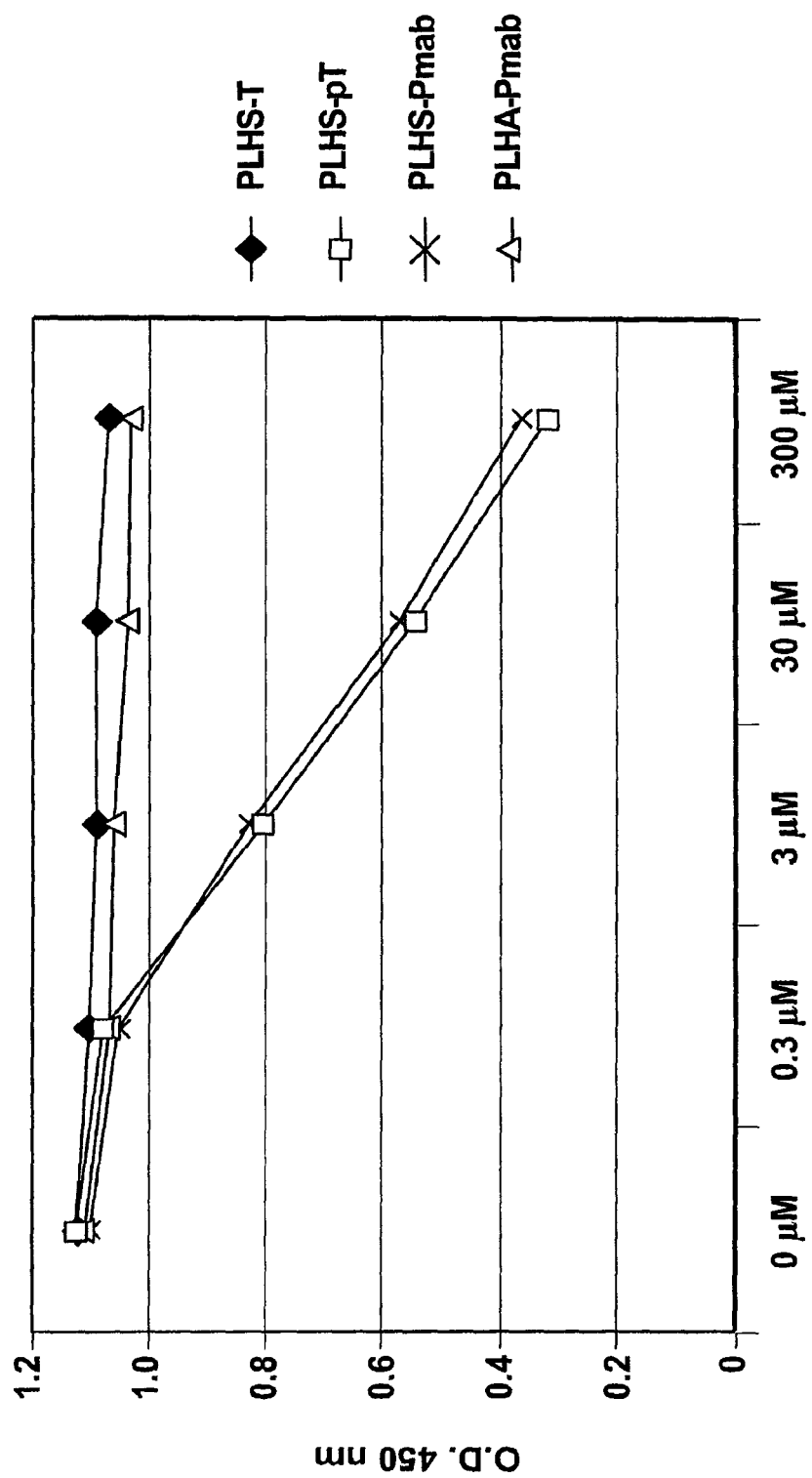

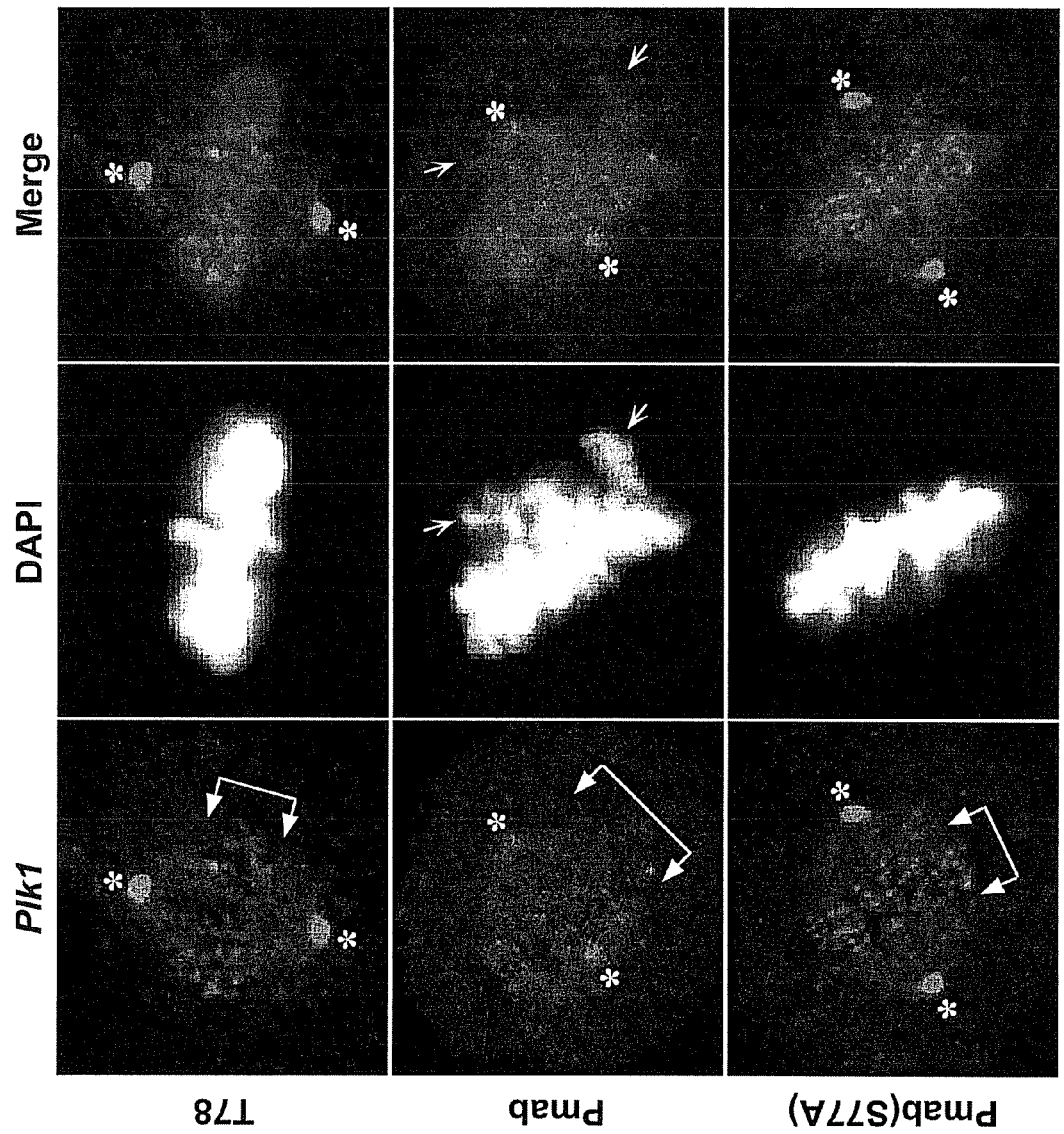

14-mer: DPPLH_S_TAIYADEE
6-mer: MQ_S_TPL (Syn. optimal)
6-mer: LH_S_TAI (Syn. opt. equiv't.)

14-mer: DPPLH_S_TAIYADEE
6-mer: MQ_S_TPL (Syn. optimal)
6-mer: PLH_S_T
6-mer: LH_S_TA

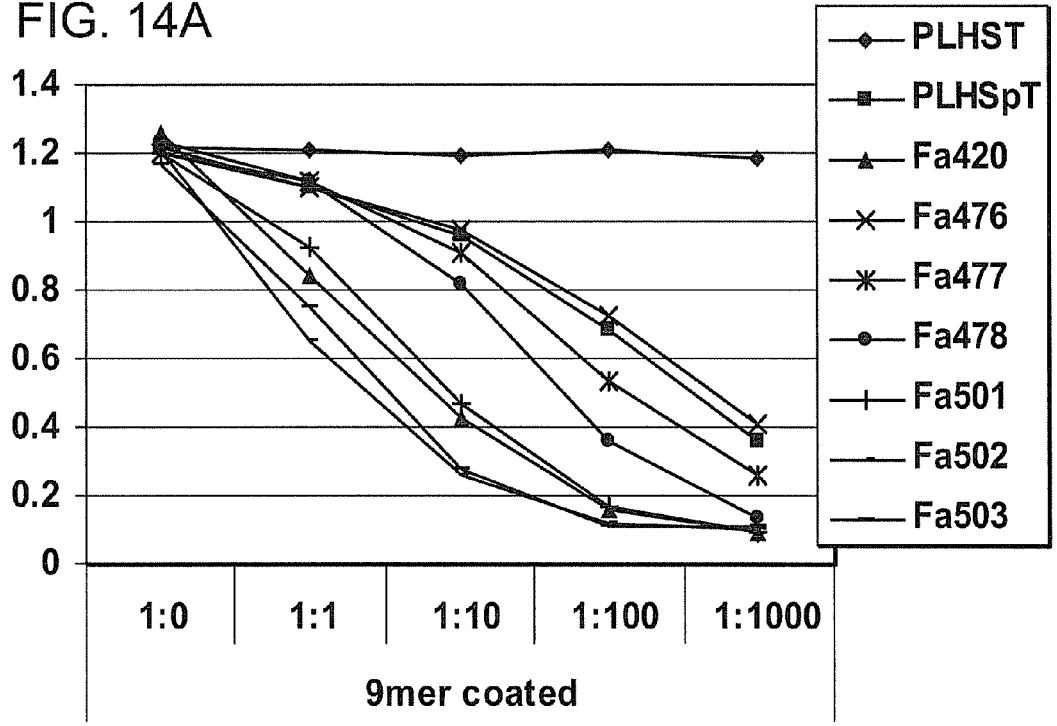
FIG. 14A 9mer coated
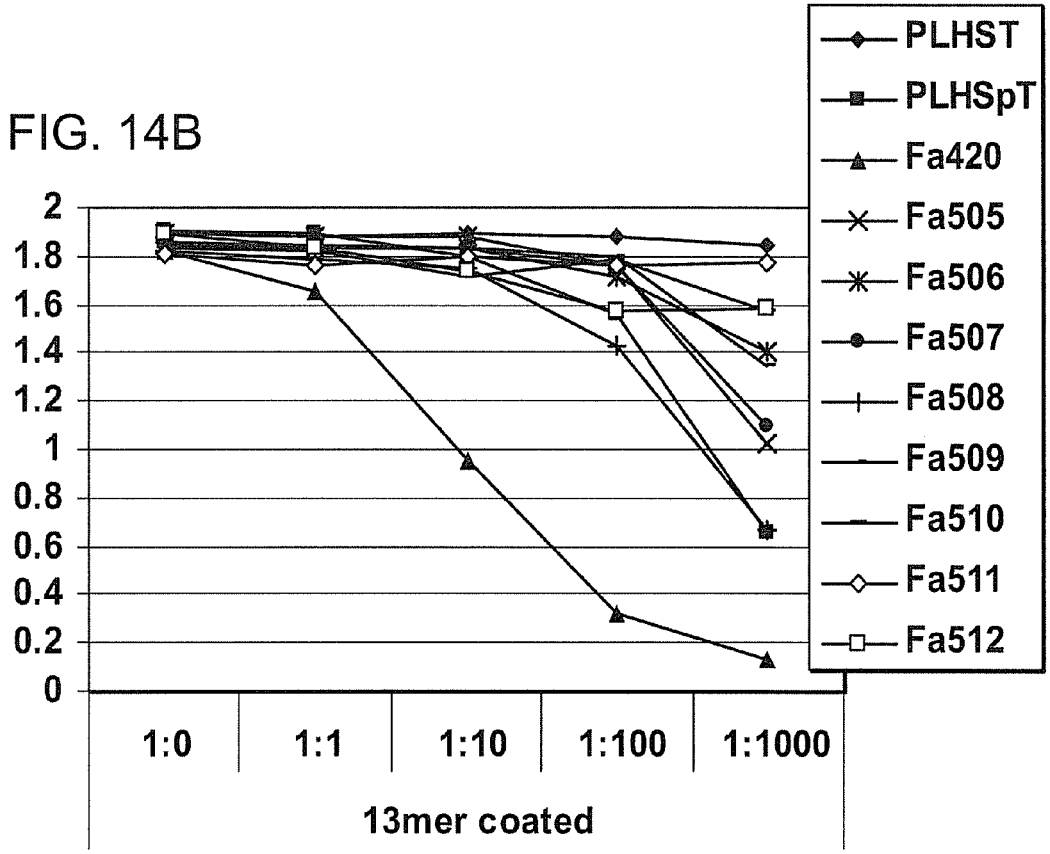
FIG. 14B 13mer coated

"no" as Cys-Ahx-PLHST;
"587" as Cys-Ahx-PLHSpT;
"563" as peptide 11;
"561" as peptide 13;
"562" as peptide 14;
"576" as peptide 12;
"611" as peptide 15;
"512" as peptide 16;

"no" as Cys-Ahx-PLHST;
"587" as Cys-Ahx-PLHSpT;
"613" as peptide 5;
"614" as peptide 7;
"615" as peptide 6;
"616" as peptide 8;

FIG. 23

Table 1. A comparison of the thermodynamic binding parameters of minimal Plk1-binding peptides

| Peptides | $K_d$ (μM) | ΔH (kcal/mol) | ΔS (cal/mol/K) | ΔG (kcal/mol) |
|---|---|---|---|---|
| MQSpTPL | 0.534 ± 0.230 | − 10.01 ± 5.53 | − 5.24 ± 1.85 | − 8.55 ± 0.57 |
| PLHSpTA | 0.262 ± 0.130 | − 11.60 ± 3.53 | − 8.83 ± 1.18 | − 8.97 ± 0.27 |
| LHSpTAI | 0.247 ± 0.050 | − 11.30 ± 2.23 | − 7.54 ± 0.75 | − 9.00 ± 0.11 |
| LHSpTA | 0.447 ± 0.110 | − 9.90 ± 0.40 | − 4.19 ± 1.33 | − 8.65 ± 0.14 |
| PLHSpT | 0.445 ± 0.180 | − 14.50 ± 5.01 | − 19.71 ± 3.38 | − 8.66 ± 0.49 |
| LHSpT | 22.100 ± 0.950 | − 6.29 ± 2.22 | − 0.20 ± 0.07 | − 6.35 ± 0.60 |
| HSpTA | 19.500 ± 1.700 | − 3.82 ± 0.25 | − 8.70 ± 0.85 | − 6.42 ± 0.05 |
| LHSTAI | no binding | no binding | no binding | no binding |

FIG. 24

Table 2. A comprehensive summary of the peptide inhibitors of Plk1

| Peptide[a] | Pull-down assay | | ITC | | XTAL[e] |
| --- | --- | --- | --- | --- | --- |
| | Plk1-binding[b] | Plk2-binding[b] | Plk1 PBD-binding[c] | Plk2 PBD-binding[d] | |
| MQSpTPL | H | M | −10.01 | −1.68 | Yes |
| DPPLHSpTAIYADEE | H | | | | |
| PLHSpTAIYAD | H | | | | |
| PLHSpTAIYA | H | | | | |
| PLHSpTAIY | H | | | | |
| PLHSpTAI | H | | | | |
| PLHSpTA | H | | −11.60 | | |
| PLHSpT | H | − | −14.50 | no binding | Yes |
| LHSpT | M/L | − | −6.29 | | |
| HSpT | − | | | | |
| SpT | − | | | | |
| LHSpTAI | H | − | −11.30 | | |
| LHSpTA | H | − | −9.90 | no binding | Yes |
| HSpTAI | M/L | | | | |
| HSpTA | M/L | − | −3.82 | | |
| SpTAI | − | | | | |
| PAHSpT | M | − | | | |
| PPHSpT | L | − | | | Yes |
| PQHSpT | H | L | | | |
| PLQSpT | H | M | | −1.10 | |
| PQQSpT | H | M | | | |
| LHSTAI | − | − | no binding | | |

[a] All the peptides used for the pull-down assays are N-terminally fused with the Cys-(CH2)₆ linker, whereas all the peptides used for the ITC analyses are N-terminally acetylated. See Table S1 for details.
[b] The levels of binding to Plk1 or Plk2 were categorized as a high (H), moderate (M), low (L), or no or negligible level of binding (−).
[c] Binding enthalpy in kcal/mol, which is indicative of productive, favorable binding contacts.
[d] Calorimetric initial heats of interaction in kcal/mol.
[e] Crystal structure (XTAL) of the Plk1 PBD-MQSpTPL complex has been described previously[12]. The other three structures have been determined in this study.

FIG. 25

Table 3. Peptides used for this study

| Length | Peptides[a] | Source |
|---|---|---|
| *Linker phospho-forms* | | |
| 14-mer | NH$_2$-C-(CH$_2$)$_6$-DPPLHSpTAIYADEE-NH$_2$ | This study |
| 10-mer | NH$_2$-C-(CH$_2$)$_6$-PLHSpTAIYAD-NH$_2$ | This study |
| 9-mer | NH$_2$-C-(CH$_2$)$_6$-PLHSpTAIYA-NH$_2$ | This study |
| 8-mer | NH$_2$-C-(CH$_2$)$_6$-PLHSpTAIY-NH$_2$ | This study |
| 7-mer | NH$_2$-C-(CH$_2$)$_6$-PLHSpTAI-NH$_2$ | This study |
| 6-mer | NH$_2$-C-(CH$_2$)$_6$-PLHSpTA-NH$_2$ | This study |
| 5-mer | NH$_2$-C-(CH$_2$)$_6$-PLHSpT-NH$_2$ | This study |
| 4-mer | NH$_2$-C-(CH$_2$)$_6$-LHSpT-NH$_2$ | This study |
| 3-mer | NH$_2$-C-(CH$_2$)$_6$-HSpT-NH$_2$ | This study |
| 2-mer | NH$_2$-C-(CH$_2$)$_6$-SpT-NH$_2$ | This study |
| 6-mer | NH$_2$-C-(CH$_2$)$_6$-LHSpTAI-NH$_2$ | This study |
| 5-mer | NH$_2$-C-(CH$_2$)$_6$-LHSpTA-NH$_2$ | This study |
| 4-mer | NH$_2$-C-(CH$_2$)$_6$-HSpTA-NH$_2$ | This study |
| 5-mer | NH$_2$-C-(CH$_2$)$_6$-HSpTAI-NH$_2$ | This study |
| 4-mer | NH$_2$-C-(CH$_2$)$_6$-SpTAI-NH$_2$ | This study |
| 5-mer | NH$_2$-C-(CH$_2$)$_6$-PAHSpT-NH$_2$ | This study |
| 5-mer | NH$_2$-C-(CH$_2$)$_6$-PPHSpT-NH$_2$ | This study |
| 5-mer | NH$_2$-C-(CH$_2$)$_6$-PQHSpT-NH$_2$ | This study |
| 5-mer | NH$_2$-C-(CH$_2$)$_6$-PLQSpT-NH$_2$ | This study |
| 5-mer | NH$_2$-C-(CH$_2$)$_6$-PQQSpT-NH$_2$ | This study |
| 5-mer | NH$_2$-C-(CH$_2$)$_6$-MLHSpT-NH$_2$ | This study[4] |
| 6-mer | NH$_2$-C-(CH$_2$)$_6$-MQSpTPL-NH$_2$ | |
| 9-mer | Biotin-C-(CH$_2$)$_6$-(CH$_2$)$_6$-DPPLHSpTAI-NH$_2$ | This study |
| *Linker non-phospho forms* | | |
| 14-mer | NH$_2$-C-(CH$_2$)$_6$-DPPLHSTAIYADEE-NH$_2$ | This study |
| 10-mer | NH$_2$-C-(CH$_2$)$_6$-PLHSTAIYAD-NH$_2$ | This study |
| 6-mer | NH$_2$-C-(CH$_2$)$_6$-LHSTAI-NH$_2$ | This study |
| 6-mer | NH$_2$-C-(CH$_2$)$_6$-PLHSTA-NH$_2$ | This study |
| 5-mer | NH$_2$-C-(CH$_2$)$_6$-PLHST-NH$_2$ | This study |
| *Linker p-T78 mimetic forms* | | |
| 5-mer | NH$_2$-C-(CH$_2$)$_6$-PLHS-Pmab-NH$_2$ | This study |
| 5-mer | NH$_2$-C-(CH$_2$)$_6$-PLHA-Pmab-NH$_2$ | This study |
| 6-mer | NH$_2$-C-(CH$_2$)$_6$-PLHS-F$_2$Pmab-A-NH$_2$ | This study |
| 6-mer | NH$_2$-C-(CH$_2$)$_6$-PLHA-F$_2$Pmab-A-NH$_2$ | This study |
| 6-mer | Biotin-(CH$_2$)$_6$-PLHS-F$_2$Pmab-A-NH$_2$ | This study |
| *No linker forms (p-T78, T78, and mimetic)* | | |
| 5-mer | Ac-PLHSpT-NH$_2$ | This study |
| 4-mer | Ac-LHSpT-NH$_2$ | This study |
| 5-mer | Ac-LHSpTA-NH$_2$ | This study |

FIG. 25 (Cont.)

Table 3. continued

| Length | Peptides[a] | Source |
|---|---|---|
| 4-mer | Ac-HSpTA-NH₂ | This study |
| 5-mer | Ac-PLHST-NH₂ | This study |
| 4-mer | Ac-LHSTA-NH₂ | This study |
| 6-mer | Ac-PLHSTA-NH₂ | This study |
| 5-mer | Ac-PLHS-Pmab-NH₂ | This study |
| 5-mer | Ac-PLHA-Pmab-NH₂ | This study |
| 6-mer | Ac-PLHS-F₂Pmab-A-NH₂ | This study |
| 6-mer | Ac-PLHA-F₂Pmab-A-NH₂ | This study |

[a] The p-T78 and T78 residues, and the phospho-Thr mimetic Pmab and F₂Pmab are marked in red.

FIG. 26

Table 4. Statistics of data collection and structure refinement

| | Crystals | | | |
|---|---|---|---|---|
| | $PBD^S$ $PBD^{S+G}$ | $PBD^{PL}$ | $PBD^{PP}$ | $PBD^{LH}$ |
| Data collection | | | | |
| Space group | $P2_1$ | $P2_12_12_1$ | $P2_12_12_1$ | $P2_1$ |
| Cell parameters | a = 33.29 Å<br>b = 102.29 Å<br>c = 68.55 Å<br>β = 93.24° | 35.19 Å<br>65.80 Å<br>104.11 Å | 35.44 Å<br>66.50 Å<br>105.82 Å | 38.31 Å<br>62.41 Å<br>46.61 Å<br>β = 94.07° |
| Molecules/a.u. | 2 | 1 | 1 | 1 |
| Resolution (Å) | 30 – 1.70 | 50 – 1.70 | 50 – 2.33 | 25 – 1.58 |
| Total reflections | 239,927 | 125,302 | 66,643 | 136,943 |
| Unique reflections | 49,748 | 28,597 | 10,764 | 28,949 |
| Completeness (%)[b] | 98.4 (85.8) | 93.7 (69.7) | 97.4 (86.5) | 96.4 (94.2) |
| Average I/σ(I) | 23.1 (3.0) | 22.6 (2.1) | 27.3 (4.9) | 17.4 (8.6) |
| $R_{merge}$ (%)[c] | 5.5 (25.9) | 5.1 (46.4) | 5.1 (26.8) | 4.3 (17.2) |
| Refinement statistics | | | | |
| R (%)[d] | 19.48 | 21.42 | 24.57 | 19.24 |
| $R_{free}$ (%)[e] | 24.28 (2.3% of data) | 26.77 (4.0% of data) | 29.32 (4.7% of data) | 22.69 (4.9% of data) |
| Rms deviations bond lengths (Å) | 0.013 | 0.017 | 0.008 | 0.009 |
| Rms deviations angles (°) | 1.5 | 1.7 | 1.3 | 1.01 |
| PDB code | 3C6I | 3C6J | 3C5L | 3FVH |

[a] Statistics given for the iodide derivative correspond to individual Friedel mates treated as independent reflections.
[b] The values in parentheses relate to the highest resolution shell.
[c] $R_{merge} = \sum |I-\langle I \rangle|/\sum I$, where I is the observed intensity, and $\langle I \rangle$ is the average intensity obtained from multiple observations of symmetry-related reflections after rejections.
[d] $R = \sum ||F_o| - |F_c||/\sum |F_o|$, where $F_o$ and $F_c$ are the observed and calculated structure factors, respectively.
[e] $R_{free}$ = defined as described previously[6].

PEPTIDE MIMETIC LIGANDS OF POLO-LIKE KINASE 1 POLO BOX DOMAIN AND METHODS OF USE

STATEMENT OF RIGHTS TO INVENTIONS MADE UNDER FEDERALLY SPONSORED RESEARCH

This work was supported by the Intramural Research Program of the National Institutes of Health and under Grant No. R01 GM60594; and the National Cancer Institute under Grant No. N01-CO-12400. The government has certain rights in the invention.

RELATED APPLICATIONS

This application is a 35 U.S.C. §371 U.S. national entry of International Application PCT/US2010/035069 (WO 2010/132869) having an International filing date of May 17, 2010, which claims priority to U.S. Provisional Patent Application No. 61/178,593 filed on May 15, 2009, and Provisional Patent Application Ser. No. 61/300,349 filed on Feb. 1, 2010, all of which are incorporated herein by reference in their entirety.

BACKGROUND

Found in various eukaryotic organisms, polo-like kinases (collectively, Plks) are a conserved subfamily of Ser/Thr protein kinases that play critical roles in cell proliferation (reviewed in refs 1,2). Plks are characterized by the presence of a highly conserved C-terminal polo-box domain (PBD) composed of two structurally-related PB1 (residues 411-489 in Plk1) and PB2 (residues 511-592) motifs (reviewed in ref 3). Multiple forms of Plks, designated Plk1, Plk2/Snk, Plk3/Prk/Fnk, and Plk4/Sak, exist in mammals. Plk4 is the most distantly related member of the Plk subfamily and one of the two Plk4 variants, Sak-a, contains only the PB1 motif near the end of an unusually long C-terminal extension. Among the Plks, Plk1 has been studied most extensively because of its ability to override cellular checkpoints and induce genetic instability, leading to oncogenic transformation of human cells (reviewed in refs 4,5). Not surprisingly, Plk1 is overexpressed in a broad spectrum of human cancers and has been proposed as a new prognostic marker for many types of malignancies. Furthermore, interference with Plk1 function induces apoptotic cell death in most tumor cells, but not in normal cells, and reduces tumor growth in mouse xenograft models (reviewed in ref 5). A Plk1 inhibitor ON01910 is presently undergoing clinical trials for the treatment of various human cancers. In contrast to the role of Plk1 in cell proliferation and tumorigenesis, the two most closely related kinases, Plk2 and Plk3, appear to play a role in checkpoint-mediated cell cycle arrest to ensure genetic stability and prevent oncogenic transformation (6, 7). Thus, specific inhibition of Plk1, but not Plk2 or Plk3, is critically important for anti-Plk1 cancer therapy.

The PBD of Plk1 plays a critical role in proper subcellular localization and mitotic functions of Plk1 (8-10) by interacting with phosphorylated Ser/Thr peptides with the invariable Ser residue at the −1 position (S-p-S/T motif)(11). Crystal structures of the Plk1 PBD in complex with artificial phosphopeptides optimized for PBD binding have revealed that the PB1 and PB2 motifs have identical folds described as β6α (a six-stranded anti-parallel β-sheet and an α-helix) and form a hetero-dimeric phosphopeptide-binding module (12,13). The phosphopeptide binds to a cleft formed between PB1 and PB2 and interacts with key amino acid residues from both polo-boxes. His538 and Lys540 from PB2 are pivotal for electrostatic interactions with the negatively charged phosphate group of phospho-Ser/Thr (p-Ser/Thr) residue, whereas Trp414 from PB1 is critical for the selection of Ser at the −1 position by engaging in two hydrogen bonding interactions and van der Waals interactions with the Ser-1 residue (12,13). These residues are conserved in the PBDs of Plk1, Plk2, and Plk3 (in short, Plk1-3), attesting to their importance (Plk4 has a distinct binding module and forms a homodimer through a single PB1 motif (14). However, minimal elements required for stable PBD binding and the interactions critical for achieving the specificity between Plk1 and its binding targets are poorly understood. Addressing these issues is pivotal in providing new insights into PBD-dependent interactions with its binding targets and designing new strategies for the development of anti-Plk1 therapeutic agents.

SUMMARY OF THE INVENTION

The invention provides compounds that bind polo-like kinases through the polo-box domain. The invention provides methods of use of the compounds and methods of synthesis of the compounds. The invention provides the compounds as pharmaceutically acceptable salts. The invention provides the compounds in pharmaceutically acceptable carriers and the use of the compounds for the preparation of a medicament. The invention further provides kits containing the compounds of the invention, and kits for synthesizing the compounds of the invention. The invention provides libraries including 2 or more compounds of the invention.

The invention provides compounds based on the structure (1):

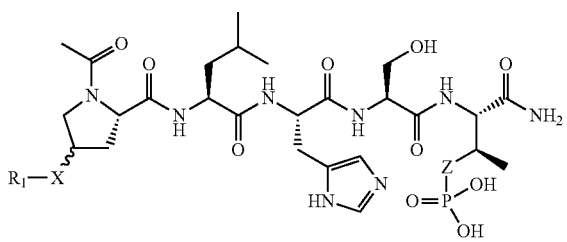

in which Z is one of O, $CH_2$, and $CF_2$;

$R_1X$ is one of: $R_1$—CH=N—O—; $R_1$—$CH_2$—$CH_2$—O—; $R_1$—C(O)—NH—O—; $R_1$—$CH_2$—$CH_2$—$CH_2$—; and $R_1$—$CH_2$—$CH_2$—S—;

$R_1$ is one of:

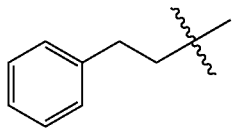
a-1

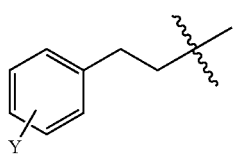
a-2

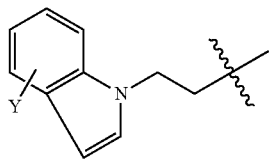
a-3

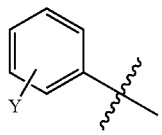
a-4

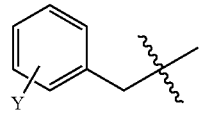
a-5

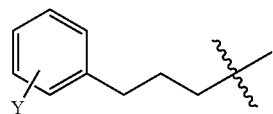
a-6

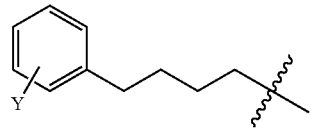
a-7 or any compound provided in Table A, such as A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-31, A-33, A-34, A-35, A-36, A-37, A-38, A-39, A-40, and A-41

Y is a group selected from the group consisting of: aryl, heteroaryl, lower alkyl, higher alkyl, lower alkene, higher alkene, halogen, amine, amide, carboxyl, olefin, and carbonyl; or any pharmaceutically acceptable salt of the compounds based on structure (1).

In certain embodiments of compound (1), Z is O; and $R_1$ is one of a-1, a-2, a-3, a-4, a-5, a-6, and a-7.

In certain embodiments of compound (1), Z is O; $R_1X$ is one of: $R_1$—CH=N—O—; and $R_1$—CH$_2$—CH$_2$—O—; and $R_1$ is a-1. In such embodiments, the compounds have the structures (2) or (3) as shown:

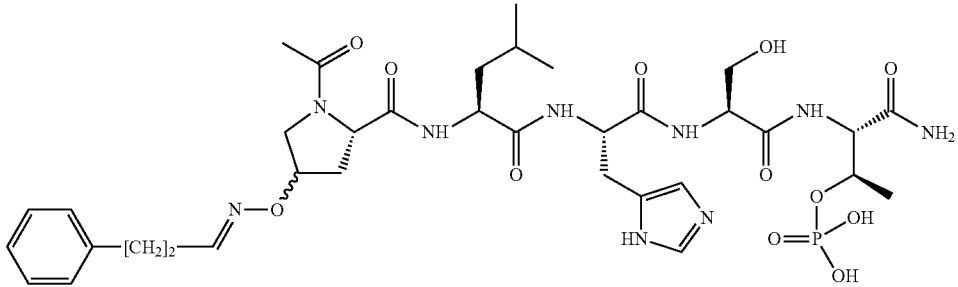
(2)

or

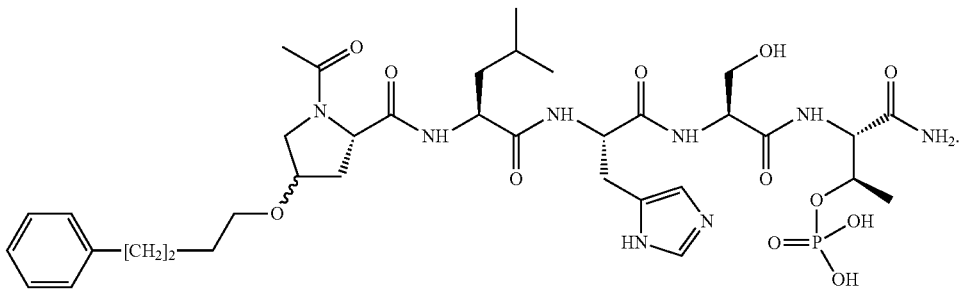
(3)

The invention provides compounds based on the structure (4):

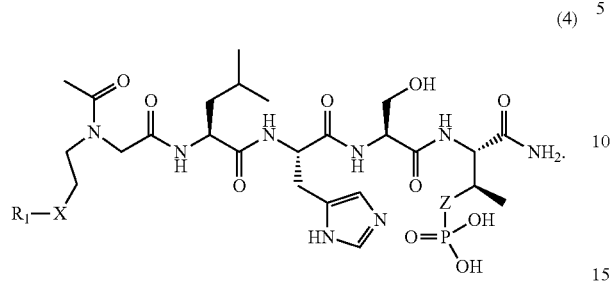
(4)

in which Z is one of: O, CH$_2$, and CF$_2$;

R$_1$X is one of: R$_1$—CH$_2$—CH$_2$—CH$_2$—; R$_1$—CH$_2$—CH$_2$—CH$_2$—CH$_2$—; R$_1$—CH$_2$—CH$_2$—S—; R$_1$—CH=N—O—; R$_1$—CH$_2$—CH$_2$—O—; and R$_1$—C(O)—NH—O—; and R$_1$ is one of:

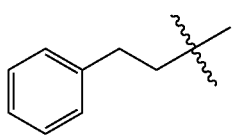
a-1

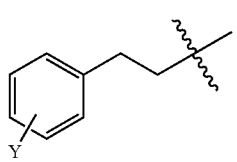
a-2

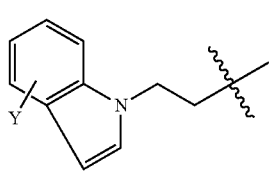
a-3

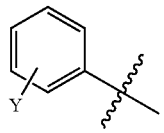
a-4

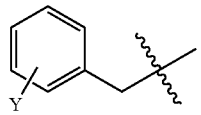
a-5

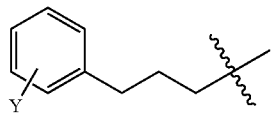
a-6

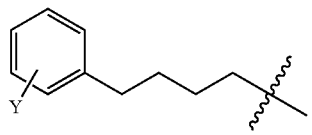
a-7 or any compound A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-31, A-33, A-34, A-35, A-36, A-37, A-38, A-39, A-40, and A-41 from Table A;

Y is a group selected from the group consisting of: aryl, heteroaryl, lower alkyl, higher alkyl, lower alkene, higher alkene, halogen, amine, amide, carboxyl, olefin, and carbonyl; or any pharmaceutically acceptable salt of the compounds based on structure (4).

In certain embodiments, the compounds based on structure (4), Z is O; and

R$_1$ is one of a-1, a-2, a-3, a-4, a-5, a-6, and a-7.

In certain embodiments, the compounds based on structure (4), Z is O; R$_1$X is one of R$_1$—CH$_2$—CH$_2$—CH$_2$— or R$_1$—CH$_2$—CH$_2$—CH$_2$—CH$_2$—CH$_2$—; and R$_1$ is a-1, providing a compound having the structure (5) as shown:

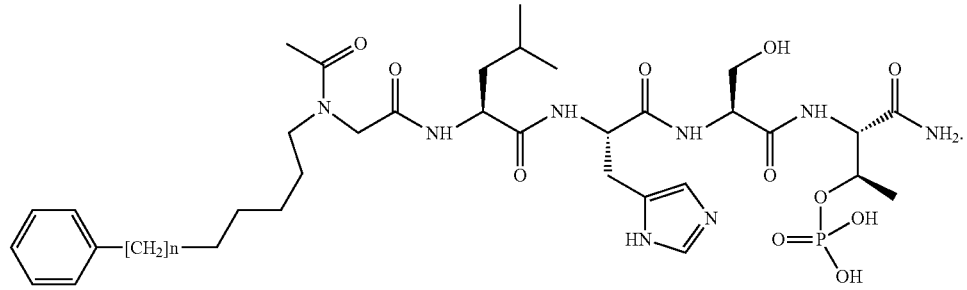
(5)

n = 1, 2

The invention provides compounds based on the structure (6):

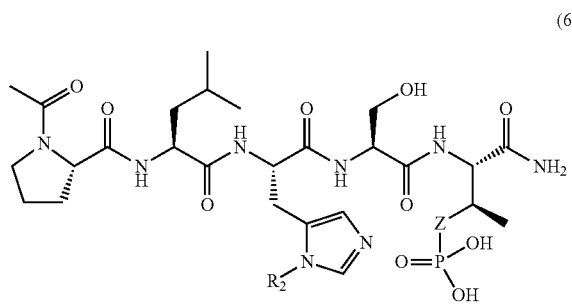

(6)

in which Z is one of O, CH$_2$, and CF$_2$;
R$_2$ is one of:

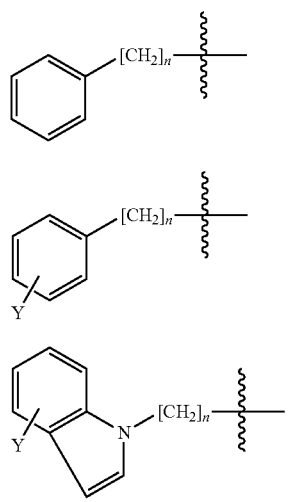

wherein n=8, 1, 2, 3, 4, 5, 6, 7, 9, or 10; and
Y is a group selected from the group consisting of: aryl, heteroaryl, lower alkyl, higher alkyl, lower alkene, higher alkene, halogen, amine, amide, carboxyl, olefin, and carbonyl; or any pharmaceutically acceptable salt of the compounds based on structure (6).

In certain embodiments of compounds based on the structure (6), Z is O.

In certain embodiments of compounds based on the structure (6), Z is O, R$_2$ is a-1, and n=8, wherein the compound has the structure of

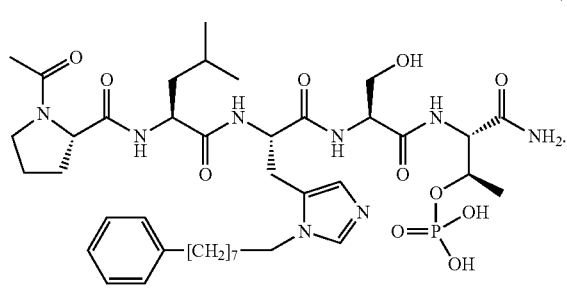

(7)

The invention provides compounds based on the structure (8):

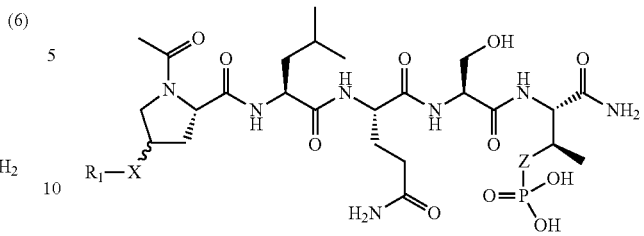

(8)

in which Z is one of O, CH$_2$, and CF$_2$;
R$_1$X is one of R$_1$—CH=N—O—; R$_1$—CH$_2$—CH$_2$—O—; R$_1$—C(O)—NH—O—; R$_1$—CH$_2$—CH$_2$—CH$_2$—; R$_1$—CH$_2$—CH$_2$—S—; and
R$_1$ is one of:

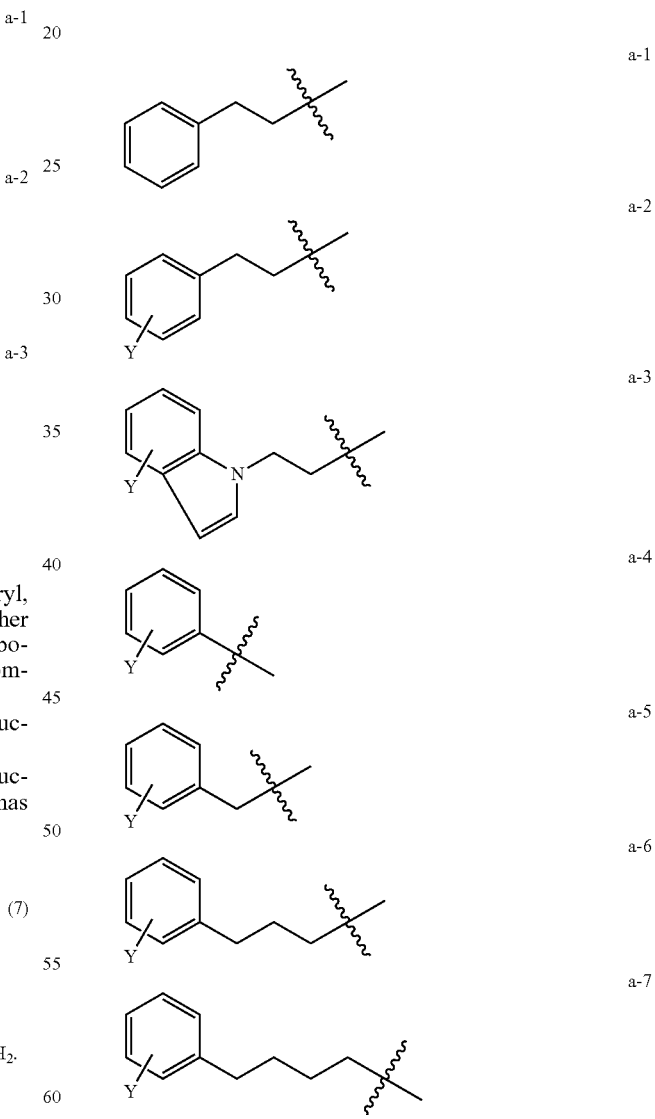

or any compound A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-31, A-33, A-34, A-35, A-36, A-37, A-38, A-39, A-40, and A-41 from Table A; and Y is one of: aryl, heteroaryl, lower alkyl, higher alkyl, lower alkene, higher alkene, halogen, amine, amide, carboxyl, olefin, and carbonyl; or any pharmaceutically acceptable salt of a compound based on the structure (8).

In certain embodiments of compounds based on the structure (8), Z is O; and $R_1$ is one of a-1, a-2, a-3, a-4, a-5, a-6, and a-7.

The invention provides compounds based on the structure (9):

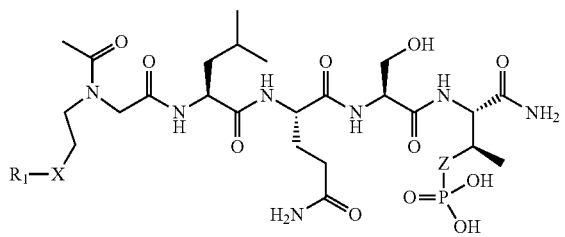

(9)

wherein Z is selected from the group consisting of O, $CH_2$, and $CF_2$;

$R_1X$ is selected from the group consisting of $R_1$—CH=N—O—; $R_1$—$CH_2$—$CH_2$—O—; $R_1$—C(O)—NH—O—; $R_1$—$CH_2$—$CH_2$—$CH_2$—; $R_1$—$CH_2$—$CH_2$—S—

$R_1$ is a group selected from the group consisting of:

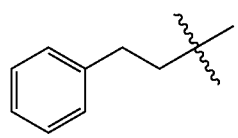

a-1

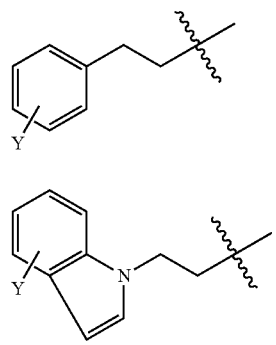

a-2 a-3

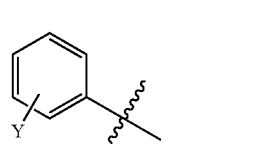

a-4

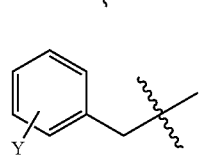

a-5

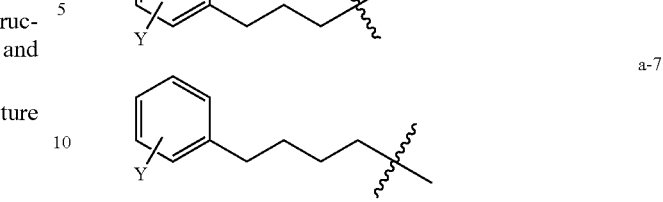

a-6 a-7 or any compound A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-31, A-33, A-34, A-35, A-36, A-37, A-38, A-39, A-40, and A-41 from Table A;

Y is a group selected from the group consisting of: aryl, heteroaryl, lower alkyl, higher alkyl, lower alkene, higher alkene, halogen, amine, amide, carboxyl, olefin, and carbonyl;

or any pharmaceutically acceptable salt of a compound based on the structure (9).

In certain embodiments, the invention provides compounds based on structure (9) in which Z is O; and $R_1$ is a group of one of a-1, a-2, a-3, a-4, a-5, a-6, and a-7.

The invention provides compounds based on the structure (10):

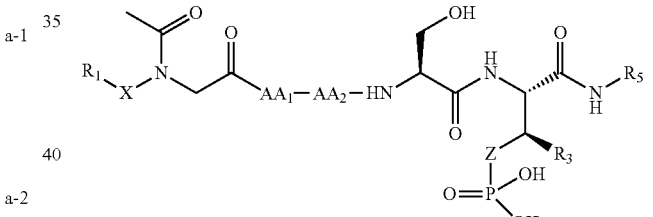

(10)

in which $R_1$ is one of

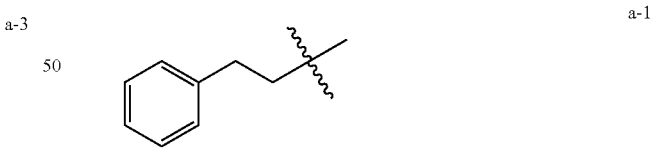

a-1

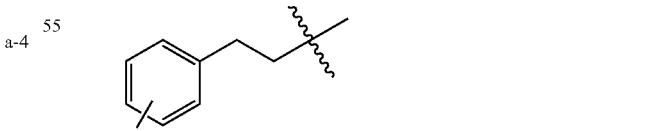

a-2

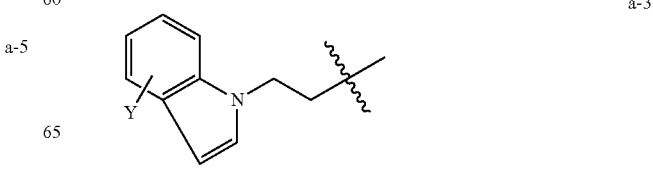

a-3

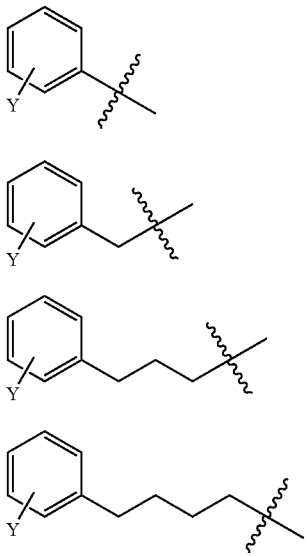

or any compound A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-31, A-33, A-34, A-35, A-36, A-37, A-38, A-39, A-40, and A-41;

Y is a group selected from the group consisting of: aryl, heteroaryl, lower alkyl, higher alkyl, lower alkene, higher alkene, halogen, amine, amide, carboxyl, olefin, and carbonyl;

$R_1$—X is selected from the group consisting of $R_1$—CH=N—O—; $R_1$—$CH_2$—$CH_2$—O—; $R_1$—C(O)—NH—O—; $R_1$—$CH_2$—$CH_2$—$CH_2$—; $R_1$—$CH_2$—$CH_2$—S—; $R_1$-lower alkyl chain; $R_1$-higher alkyl chain; and $R_1$-lower heteroalkyl or $R_1$-higher heteroalkyl wherein said heteroalkyl comprises a group selected from the group consisting of: alkenyl, aryl, heteroaryl, cycloalkyl, heterocycloalkyl, amide, ester, oxime, ether or thioether;

$AA_1$ is an amino acid Cys, Asp, Glu, Phe, Gly, His, Ile, Lys, Leu, Met, Asn, Pro, Gln, Arg, Ser, Thr, Val, Trp, or Tyr; or any non-natural amino acid except alanine analogs;

$AA_2$ is an amino acid His, Gln, Ala, Cys, Glu, Phe, His, Ile, Met, Asn, Ser, Thr, Val, or Tyr; and Z is one of O, $CH_2$, and $CF_2$;

$R_3$ is one of —$CH_3$ and —H; and $R_5$ is one of —H or Gly; or any pharmaceutically acceptable salt of a compound based on the structure (10).

The invention provides compounds based on the structure (11):

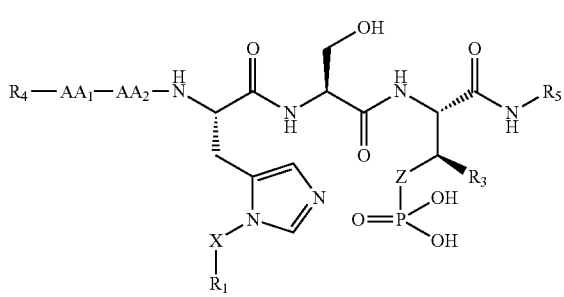

(11)

in which $R_1$—X is one of $R_1$—CH=N—O—; $R_1$—$CH_2$—$CH_2$—O—; $R_1$—C(O)—NH—O—; $R_1$—$CH_2$—$CH_2$—$CH_2$—; $R_1$—$CH_2$—$CH_2$—S—; $R_1$-lower alkyl chain; $R_1$-higher alkyl chain; and $R_1$-lower heteroalkyl or $R_1$-higher heteroalkyl wherein said heteroalkyl comprises a group selected from the group consisting of: alkenyl, aryl, heteroaryl, cycloalkyl, heterocycloalkyl, amide, ester, oxime, ether or thioether;

$R_1$ is one of

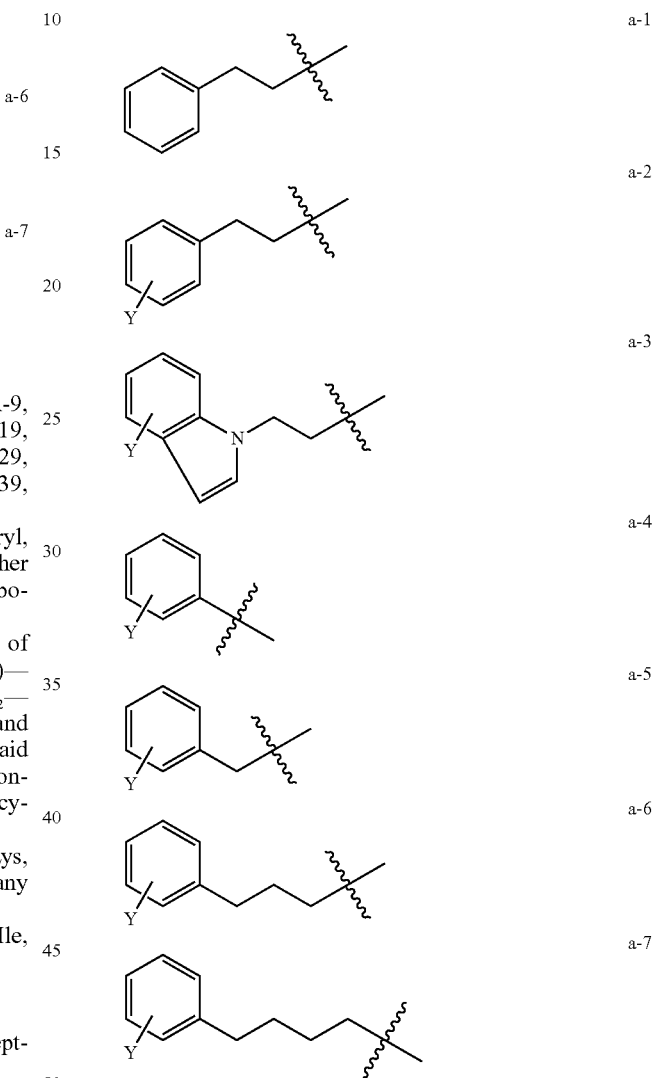

or any compound A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-31, A-33, A-34, A-35, A-36, A-37, A-38, A-39, A-40, and A-41; Y is one of the group of: aryl, heteroaryl, lower alkyl, higher alkyl, lower alkene, higher alkene, halogen, amine, amide, carboxyl, olefin, and carbonyl;

$R_3$ is H or any acyl group;

Z is O, $CH_2$, and $CF_2$;

$AA_1$ is an amino acid of the group consisting of Cys, Asp, Glu, Phe, Gly, His, Ile, Lys, Leu, Met, Asn, Pro, Gln, Arg, Ser, Thr, Val, Trp, and Tyr; and any non-natural amino acid except alanine analogs;

$AA_2$ is an amino acid of group consisting of His, Gln, Ala, Cys, Glu, Phe, His, Ile, Met, Asn, Ser, Thr, Val, and Tyr; and $R_5$ is one of —H or Gly;

or any pharmaceutically acceptable salt of a compound based on the structure (11).

The invention provides compounds based on the structure (12):

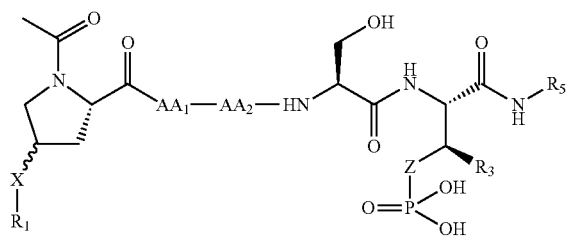

(12)

in which $R_1$—X is one of $R_1$—CH=N—O—; $R_1$—CH$_2$—CH$_2$—O—; $R_1$—C(O)—NH—O—; $R_1$—CH$_2$—CH$_2$—CH$_2$—; $R_1$—CH$_2$—CH$_2$—S—; $R_1$-lower alkyl chain; $R_1$-higher alkyl chain; and $R_1$-lower heteroalkyl or $R_1$-higher heteroalkyl wherein said heteroalkyl comprises a group selected from the group consisting of: alkenyl, aryl, heteroaryl, cycloalkyl, heterocycloalkyl, amide, ester, oxime, ether or thioether;

$R_1$ is one of:

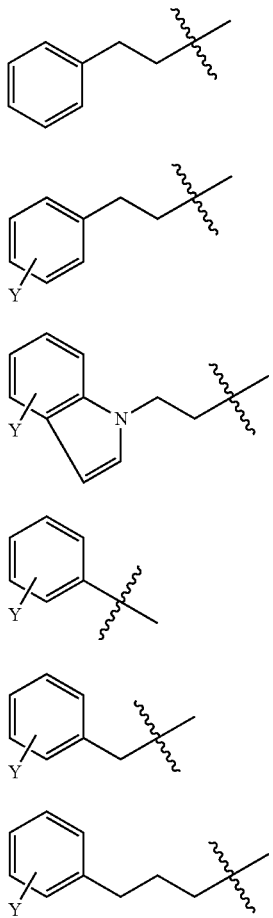

a-1 a-2 a-3 a-4 a-5 a-6

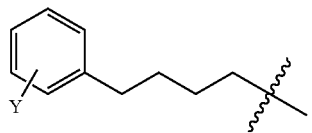

a-7 or any compound A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-31, A-33, A-34, A-35, A-36, A-37, A-38, A-39, A-40, and A-41;

Y is a group selected from the group consisting of: aryl, heteroaryl, lower alkyl, higher alkyl, lower alkene, higher alkene, halogen, amine, amide, carboxyl, olefin, and carbonyl Z is selected from the group consisting of O, CH$_2$, and CF$_2$;

AA$_1$ is an amino acid of the group consisting of Cys, Asp, Glu, Phe, Gly, His, Ile, Lys, Leu, Met, Asn, Pro, Gln, Arg, Ser, Thr, Val, Trp, and Tyr; and any non-natural amino acid except alanine analogs;

AA$_2$ is an amino acid of group consisting of His, Gln, Ala, Cys, Glu, Phe, His, Ile, Met, Asn, Ser, Thr, Val, and Tyr; and R$_3$ is selected from the group consisting of —H and CH$_3$; and R$_5$ is H or glycine;

or any pharmaceutically acceptable salt of a compound based on the structure (11).

The invention provides compounds having the following structures:

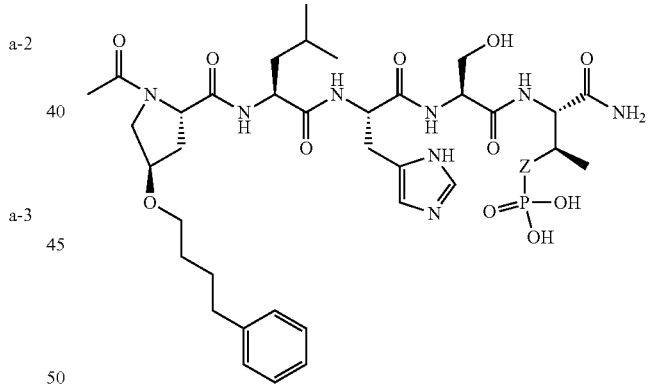

(13)

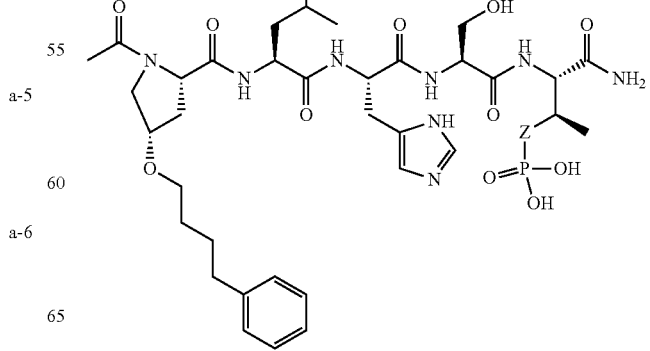

(14)

-continued
(15)
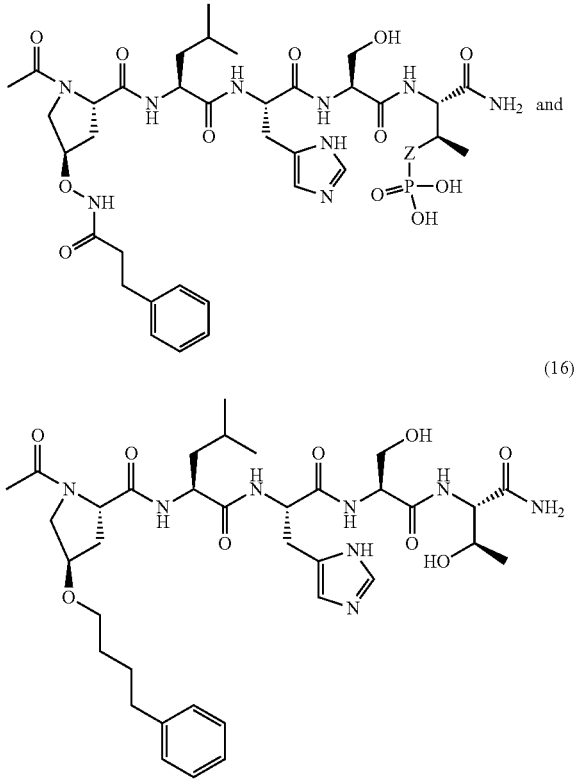
(16)
in which Z is one of O, CH$_2$, and CF$_2$;
or a pharmaceutically acceptable salt of a compound based on structure (13), (14), (15), or (16).
The invention provides compounds based on the structures (17) and (18):
(17)
(18)
in which R$_7$ is one of:
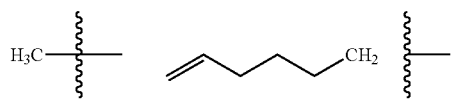
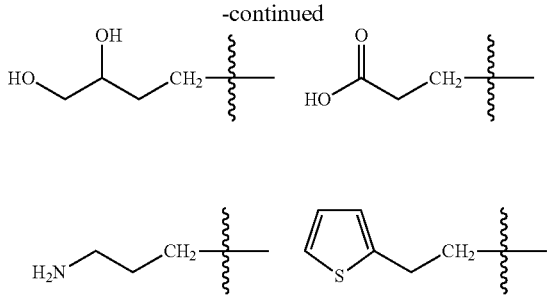
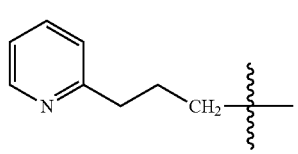
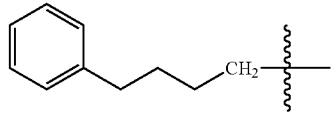
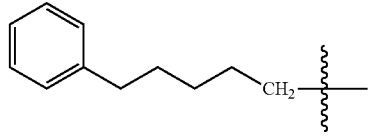
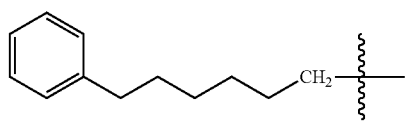
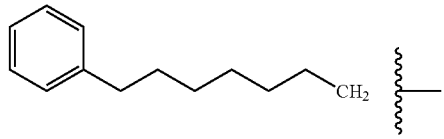
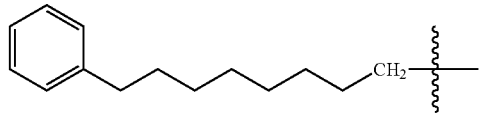
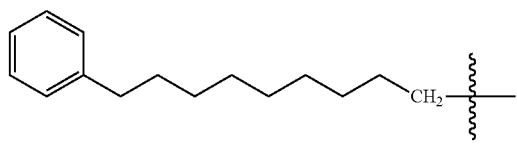

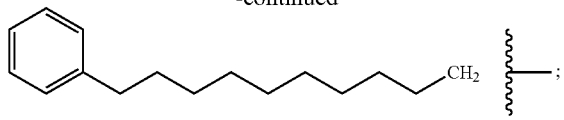

or a pharmaceutically acceptable salt of a compound based on one of structures (17) or (18).

The invention provides compounds based on structures (19) and (20):

(19)

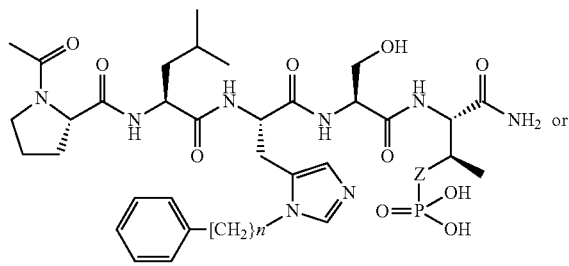

(20)

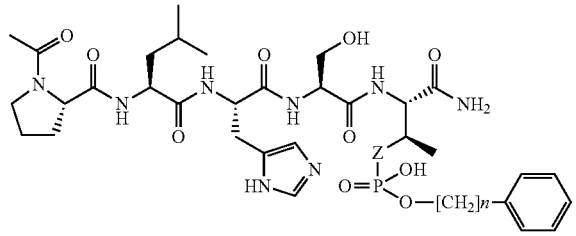

in which n is 7 or 8;

Z is one of O, $CH_2$, and $CF_2$;

or a pharmaceutically acceptable salt of a compound based on structure (19) or (20).

The invention provides compounds based on structures (21) and (22):

(21)

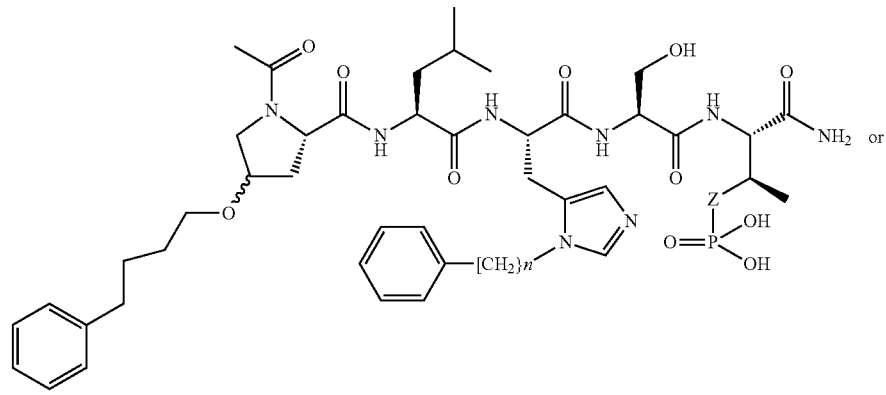

(22)

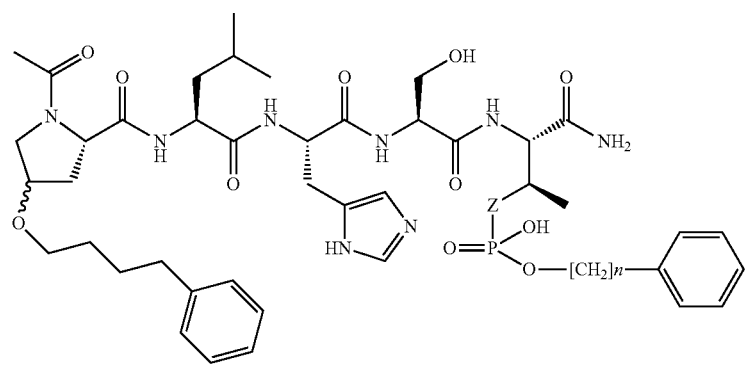

in which n is 2, 3, 4, 5, 6, 7, 8, 9, or 10; and Z is one of O, $CH_2$, and $CF_2$; or a pharmaceutically acceptable salt compound based on structure (21) or (22).

The invention provides compounds based on structure (23):
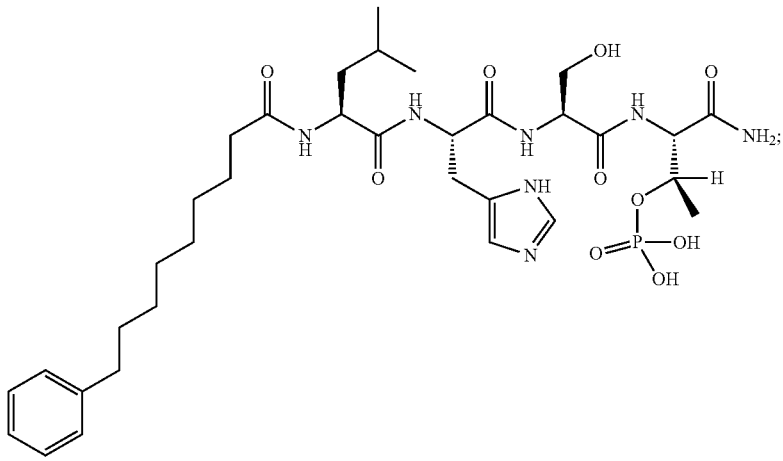
(23)
or a pharmaceutically acceptable salt of a compound based on structure (23).
The invention provides compounds based on structure (24):
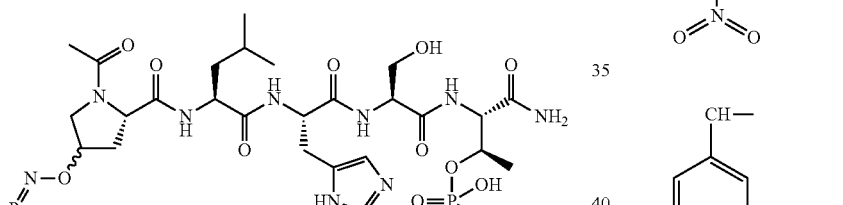
(24)
in which $R_1$ is one of:
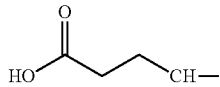
aa
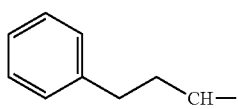
ab
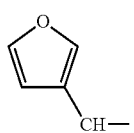
ac
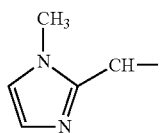
ad
-continued
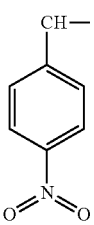
ae
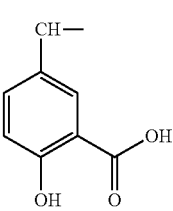
af
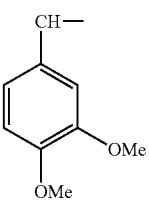
ag
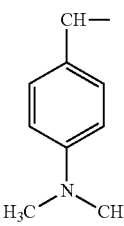
ah
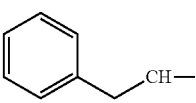
ai -continued aj [structure: 3-phenylpropyl-CH—]

ak [structure: 2-methylphenethyl-CH—]

al [structure: 3-methylphenethyl-CH—]

am [structure: 4-methylphenethyl-CH—]

an [structure: 3-methoxyphenethyl-CH—]

ao [structure: 3-bromophenethyl-CH—]

ap [structure: 3-biphenylethyl-CH—]

and an R₁ group derived from any aldehyde provided herein, such as those in Table A; in which the undefined sterobonds are either cis or trans.

The invention provides compounds based on structure (25):

(25)

[structure of peptide with R₉, R₈, N, leucine, histidine, serine, threonine-phosphate, NH₂]

in which R₉ is H or acetyl; and
R₈ is one of:

a [ˉH₂C-CH₂-CH₂-CH₃]

-continued b [cyclopentyl-CH⁻]

c [cyclohexyl-CH₂⁻]

d [ˉH₂C-CH₂-CO₂Hˉ]

e [ˉH₂C-CH₂-NH₂]

f [benzyl CH₂⁻]

g [ˉHC(S)-phenyl]

h [3,5-dimethoxybenzyl CH₂⁻]

i [furan-2-yl-CH₂⁻]

j [3,4-difluorobenzyl CH₂⁻]

k [ˉHC(R)-phenyl]

-continued

[Structures labeled l, m, n, o, p, q, r showing: 1-naphthylmethyl (CH₂-), benzyl (PhCH₂-), phenethyl (PhCH₂CH₂-), phenylpropyl, phenylbutyl, phenylpentyl, phenylhexyl (CH₂- groups with increasing alkyl chain lengths attached to phenyl)]

or

—(CH$_2$)$_n$—OPO$_3$H$_2$ wherein n=2, 3, 4, 5, 6, or 7;

or any pharmaceutically acceptable salt based on structure (25).

The invention provides compounds based on the structure:

(26)

[Chemical structure of compound 26: peptide with R₁₀ group, acetyl, leucine, histidine, serine, threonine-phosphate, amide]

wherein R$_{10}$ comprises —(CH$_2$)$_n$—OPO$_3$H$_2$ wherein n=2, 3, 4, 5, 6, or 7; or any pharmaceutically acceptable salt based on the structure of compound (26).

The invention further provides compounds FA505, FA506, FA507, FA510, FA511, and FA512 having structures:

[Structure FA505 — isomer 1]

[Structure FA506 — isomer 2]

[Structure FA510]

[Structure FA511]

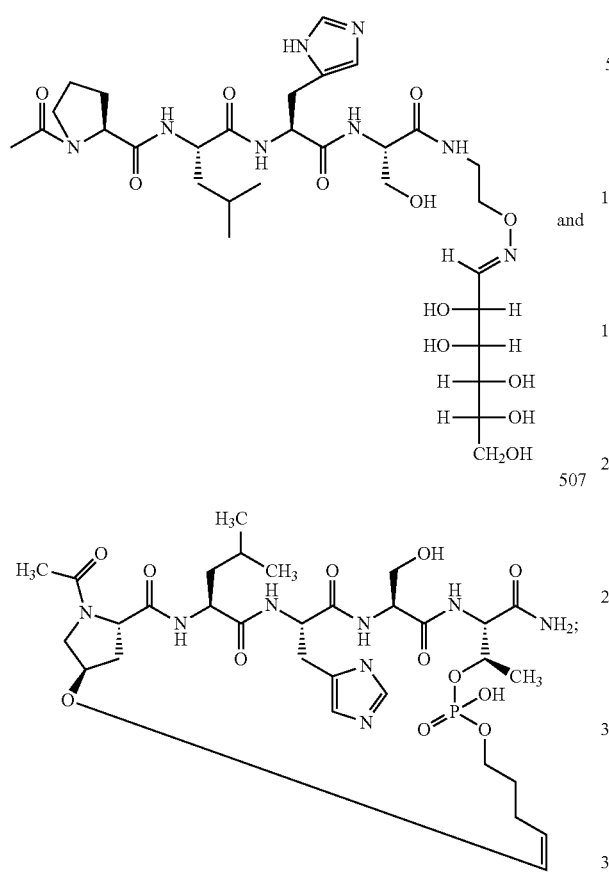

or any pharmaceutically acceptable salt of any of compounds 505, 506, 507, 510, 511, and 512.

The invention provides a number of compounds in Tables 7 to 12 including compounds FA550-FA553. The invention includes pharmaceutically acceptable salts of any of the compounds provided in Tables 7 to 12 and compounds FA550-FA553.

The invention provides compositions including any of the compounds of the invention a pharmaceutically acceptable carrier, for use, for example, for the preparation of a medicament. The medicament can be, for example, a medicament for the prevention, amelioration, or treatment of a hyperproliferative disorder such as cancer.

As such, the compounds of the invention can be used in methods for the prevention, amelioration, or treatment of a subject for a hyperproliferative disorder. Such methods can further include identification of a subject suffering from or suspected of suffering from a hyperproliferative disorder and/or monitoring the subject for prevention, amelioration, or treatment of a hyperproliferative disorder. In certain embodiments, the hyperproliferative disorder is cancer. Cancers can be characterized as solid tumors and non-solid tumors. Cancers include, but are not limited to Acute Lymphoblastic Leukemia, Acute Myeloid Leukemia, Adrenocortical Carcinoma, Basal Cell Carcinoma, Bladder Cancer, Bone Cancer, Brain Tumor, Breast Cancer, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Esophageal Cancer, Ewing Family of Tumors, Retinoblastoma, Gastric (Stomach) Cancer, Gastrointestinal Tumors, Glioma, Head and Neck Cancer, Hepatocellular (Liver) Cancer, Hodgkin Lymphoma, Islet Cell Tumors (Endocrine Pancreas), Kidney (Renal Cell) Cancer, Laryngeal Cancer, Lung Cancer, Non-Small Cell, Lung Cancer, Small Cell, Lymphoma, Medulloblastoma, Melanoma, Pancreatic Cancer, Prostate Cancer, Renal Cancer, Rectal cancer, Thyroid Cancer.

The invention provides compounds for use in synthetic methods, such as compounds having structure (27)

(27)

Pmab in which the isomer shown is at least 60%, 70%, 80%, 85%, 90% or 95% of the compound present.

The invention provides kits containing at least one compound of the inventions and instructions for use. The invention provides kits having 2, 3, 4, 5, 6, 7, 8, 9, or 10 compounds.

The invention provides libraries including at least two compounds of the invention.

DEFINITIONS

An "agent" is understood herein to include a therapeutically active compound or a potentially therapeutically active compound. An agent can be a previously known or unknown compound. As used herein, an agent is typically a non-cell based compound, however, an agent can include a biological therapeutic agent, e.g., peptide or nucleic acid therapeutic, cytokine, antibody, etc.

An "agonist" is understood herein as a chemical substance capable of initiating the same reaction or activity typically produced by the binding of an endogenous substance or ligand to its target. An "antagonist" is understood herein as a chemical substance capable of inhibiting the reaction or activity typically produced by the binding of an endogenous substance (e.g., an endogenous agonist) to its target to prevent signaling through a receptor, to prevent downstream signaling, or to prevent cellular events (e.g., progression through cell cycle) that are the normal result of activation of the target. The antagonist can bind directly to the target or can act through other proteins or factors required for signaling. Agonists and antagonists can modulate some or all of the activities of the endogenous substance or ligand that binds to the target. Antagonists are typically characterized by determining the amount of the antagonist is required to inhibit the activity of the endogenous agonist. For example, an inhibitor at 0.01-, 0.1-, 1-, 5-, 10-, 50-, 100-, 200-, 500-, or 1000-fold molar concentration relative to the agonist can inhibit the activity of the agonist by at least 10%, 50%, 90%, or more.

As used herein "amelioration" or "treatment" is understood as meaning to lessen or decrease at least one sign, symptom, indication, or effect of a specific disease or condition. For example, amelioration or treatment of cancer can be determined using the standard RECIST (Response Evaluation Criteria in Solid Tumors) criteria including the assessment of tumor burden, by survival time, reduced presence of tumor markers (e.g., prostate specific antigen), or any other clinically acceptable indicators of disease state or progression. Amelioration and treatment can require the administration of more than one dose of an agent or therapeutic. As used herein, "prevention" is understood as to limit, reduce the rate or degree of onset, or inhibit the development of at least one sign or symptom of a disease or condition. For example, a subject having a genetic predisposition to develop a disease may develop disease later in life, e.g., delay of BRCA1 or BRCA2 related breast cancer development from third or fourth decade of life to fifth or beyond. Prevention can require the administration of more than one dose of an agent or therapeutic.

As used herein, an "aminooxy-containing amino acid" can be a modified proline, or an amino acid modified to provide a universal scaffold for modification with an aldehyde. Exemplary structures are provided:

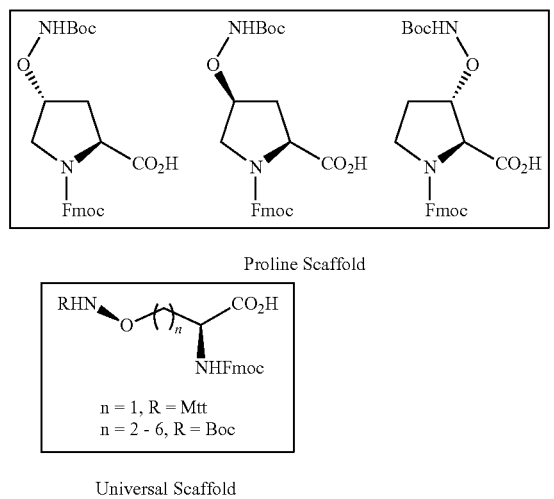

Proline Scaffold

Universal Scaffold

Chemical classes and groups are provided herein and referred to by chemical names, common names, and/or chemical structures. In the absence of an explicit definition herein, definitions of chemical structures can be found in chemical dictionaries, science textbooks, such as organic chemistry textbooks, or in databases such as the IUPAC Compendium of Chemical Terminology which can be accessed at Hypertext Transfer Protocol://old.iupac.org/publications/compendium/. Chemical classes and groups commonly referred to herein are provided as follows.

As used herein, an "alkene group" is understood as an acyclic branched or unbranched hydrocarbons having one carbon-carbon double bond and the general formula $C_nH_{2n-1}$. A "lower alkene" is understood as an alkyl of the formula $—C_nH_{2n-1}$ wherein n is less than or equal to 6. A "higher alkene" is understood as an alkyl of the formula $—C_nH_{2n-1}$ wherein n is greater than or equal to 6. Acyclic branched or unbranched hydrocarbons having more than one double bond are alkadienes, alkatrienes, etc. Heteroalkenes are analogues of alkenes in which a doubly bonded carbon atom is replaced by a heteroatom.

As used herein, "alkyl group" is understood as a univalent group derived from alkanes by removal of a hydrogen atom from any carbon atom $—C_nH_{2n+1}$. The groups derived by removal of a hydrogen atom from a terminal carbon atom of unbranched hydrocarbons form a subclass of normal alkyl (n-alkyl) groups $H(CH_2)_n$. The groups $RCH_2$, $R_2CH(R\neq H)$, and $R_3C$ ($R\neq H$) are primary, secondary and tertiary alkyl groups, respectively. A "lower alkyl" is understood as an alkyl of the formula $—C_nH_{2n+1}$ wherein n is less than or equal to 6. A "higher alkyl" is understood as an alkyl of the formula $—C_nH_{2n+1}$ wherein n is greater than or equal to 6.

As used herein, an amide is understood as a derivative of an oxoacids in which an acidic hydroxy group has been replaced by an amino or substituted amino group. Compounds having one, two or three acyl groups on a given nitrogen are generically included and may be designated as primary, secondary and tertiary amides, respectively, e.g. PhC(=O)NH₂ benzamide, CH₃S(=O)₂NMe₂ N,N-dimethylmethanesulfonamide, [RC(=O)]₂NH secondary amides (see imides), [RC(=O)]₃N tertiary amides, PhP(=O)(OH)NH₂ phenylphosphonamidic acid. An amide group as used herein is understood as a group with —NH₂, NHR and NR₂. Amide groups should not be distinguished by means of the terms primary, secondary and tertiary.

As used herein, amine is understood as Compounds formally derived from ammonia by replacing one, two or three hydrogen atoms by hydrocarbyl groups, and having the general structures RNH₂ (primary amines), R₂NH (secondary amines), R₃N (tertiary amines). An amino group is understood as having the structure —NH₂, —NHR, or —NR₂.

As used herein, "aryl group" is understood as refers to any functional group or substituent derived from a simple aromatic ring, may it be phenyl, thiophene, indolyl, etc (see IUPAC nomenclature, goldbook.iupac.org/A00464.html). Aryl groups derived from arenes by removal of a hydrogen atom from a ring carbon atom. Groups similarly derived from heteroarenes are sometimes subsumed in this definition. "Aryl" is used for the sake of abbreviation or generalization. For example, a simple aryl group is phenyl, $C_6H_5$; it is derived from benzene. The tolyl group, $CH_3C_6H_4$, is derived from toluene (methylbenzene). The xylyl group, $(CH_3)_2C_6H_3$, is derived from xylene (dimethylbenzene). The class of heterocyclyl groups derived from heteroarenes by removal of a hydrogen atom from any ring atom; an alternative term is hetaryl.

As used herein, "carboxylic acid" is understood as a group having the structure RC(=O)OH. A carboxylic acid group is understood to denote the —C(=O)OH group including its carbon atom.

As used herein, "carbonyl group" is understood as a group containing the carbonyl group, C=O. The term is commonly used in the restricted sense of aldehydes and ketones, however as used herein it includes carboxylic acids and derivatives.

As used herein, a "halogen" is understood as an element located in Group VIIA of the periodic table. Halogens are reactive nonmetals having seven valence electrons. Halogen groups include —F, —Cl, —Br, and —I.

As used herein, modification of a class of chemical group with the term "hetero" is understood as the class of functional groups derived from the particular class of the functional group by removal of a hydrogen atom from any carbon atom.

"Heterocyclyl" groups as used herein are univalent groups formed by removing a hydrogen atom from any ring atom of a heterocyclic compound.

As used herein, "olefin group" is understood as an acyclic and or cyclic hydrocarbon having one or more carbon-carbon double bonds, apart from the formal ones in aromatic compounds. The class olefins subsumes alkenes and cycloalkenes and the corresponding polyenes.

Structures are provided in which a group is indicated as potentially being attached at any position of the ring as shown:

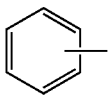

In compounds, amino acid positions are determined relative to the phosphothreonine which is arbitrarily defined as position zero (0). Amino acids to the C-terminus of the peptide (to the right) are indicated as positions +1 (adjacent to the phosphothreonine), +2 (adjacent to the +1 position, but not the phosphothrenine), etc. Similarly, amino acids towards the N-terminus are defined as positions −1 (adjacent to the phosphothreonine), −2 (adjacent to the −1 position, but not the phosphothrenine), etc.

"Contacting a cell" is understood herein as providing an agent to a test cell e.g., a cell to be treated in culture or in an animal, such that the agent or isolated cell can interact with the test cell or cell to be treated, potentially be taken up by the test cell or cell to be treated, and have an effect on the test cell or cell to be treated. The agent or isolated cell can be delivered to the cell directly (e.g., by addition of the agent to culture medium or by injection into the cell or tissue of interest), or by delivery to the organism by an enteral or parenteral route of administration for delivery to the cell by circulation, lymphatic, or other means.

As used herein, "changed as compared to a control" sample or subject is understood as having a level of the analyte or diagnostic or therapeutic indicator to be detected at a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., PSA) or a substance produced by a reporter construct (e.g., β-galactosidase or luciferase). Depending on the method used for detection the amount and measurement of the change can vary. For example, a change in the amount of cleavage of analyte present will depend on the exact reaction conditions and the amount of time after exposure to the agent the sample is collected. Changed as compared to a control reference sample can also include decreased binding of a ligand to a receptor in the presence of an antagonist or other inhibitor. Determination of statistical significance is within the ability of those skilled in the art.

As used herein, "detecting", "detection" and the like are understood that an assay performed for identification of a specific analyte in a sample or a product from a reporter construct in a sample. Detection can also include identification of activation of a kinase or other enzyme. Detection can include the identification of a mutation in a gene sequence, such as a point mutation, a deletion of all or part of the coding sequence or transcriptional/translational regulatory sequences of the gene, a truncation of the gene sequence, or any other alteration that can alter the expression level or the sequence of the protein expressed by the gene, particularly when the alteration of the sequence results in a phenotypic change in the subject. Detection can include the determination of the size of a tumor, the presence or absence of metastases, the presence or absence of angiogenesis. The amount of analyte detected in the sample can be none or below the level of detection of the assay or method.

By "diagnosing" as used herein refers to a clinical or other assessment of the condition of a subject based on observation, testing, or circumstances for identifying a subject having a disease, disorder, or condition based on the presence of at least one sign or symptom of the disease, disorder, or condition. Typically, diagnosing using the method of the invention includes the observation of the subject for other signs or symptoms of the disease, disorder, or condition by physical examination, imaging, further laboratory tests, etc.

As used herein, a "diagnostic marker" is understood as one or more signs or symptoms of a disease or condition that can be assessed, preferably quantitatively to monitor the progress or efficacy of a disease treatment or prophylactic treatment or method. A diagnostic marker can be a substance that is released by a tumor (e.g., antigens such as PSA or enzymes). A diagnostic marker can be tumor size and/or grade of tumor and/or growth rate of tumor. A diagnostic marker can be the presence or absence of angiogenesis. A diagnostic marker can be a change in blood counts or cellular function measured in an in vitro assay, or the presence and characteristics of metastases (number and size).

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the expression profile or profiles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as a improvement of symptoms, a cure, a reduction in disease signs or symptoms, extension of life, improvement in quality of life, or other effect generally recognized as positive by medical doctors familiar with treating the particular type of disease or condition.

As used herein, "Fmoc" is understood as 9-Fluorenylmethyloxycarbonyl having the molecular formula $C_{15}H_{11}ClO_2$. The structure of this protective group is well known.

As used herein, "heterologous" as in "heterologous protein" is understood as a protein not natively expressed in the cell in which it is expressed. The heterologous protein may be, but need not be, from a different species.

The term "hyperproliferative disorder" or "neoplasia" includes malignancies characterized by excess cell proliferation or growth, or reduced cell death. In specific embodiments, the term "cancer" includes but is not limited to carcinomas, sarcomas, leukemias, and lymphomas. The term "cancer" also includes primary malignant tumors, e.g., those whose cells have not migrated to sites in the subject's body other than the site of the original tumor, and secondary malignant tumors, e.g., those arising from metastasis, the migration of tumor cells to secondary sites that are different from the site of the original tumor. Tumors include solid tumors (i.e., non-blood tumors) and blood tumors. Cancers include, but are not limited to, Acute Lymphoblastic Leukemia, Acute Myeloid Leukemia, Adrenocortical Carcinoma, Basal Cell Carcinoma, Bladder Cancer, Bone Cancer, Brain Tumor, Breast Cancer, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Esophageal Cancer, Ewing Family of Tumors, Retinoblastoma, Gastric (Stomach) Cancer, Gastrointestinal Tumors, Glioma, Head and Neck Cancer, Hepatocellular (Liver) Cancer, Hodgkin Lymphoma, Islet Cell Tumors (Endocrine Pancreas), Kidney (Renal Cell) Cancer, Laryngeal Cancer, Lung Cancer, Non-Small Cell, Lung Cancer, Small Cell, Lymphoma, Medulloblastoma, Melanoma, Pancreatic Cancer, Prostate Cancer, Renal Cancer, Rectal cancer, Thyroid Cancer.

As used herein, "isolated" or "purified" when used in reference to a polypeptide means that a naturally polypeptide or protein has been removed from its normal physiological environment (e.g., protein isolated from plasma or tissue) or is synthesized in a non-natural environment (e.g., artificially synthesized in an in vitro translation system). Thus, an "isolated" or "purified" polypeptide can be in a cell-free solution or placed in a different cellular environment (e.g., expressed in a heterologous cell type). The term "purified" does not imply that the polypeptide is the only polypeptide present, but that it is essentially free (about 90-95%, up to 99-100% pure) of cellular or organismal material naturally associated with it, and thus is distinguished from naturally occurring polypeptide. Similarly, an isolated nucleic acid is removed from its normal physiological environment. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition.

As used herein, "kits" are understood to contain at least the non-standard laboratory reagents for use in the methods of the invention. For example, a kit can include at least one of, preferably at least two of at least one peptide for modification, one or more aldehyde molecules for modification of peptides, and instructions for use, all in appropriate packaging. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

The term "label" or "detectable label" as used herein refers to any atom or molecule which can be used to provide a detectable (preferably quantifiable) signal, and which can be attached to a chemical compound, a nucleic acid or protein. Labels may provide signals detectable by fluorescence, radioactivity, colorimetry, gravimetry, X-ray diffraction or absorption, magnetism, enzymatic activity, and the like. Various methods of labeling polypeptides and glycoproteins are known in the art and may be used. Examples of labels for polypeptides include, but are not limited to, the following: radioisotopes (e.g., $^3$H), fluorescent labels (e.g., FITC, rhodamine, lanthanide phosphors), enzymatic labels (e.g., horseradish peroxidase, beta-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. In others, the label is part of the fusion protein, e.g. Green Fluorescent Protein (GFP), Yellow Fluorescent Protein (YFP).

"Library" as used herein is understood to be a chemical library. Chemical libraries include two or more compounds (10 or more, 50 or more, 100 or more, 200 or more, 500 or more, 1000 or more, 5000 or more, 10,000 or more, etc.; or any range bracketed by the noted values), preferably that have structural and/or potential functional properties. Libraries can be used, for example for screening assays to select compounds with desired activities, e.g., kinase binding, kinase stimulating, kinase inhibiting activity.

"Obtaining" is understood herein as manufacturing, purchasing, or otherwise coming into possession of.

As used herein, "oligonucleotide sequence" is understood as a non-coding nucleic acid sequence prepared by chemical synthesis methods or by transcription from a construct including an appropriate promoter sequence. A double stranded RNA oligonucleotide sequence as used herein includes a single strand forming a hairpin structure (e.g., shRNA) or joined by other non-nucleic acid linkages, or two separate strands annealed to form a double stranded structure.

An "oxime modified peptide" and the like are understood as a peptide in which at least one amino acid includes an aminooxy group, —O—NH$_2$, that will be reacted with an aldehyde to make a oxime modified peptide. In an embodiment, the aminooxy containing peptide is reacted with a library of aldehyde compounds to provide a library of oxmine modified peptides. An exemplary reaction scheme is shown:

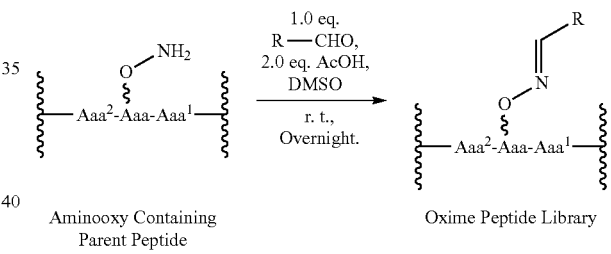

Aminooxy Containing Parent Peptide

Oxime Peptide Library

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. For example, pharmaceutically acceptable carriers for administration of cells typically is a carrier acceptable for delivery by injection, and do not include agents such as detergents or other compounds that could damage the cells to be delivered. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol;

esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, intramuscular, intraperotineal, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect.

A "peptide" as used herein is understood as two or more independently selected natural or non-natural amino acids joined by a peptide bond. A peptide can include 2, 3, 4, 5, 6, 7, 8, 9, 10, 11, 12 or more natural or non-natural amino acids joined by peptide bonds.

A "peptide-peptoid hybrid" as used herein is understood as a peptide in which at least one amino acid comprises the non-natural amino acid N-alkylglycine having the below structure.

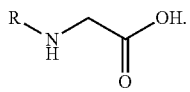

"Peptoids" are polymers of N-substituted glycine residues (NSG). These have emerged as an important class of peptide mimetic that can retain bioactivity while exhibiting resistance to proteolytic degradation. Peptide-peptoid hybrids containing both peptide and NSG residues have also shown significant utility. Examples are provided by the replacement of key Pro residues with NSG residues in WW and SH3 domain-binding peptides to achieve greater ligand selectivity and affinity (32).

As used herein, pharmaceutically acceptable salts include, without limitation, the tartrate, succinate, tartarate, bitartarate, dihydrochloride, salicylate, hemisuccinate, citrate, maleate, hydrochloride, carbamate, sulfate, nitrate, and benzoate salt forms thereof, as well as combinations thereof and the like. Any form of peptide mimentic is suitable for use in the methods of the present invention, e.g., a pharmaceutically acceptable salt of a peptide mimentic, a free base of a peptide mimentic, or a mixture thereof.

As used herein, "plurality" is understood to mean more than one. For example, a plurality refers to at least two, three, four, five, or more.

A "polo-like kinase" or "Plk" as used herein collectively refers to the proteins called Plk-1, (human sequence available as under Accession No. P53350.1 GI:1709658; mouse sequence available under Accession No. Q07832.2 GI:1709659; rat sequence available under Accession No. Q62673.1 GI:12230396; Pan troglodytes sequence available under Accession No. XP_001163585.1 GI:114661620); Plk-2 (human sequence available under Accession No. Q9NYY3.3 GI:22096374); Plk-3 (human sequence available under Accession No. Q9H4B4.2 GI:51338822); and Plk-4 (human sequence available under Accession No. O00444.3 GI:160113150), from any organism, preferably a mammalian organism, preferably from a human organism. Such proteins can be encoded by any nucleic acid that provides the appropriate translation product; however, in certain embodiments, the polo-like kinases are encoded by the native genes which can easily be identified using GenBank or any of a number of publicly available databases. All GenBank Nos. incorporated herein by reference as of the filing date of the instant application.

"Reporter construct" as used herein is understood to be an exogenously inserted gene, often present on a plasmid, with a detectable gene product, under the control of a promoter sequence. The activity of the promoter is modulated upon signaling through one or more known cellular pathways. Preferably, the gene product is easily detectable using a quantitative method. Common reporter genes include luciferase and beta-galactosidase. The reporter construct can be transiently inserted into the cell by transfection or infection methods. Alternatively, stable cell lines can be made using methods well known to those skilled in the art, or cells can be obtained from transgenic animals expressing a reporter construct. The specific reporter gene or method of detection is not a limitation of the invention.

"RNA interference" refers to a target directed disruption of expression from a particular RNA transcript using a double stranded RNA molecule, either a siRNA or a shRNA. "siRNA" refers to a small interfering RNA, sometimes known as short interfering RNA or silencing RNA, is a class of 20-25 nucleotide-long double-stranded RNA molecules involved in the RNA interference (RNAi) pathway, where it interferes with the expression of a specific gene. SiRNAs have a well-defined structure: a short (usually 21-nt) double strand of RNA (dsRNA) with 2-nt 3' overhangs on either end. However, siRNAs can vary in length from about 19 to about 24 nucleotides in length. Each strand has a 5' phosphate group and a 3' hydroxyl (—OH) group. Structures of siRNAs and methods for design are provided, for example in WO02/44321, incorporated herein by reference. As used herein, "small hairpin RNA" or "short hairpin RNA" (shRNA) is a sequence of RNA that makes a tight hairpin turn that can be used to silence gene. A shRNA is composed of a single-stranded RNA with two self-complementary regions that allow the RNA to fold back upon itself and form a stem-loop structure with an intramolecular duplex region and an unpaired loop region.

A "sample" as used herein refers to a biological material that isolated from its environment (e.g., blood or tissue from an animal, cells, or conditioned media from tissue culture) and is suspected of containing, or known to contain an analyte, such as a tumor cell or a product from a reporter construct. A sample can also be a partially purified fraction of a tissue or bodily fluid. A reference sample can be a "normal" sample, from a donor not having the disease or condition fluid, or from a normal tissue in a subject having the disease or condition (e.g., normal tissue vs. tumor tissue). A reference sample can also be from an untreated donor or cell culture not treated with an active agent (e.g., no treatment or administration of vehicle only) and/or stimulus. A reference sample can also be taken at a "zero time point" prior to contacting the cell or subject with the agent or cell to be tested.

"Small molecule" as used herein is understood as a compound, typically an organic compound, having a molecular weight of no more than about 1500 Da, 1000 Da, 750 Da, or 500 Da. In an embodiment, a small molecule does not include a polypeptide or nucleic acid including only natural amino acids and/or nucleotides.

An agent, antibody, polypeptide, nucleic acid, or other compound "specifically binds" a target molecule, e.g., antigen, polypeptide, nucleic acid, or other compound, when the target molecule is bound with at least 100-fold, preferably at least 500-fold, preferably at least 1000-fold, preferably at least a 5000-fold, preferably at least a 10,000-fold preference as compared to a non-specific compounds, or a pool of non-specific compounds. Specifically binds can be used in relation to binding one of two or more related compounds that have physically related structures, e.g., two kinases, particularly 2 polo-like kinases. For example, an agent, antibody, polypeptide, nucleic acid, or other compound can "specifically bind" one polo-like kinase (e.g., Plk1) with at least a 10-fold, 50-fold, 100-fold, 500-fold, 1000-fold, 5000-fold, 10,000-fold or more preference over another polo-like kinase, e.g., Plk2, Plk3, or Plk4. Binding preferences and affinities, absolute or relative, can be determined, for example by determining the affinity for each pair separately or by the use of competition assays or other methods well known to those of skill in the art.

A "subject" as used herein refers to living organisms. In certain embodiments, the living organism is an animal. In certain preferred embodiments, the subject is a mammal. In certain embodiments, the subject is a domesticated mammal. Examples of subjects include humans, monkeys, dogs, cats, mice, rats, cows, horses, goats, and sheep. A human subject may also be referred to as a patient.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions such as cancer is within the ability of those in the art. Subjects suffering from, and suspected of suffering from, a specific disease, condition, or syndrome are not necessarily two distinct groups.

"Therapeutically effective amount," as used herein refers to an amount of an agent which is effective, upon single or multiple dose administration to the cell or subject, in prolonging the survivability of the patient with such a disorder beyond that expected in the absence of such treatment.

An agent can be administered to a subject, either alone or in combination with one or more therapeutic agents, as a pharmaceutical composition in mixture with conventional excipient, e.g., pharmaceutically acceptable carrier, or therapeutic treatments such as radiation.

The pharmaceutical agents may be conveniently administered in unit dosage form and may be prepared by any of the methods well known in the pharmaceutical arts, e.g., as described in Remington's Pharmaceutical Sciences (Mack Pub. Co., Easton, Pa., 1985). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain agents.

It will be appreciated that the actual preferred amounts of active compounds used in a given therapy will vary according to e.g., the specific compound being utilized, the particular composition formulated, the mode of administration and characteristics of the subject, e.g., the species, sex, weight, general health and age of the subject. Optimal administration rates for a given protocol of administration can be readily ascertained by those skilled in the art using conventional dosage determination tests conducted with regard to the foregoing guidelines.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

The term "transfection" as used herein refers to the introduction of a transgene into a cell. The term "transgene" as used herein refers to any nucleic acid sequence which is introduced into the genome of a cell by experimental manipulations. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment) and the like.

The term "stable transfection" or "stably transfected" refers to the introduction and integration of a transgene into the genome of the transfected cell. The term "stable transfectant" refers to a cell which has stably integrated one or more transgenes into the genomic DNA.

The term "transient transfection" or "transiently transfected" refers to the introduction of one or more transgenes into a transfected cell in the absence of integration of the transgene into the host cell's genome. The term "transient transfectant" refers to a cell which has transiently integrated one or more transgenes.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications (e.g. deletions, substitutions, etc.) in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof. Chemical bonds not specifically defined as cis- or trans- can be either cis- or trans. The compounds of the invention can include mixtures of stereoisomers of the compounds or may include only specific stereoisomers, or may only include specific stereoisomers at specific positions.

All oligonucleotide sequences are written from the 5'-end to the 3'-end unless otherwise specifically noted.

Any compositions or methods provided herein can be combined with one or more of any of the other compositions and methods provided herein.

BRIEF DESCRIPTION OF THE FIGURES

FIG. 1A-D. Minimization of PBIP1 p-T78 peptide that binds to the mammalian polo-like kinase Plk1. (A-C), Various lengths of N-terminal Cys-(CH$_2$)$_6$-fused T78 peptides were cross-linked to the beads using SulfoLink (A) and then tested for their ability to bind to Plk1. The Ser residue (blue) in (A, right) indicates the invariable Ser77 residue critical for the PBD binding. For comparison, a shortened form of the previously characterized synthetic peptide optimized for the Plk1 PBD binding (MQSpTPL)13 was included. (D) A 6-mer T78 peptide (LHSpTAI) analogous to the synthetic optimal peptide (MQSpTPL) efficiently precipitated Plk1. Numbers indicate the efficiency of Plk1 precipitation by each peptide relative to the Plk1 signal in the input.

FIG. 4A-G. A 5-mer p-T78 mimetic peptide (PLHS-Pmab) induces mitotic arrest by specifically inhibiting Plk1 localization. (A), Illustration of a nonhydrolyzable p-Thr derivative, Pmab (Top), used for the synthesis of mimetic peptides. The indicated, bead-immobilized, peptides were incubated with mitotic HeLa lysates in the presence of phosphatase inhibitors, and then analyzed as in FIG. 1A. T78, C—(CH$_2$)$_6$-PLHST; p-T78, C—(CH$_2$)$_6$-PLHSpT; Pmab, C—(CH$_2$)$_6$-PLHS-Pmab; Pmab(S77A), C—(CH$_2$)$_6$-PLHA-Pmab. (B), The same peptides used in (A) were incubated with the mixture of HeLa lysates expressing the kinase-inactive Flag-Plk1(K82M), Flag-Plk2(K108M), or Flag-Plk3 (K52R). Bead-associated proteins were analyzed as in FIG. 2A. The membrane was stained with Coomassie (CBB). (C), To quantitatively determine the efficiency of PBD-binding inhibition by the indicated peptides, an ELISA-based inhibition assay was performed as described in the Methods. The level of HA-EGFP-Plk1 bound to an immobilized biotinylated p-T78 peptide was quantified in the presence of various amounts of the indicated competitor peptides. (D-E), HeLa cells arrested in S phase by thymidine treatment were released into fresh medium. Two hours after release, all the cells (~150 cells) in a single grid were microinjected with a mixture containing 2.5 mM of the indicated peptide and 30 ng/μl of pEGFP-C1 vector (to visualize the injected cells), and then further incubated. Cells were photographed 12 h after releasing from the S phase block (D). Reduction in the total cell number was frequently apparent due to the loss of floating dead cells. To monitor cell cycle progression, the percentages of mitotic cells were quantified at the indicated time points (E). Bars, standard deviation. (F-G), Cells microinjected similarly as in (D) were fixed and immunostained with anti-Plk1 antibody (F). Images were acquired from EGFP-positive cells. Asterisks, centrosome-localized Plk1 signals; arrowed brackets, kinetochore-localized Plk1 signals; arrows, misaligned chromosomes. Fluorescence intensities for centrosome-localized (n>20 centrosomes) or kinetochore-localized (n>45 kinetochores, average of 6 kinetochores per cell) anti-Plk1 signals were quantified as described in the Methods (G). Bars (red), the averages of relative fluorescence intensities.

FIG. 14A-B. ELISA based inhibition assay. To quantitatively determine the efficiency of PBD-binding inhibition by the indicated peptides, an ELISA-based inhibition assay was carried out. The level of HA-EGFP-Plk1 bound to an immobilized biotinylated p-T78 peptide was quantified in the presence of various amounts of the competitor peptides.

FIG. 23. Table 1. A comparison of the thermodynamic binding parameters of minimal Plk1-binding.

FIG. 24. Table 2. A summary of the peptide inhibitors of Plk1.

FIG. 25. Table 3. Peptides used in the present disclosure.

FIG. 26 Table 4. Statistics of data collection and structure refinement.

DETAILED DESCRIPTION

Figure 1A:
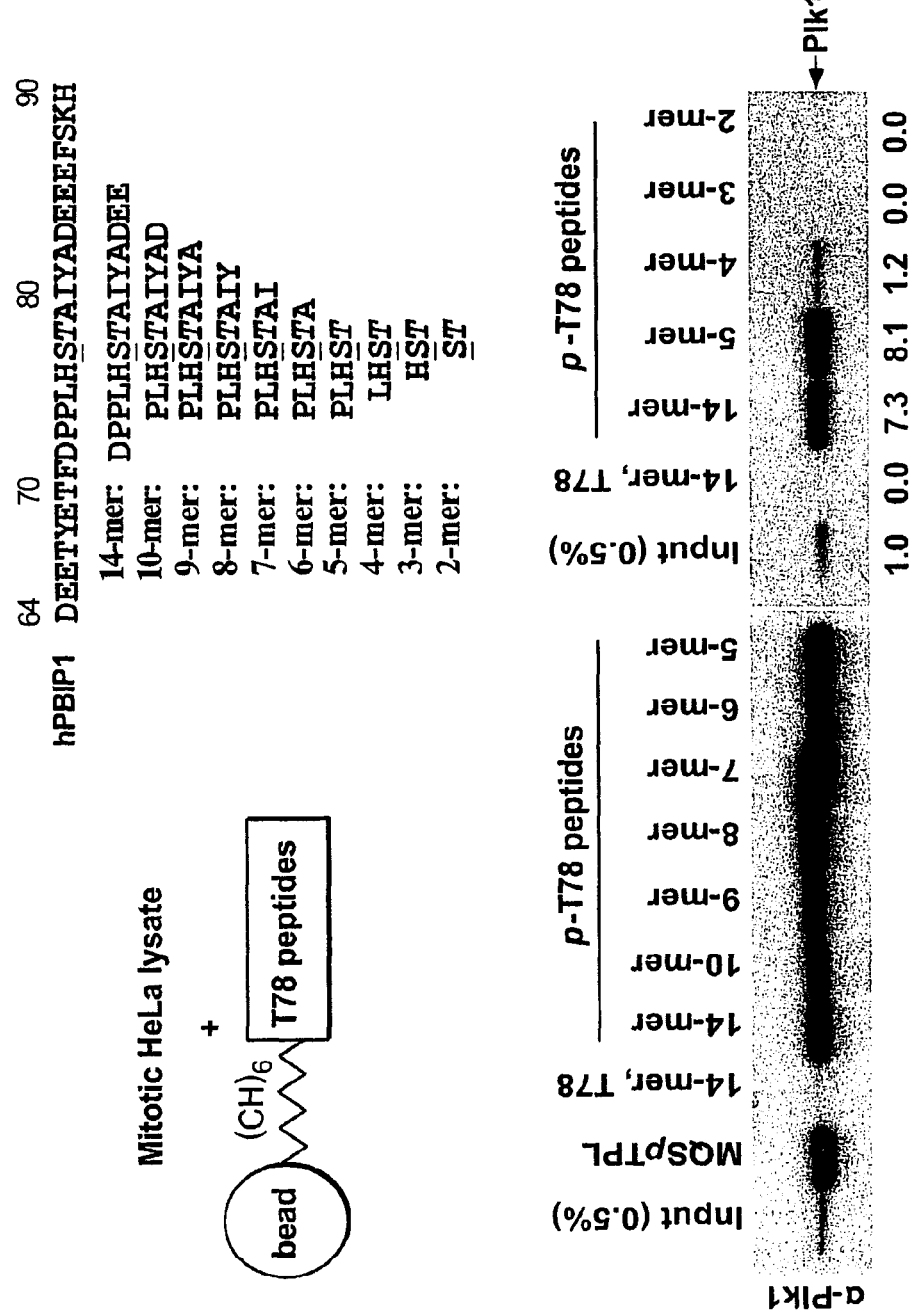

Polo-like kinases (Plks) are a conserved subfamily of Ser/Thr protein kinases that play pivotal roles in cell proliferation. Since Plk1 overexpression is closely associated with oncogenesis, Plk1 is considered an attractive target for anti-cancer therapy. The polo-box domain (PBD) uniquely found in the C-terminal non-catalytic region of Plks forms a phospho-epitope-binding module for protein-protein interaction. Provided herein is the identification of minimal phosphopeptides that specifically interacted with the PBD of Plk1, but not the two closely-related Plk2 and Plk3, with a high affinity. Comparative binding studies and analyses of the crystal structures of the Plk1 PBD in complex with a minimal phosphopeptide (PLHSpT) or its derivative PPHSpT, LHSpTA, or no peptide revealed that the C-terminal SpT dipeptide functions as a high affinity anchor, whereas the N-terminal PLH residues are critical for providing both specificity and affinity to the PBD. Testing of minimal phospho-Thr mimetic peptides demonstrated that inhibition of the PBD of Plk1 is sufficient to induce mitotic arrest and apoptotic cell death. Thus, the mode of PLHSpT binding to the PBD may provide an important template for designing anti-Plk1 therapeutic agents.

Also provided herein are high affinity analogues bearing non-natural amino acids as well as peptide-peptoid hybrids (containing N-alkylglycine residues).

Further provided herein are methods for the generation of stereoselective synthesis of protected phosphonate-based pThr mimetics and their application in the preparation of phosphatase-stable variants of these peptides.

The compositions and methods provided herein represent new approaches to the design and synthesis of PBD-binding antagonists that can lead to the development of further therapeutically relevant PBD-directed agents.

Over-expression of Plk1 induces neoplastic transformation of human cells, whereas interference with Plk1 function induces apoptosis in tumor cells but not in normal cells. Moreover, Plk1 over-expression is associated with aggressive disease stage and poor patient survival in various types of cancers (5). Over the years, efforts have been made to generate anti-Plk1 inhibitors, resulting in several compounds (BI 2536, GSK Compound 1, Cyclapolin 1, DAP81, and TAL) developed to competitively inhibit the kinase activity or substrate recognition of Plk1 (5). However, largely because of the structural similarities among the catalytic domains of all Plks and other related kinases, it has been difficult to generate Plk1-specific inhibitors. Thus, since the non-catalytic PBD is found only in the members of the Plk subfamily, development of novel inhibitors that target the PBD of Plk1 may prove to be an alternative strategy for selectively targeting Plk1.

While conducting studies on the interaction between Plk1 and its physiological binding target PBIP1, a minimal phosphopeptide derived from the Thr78 region of PBIP1 was identified that exhibits a high level of affinity and specificity for the Plk1 PBD. Testing of a non-hydrolyzable p-T78 mimetic peptide demonstrated that inhibition of the Plk1 PBD function results in a chromosome congression defect that leads to mitotic arrest and apoptotic cell death, as observed previously in cells expressing a dominant-negative PBD (10,19). Since interference with Plk1 function induces apoptosis in most tumor cells but not in normal cells (5), these findings demonstrate that inhibition of the PBD function is sufficient to interfere with cell proliferation activity of tumor cells. Furthermore, data presented here directly provide the proof-of-principle that specific inhibition of Plk1 PBD is achievable by a small mimetic peptide or its relevant compounds.

It has been demonstrated that SpT-dependent electrostatic interactions with His538 and Lys540 residues are critical for the interaction between optimal peptides (PMQSpTPL and MQSpTPL) and the Plk1 PBD12,13. Comparative in vitro binding studies and analyses of the phosphopeptide-binding pockets of PBDS+G and PBDS with PBDPL, PBDPP, and PBDLH revealed that, in addition to the SpT motif of the phosphopeptide that acts as a high affinity anchor, the N-terminal residues provide additional binding affinity and specificity to the Plk1 PBD through three distinct interactions. First, the polar contact between the carbonyl oxygen N-terminal to the Leu-3 of PLHSpT or LHSpTA and the guanidinium moiety of Arg516 of Plk1 PBD provides a molecular basis for a high affinity and specificity interaction. Second, docking of the N-terminal Pro-4 side chain into the pocket generated by the surrounding Trp414 and Phe535 offers additional affinity and likely another level of specificity to the interaction. Notably, the PBDs from both Plk2 and Plk3 possess Lys and Tyr residues at positions analogous to the Plk1 Arg516 and Phe535 residues, respectively, in Plk1, and, as a consequence, may fail to generate as favorable an environment to accommodate the N-terminal Pro residue. Third, peptide pull-down assays demonstrate that the His-2 residue adds another layer of Plk1 PBD specificity, although the underlying mechanism is not clearly understood at present.

Besides each amino acid residue of the p-T78 peptide involved in defining the Plk1 binding affinity and specificity, the positions of the phosphopeptide and glycerol in the pocket, along with the network of water molecules that mediate contacts between the phosphopeptide and the PBD, suggest that both the glycerol and the network of water molecules surrounding the phosphopeptide could be important elements of the PBD recognition by phosphopeptides. Furthermore, the structures of the $PBD^{S+G}$, $PBD^S$, and $PBD^{PL}$ were remarkably similar, hinting that the other glycerol molecule and the sulfate anion occupying the phosphopeptide-binding cleft may substitute the role of the SpT dipeptide.

The data provided herein demonstrate that the Plk1 PBD-binding pocket accommodates (i) the core SpT motif, (ii) the N-terminal hydrophobic residue, (iii) glycerol, and (iv) a network of contacting water molecules. A combination of some or all of these four elements could be potentially used for targeted drug design. Better understanding of the PBD interaction as well as further isolation and development of PBD-binding agents would greatly facilitate the discovery of a new class of Plk1-specific anti-cancer therapeutic agents.

The invention provides method of making compounds of any of the formulae herein using any one, or combination of, reactions delineated herein. The method can include the use of one or more intermediates or chemical reagents delineated herein.

Another aspect is an isotopically labeled compound of any of the formulae delineated herein.

Such compounds have one or more isotope atoms which may or may not be radioactive (e.g., $^3$H, $^2$H, 14C, $^{13}$C, $^{35}$S, $^{32}$P, $^{125}$I, and $^{131}$I) introduced into the compound. Such compounds are useful for drug metabolism studies and diagnostics, as well as therapeutic applications.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt form, respectively. For example, a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Prodrug derivatives of the compounds of the invention can be prepared by methods known to those of ordinary skill in the art (e.g., for further details see Saulnier et al., (1994), *Bioorganic and Medicinal Chemistry Letters, Vol.* 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present invention. All crystal forms of the compounds described herein are expressly included in the present invention.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

In the Examples, the compound numbers refer to the compounds described in the Example. Efforts have been made to provide cross references to the same compound in other examples labeled with a different reference number.

Example 1

Materials and Methods

Methods
General.

All experiments involving moisture-sensitive compounds were conducted under dry conditions (positive argon pressure) using standard syringe, cannula, and septa apparatus. Solvents: All solvents were purchased anhydrous (Aldrich) and used directly. HPLC-grade hexanes, EtOAc, CH2Cl2, and MeOH were used in chromatography. TLC: analytical TLC was performed on Analtech precoated plates (Uniplate, silica gel GHLF, 250 microns) containing a fluorescence indicator; NMR spectra were recorded using a Varian Inova 400 MHz spectrometer. The coupling constants are reported in Hertz, and the peak shifts are reported in the δ (ppm) scale. Low resolution mass spectra (ESI) was measured with Agilent 1200 LC/MSD-SL system, and high resolution mass spectra (ESI or APCI) was measured by UCR Mass Spectrometry Facility, Department of Chemistry, University of California, 3401 Watkins Dr., Riverside Calif., 92521. Optical rotations were measured on a Jasco P-1010 polarimeter at 589 nm. IR spectra were obtained neat with a Jasco FT-IR/615 spectrometer.

Synthesis of Peptides.

The list of peptides used in this study is shown in Table 3. Peptides were synthesized using a 9-Fluorenylmethoxycarbony (Fmoc)-based solid-phase method on Rink amide resin (0.36 mmol/g) (Novabiochem, San Diego, Calif.) at the 0.1 mmol scale. Briefly, Fmoc-protected amino acids (2.5-fold molar excess) were sequentially condensed using 0.25 mmol of N,N'-diisopropylcarbodiimide(DIC)/N-hydroxybenzotriazole (HOBt) dissolved in dimethylformamide. Fmoc deprotection was achieved by 20% piperidine/N-methylpyrrolidinone. The synthesis of protected (2S,3R)-2-amino-3-methyl-4-phosphonobutyric acid (Pmab) and its incorporation into peptides will be reported separately. For peptide-based pull-down assays, peptides bearing the N-terminal Cys-$(CH_2)_6$ linkers (1 mM stock) were cross-linked to the beads using SulfoLink Coupling gel (Pierce, Rockford, Ill.).

Peptide-Binding, GST-PBD Pull-Down, and ELISA-Based PBD-Binding Inhibition Assays.

Peptide binding and GST-PBD pull-down assays were performed as described previously (15). An ELISA-based PBD-binding inhibition assay was carried out using an immobilized biotinylated 9-mer p-T78 peptide {Biotin-C—$(CH_2)_6$—$(CH_2)_6$-DPPLHSpTAI-$NH_2$} and the cellular lysates expressing HA-EGFP-Plk1.

Isothermal titration calorimetry analyses. The calorimetric titrations were carried out using purified recombinant PBDs (for Plk1 and Plk2) from bacterial cells and the indicated peptides. Further details are presented in Online Supplemental Materials.

Crystallization, Data Collection, and Refinement.

All initial crystallization screens for the Plk1PBD-PLH-SpT complex were performed on an Art Robbins *Phoenix* Liquid Handling System using Index (Hampton Research, Aliso Viejo, Calif.) and PEGs (Qiagen, Valencia, Calif.) crystallization kits. All subsequent crystals were grown using the hanging-drop vapor diffusion method at room temperature. PBD and the kinase domain of Plk1 were concentrated to ~30 mg/ml in buffer A (20 mM Tris-Cl, pH 8.0, 500 mM NaCl, 3 mM DTT). The phosphopeptide Ac-PLHSpT was dissolved in buffer A. The phosphopeptide and PBD were added in 2:1 stoichiometric ratio, respectively, and the final concentration was adjusted to ~15 mg/ml. Crystals of this complex were grown by adding 1 µl of this complex to 1 µl of well solution (0.2 M di-potassium phosphate, 20% w/v PEG 3350). The complex between PBD and kinase domain was formed similarly using a 1:1 stoichiometric ratio, and 0.2 M lithium sulfate monohydrate, 0.1 M Bis-Tris, pH 5.5, 25% w/v PEG 3350 as the well solution. Crystals formed within one week and were soaked for 5 minutes in mother liquor constituted with 20% v/v glycerol prior to flash-freezing in liquid nitrogen. The complex of PBD and Ac-PLHSpT crystallized in the space group $P2_12_12_1$ (a=35.19 Å, b=65.76 Å, c=104.11 Å). The kinase domain of Plk1 precipitated and PBD crystallized in the space group P21 (a=35.29 Å, b=102.29 Å, c=68.55 Å, β=93.24°).

Crystals of the Plk1 PBD-PPHSpT complex were obtained in a similar fashion using a well solution of 0.1 M MES buffer (pH 6.0) containing 15% PEG 3350. The crystals were soaked for 5 minutes in the mother liquor constituted with 15% v/v glycerol, 10 mM DTT and 2 mM of the phosphopeptide Ac-PPHSpT prior to freezing in liquid nitrogen. This complex crystallized in the space group $P2_12_12_1$ (a=35.44 Å, b=66.50 Å, c=105.82 Å). All data were collected at 100K. The data for PBD, and PBD in complex with Ac-PLHSpT were collected at the SER-CAT beamline 22-ID, at the Advanced Photon Source (APS), on a MAR 300CCD detector. The data for the complex of PBD and Ac-PPHSpT were collected at APS beamline 24-ID-C at 100 K. All data were processed and scaled using the HKL2000 package20. Phasing of the data was done by molecular replacement using a previously published structure (PDB ID; 1UMW). The structures were refined independently of each other with the program REFMAC521 and CNS1.122. Model building was performed using Coot (23) and XtalView (24) (Table 4).

Crystals of the Plk1 PBD-LHSpTA complex were grown by hanging drop vapour diffusion using 1 µl of protein solution (12 mg/ml in 10 mM Tris-Cl, pH 8.0, 0.5 M NaCl, 10 mM DTT, 2 mM Ac-LHSpTA-$NH_2$ peptide) mixed with 1 µl of well solution consisting of 32.5% PEG 2000 MME, 0.1 M Tris-Cl, pH 8.5, 0.2 M trimethyl-amine N-oxide. Crystals grew overnight at room temperature. For data collection, a crystal was looped from the drop and flash frozen by direct transfer to a cryostream at 100 K. Data were collected with a rotating anode home source on a Rigagku R-axis IV detector and processed using the HKL2000 package20. A molecular replacement solution was found with AMoRe (25). Initial refinement was done with CNS 1.2126 with manual model fitting using XtalView (24). The final rounds of refinement were completed in PHENIX 1.3 (27) with the addition of riding hydrogens.

Synthesis of $F_2$Pmab-Containing Mimetic Peptide.

Synthesis of 2-amino-4,4-difluoro-3-methyl-4-phosphobutanoic acid ($F_2$Pmab)-containing peptides were carried out by employing a tert-butoxycarbonyl (Boc)-based solid-phase method on 4-methylbenzhydrylamine (MBHA) resin as described previously. For peptide-based pull-down assays, peptides bearing the N-terminal Cys-$(CH_2)_6$ linker (1 mM stock) were cross-linked to the beads using SulfoLink Coupling gel (Pierce, Rockford, Ill.). An initial attempt to synthesize a 5-mer PLHS-$F_2$Pmab mimetic peptide did not yield sufficient amounts because of an inefficient coupling of $F_2$Pmab to the resin. Thus, we synthesized a 6-mer $F_2$Pmab-containing peptide (PLHS-$F_2$Pmab-A) and then examined its affinity and specificity to Plk1 in comparison to those of the corresponding p-T78 peptide.

Peptide and GST-PBD Pull-Down Assays.

For Plk1 pull-down assays with immobilized peptides, we used total lysates prepared from mitotic HeLa cells. HeLa cells contain no mutations in Plk1 coding sequence and the level of Plk1 expression is high (2). Cells treated with 200 ng/ml of nocodazole for 16 h were lysed in TBSN buffer {20 mM Tris-Cl (pH8.0), 150 mM NaCl, 0.5% NP-40, 5 mM EGTA, 1.5 mM EDTA, 0.5 mM $Na_3VO_4$, 20 mM p-nitrophenyl phosphate, and protease inhibitor cocktail (Roche, Nutley, N.J.)}, and then clarified by centrifugation at 15,000×g for 20 min at 4° C. The resulting lysates were incubated with bead-immobilized peptides (40 µM per binding) for 2 h, precipitated, washed, and then boiled in sodium dodecyl sulfate (SDS) sample buffer to elute the associated proteins. Samples were separated by 10% SDS-polyacrylamide gel electrophoresis (PAGE), and then either stained with silver or transferred to PVDF membrane for immunoblotting analysis with anti-Plk1 antibody using the enhanced chemiluminescence (ECL) detection system (Pierce).

To investigate the binding specificity of p-T78 peptides to various Plks, Flag-Plk1 (K82M), Flag-Plk2(K108M)3 or Flag-Plk3(K52R) (a gift of Wei Dai, New York University School of Medicine, NY) construct was first transfected into HeLa cells. Cellular lysates were prepared as above, mixed, and then incubated in TBSN buffer with the immobilized peptides indicated.

To determine whether PLHSpT binds to the phosphate pincer cleft of the PBD, bead-immobilized PLHSpT or the respective non-phospho PLHST control peptide was incubated with soluble control GST, GST-PBD, or GST-PBD (H538A K540M)$_4$ for 2 h, washed, and then precipitated fraction was analyzed.

For p-Cdc25C pull-down assays, either bead-bound GST-PBD or the corresponding GST-PBD(H538A K540M) mutant was incubated with mitotic HeLa lysates in TBSN buffer supplemented with 2 mM DTT. To test the ability of the indicated peptides to compete the PBD-p-Cdc25C interaction, lysates were pre-incubated with GST-PBD for 1.5 h prior to the addition of the indicated peptides. Lysates were then incubated for additional 1.5 h, washed in the binding buffer, and then analyzed. For competition of the interaction between p-Cdc25C and endogenous Plk1, mitotic lysates were prepared in TBSN and incubated with the indicated peptides for 1 h before subjecting to immunoprecipitation with anti-Plk1 antibody.

ELISA-Based PBD-Binding Inhibition Assay.

A biotinylated 9-mer p-T78 peptide {Biotin-C—$(CH_2)_6$—$(CH_2)_6$-DPPLHSpTAI-$NH_2$} or a biotinylated 13-mer p-T78 peptide {Biotin-$(CH_2)_6$—CETFDPPLHSpTAI-$NH_2$} was first diluted with coating solution (KPL Inc., Gaithersburg, Md.) to the final concentration of 0.3 µM, and then 50 µl of the resulting solution was immobilized onto a 96-well streptavidin-coated plate (Nalgene Nunc, Rochester, N.Y.). To block the unoccupied sites, wells were washed once with PBS+ 0.05% Tween 20 (PBST) and incubated with 200 µl of PBS+ 1% BSA (blocking buffer) for 1 h. Mitotic 293A lysates expressing HA-EGFP-Plk1 (5) were prepared in TBSN buffer. The resulting lysates (60 µg total lysates in 100 µl) were applied onto the biotinylated peptide-coated ELISA wells immediately after mixing with the indicated amount of the competitor peptides, and then incubated with constant rocking for 1 h at 25° C. To terminate the reaction, ELISA plates were washed 4 times with PBST. For detection of the bound HA-EGFP-Plk1, plates were incubated for 2 h with 100 µl/well of monoclonal anti-HA antibody at a concentration of 0.5 µg/ml in the blocking buffer. After washing the plates 5 times, 100 µl of an HRP-conjugated secondary antibody diluted to 1:1000 in the blocking buffer was added onto each well and incubated for 1 h. Afterward, the plates were washed 5 times with PBST and incubated with 100 µl/well of 3,3',5,5'-Tetramethylbenzidine solution (TMB) (Sigma, St. Louis, Mo.) as substrate until reaching a desired absorbance. The reactions were terminated by the addition of 1N $H_2SO_4$ and the optical densities for each sample were measured at 450 nm by using an ELISA plate reader (Molecular Device, Sunnyvale, Calif.).

Similar methods were used for the ELISA assays shown in FIGS. 14, 17, 19, and 20.

Isothermal titration calorimetry analyses. The calorimetric titrations were performed on a VP-ITC titration calorimeter (Microcal, Inc., Northampton, Mass.). In a typical experiment, 5 µl aliquots of a phosphorylated peptide were injected from a 250 µl syringe into a rapidly mixing (300 rpm) solution of Plk1 PBD (cell volume=1.3472 ml). Control experiments involved injecting identical amounts of the peptide solution into buffer without Plk1 PBD. The concentrations of Plk1 PBD were 0.033-0.052 mM, and those of the peptides were 0.145-0.365 mM, all concentration values determined by amino acid analysis. Titrations were carried out at 25° C. in 20 mM Tris-Cl (pH 7.5), 100 mM NaCl, 3 mM DTT. The isotherms, corrected for dilution/buffer effects, were fit using the Origin ITC Analysis software according to manufacturer's protocols. A nonlinear least-square method was used to fit the titration data and to calculate the errors. Consistent with the structural data, a 1:1 stoichiometry was assumed and the data were fit to a one-site binding model. From the binding curve, values for enthalpy and binding affinity were extracted. Thermodynamic parameters were calculated using $\Delta G = -RT\ln K_a$, $\Delta G = \Delta H - T\Delta S$.

Cloning, Protein Expression, and Purification.

Two forms of Plk1 PBD (residues 326-603 and residues 367-603) were expressed as fusion constructs with an N-terminal $His_6$-DsRed tag in a vector based on pDEST-527 (Addgene, Cambridge, Mass.). Another form of Plk1 PBD (residues 371-603) was expressed with an N-terminal $His_6$-MBP tag in a vector based on pET-28a (Novagen, Madison, Wis.). A TEV protease cleavage site was engineered between the tag and PBD. The vectors were expressed in either *E. coli* BL21(DE3)pLysS or Rosetta 2 cells (Novagen) with similar yield. Cells were grown to an optical density of 0.4 at 30° C. with vigorous shaking. The cultures were cooled to 20° C., induced by addition of IPTG to a final concentration of 0.4 mM, and incubated for 12 h. The cells were harvested and the pellets were frozen prior to lysis. All subsequent purification was done at 4° C. The frozen pellets were thawed in buffer A (20 mM Tris-Cl, pH 8.0, 500 mM NaCl, 3 mM DTT) and lysed by addition of 4% v/v BugBuster 10× protein extraction reagent (Novagen) and 0.1 mg/ml of DNase I (Sigma). The lysate was centrifuged at 40000×g for 30 minutes to pellet the cell debris and filtered through a 0.2 µm filter. The lysate was loaded onto HisTrap HP columns (Amersham Biosciences, Piscataway, N.J.) with 100 mM imidazole, washed with 100 mM imidazole in buffer A, and eluted with 500 mM imidazole in buffer A. The peaks containing the fusion protein were digested with TEV protease (1:100 molar ratio) overnight by dialysis against buffer A. The digestion was reloaded onto HisTrap HP column without imidazole, washed with buffer A, and eluted with 80 mM imidazole in buffer A. A HiLoad 16/60 Superdex 75 gel filtration column (Amersham) equilibrated with buffer A was used as the final step in purification. Full length PBD was dialyzed against a low salt buffer (20 mM Tris-Cl, pH 7.5, 100 mM NaCl, 3 mM DTT), and used in calorimetry experiments. The truncated forms of PBD were used for crystallography. The kinase domain of Plk1 (residues 1-337) was purified in the same manner. His$_6$-MBP constructs were purified by Ni metal affinity chromatography, loaded on to an amylose-agarose column, and then eluted with 50 mM maltose in a buffer {10 mM Tris (pH 8), 0.5 M NaCl, 2 mM DTT}. The resulting protein was digested with TEV protease to cleave the tag, flowed through Ni column, and then finally subjected to gel filtration. The PBD of human Plk2 (residues 373 to 685) was cloned as a MBP fusion with a TEV protease cleavage site and purified as the same fusion with PBD of Plk1.

Cell Culture and Microinjection.

HeLa cells were cultured as subconfluent monolayers under the conditions recommended by American Type Culture Collection (Manassas, Va.). To acutely inhibit the Cdc2 kinase activity, HeLa cells arrested with 200 ng/ml of nocodazole for 16 h were treated with 200 nM of BMI-1026 for 10 min. No mitotic exit was observed during the period of 10 min BMI-1026 treatment. For microinjection experiments with the Pmab-containing mimetic peptides, cells were arrested for 16 h with 2.5 mM thymidine (Sigma) and released into fresh medium. Two hours after release from the S phase block, the indicated peptides (2.5 mM stock in PBS) were microinjected into the cells using Eppendorf® Transjector 5246 (Eppendorf®, Westbury, N.Y.) at the 150 hPa pressure level and the 0.5 second injection time. All the cells in a single grid were injected and then further incubated to monitor cell cycle progression. For microinjection experiments with the F$_2$Pmab-containing mimetic peptides, cells were arrested with 2.5 mM thymidine for 16 h twice with a 9 h release interval, and then released into fresh medium. Seven hours after release from the G1/S phase block, the indicated peptides (4 mM stock in PBS) were microinjected similarly as above. Where indicated, peptides containing the final concentration of 30 ng/µl of pEGFP-C1 vector (Clontech®, Mountain View, Calif.) were used to visualize the injected cells.

To determine the level of Plk1 delocalization by the microinjected PLHS-Pmab peptide, cells were released for 5 h from the single thymidine (S phase) block and then microinjected. Four hours after microinjection, cells were fixed and subjected to immunostaining analyses as described below.

Similar methods were used for the experiments shown in FIG. 16 using the peptides indicated. HeLa cells were arrested at the G1/S boundary by double thymidine treatment and released into fresh medium. Six hours after release, the cells were microinjected with a mixture of 3 mM of peptides 21, 23 or 24 and 30 ng/µL of pEGFP-C1 vector and the cells were then photographed 15 h after G1/S release. Co-injected EGFP plasmid provided a convenient marker to identify the microinjected cells.

Electroporation.

For the purpose of investigating a long term effect of the peptide, a 6-mer Biotin-conjugated p-T78 mimetic peptide {Biotin-(CH)$_6$-PLHS-F$_2$Pmab-A-NH$_2$} was electroporated into asynchronously growing HeLa cells using a Bio-Rad® Gene Pulser (Bio-Rad® Laboratories, Hercules, Calif.) at 250 µFD and 300 V. Cells were then incubated for 2 days, fixed, and then subjected to immunostaining analysis.

Indirect Immunofluorescence and Confocal Microscopy.

Indirect immunostaining was carried out as described previously (5) using anti-Plk1 antibody (Santa Cruz Biotechnologies, Santa Cruz, Calif.) and anti-CREST antiserum (Cortex Biochem, San Leandro, Calif.). All the appropriate secondary antibodies were purchased from Jackson ImmunoResearch Laboratories, Inc. (West Grove, Pa.). Biotinylated F$_2$Pmab-positive cells were detected by co-staining with FITC-conjugated Streptavidin (Invitrogen®, Carlsbad, Calif.). Chromosomes were visualized with 4',6-diamidino-2-phenylindole (DAPI) (Sigma). Digital images were collected with a Zeiss LSM510 confocal microscope. For the quantification of the fluorescence signal intensities, images of unsaturated fluorescence signals were acquired with the same laser intensity at 512×512 pixels and 12-bit resolution. Fluorescence intensities for localized signals were determined after subtracting the background signal intensities using Zeiss AIM confocal software.

Example 2

Identification of Minimal p-T78 Peptides that Bind to the PBD of Plk1

Figure 5:
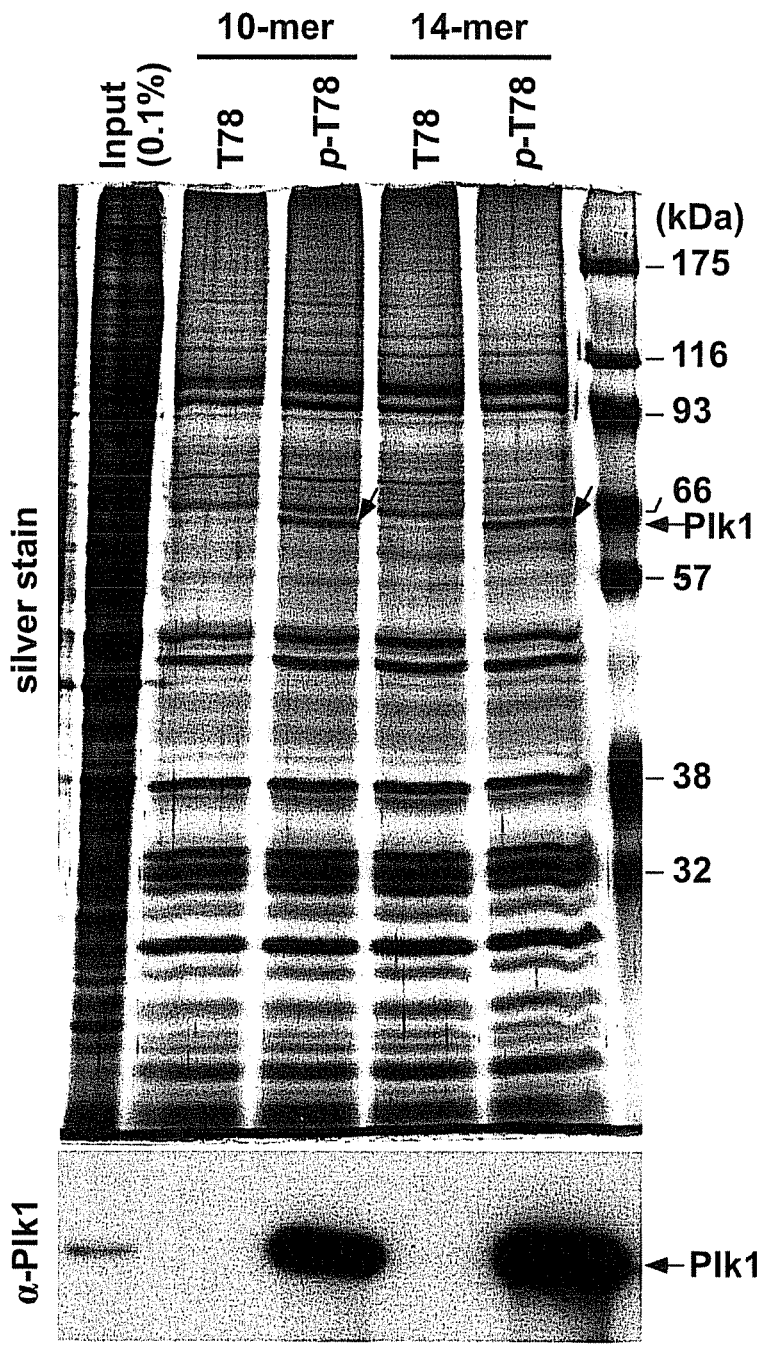
FIG. 5. p-T78 peptides, but not the respective non-phospho forms, precipitate Plk1 as the major binding protein from mitotic HeLa lysates. Mitotic lysates were prepared in TBSN buffer containing 20 mM p-nitrophenyl phosphate to inhibit dephosphorylation of p-T78 peptides. The resulting lysates were incubated with bead-immobilized non-phospho T78 (T78) or p-T78 peptides (10-mer and 14-mer) shown in FIG. 1A. Bead-associated proteins were separated in 10% SDS-PAGE, and stained with silver (Top) or immunoblotted with anti-Plk1 antibody (Bottom). Arrows, Plk1 precipitated with p-T78 peptides.

PBIP1/MLF1IP/KLIP1/CENP-50/CENP-U (PBIP1 hereafter) was isolated as a PBD-interacting protein critical for Plk1 localization to the centromeres (15) and for proper chromosome segregation (15-18). Further investigation on the Plk1-PBIP1 interaction shows that the PBD of Plk1 binds to the T78 region of PBIP1 in a phospho-dependent manner (15). To better understand the binding nature of Plk1PBD to the S77-p-T78 motif, various p-T78 peptides for in vitro binding analyses were synthesized. Consistent with the previous observation (15), a bead-immobilized 10-mer or 14-mer phospho-T78 (p-T78) peptide, but not the respective non-phospho forms, precipitated Plk1 from mitotic HeLa cells as the major binding protein (FIG. 5; note that the pull-down assays were performed in the presence of phosphatase inhibitors to prevent dephosphorylation of p-T78 peptides). To determine a minimal sequence of the T78 motif that is sufficient for the interaction, a systematic deletion analysis starting from the 10-mer p-T78 peptide (PLHSpTAIYAD) was carried out and the ability of each resulting peptide to bind to Plk1 was tested. Surprisingly, removal of all the amino acid residues C-terminal to the p-T78 residue did not diminish the level of Plk1 binding (FIG. 1A, left), suggesting that these C-terminal residues after p-T78 are dispensable for the PBD binding. Further N-terminal deletion analyses of PLHSpT showed that LHSpT lacking the N-terminal Pro possessed a greatly diminished (~7 fold) binding affinity to Plk1, while HSpT lacking both the Pro and Leu residues did not exhibit any significant level of binding (FIG. 1A, right). These data suggest that PLHSpT binds to Plk1 as efficiently as the initial 10- or 14-mer p-T78 peptide and that, besides the SpT dipeptide, the N-terminal Pro-Leu motif is critically required to provide an additional level of affinity to the PBD.

Figure 12B:
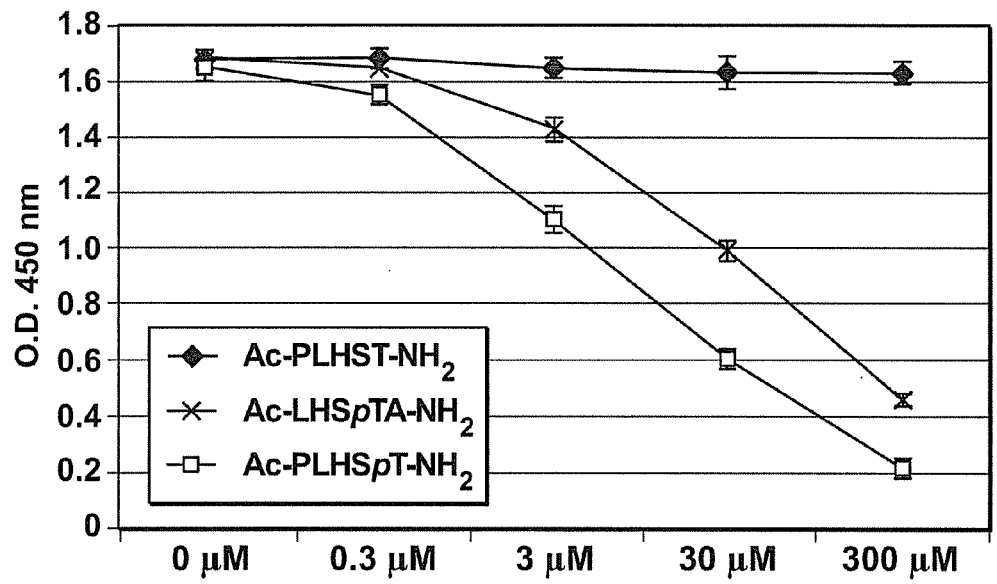
FIG. 12A-B. Comparative analyses of the PBD inhibition by two minimal p-T78 peptides, Ac-PLHSpT-NH$_2$ and Ac-LHSpTA-NH$_2$. (A), Schematic diagram illustrating the PBD-binding inhibition assay. The biotinylated p-T78 peptide {Biotin-C—(CH$_2$)$_6$—(CH$_2$)$_6$-DPPLHSpTAI-NH$_2$} (green dot with wiggled p-T78 peptide) was immobilized on the avidin-coated ELISA wells, and then incubated with HeLa lysate expressing HA-EGFP-Plk1 in the presence of a competitor peptide (red). After incubation, plates were washed and the level of HA-EGFP-Plk1 bound to the biotinylated peptide was quantified by incubating the ELISA wells with anti-HA antibody (blue), followed by HRP-conjugated secondary antibody (the green antibody with a black dot). The yellow and red asterisks indicate 3,3',5,5'-Tetramethylbenzidine (TMB) substrate and its reaction product, respectively, generated by HRP. (B), To determine the efficiency of the PBD inhibition by the indicated peptide, the HA-EGFP-Plk1-expressing HeLa lysates were added onto the ELISA wells immediately after mixing with various amounts of the peptide. Reproducibly, Ac-PLHSpT-NH$_2$ exhibited a higher level of PBD inhibition than Ac-LHSpTA-NH$_2$, suggesting that the Pro-4-dependent hydrophobic interactions of Ac-PLHSpT-NH$_2$ with the Trp414 and Phe535 residues as shown in FIG. 10 are stronger than the van der Waals contacts generated by the Ala+1 residue in Ac-LHSpTA-NH$_2$. Bars, standard deviation.

To eliminate the bias of the deletion scheme that was followed, the question of whether other 5-mer peptides encompassing the SpT motif efficiently bind to Plk1 was also tested. Interestingly, LHSpTA, which lacks the N-terminal Pro but bears the C-terminal Ala, bound to Plk1 almost as efficiently as PLHSpT (FIG. 1B, left; see also FIGS. 2B and 12B), suggesting that loss of the N-terminal Pro can be largely compensated by the addition of the C-terminal Ala. However, HSpTAI, lacking both Pro and Leu but instead bearing two additional C-terminal residues following the SpT motif, bound to Plk1 only weakly (FIG. 1B, right), thus underlining the importance of the Leu-3 residue in the absence of the Pro-4 residue (see FIG. 10 for molecular level details). A high level of interaction between LHSpTA and PBD was somewhat unexpected, because previous data showed that the Pro, Cys, and Gly residues are selected for the residue at the p-Thr+1 position13. Among the 4-mers, both LHSpT and HSpTA bound to Plk1 better than SpTAI (FIG. 1C), suggesting that the central PBD-binding motif in the T78 region of PBIP1 is built around the core sequences of LHSpT and HSpTA. Consistent with the strong binding affinity of the p-T78 peptides, comparative binding studies between a short form of the previously characterized optimal PBD-binding peptide (MQSpTPL)13 and the analogous p-T78 peptide (LHSpTAI) showed that the binding affinity of the latter is equivalent to that of the former (FIG. 1D).

Example 3

Figure 2A:
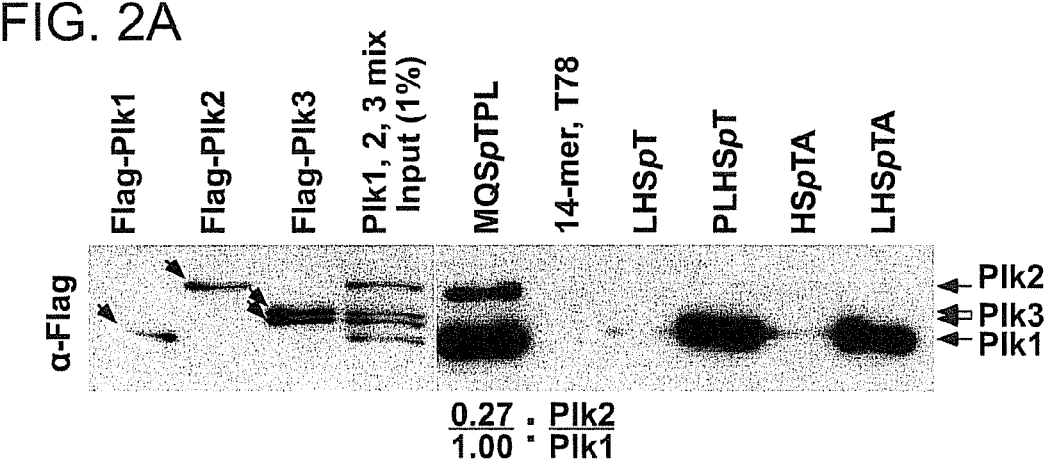
FIG. 2A-F. Minimal p-T78 peptides specifically bind to Plk1 with a high affinity. (A) HeLa lysates expressing the kinase-inactive Flag-Plk1(K82M), Flag-Plk2(K108M), or Flag-Plk3(K52R) were mixed before incubating with the indicated T78 peptides cross-linked to the beads. The synthetic optimal peptide (MQSpTPL) was included as a comparison. Precipitates were immunoblotted with anti-Flag antibody. Numbers indicate the fraction of Plk2 over Plk1 bound to the peptide. Arrows indicate Flag-Plk1, 2, 3 proteins. (B), Mitotic HeLa lysates were incubated with the indicated bead-bound peptides. Co-precipitating proteins were analyzed by silver staining. Arrows, Plk1 precipitated with p-T78 peptides. (C), Soluble control GST, GST-PBD, or GST-PBD(H538A K540M) was incubated with the indicated T78 peptides immobilized to the beads. Bound proteins were immunoblotted with anti-GST antibody. (D), Isothermal titration calorimetry for the p-T78 peptides was performed using purified Plk1 PBD. Representative calorimetric isotherms for the binding of two 5-mers (PLHSpT and LHSpTA) to the PBD are shown. The solid lines represent fits to the data. The overall ΔH (kcal/mol) is easily observed as the difference between the pre- and the post-binding baselines extrapolated along the y-axis. (E), To test the ability of the indicated peptides to disrupt the Plk1-p-Cdc25C interaction, mitotic HeLa lysates were pre-incubated with bead-bound GST-PBD for 1.5 h prior to the addition of the indicated peptides. After additional 1.5 h incubation, GST-PBD-binding proteins were precipitated and analyzed as in (A). Detection of GST-PBD in the anti-Cdc25C blot is the result of previous immunoblotting with anti-GST antibody. Numbers indicate relative efficiency of p-Cdc25C pull-down by GST-PBD. (F), Mitotic HeLa lysates were treated with the indicated peptide prior to immunoprecipitation with either control (cont.) antibody or anti-Plk1 antibody. Plk1 immunoprecipitates were analyzed with the indicated antibodies. Asterisk, a cross-reacting protein.
Figure 2B:
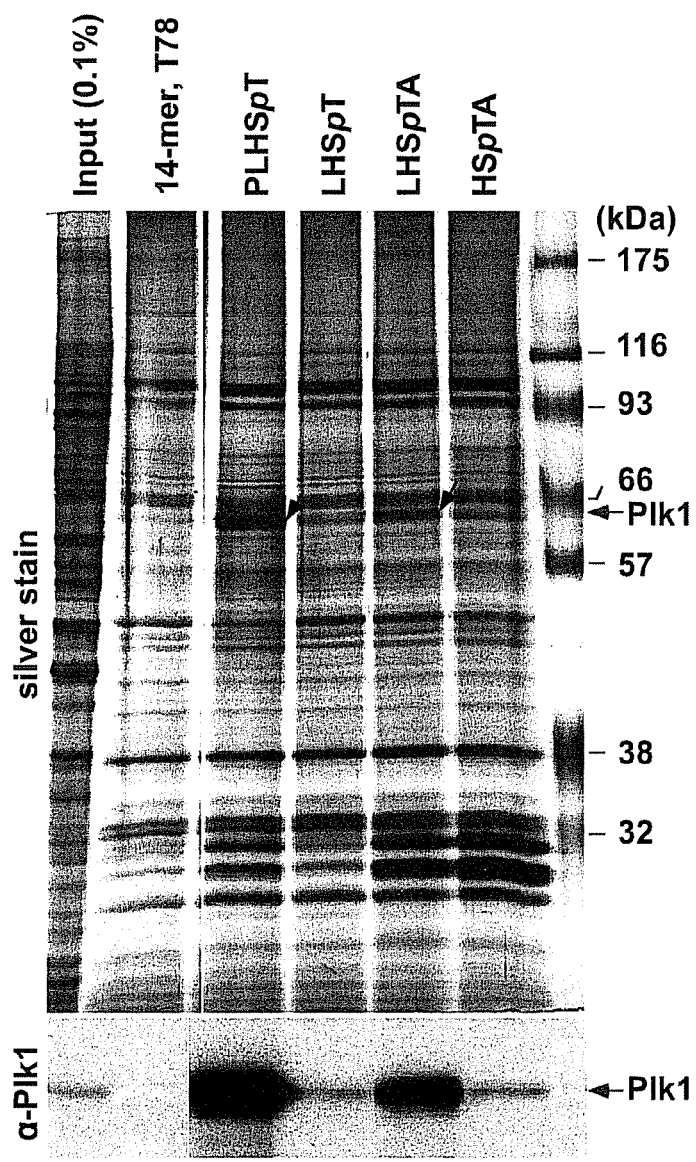
Figure 2C:
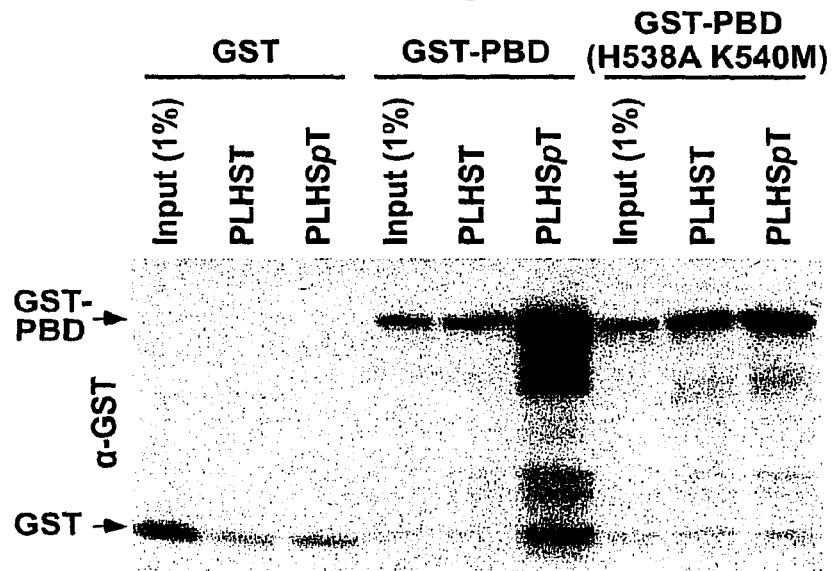
Figure 6:
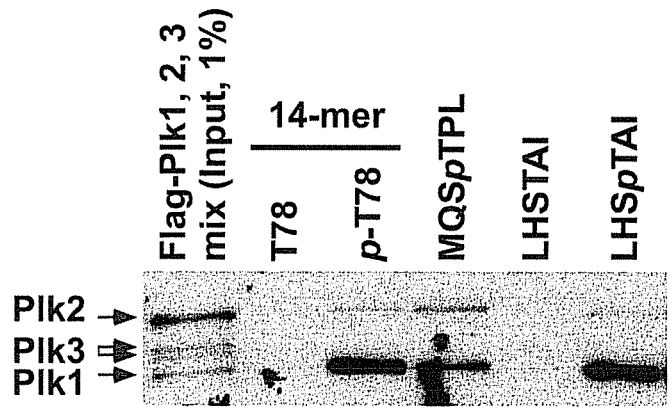
FIG. 6. A 6-mer T78 peptide (LHSpTAI) analogous to the synthetic optimal peptide (MQSpTPL) preferentially precipitates Plk1, whereas MQSpTPL binds to both Plk1 and, at a reduced level, Plk2. The mixture of HeLa lysates expressing the kinase-inactive Plk1(K82M), Flag-Plk2(K108M), or Flag-Plk3(K52R) was incubated with the indicated peptides cross-linked to the beads. Precipitates were washed, separated, and then subjected to immunoblotting analysis with anti-Flag antibody.
Figure 7:
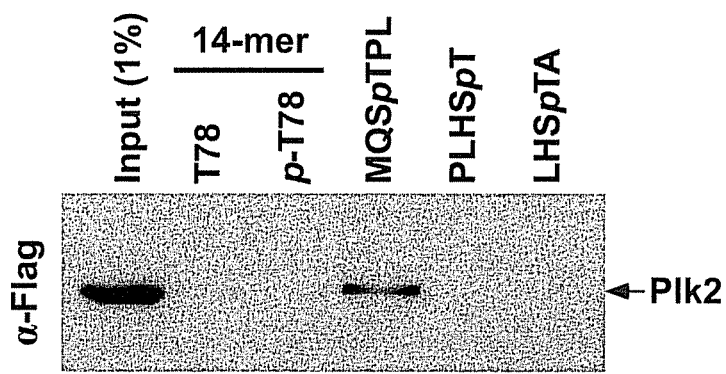
FIG. 7. The synthetic optimal PBD-binding peptide (MQSpTPL) (4) binds to Plk2. HeLa lysates expressing Flag-Plk2 were incubated with the immobilized peptides indicated under the conditions described in the Materials and Methods (Example 1). Precipitates were analyzed as in FIG. 2A.

A Specific and High Affinity Binding Between Minimal p-T78 Peptide and the Plk1 PBD Next, the specificity of the minimized p-T78 peptides against Plk1 PBD was tested. Because of the distinct binding nature of Plk4 PBD, Plk4 was not included in these analyses. The results showed that, similar to the initial 14-mer peptide, minimized p-T78 peptides specifically precipitated Plk1 from lysates containing similar levels of Plk1, Plk2, and Plk3 (FIG. 2A and FIG. 6). In contrast, the 6-mer optimal MQSpTPL peptide precipitated Plk2 with ~27% efficiency of Plk1 precipitation under the same conditions (FIG. 2A), suggesting that it possesses a significantly lower Plk1 specificity than PLHSpT. Consistent with this notion, MQSpTPL but not the p-T78 peptides, precipitated Plk2 from the HeLa lysates expressing Plk2 alone (FIG. 7). Remarkably, although much shorter in length than the initial 14-mer peptide, a minimal p-T78 peptide, PLHSpT, exhibited an undiminished Plk1 specificity and precipitated Plk1 as the only major binding protein from the total HeLa lysates (FIG. 2B). Another 5-mer, LHSpTA, also displayed a similar but somewhat reduced level of Plk1 affinity (FIG. 2B). These observations suggest that elements critical for Plk1-binding affinity and specificity reside within these minimal sequences. Further examination with PLHSpT showed that it specifically bound to GST-fused PBD (GST-PBD), but only weakly to the corresponding GST-PBD (H538A, K540A) phosphate pincer mutant (FIG. 2C), indicating that an intact phosphoepitope-binding module is required for the PLHSpT-Plk1 PBD interaction.

Figure 2D:
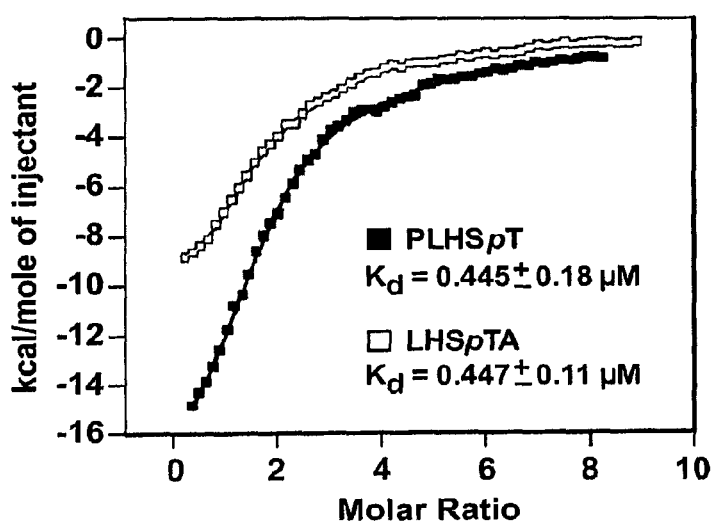

Next, out isothermal titration calorimetry analyses were carried out with recombinant Plk1 PBD and quantified the binding parameters of the minimal p-T78 peptides. Among the minimal peptides tested, a 5-mer PLHSpT mediated the best binding contacts with the PBD ($\Delta H=-14.5$ kcal/mol) (FIG. 2D), although it exhibited an equivalent binding affinity overall (Kd~0.45 µM) with another 5-mer peptide, LHSpTA. Under the same conditions, the synthetic optimal 6-mer peptide, MQSpTPL, bound to PBD with a Kd of 0.534 µM (Table 1), a value similar to those of the 5-mer p-T78 peptides. The two other ti-mer peptides (PLHSpTA and LHSpTAI) displayed slightly higher affinities than the 5-mer peptides, whereas the 4-mers (LHSpT and HSpTA) exhibited much lower affinities (Table 1).

To test the specificity of binding of the above peptides, calorimetry binding experiments were conducted with recombinant Plk2 PBD. Saturable binding was not observed and, as a result of the lack of a binding curve in all cases, values for binding enthalpy or binding affinity could not be extrapolated. However, a clear difference in the initial heats of interaction of the peptides was observed above the limits of detection (1 kcal/mol) of the instrument. The two minimal p-T78 peptides, PLHSpT and LHSpTA, exhibited virtually no interactions with Plk2 (only baseline heats were detected), whereas MQSpTPL titrated into Plk2 PBD produced initial heats of −1.68 kcal/mol (Table 2). These results further corroborate the specificity of the minimal p-T78 peptides for Plk1 over Plk2.

Example 4 p-T78 Peptide Disrupts the PBD-Cdc25C Interaction

Figure 2F:
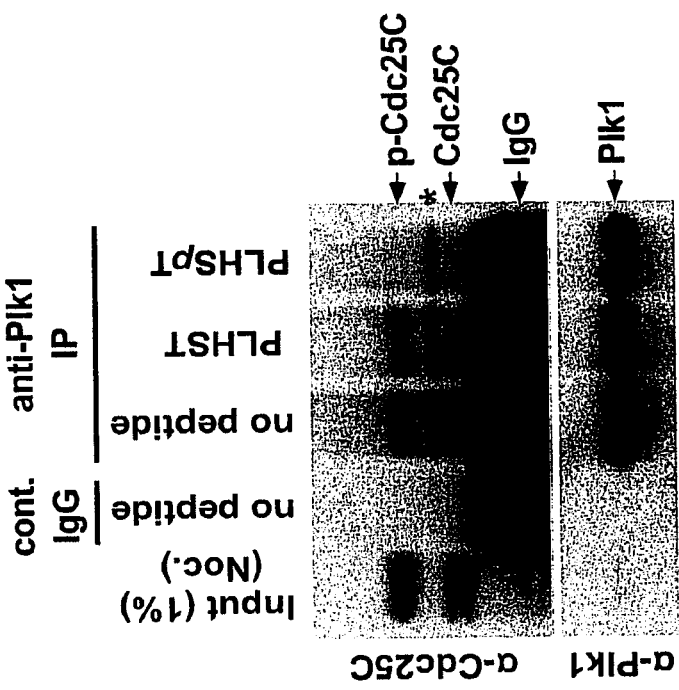
Figure 2E:
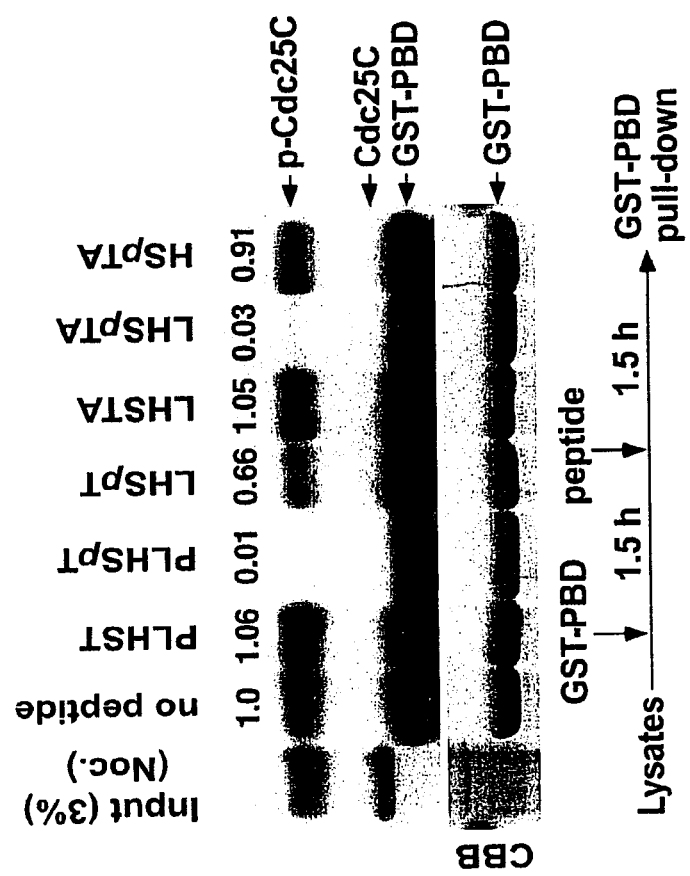
Figure 8A:
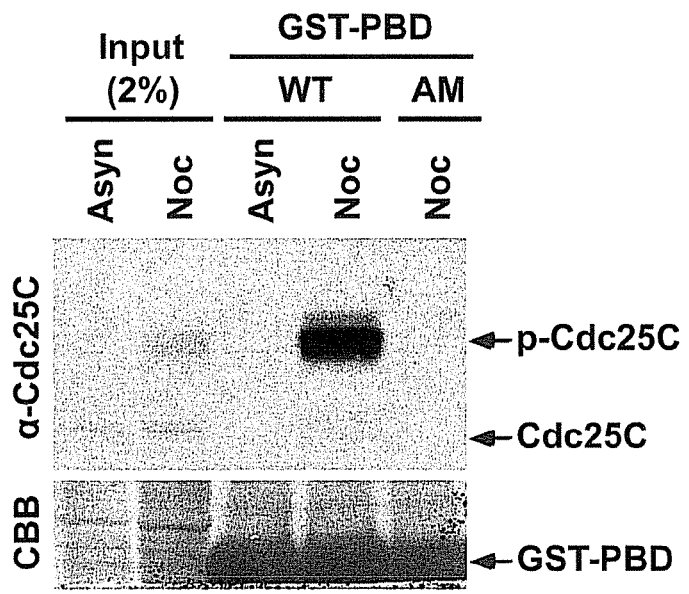
FIG. 8A-B. Concentration-dependent inhibition of the Plk1-p-Cdc25C interaction by minimal p-T78 peptides. (A), Either asynchronous (Asyn) or mitotic (Noc) HeLa lysates were incubated with bacterially-expressed GST-PBD or the GST-PBD(H538A K540M) mutant. GST-PBD-binding proteins were precipitated, washed, and then blotted with anti-Cdc25C antibody. The same membrane was stained with Coomassie (CBB). (B), Mitotic HeLa lysates were pre-incubated with bead-bound GST-PBD for 1.5 h before the addition of the peptides at the concentrations indicated. After additional 1.5 h incubation, GST-PBD-binding proteins were precipitated and analyzed as in (A). GST-PBD was also detected in the anti-Cdc25C blot as a result of previous immunoblotting with anti-GST antibody. Numbers indicate relative efficiency of the p-Cdc25C pull-down by GST-PBD.
Figure 8B:
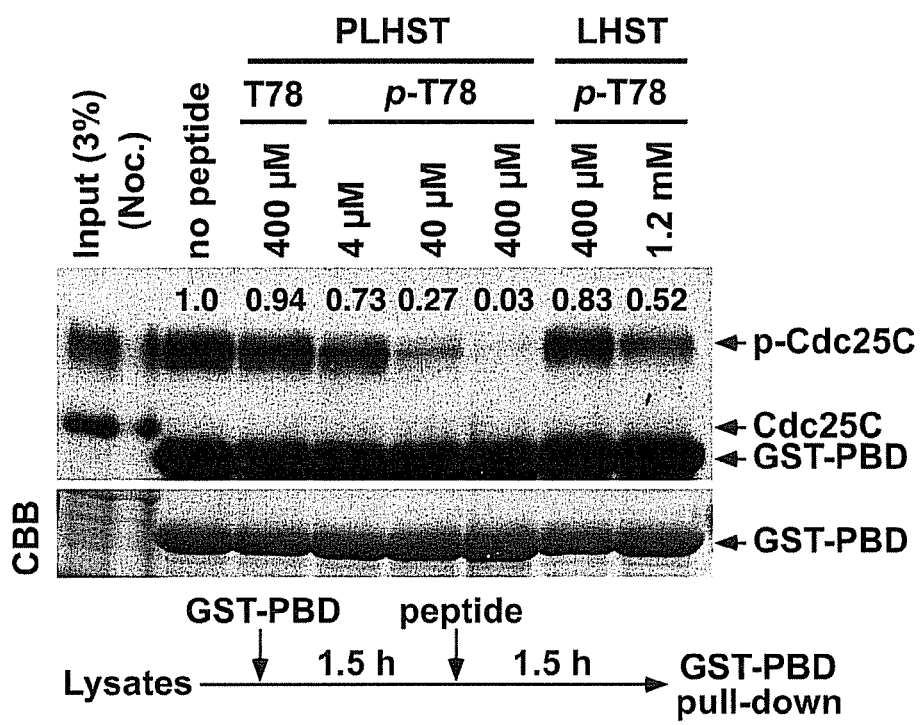

Next, the minimal p-T78 peptides were examined to determine if they have the capacity to interfere with the interaction between Plk1 PBD and its physiological binding target, phospho-Cdc25C (p-Cdc25C). In agreement with the previous finding, GST-PBD precipitated p-Cdc25C, but not the unphosphorylated form, from mitotic HeLa cells (13) (FIG. 8A). Addition of PLHSpT, but not the respective non-phosphopeptide, into the mitotic lysates disrupted the pre-formed PBD-p-Cdc25C complex in both a phospho- and concentration-dependent manner (FIG. 8B). LHSpT also interfered with the PBD-p-Cdc25C interaction, although it was much less effective than PLHSpT (FIG. 8B). In a separate experiment, we found that LHSpTA disrupted the pre-formed PBD-p-Cdc25C complex nearly as efficiently as PLHSpT, whereas both LHSpT and HSpTA disrupted the complex weakly (FIG. 2E). Consistent with these observations, PLHSpT, but not the corresponding non-phosphorylated peptide, disrupted the in vivo Plk1-p-Cdc25C interaction efficiently (FIG. 2F). These data demonstrate that p-T78 peptides interrupt the interaction between the PBD and its binding targets by competitively binding to the PBD.

Example 5

The Binding Nature of the Plk1 PBD

Figure 3A:
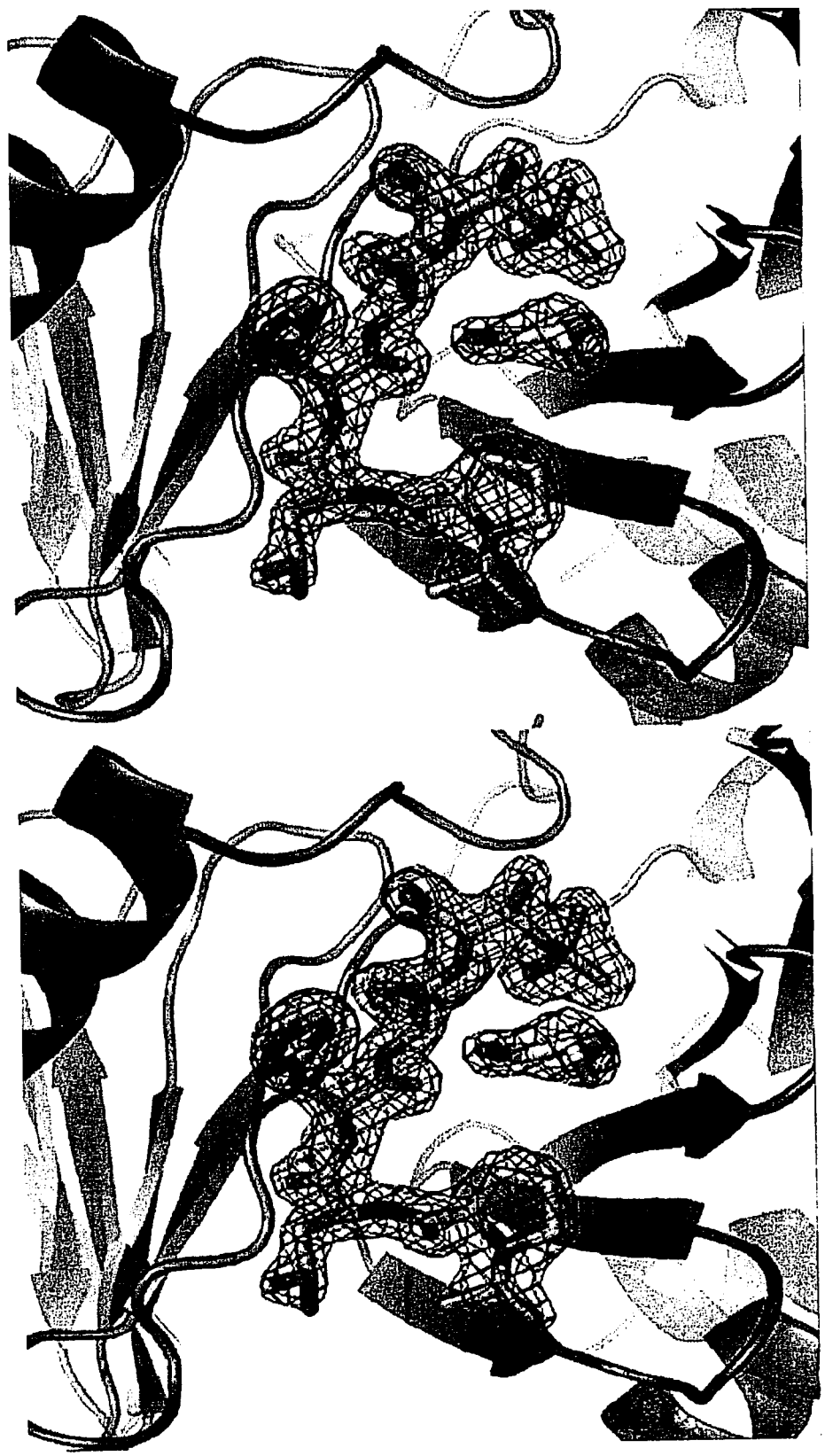
FIG. 3A-F. The nature of PBD binding and specificity. (A-C), Stereo image of the PBD phosphopeptide-binding pocket. In all images, PLHSpT is drawn in green and the associated glycerol in the binding pocket of PBDPL is in yellow. PDB ID for PBDPL; 3C6J. (A), The 2Fo-Fc electron density is contoured to 1.5σ around PLHSpT and its associated glycerol molecule in blue mesh. (B), The PBD residues involved in binding of PLHSpT are labeled and shown in cyan. All water molecules that form an interface between the phosphopeptide and PBD are drawn in red mesh. (C), Superposition of PLHSpT (green), PPHSpT (cyan), MQSpTPL (magenta), and PMQSpTPL (grey). PDB ID for PBDPP; 3C5L. (D-E), The mixture of HeLa lysates expressing the kinase-inactive Flag-Plk1(K82M), Flag-Plk2(K108M), or Flag-Plk3(K52R) was subjected to pull-down assays as in FIG. 2A with the indicated 5-mer wild-type (PLHSpT) and mutants cross-linked to the beads. The respective non-phospho-T78 peptide (PLHST) was used as a control. The numbers at the top of the blot indicate the relative efficiency of Plk2 precipitation, whereas the numbers at the bottom denote the relative efficiency of Plk1 precipitation. (F), Illustration depicting the nature of the interactions between the SpT-containing peptides and the Plk1 PBD. Alignment of minimal p-T78 peptides and synthetic optimal peptides showed that, in addition to the critical SpT motif, the N-terminal Pro-4 and Met-3 residues are important to stabilize the interactions by docking into a hydrophobic core surrounded by the Trp414, Phe535 and Arg516 residues in Plk1 PBD. The His-2 residue is important for Plk1 specificity since substitution of Gln for His enhances Plk2 binding. The Ala+1 or Pro+1 residue is central for guiding a priming kinase to phosphorylate the Thr residue.
Figure 3B:
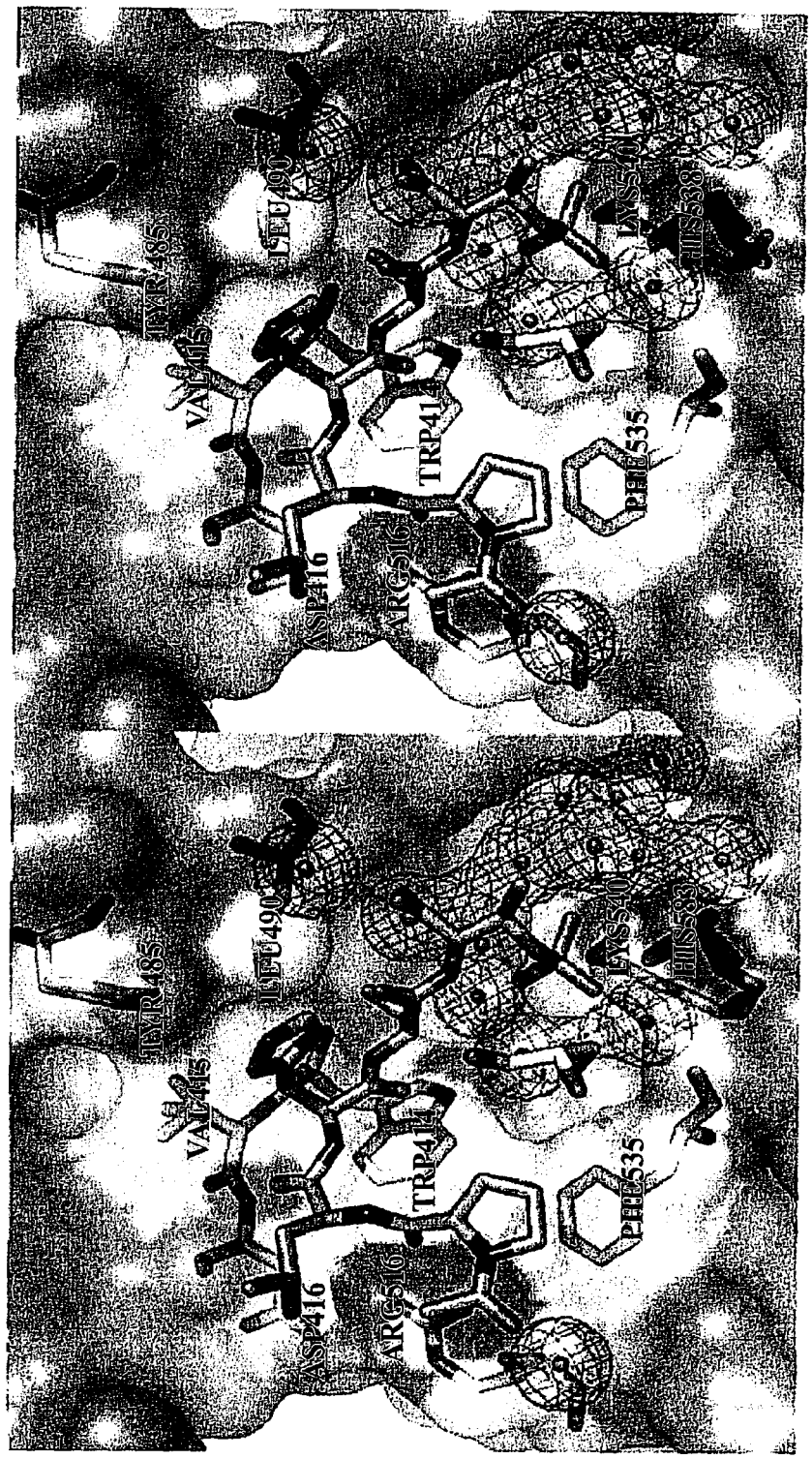
Figure 3C:
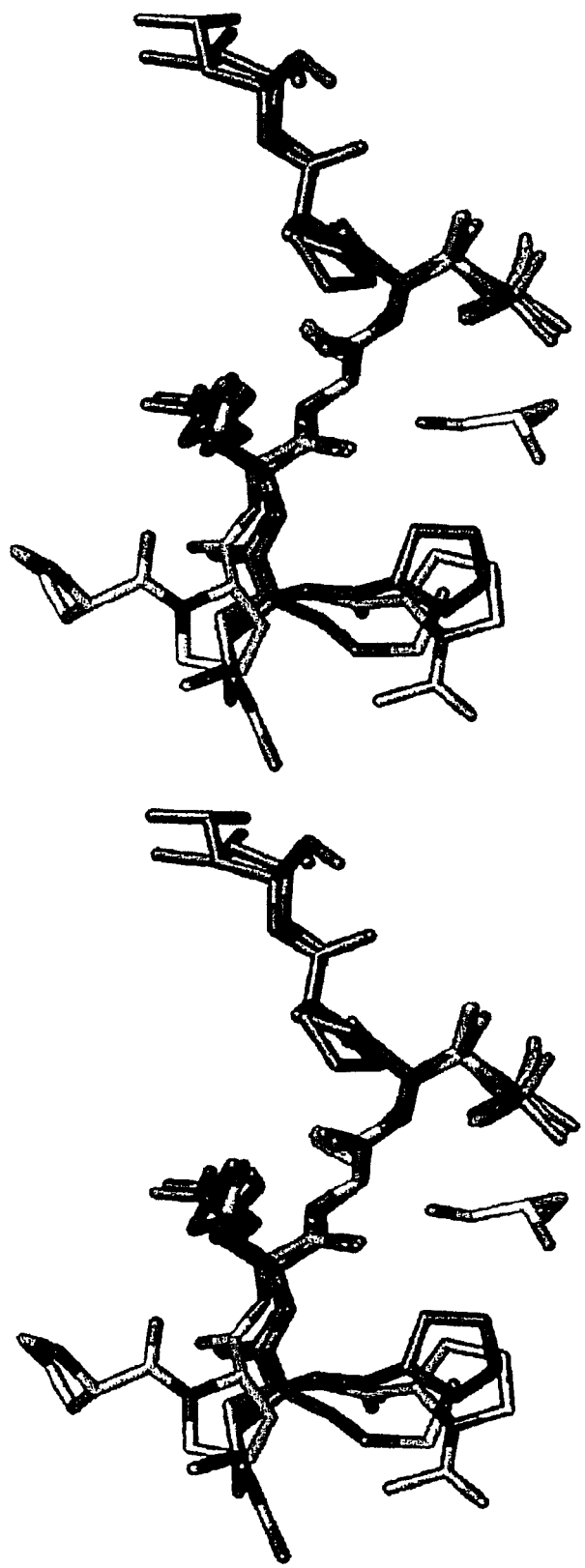
Figure 9:
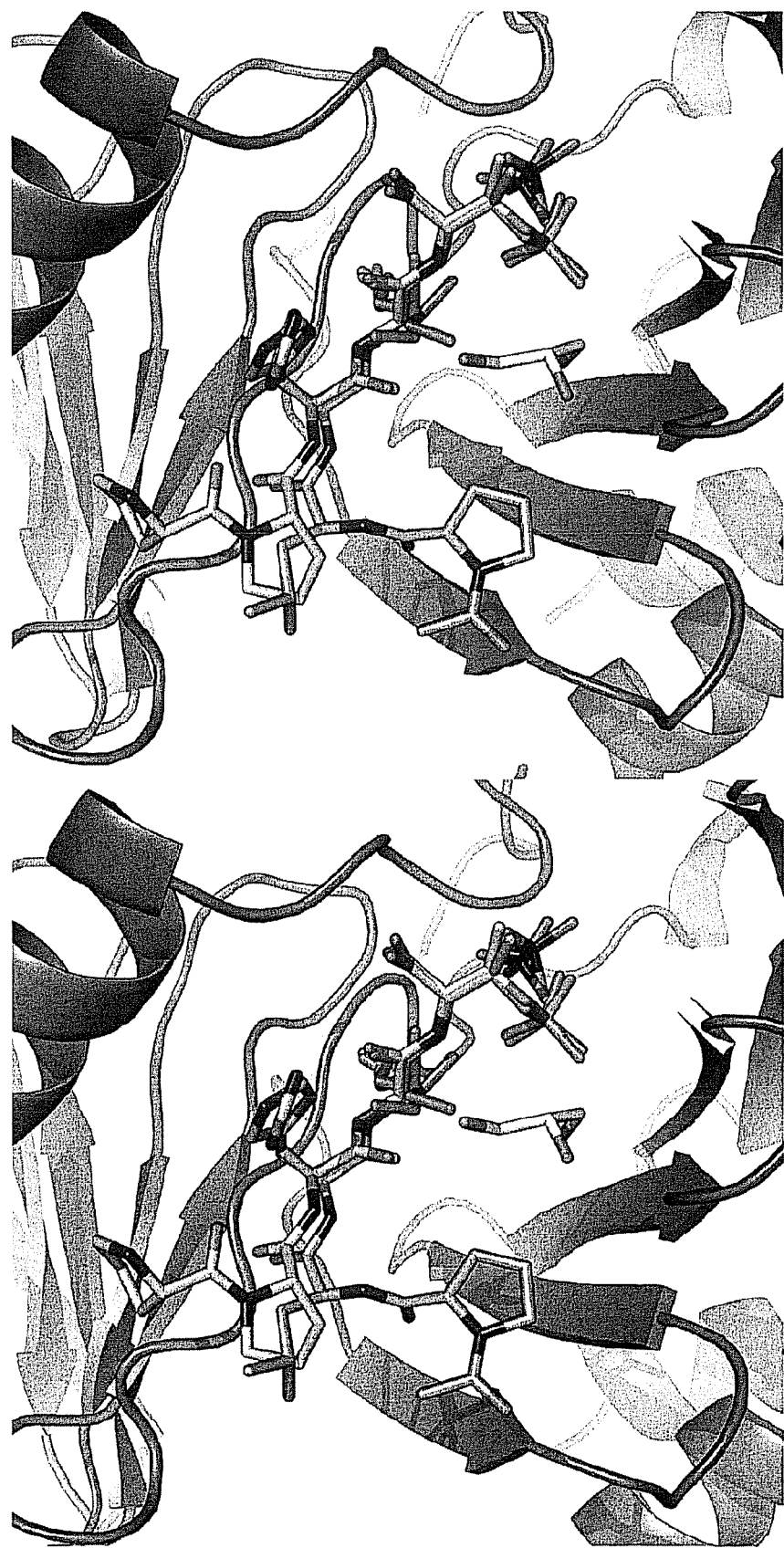
FIG. 9. Superposition of the phosphopeptide-binding pockets of PBDPL, PBDPP, PBDS+G, and PBDS. PBD is drawn in grey. PLHSpT is in green and its associated glycerol molecule is in yellow. PPHSpT is drawn in cyan. The glycerol molecule (two half-occupancy conformations at the Ser-1 position) of PBDS+G is drawn in magenta. The two sulfate anions of PBDS+G and PBDS are drawn with the sulfur atoms in black and oxygen atoms in red. Remarkable structural similarities among the PBDS+G, PBDS, and PBDPL hint that the glycerol molecule and the sulfate anion are capable of substituting the role of the SpT dipeptide. The differences in the exact positions of sulfate and phosphate groups could be due to the fact that the sulfate is a free anion, whereas the phosphate is covalently linked to the phosphopeptide. PDB ID for PBDS+G and PBDS; 3C6I.

Since PLHSpT exhibited a high affinity and specificity to Plk1 PBD, the binding nature of this peptide to the PBD was investigated to determine the interactions critical for Plk1 specificity, especially on its N-terminus. To this end, the crystal structures of the Plk1 PBD in complex with the phosphopeptides PLHSpT (hereon referred to as $PBD^{PL}$) and PPHSpT ($PBD^{PP}$; to examine the importance of the N-terminal residue for the interaction) were solved at 1.7 Å and at 2.3 Å resolution, respectively (FIGS. 3A-C and Table 4). Additionally, an attempt was made to crystallize a complex by mixing the PBD (without phosphopeptide) and the kinase domain, each expressed and purified separately. However, the kinase domain precipitated and only the PBD was found in a diffraction quality crystal. This novel crystal form contained two PBD molecules per asymmetric unit, referred to as $PBD^{S+G}$ (with sulfate and glycerol) and $PBD^S$ (with sulfate only) for chains A and B, respectively (FIG. 9). Several strong peaks of positive difference density were found in the Fo-Fc maps for $PBD^{PL}$, $PBD^{S+G}$, and $PBD^S$, which could not be interpreted as water molecules. These peaks were modeled as sulfate, glycerol, and ethylene glycol molecules. $PBD^{PL}$ contained a glycerol molecule in the phosphopeptide-binding cleft (FIG. 3A-B), occupying a cavity formed by the phosphopeptide, two water molecules, and PBD. The three hydroxyl groups of this glycerol molecule were involved in hydrogen bonding with the backbone carbonyls of the phosphopeptide and PBD, the phosphate group of p-Thr, and one of the water molecules. PBD$^{S+G}$ and PBD$^S$ contained a sulfate anion in the same pocket (FIG. 9), in the region normally occupied by the phosphate of p-Thr. The choice of modeling the density in this pocket as sulfate instead of phosphate stemmed from the presence of 0.3 M lithium sulfate in the crystallization media. PBD$^{S+G}$ contained a glycerol molecule in the phosphopeptide-binding cleft (FIG. 9). This glycerol molecule was located at the −1 position, normally occupied by the Ser residue when a phosphopeptide is in the binding cleft (FIG. 9). The L2 loop in PBD$^S$ is much less ordered than in the PBD$^{S+G}$ structure. Analysis of contacts with symmetry-related molecules showed that this difference in the degree of order observed in the L2 region is likely caused by crystal packing. Notably, the structures for the PBD$^{S+G}$, PBD$^S$, and PBD$^{PL}$ were remarkably similar among themselves, raising the possibility that the glycerol molecule and the sulfate anion are capable of mimicking the role of the SpT dipeptide in the PBD binding.

Example 6

The Role of the N-Terminal Residues of p-T78 Peptide for Plk1 Binding Affinity and Specificity Close inspection of the structure of the PLHSpT-PBD complex revealed that, in addition to the previously described SpT-dependent interactions (12,13), the N-terminal Pro residue is crucial for providing additional stability to the PBD binding by engaging in two discrete yet interconnected interactions. The carbonyl oxygen of the N-terminal Pro residue was in polar contact (i.e., hydrogen-bonding interaction) with the guanidinium moiety of Arg516, while the pyrrolidine ring of the Pro residue enhanced the interaction by docking into a shallow hydrophobic pocket generated by the surrounding Trp414 and Phe535 (FIGS. 3A-B). The importance of the latter interaction with the Pro-binding pocket was manifest by the observation that LHSpT, which can still form the polar contact with Arg516 through the carbonyl oxygen N-terminal to the Leu-3 residue, exhibited ~50-fold weaker binding than PLHSpT (Table 1).

Figure 3D:
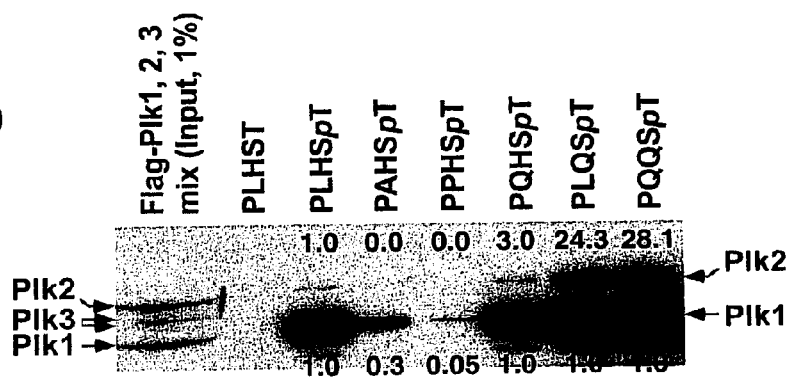

The critical role of the N-terminal Pro residue in PBD binding was directly demonstrated in experiments with PPHSpT. Here, the N-terminal Pro at the −4 position of PPHSpT was flipped out of the Pro-binding pocket and was unable to generate the polar contact and hydrophobic interactions because the Pro-3 residue locks the backbone of the phosphopeptide in a conformation opposite to that of PLHSpT (FIG. 3C). The effect of removal of the N-terminal Pro from the Pro-binding pocket and loss of the polar contact with the guanidinium moiety of Arg516 was reflected in the drastically diminished (20-fold) binding affinity of PPHSpT to Plk1 (FIG. 3D). In a separate experiment, a Pro-4 to Met-4 mutant, MLHSpT, exhibited a greatly diminished level of Plk1 PBD binding (FIG. 3E), further highlighting the importance of the Pro-4 residue in stably binding into the pocket. Consistent with these observations, the Pro-4 residue in PMQSpTPL docked into the Pro-binding pocket13 (FIG. 3C), while, in the absence of the N-terminal Pro-4, the side chain of the N-terminal unacetylated (i.e., free amine) Met-3 in MQSpTPL extended into the Pro-binding pocket (12) (FIG. 3C).

Figure 10A:
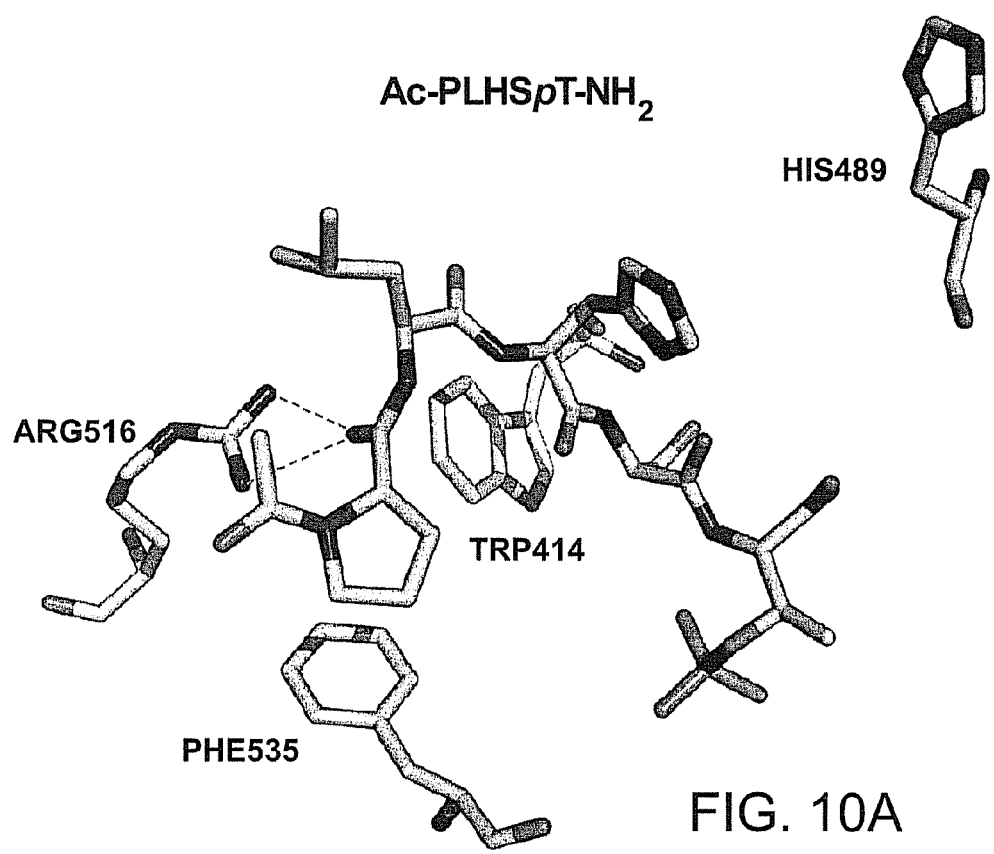
FIG. 10A-B. Comparative analyses on the structures of the PBD in complex with Ac-PLHSpT-NH$_2$ or Ac-LHSpTA-NH$_2$. The core PBD-binding mode for (B)Ac-LHSpTA-NH$_2$ and (A)Ac-PLHSpT-NH$_2$ remains largely the same. It is noteworthy that, in the Ac-PLHSpT-NH$_2$ structure, the carbonyl oxygen of the peptide bond between the Pro-4 and the Leu-3 is hydrogen-bonded to the guanidinium moiety of Arg516 of PBD (two red dotted lines). Similarly, by mimicking a peptide bond in the non-terminal regions of any peptide or protein, the N-terminal acetyl carbonyl oxygen in Ac-LHSpTA-NH$_2$ is in hydrogen bond with Arg516 (two red dotted lines). Notably, the PBDs from both Plk2 and Plk3 possess the Lys and Tyr residues at the positions analogous to the Arg516 and Phe535, respectively, of Plk1 PBD, suggesting that the Arg516 and Phe535 residues are likely important for Plk1 PBD-binding specificity. Since both Ac-PLHSpT-NH$_2$ and Ac-LHSpTA-NH$_2$ exhibited a high Plk1 specificity, the hydrogen bond generated between the carbonyl oxygen N-terminal to Leu-3 and the guanidinium moiety of Arg516 of Plk1 PBD could be critical for achieving the Plk1 specificity. However, mutations of the analogous Lys and Tyr residues in Plk2 and Plk3 to Arg and Phe, respectively, {i.e., Plk2(K607R, Y626F) and Plk3 (K568R, Y587F) mutations} failed to enhance the ability of Plk2 and Plk3 to bind to the synthetic optimal peptide (MQSpTPL). Rather, they eliminated the moderate level of the interaction normally observed between Plk2 and the latter peptide. These observations suggest that a broader primary sequence context of the PBD is likely important in properly forming the phosphopeptide-binding module and preserving the overall structural integrity of the PBD. PDB ID for PBD$^{LH}$; 3FVH.
Figure 10B:
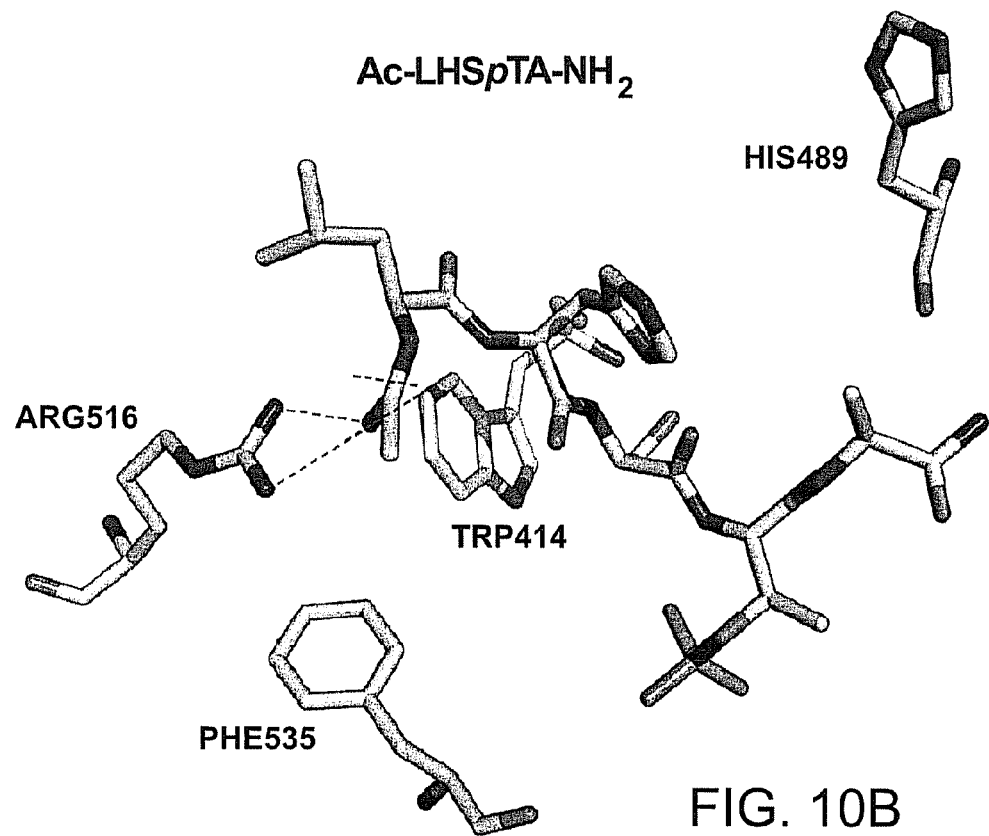

It is noteworthy that LHSpTA also exhibited a high level of Plk1 PBD binding affinity and specificity even in the absence of the Pro-4 residue (FIGS. 2A-B, 2D, and 7). Analyses of the crystal structure of the Plk1 PBD in complex with LHSpTA (PBD$^{LH}$, Table 4) revealed that, similar to the Leu-3 of PLHSpT, the N-terminal Leu-3 side chain of LHSpTA was directed into an intramolecular cavity and did not appear to be involved in interactions with the surrounding PBD residues (FIG. 10). The N-terminal acetyl carbonyl of LHSpTA was also in polar contact with Arg516, thus substituting the interaction engaged by the carbonyl oxygen of the Pro-4 of PLHSpT Unlike Plk1, both Plk2 and Plk3 possess the Lys residue (Lys607 and Lys568, respectively) at the position analogous to the Plk1 Arg516, suggesting that the observed polar contact is Plk1-specific. Since both PLHSpT and LHSpTA exhibit a high level of Plk1 PBD-binding specificity, this polar contact between the carbonyl oxygen N-terminal to the Leu-3 and the guanidinium moiety of the Arg516 is likely one of the major determinants of Plk1 PBD specificity. In addition, loss of the interactions between the pyrrolidine ring of the Pro-4 residue and the Pro-binding pocket, as a result of the lack of the N-terminal Pro residue in LHSpTA, appeared to be largely compensated by the van der Waals contacts generated by the C-terminal Ala+1 residue (FIG. 10), thus explaining how LHSpTA could achieve a relatively high affinity binding to the Plk1 PBD.

Apart from the phosphopeptide backbone region of the Leu-3 as mentioned above, the weak sum electron density (|Fo|-|Fc|) observed in the PBD$^{PL}$ structure in FIG. 3A suggested that the Leu side chain region is disordered and may not be involved in specific interactions with PBD. However, mutation of the Leu-3 of PLHSpT to Ala significantly diminished (~3-fold) the level of Plk1 binding, while the mutation to Gln did not alter the Plk1 affinity (rather, it appeared to increase the level of Plk2 binding) (FIG. 3D). Since the Leu-3 side chain does not appear to interact with other PBD residues, it is possible that the bulky side chain in the Leu or Gln residue contributes indirectly to the PBD binding by limiting the conformational flexibility of the phosphopeptide backbone in a way that the N-terminal Pro can better dock into the Pro-binding pocket.

The importance of the His at the −2 position for Plk1 specificity was next examined. In the crystal structure, the side chain of the His-2 residue did not directly mediate contacts with PBD residues (FIG. 3A-B). Strikingly, mutation of the His-2 to Gln substantially increased (24-fold) the level of Plk2 binding (FIG. 3D). In calorimetry experiments, titration of the PLQSpT mutant into Plk2 PBD produced initial heats of interaction on the order of −1.1 kcal/mol as compared to virtually baseline heats for the parent PLHSpT (Table 2), suggesting that the mutant peptide mediates binding contacts with Plk2 PBD, whereas the parent peptide is selective only for Plk1 PBD. Since the NΔ1 of His at the −2 position was involved in a hydrogen bond with the carbonyl oxygen of Ser at the −1 position, it has been speculated that the hydrogen bond between these two residues is critical for conferring Plk1 specificity. Alternatively, the presence of a Gln residue at the −2 position could be important for strong Plk2-mediated interactions.

Figure 3E:
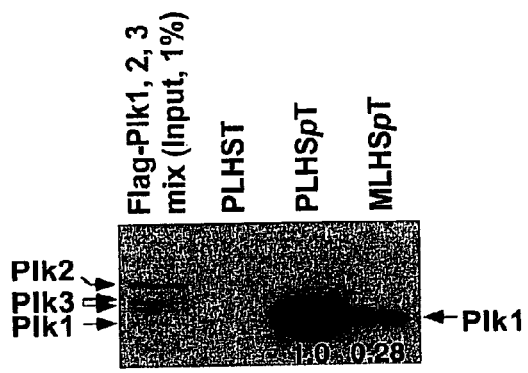
Figure 3F:
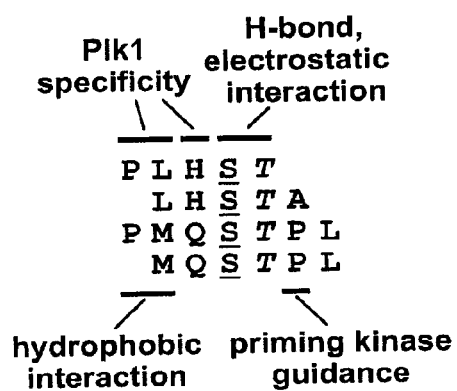

Taken together, the results provided herein demonstrate that the N-terminal Pro-Leu motif at the −4 and −3 positions is crucial for high affinity and specificity interactions with Plk1 PBD, while the His residue at the −2 position is important to assure an additional layer of Plk1 specificity (FIG. 3E). These findings explain in part why MQSpTPL, bearing the N-terminal Met for the Pro-binding pocket and lacking the critical His-2 residue, exhibits a low Plk1 specificity with a significant level of Plk2 affinity. In addition, the T78 residue in PBIP1 is followed by Ala in place of the commonly found Pro residue. Since Plk1, but not the Pro-directed Cdc2, is responsible for generating the p-T78 epitope, the Ala+1 residue may play a critical role in directing a non-Pro-directed kinase to phosphorylate the T78 residue (FIG. 3E).

Example 7

Inhibition of the Function of the Plk1 PBD by a p-T78 Mimetic Peptide

Figure 11A:
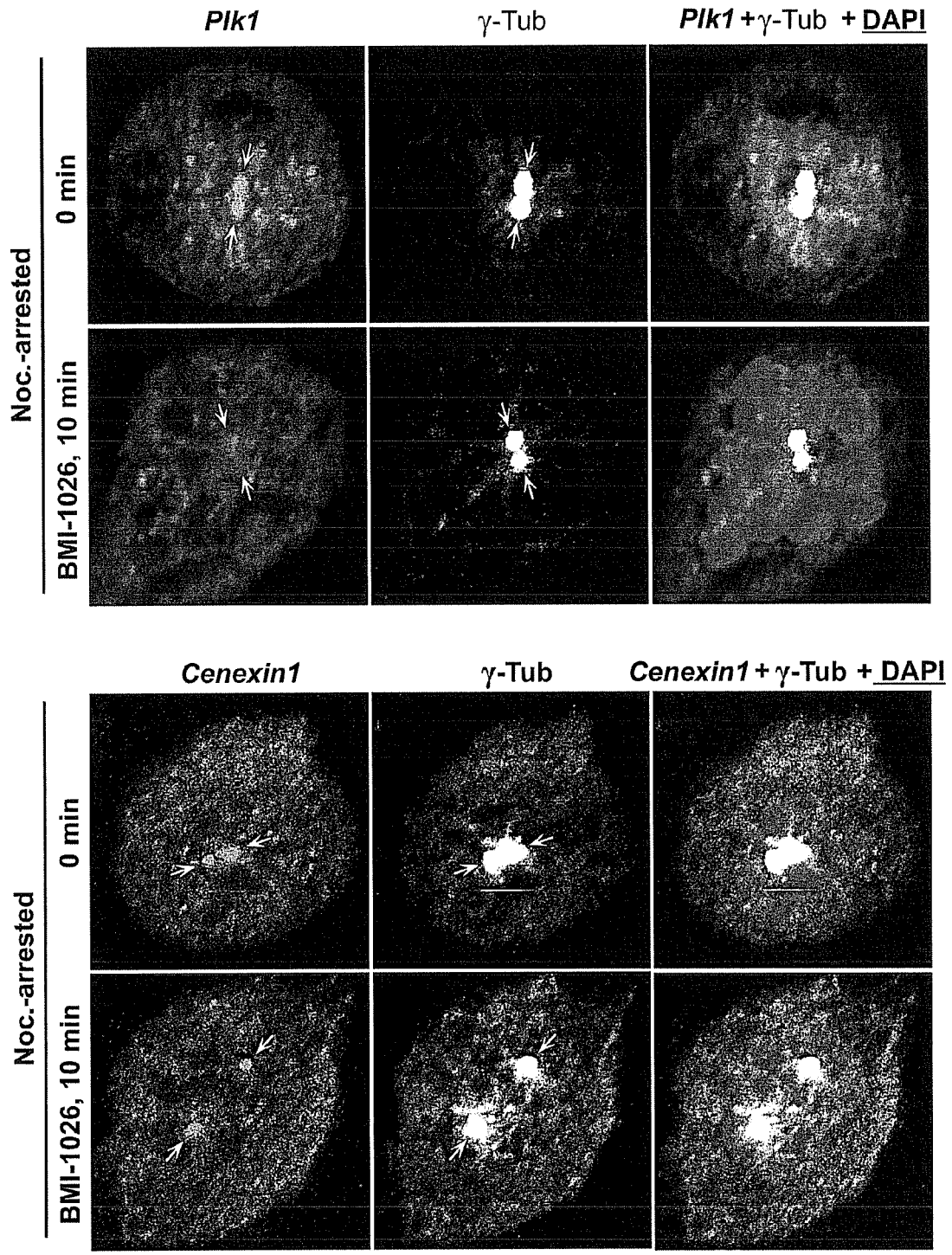
FIG. 11A-B. Acute inhibition of Cdc2 activity induces Plk1 delocalization from the centrosomes. (A), Mitotic HeLa cells were prepared by the addition of 100 ng/ml of a microtubule-depolymerizing drug, nocodazole, for 16 h. The resulting cells were further treated with 200 nM of a Cdk1 inhibitor, BMI-1026[7], for 10 min, fixed and then immunostained with anti-Plk1 and anti-γ-tubulin antibodies (Top) or anti-hCenexin1 and anti-γ-tubulin antibodies (Bottom). Cells did not exit from mitosis during the 10 min treatment, as evidenced by the pre-anaphase chromosomal DNA morphology. Inhibition of Cdc2 activity greatly diminished the level of centrosomal Plk1 signals, whereas it did not significantly alter the level of another centrosomal protein, hCenexin1. Since Cdc2 is one of the major priming kinases for the PBD-binding sites, these observations suggest that disruption of the PBD-dependent protein-protein interaction is sufficient to impair Plk1 localization and therefore its function. γ-tubulin signals mark the position of centrosomes. Arrows, centrosomes. (B), Quantification of the centrosome fluorescence intensities for Plk1 and hCenexin1 was carried out as described in the Examples.
Figure 11B:
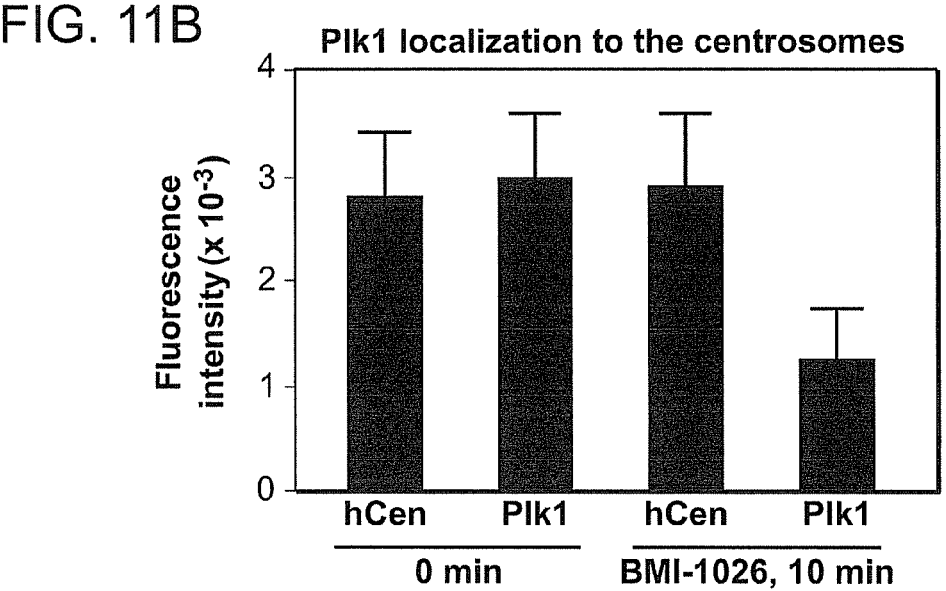
Figure 12A:
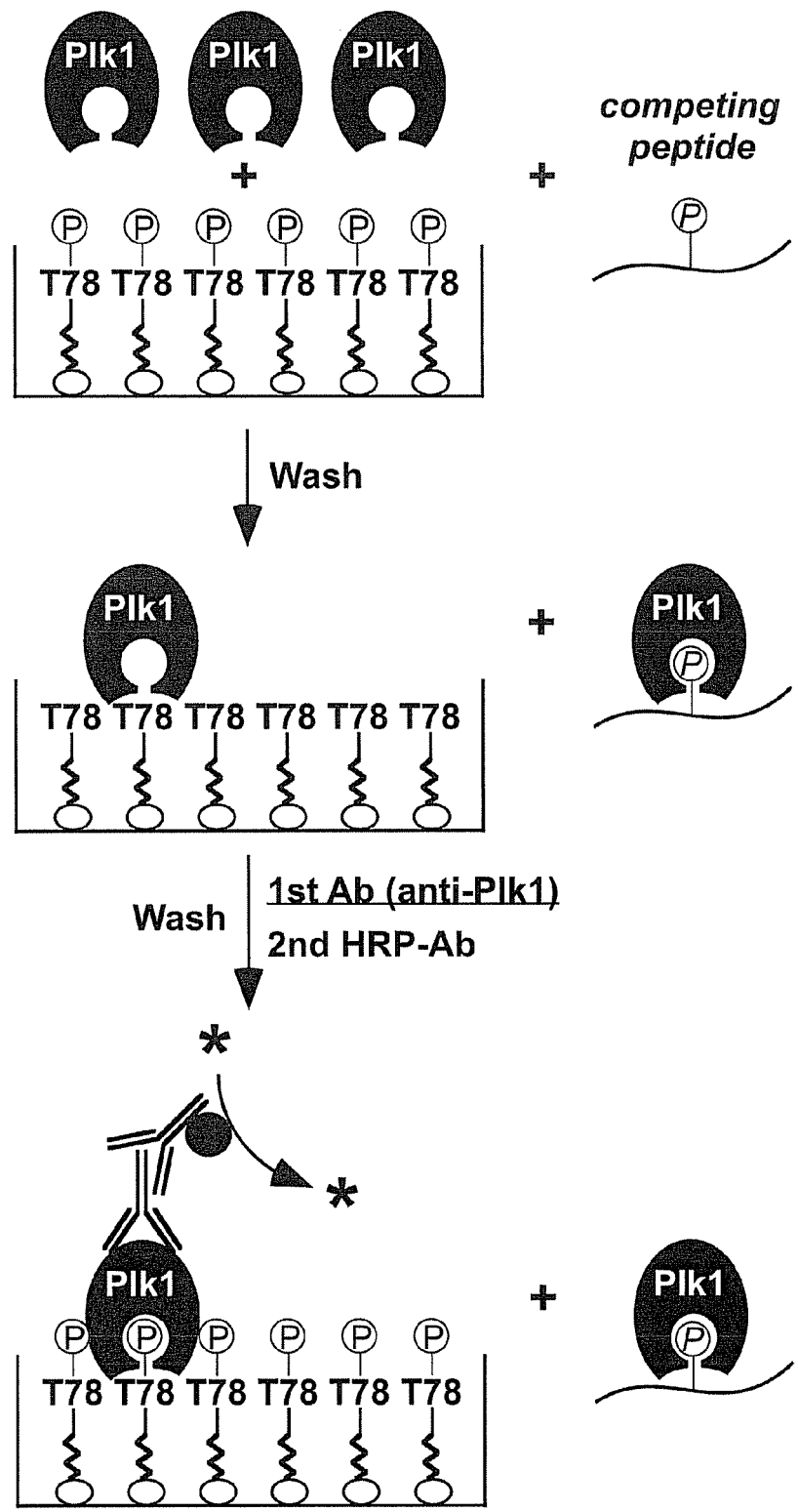
Figure 13B:
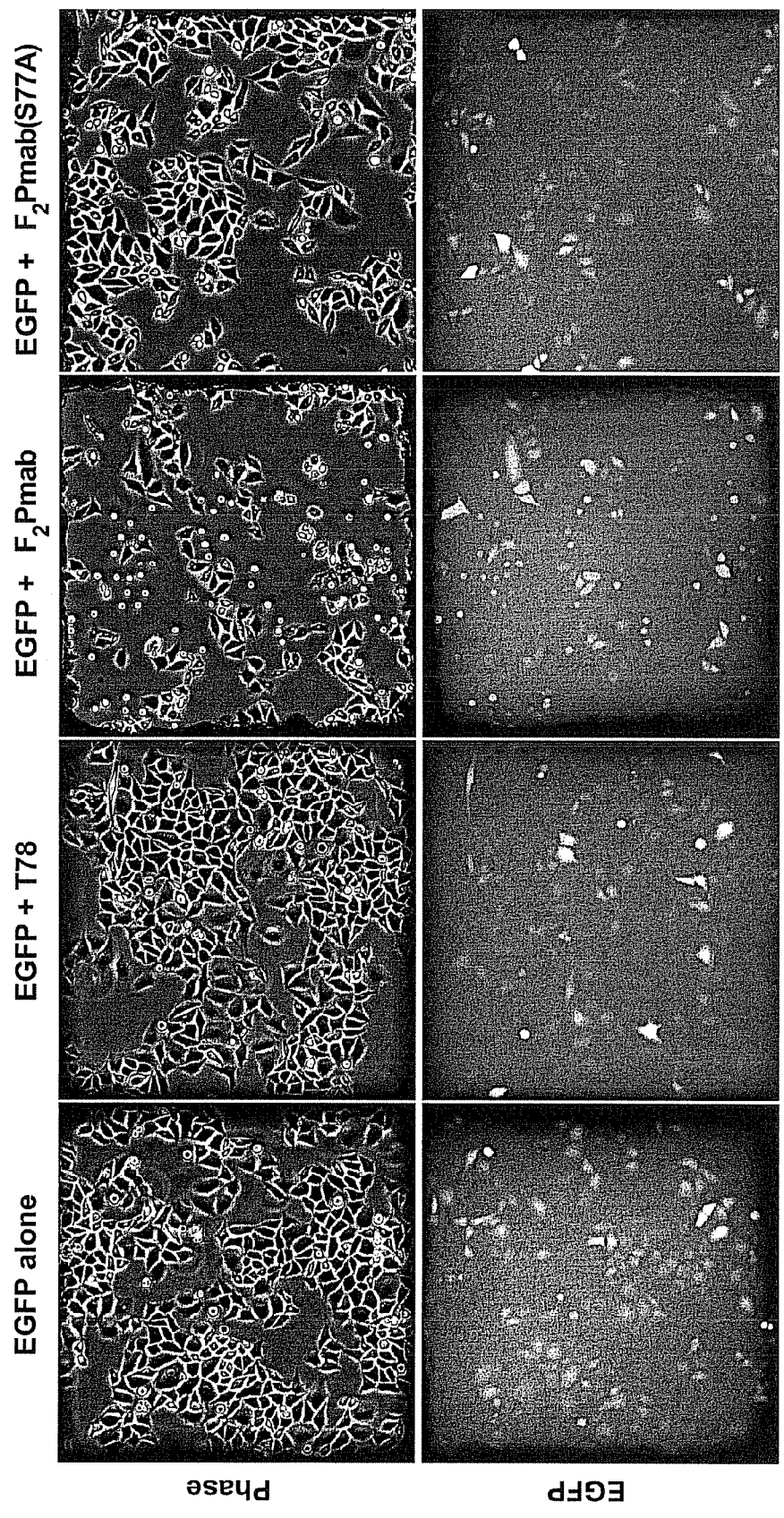
Figure 13C:
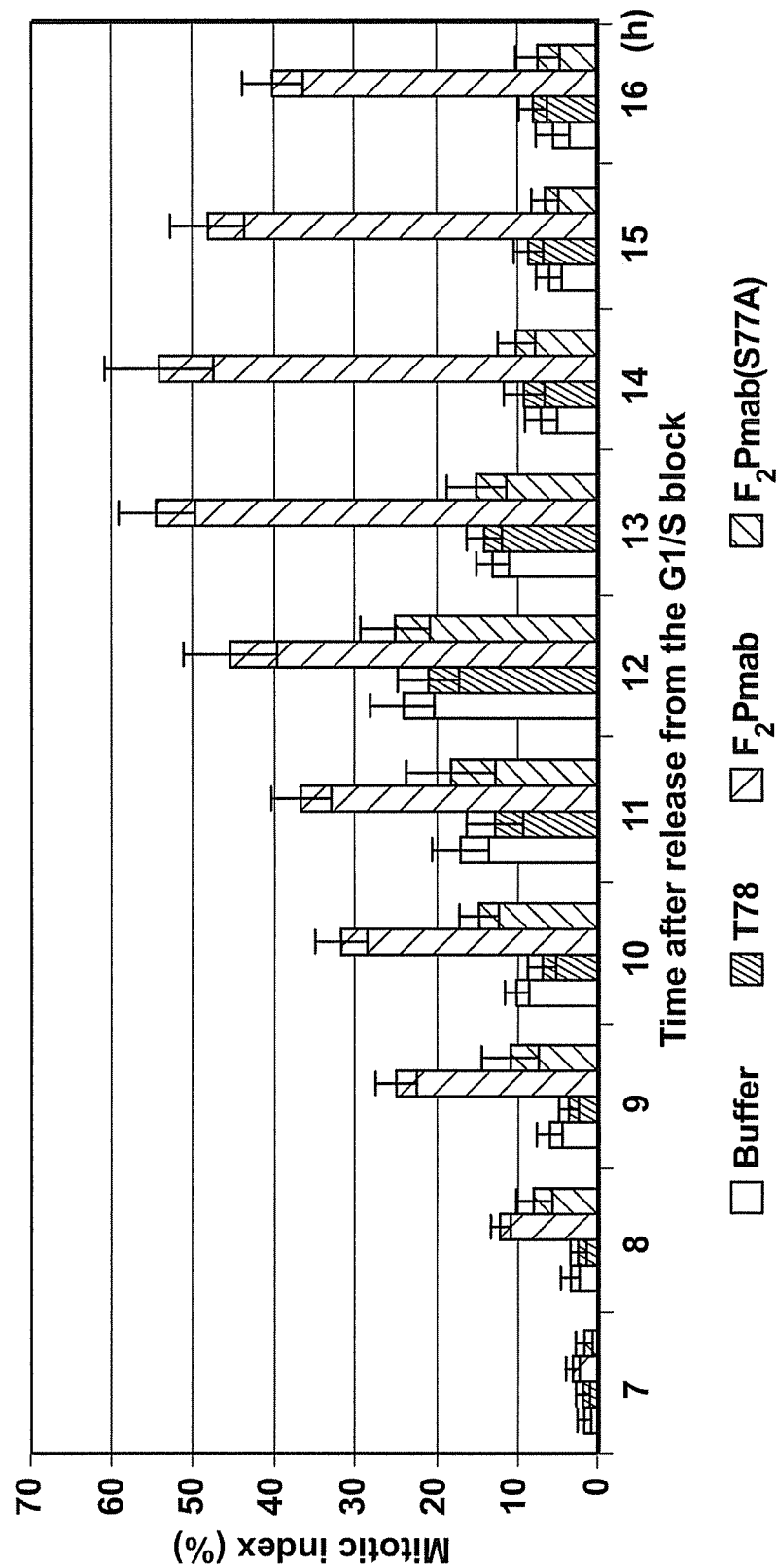
Figure 13D:
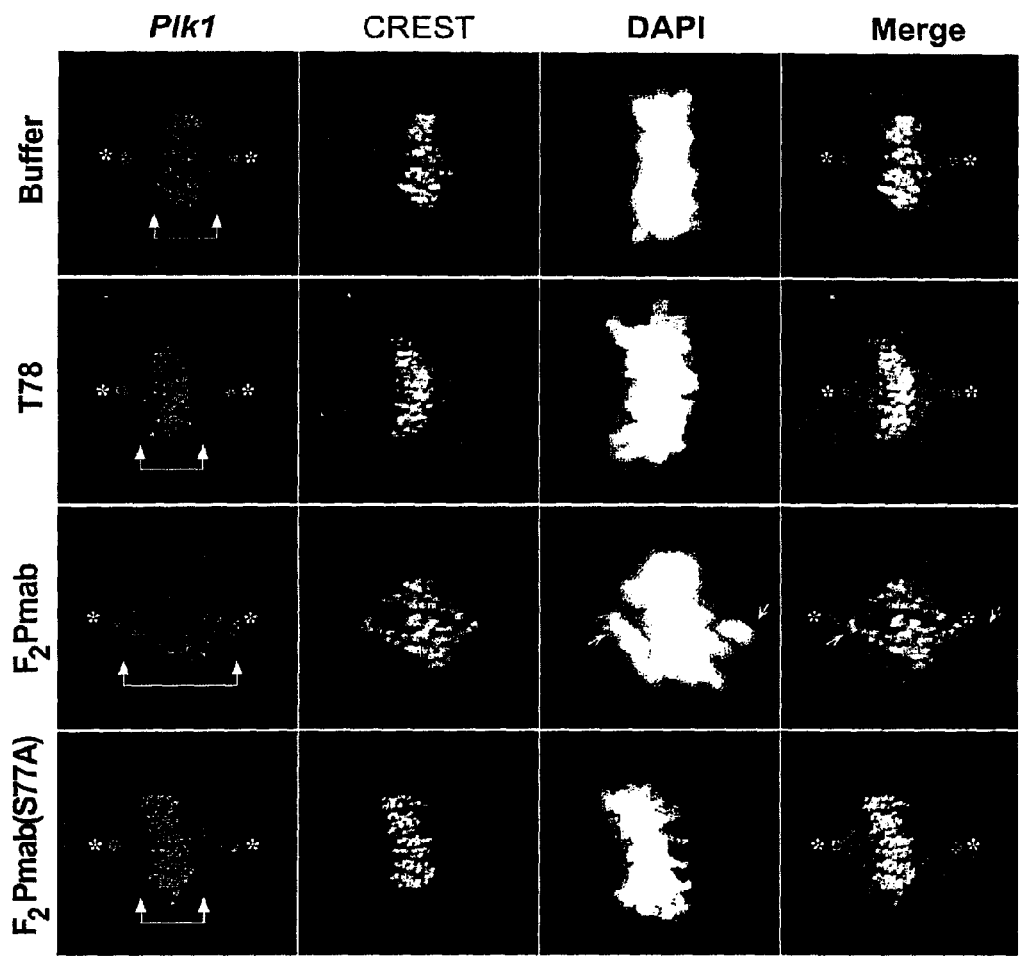
Figure 13E:
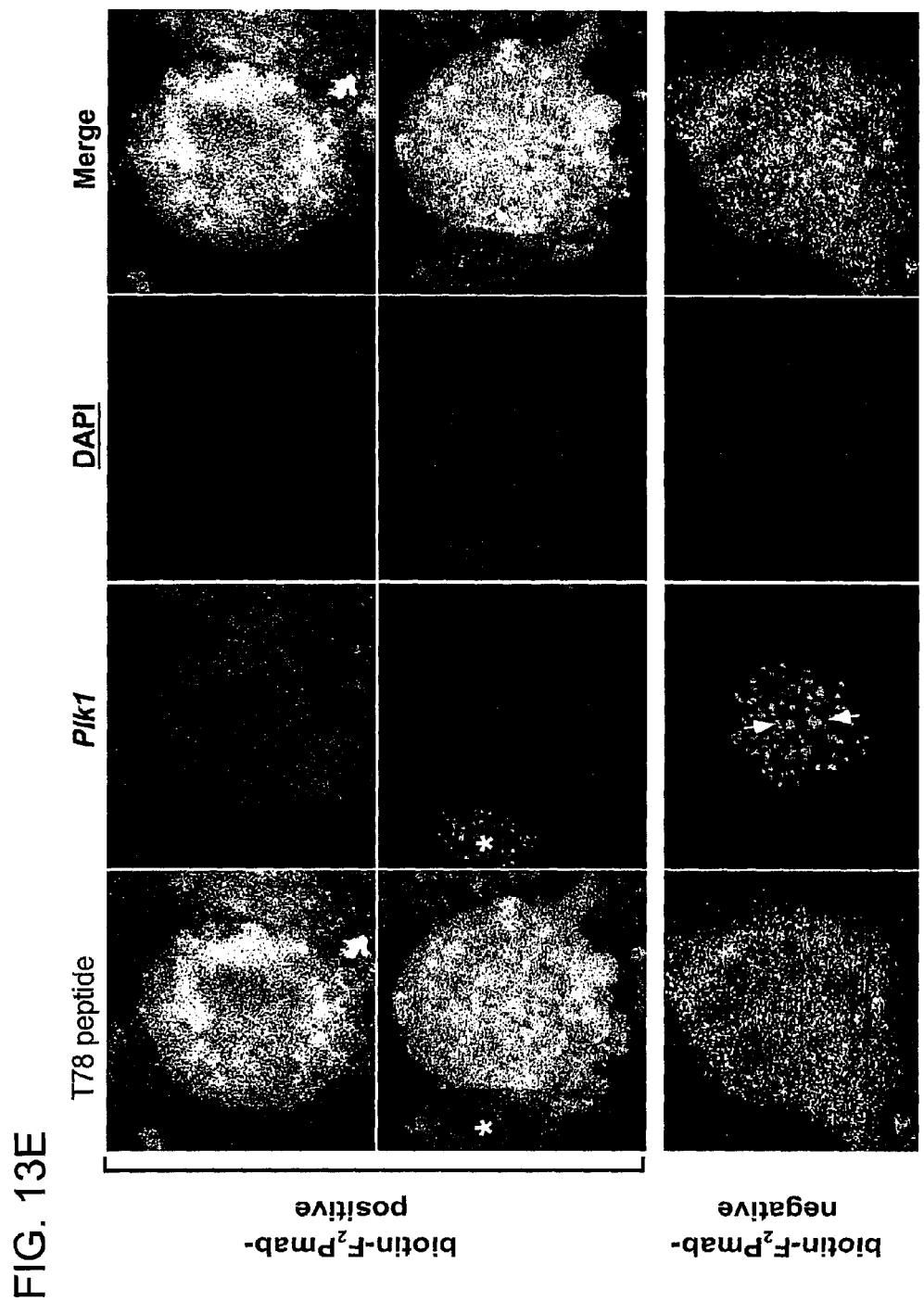
Figure 13F:
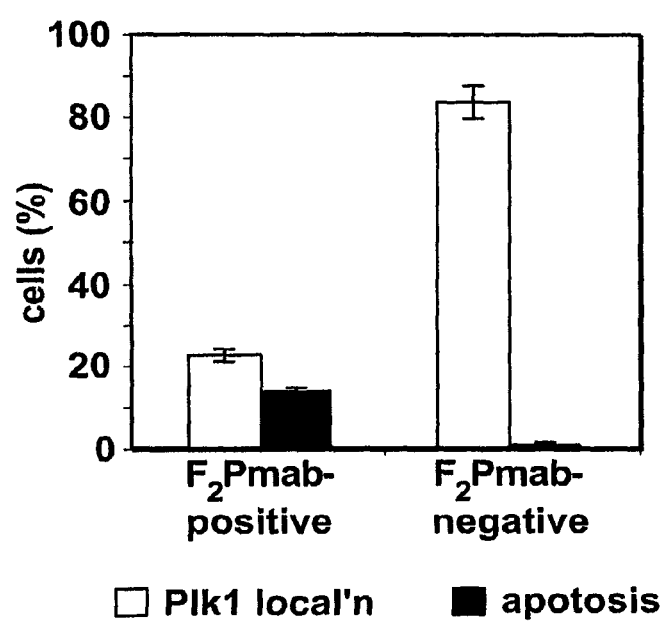
Figure 15A:
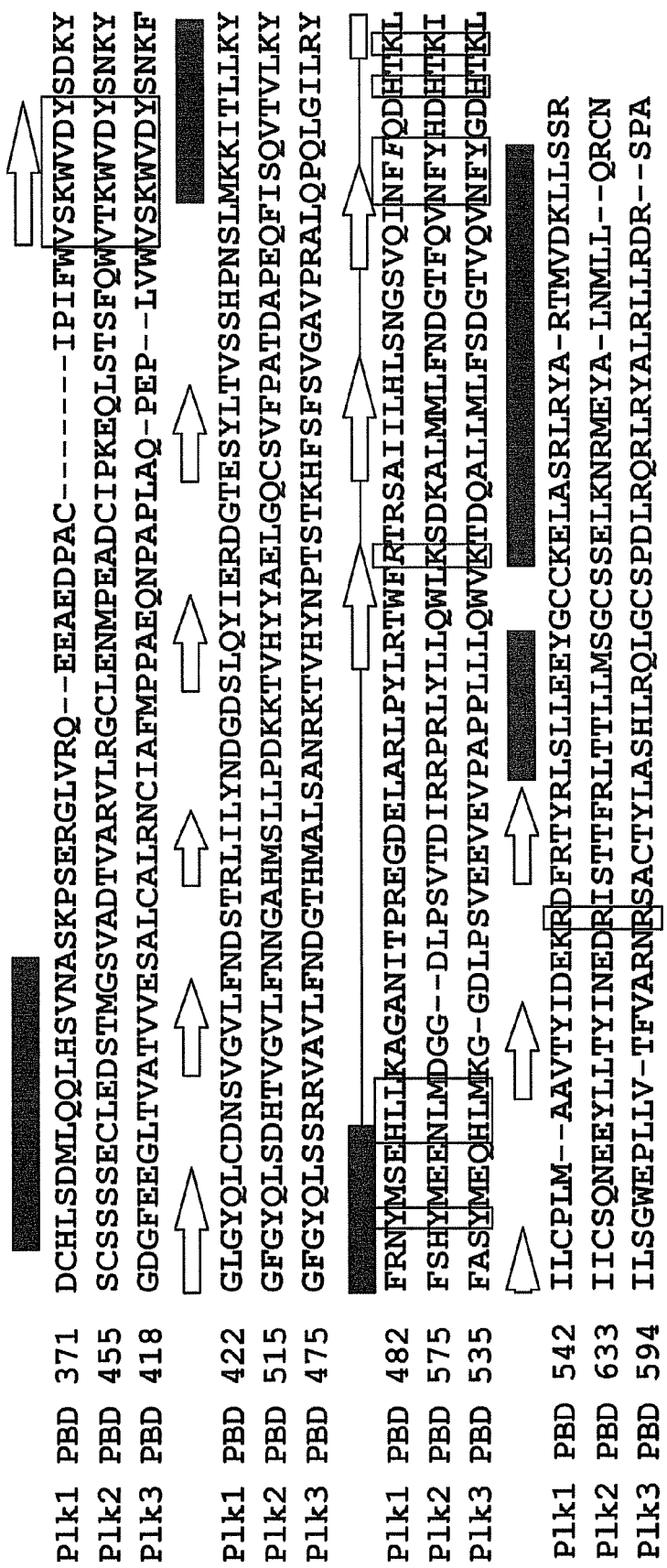
FIG. 15A-B. Mutations of the residues of Plk2 and Plk3 at positions analogous to the Arg516 and the Phe535 residues in Plk1 fail to enhance the binding affinity to the synthetic optimal peptide, MQSpTPL, or the p-T78 minimal peptide, PLHSpT. (A), Sequence alignment for the PBDs from Plk1, Plk2, and Plk3. The homology modeling for the PBDs was carried out using MOE-Homology modeling program and MOE-Align module (MOE, version 2005.06, Chemical Computing Group, Montreal, Quebec, Canada. 2005). The secondary structures of Plk1 PBD are shown as red bars for α-helices and blue arrows for β-strands. The residues that are potentially involved in generating the phosphoepitope-binding module of the PBD are marked in boxes. The two critical residues for binding the N-terminal Pro residue of PLHSpT (Arg516 and Phe535) and their analogous residues in Plk2 and Plk3 (the Lys607 and Tyr626 residues of Plk2 and the Lys568 and Tyr587 residues of Plk3) are indicated in red. To examine whether the introduction of the Plk1-specific Arg and Phe residues to the analogous positions in Plk2 and Plk3 allows the latter proteins to better bind to the MQSpTPL or PLHSpT peptide, we generated Flag-Plk2(K607R, Y626F) and Flag-Plk3(K568R,Y587F) double mutants. Since a block of the Arg or Phe-bearing sequences in Plk1 could be important in positioning the Arg and Phe residues in close proximity with the N-terminal residues of the phosphopeptides, we also introduced multiple mutations into Plk2 and Plk3 at the positions analogous to the Arg and Phe-bearing motifs in Plk1, thus yielding Flag-Plk2(L606F, K607R, S608T, D609R, K610S, Y626F, H627Q) and Flag-Plk3(V567F, K568R, D570R, Q571S, Y587F, G588Q) mutants. (B) To examine the ability of these mutants to bind to the minimal peptides, HeLa cells were first transfected with these constructs. The resulting total cellular lysates prepared similarly as in FIG. 2A were subjected to pull-down assays with the immobilized MQSpTPL or its control non-phosphopeptide. However, none of the Plk2 and Plk3 mutants exhibited an enhanced affinity to MQSpTPL. Rather, these mutations eliminated the moderate level of the Plk2 binding affinity to the latter. Similar results were obtained with the immobilized PLHSpT as well. These observations suggest that the amino acid sequences that are not directly involved in interacting with the phosphopeptide are also important in forming the phosphoepitope-binding module and preserving the overall structural integrity of the PBD.
Figure 15B:
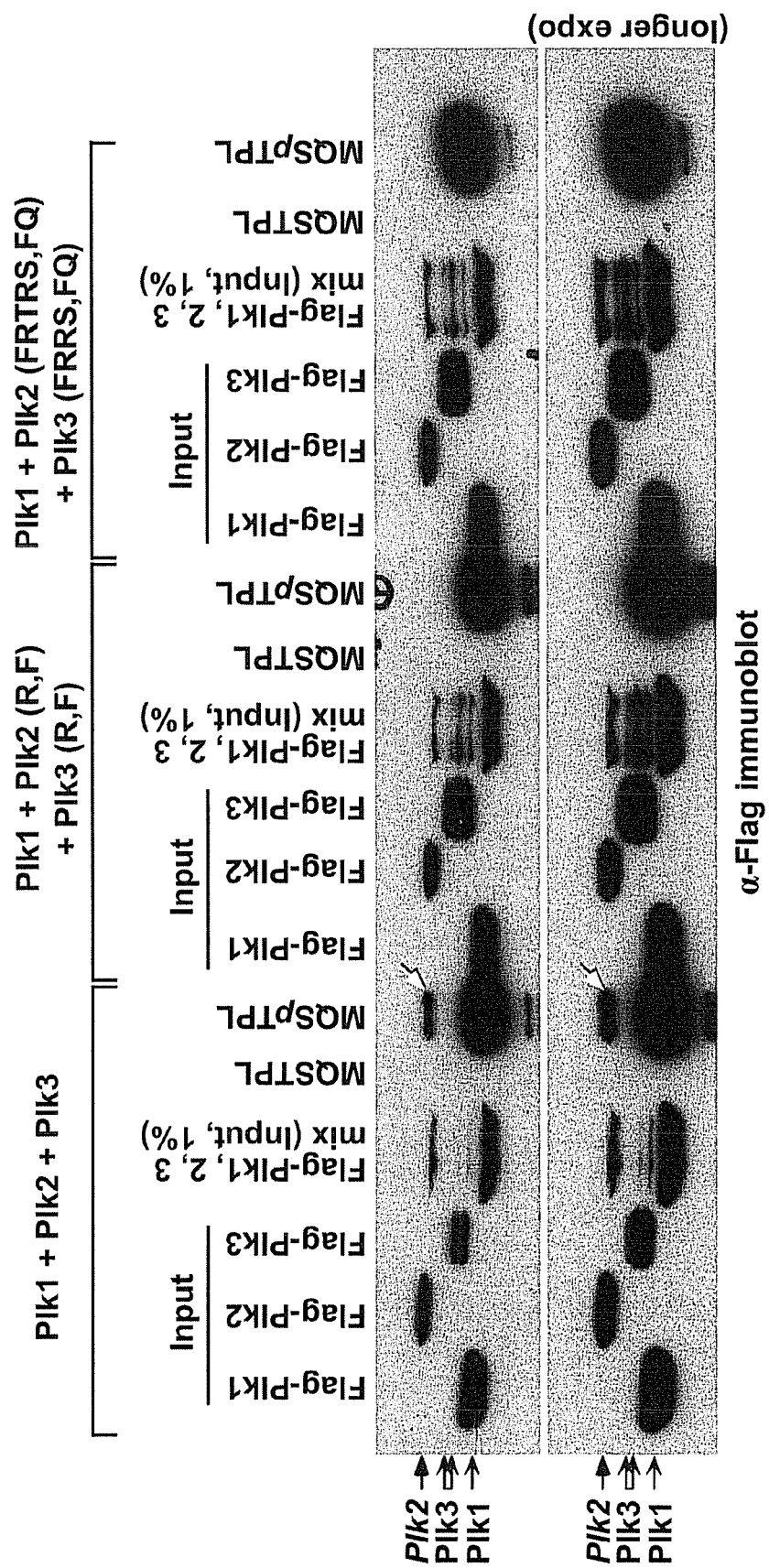

A growing body of evidence suggests that the PBD-dependent interactions with various S-p-S/T-containing targets are critical for Plk1 localization to the centrosomes, kinetochores, and mid-body. In line with this notion, acute inhibition of the activity of Cdc2, one of the major kinases that prime the PBD-binding sites, drastically diminished the level of Plk1 localization to the centrosomes and kinetochores in prometaphase cells (FIG. 11). This observation, together with the high affinity and specificity of the minimal p-T78 peptides to the Plk1 PBD, prompted us to test whether the minimal p-T78 peptides can interfere with the function of Plk1 by disrupting its localization in vivo. Consistent with the PBD pull-down assays, PLHSpT, but not the respective non-phosphopeptide, efficiently inhibited the p-T78-dependent PBD interaction in vitro, while LHSpTA inhibited the PBD at a moderately reduced level (FIG. 12). Since the phosphate group of the T78 residue is strictly required for the PBD binding but is susceptible to dephosphorylation by intracellular phosphatase activity, phosphatase-resistant p-Thr mimetic, (2S,3R)-2-amino-3-methyl-4-phosphonobutyric acid (Pmab) was synthesized, in protected form and incorporated it into peptides in place of the p-Thr residue (FIG. 4A). The bead-immobilized PLHS-Pmab precipitated Plk1, but not Plk2 or Plk3, from mitotic HeLa cells as efficiently as the respective PLHSpT peptide (the experiment was carried out in the presence of phosphatase inhibitors) (FIG. 4A-B). As expected if the binding were PBD-dependent, a mutation of the invariably required Ser-1 residue to Ala {PLHA-Pmab; in short, Pmab(S77A)} abolished the Plk1 binding. Furthermore, the PLHS-Pmab peptide, but not the respective Pmab (S77A) mutant, efficiently interfered with a p-T78-dependent Plk1PBD interaction (FIG. 4C), suggesting that the PLHS-Pmab peptide is suitable for testing the PBD inhibition in vivo.

Figure 4D:
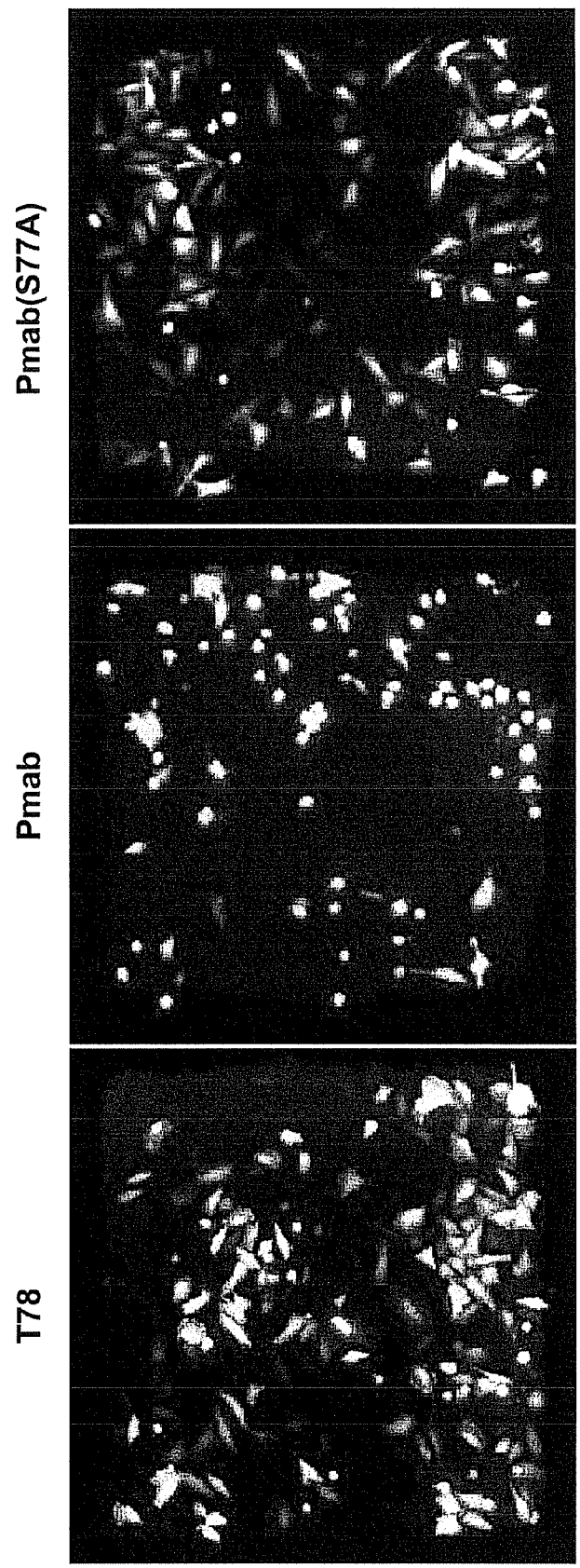
Figure 4E:
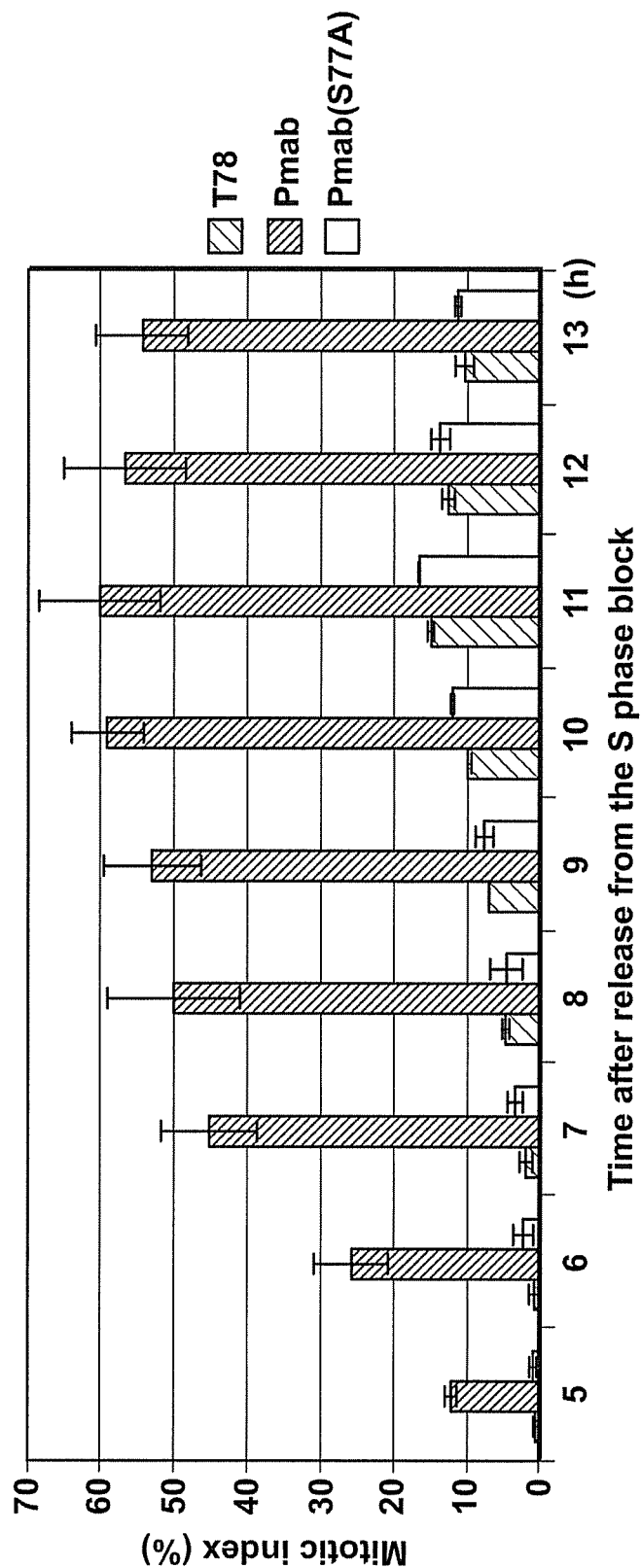
Figure 4G:
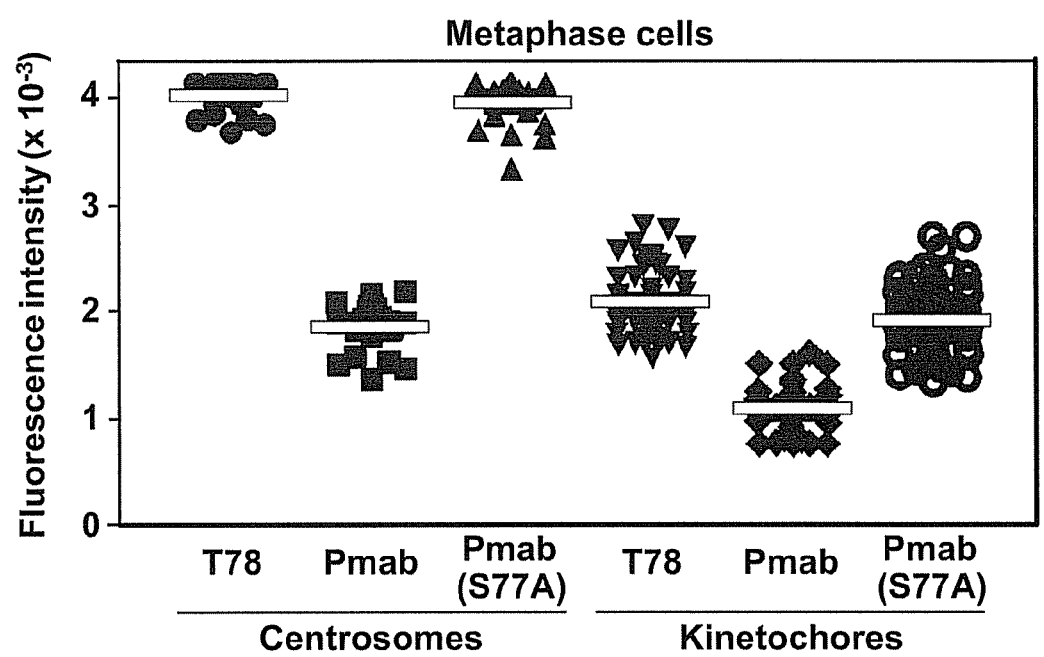
Figure 13A:
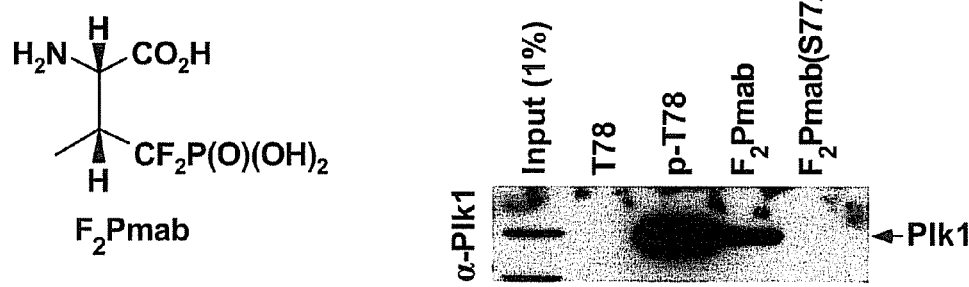
FIG. 13. A 6-mer, p-T78 mimetic, peptide (PLHS-F$_2$Pmab-A), but not the respective PLHA-F$_2$Pmab-A mutant, induces a mitotic arrest and apoptotic cell death in HeLa cells. (A), Illustration of a nonhydrolyzable p-Thr derivative, F$_2$Pmab (Left), used for the synthesis of mimetic peptides. The indicated peptides cross-linked to the beads were incubated with mitotic HeLa lysates in the presence of phosphatase inhibitors, precipitated, and then analyzed as in FIG. 1A. The immobilized C—(CH$_2$)$_6$-PLHS-F$_2$Pmab-A peptide (F$_2$Pmab), but not the C—(CH$_2$)$_6$-PLHA-F$_2$Pmab-A mutant {in short, F$_2$Pmab(S77A)}, precipitated Plk1 at a level a few fold lower than that of the control C—(CH$_2$)$_6$-PLHSpTA peptide. (B—C), Cells were arrested at the G1/S boundary by double thymidine treatment and then released into fresh medium. Seven hours after release, all the cells in a single grid were microinjected with a mixture containing 4 mM of the indicated peptides and 30 ng/μl of pEGFP-C1 vector, and then further incubated. Cells were photographed 16 h after G1/S release (9 h after microinjection) (B). Co-injection of the green fluorescent EGFP plasmid provided a convenient indicator for the level of microinjected peptides. Among the cells microinjected with PLHS-F$_2$Pmab-A, a majority of the EGFP-positive cells were rounded-up. Reduction in the total cell number in (C) was the result of loss of floating dead cells. The percentages of mitotic cells were quantified at the indicated time points to monitor cell cycle progression. Bars, standard deviation. (D), Cells at the 13 h time point in (C) were co-stained with anti-Plk1 antibody and anti-CREST antiserum. Asterisks, centrosome-localized Plk1 signals; Arrowed brackets, kinetochores-localized Plk1 signals; barbed arrows, misaligned chromosomes. (E-F), Electroporation of HeLa cells with the F$_2$Pmab-bearing peptide leads to Plk1 delocalization and apoptotic cell death. HeLa cells were electroporated with biotinylated PLHS-F$_2$Pmab-A peptide (biotin-F$_2$Pmab). Two days after electroporation, cells were stained with FITC-streptavidin and anti-Plk1 antibody to determine the biotin-F2Pmab-positive and biotin-F$_2$Pmab-negative cells (E). Among these populations, cells exhibiting proper Plk1 localization or apoptotic chromosome morphology were quantified (F). An asterisk in (E) indicates a poorly electroporated (weak biotin-F$_2$Pmab) cell that displays localized Plk1 signals. Arrows indicate centrosomes.

Microinjection studies using HeLa cells released from an S phase block were performed to examine the effect of the Pmab-containing mimetic peptide in vivo and to overcome poor membrane permeability of a negatively charged peptide. Cells microinjected with the non-phospho T78 peptide proceeded through the cell cycle normally. However, as expected if the function of Plk1 were inhibited, the Pmab peptide, but not the respective Pmab(S77A) mutant, induced a drastic mitotic arrest in ~60% of the microinjected population. Reminiscent of the phenotype associated with the loss of the PBD function ~25% of the arrested population (n>180 cells) exhibited a chromosome congression defect (FIG. 4D-F). Due to the increasing level of apoptotic cell death following a prolonged mitotic block, the total numbers of arrested cells began to shrink at later time points (the 12 h and 13 h time points in FIG. 4E). Consistent with these observations, the Pmab peptide, but not the respective Pmab(S77A) or non-phospho T78 peptide, interfered with Plk1 localization at both mitotic centrosomes and kinetochores and diminished Plk1 fluorescence signals (FIG. 4F-G) to a level similar to that observed after the treatment of the Cdk1 inhibitor, BMI-1026 (FIG. 11). In a second experiment, another type of p-T78 mimetic peptide, a 6-mer $F_2$Pmab-containing PLHS-$F_2$Pmab-A was synthesized (synthesis of a 5-mer PLHS-$F_2$Pmab mimetic peptide did not yield sufficient amounts because of an inefficient coupling of $F_2$Pmab to the resin), and examined for its effect in HeLa cells (FIG. 13A). Although not as efficient as the PLHS-Pmab peptide likely as a result of a strong electronegativity of the difluoride, PLHS-$F_2$Pmab-A, but not the respective $F_2$Pmab(S77A) mutant, significantly precipitated Plk1 (FIG. 13A), and, as such, induced defects in proper Plk1 localization and chromosome congression that ultimately led to mitotic arrest and apoptotic cell death (FIG. 13B-F) Taken together, these data strongly suggest that inhibition of the PBD by the p-T78 mimetic peptide is sufficient to interfere with subcellular localization and mitotic functions of Plk1.

Example 8

Application of Oxime-Based Post Solid-Phase Diversification to Optimization of Polo Box Domain-Binding Peptides Plk1 possesses a phosphopeptide-binding PBD that is essential for intracellular localization and substrate recognition. Because PBDs are unique to Plks, they are ideal targets for selectively inhibiting Plk1 functions. By examining various PBD-binding phosphpeptides, a 5-mer phosphopeptide "PLHSpT" that specifically interacts with the Plk1 PBD with a high affinity (Kd=0.45 µM), but not with the two closely-related Plk2 and Plk3, has been identified (29).

Taking advantage of the facile condensation of aminooxy functionality and carbonyl groups, aminooxy handles were incorporated into proteins consensus recognition sequences and used these for post-solid phase construction of peptide libraries bearing tethered components. These libraries can be easily assembled and directly evaluated without purification (30-31). Provided herein are PDB-binding peptides generated by this method. Based on the previously identified parent peptide "PLHSpT" the amino-terminal proline was replaced by trans and cis-4-aminooxy proline 1 and 2 (31) to provide the aminooxy-containing peptides 4 and 5. This approach allowed library diversification at this residue with maintenance of the parent proline pyrrolidine ring system as shown.

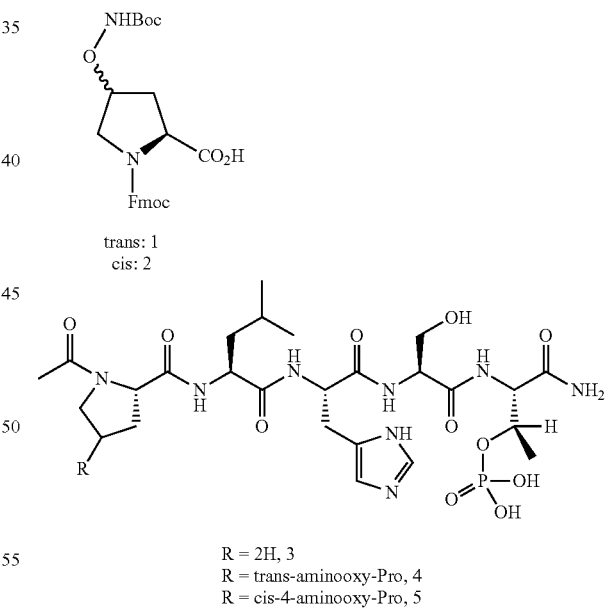

R = 2H, 3
R = trans-aminooxy-Pro, 4
R = cis-4-aminooxy-Pro, 5

Structure of protected 4-aminooxy prolines (1 and 2) and peptide products 4 and 5.

Oxime-containing peptide libraries were then prepared by conjugating peptides 4 and 5 with ten selected aldehydes. The resulting libraries were directly evaluated by competing with immobilized wild type peptide in ELISA-based Plk1 pull-down assays using cell lysates. The oxime peptides 4-b and 5-b showed enhanced binding potency as compared to the parent 5-mer sequence.

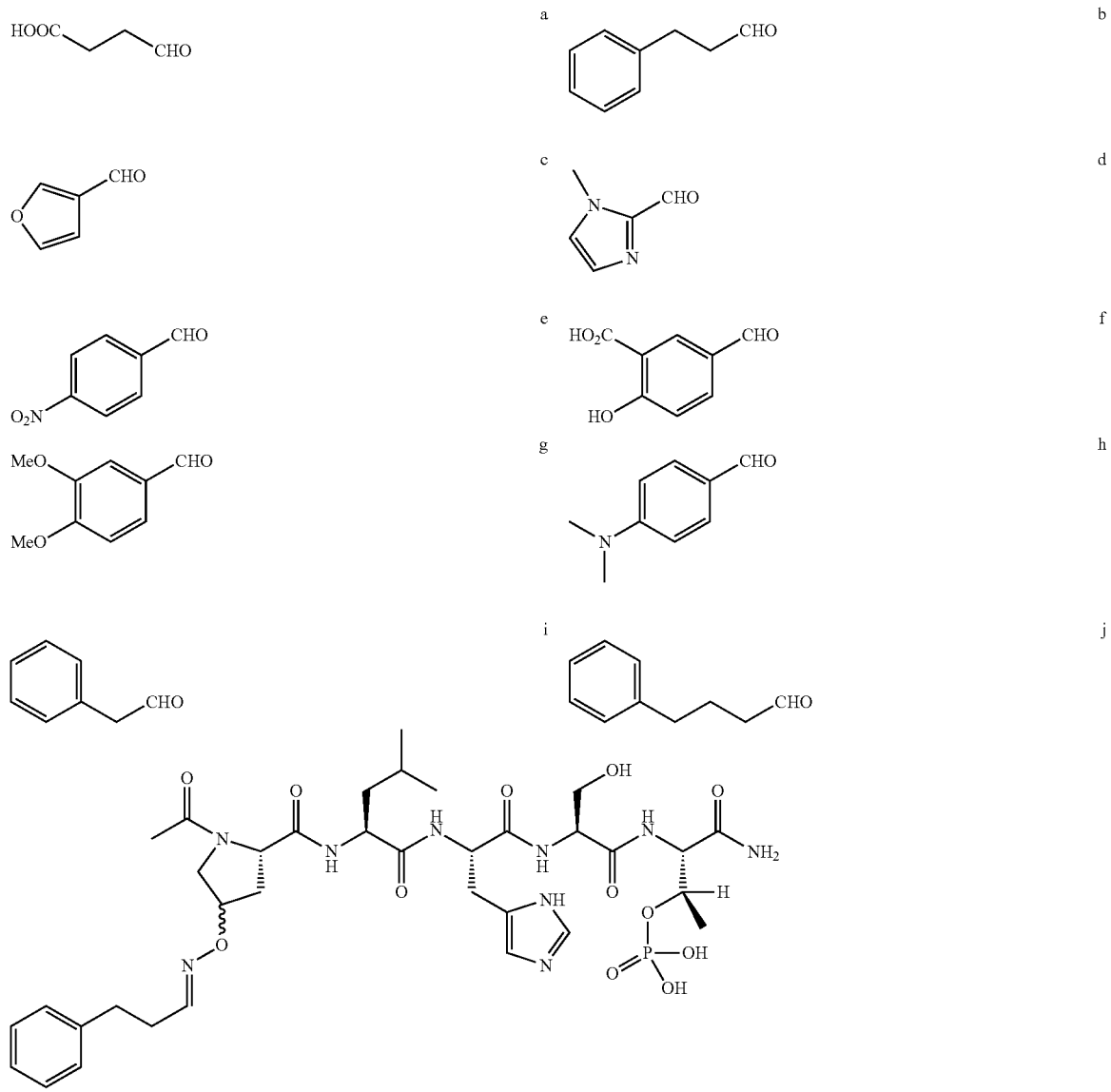

Trans-4-aminooxy-Pro: 4-b
Cis-4-aminooxy-Pro: 5-b

Aldehydes for preparation of oxime-peptides and structure of 4b and 5b.

Isothermal titration calorimetric PBD binding experiments were conducted for 4b and 5b. These experiments confirmed the ELISA data from cell lysates and provided $K_d$ values of 47.5 nM and 71.7 nM for 4b and 5b, respectively (Table 5). calorimetric data also suggested that 4b and 5b exhibit high enthalpic advantages, but they are accompanied by high entropic disadvantages. This indicated further binding affinity enhancement could be achieved for these peptides by induction of conformational constraint.

TABLE 5

| Peptide | $K_d$ (μM) | ΔH (kcal/mol) | ΔS (cal/mol*K) | ΔG (kcal/mol) | N (peptide:plk1) |
|---|---|---|---|---|---|
| 4b | 0.048 ± 0.020 | −22.50 ± 0.32 | −40.87 ± 1.26 | −10.10 ± 0.38 | 0.49 ± 0.03 |

TABLE 5-continued

| Peptide | $K_d$ (μM) | ΔH (kcal/mol) | ΔS (cal/mol*K) | ΔG (kcal/mol) | N (peptide:plk1) |
|---|---|---|---|---|---|
| 5b | 0.072 ± 0.030 | −25.30 ± 0.20 | −50.86 ± 0.73 | −9.90 ± 0.22 | 0.48 ± 0.03 |
| 3 | 0.445 ± 0.180 | −14.5 ± 5.01 | −18.91 ± 3.32 | −8.80 ± 0.50 | 1.46 ± 0.03 |

Replacing the pThr residue with a non-charged moiety would likely enhance cellular bioavailability. To rapidly explore a wide range of replacement functionality at the C-terminal position, the aminooxy-containing peptide 6 is prepared for post-solid-phase oxime diversification leading to products of type 7, which are amenable to direct biological evaluation without purification.

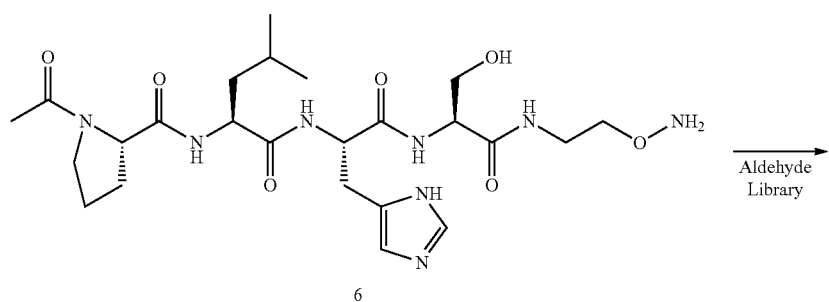
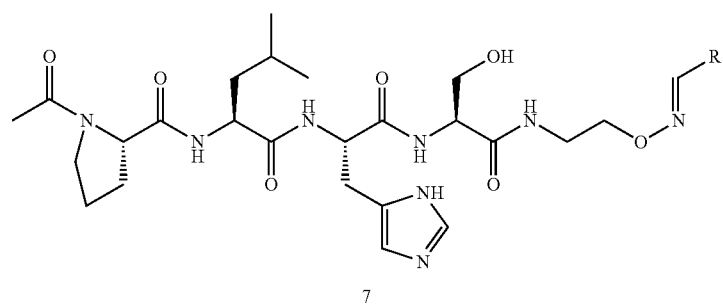
Oxime library approach to replacing the pThr residue. Possible aldehydes for reaction with the oxime-containing peptide include, but are not limited to:
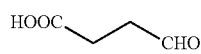
a
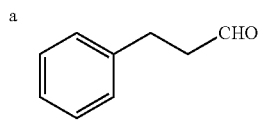
b
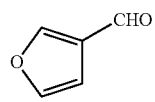
c
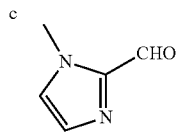
d
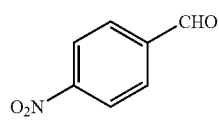
e
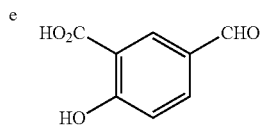
f
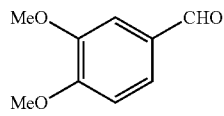
g
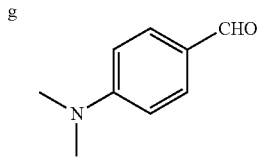
h
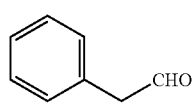
i
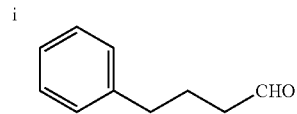
j

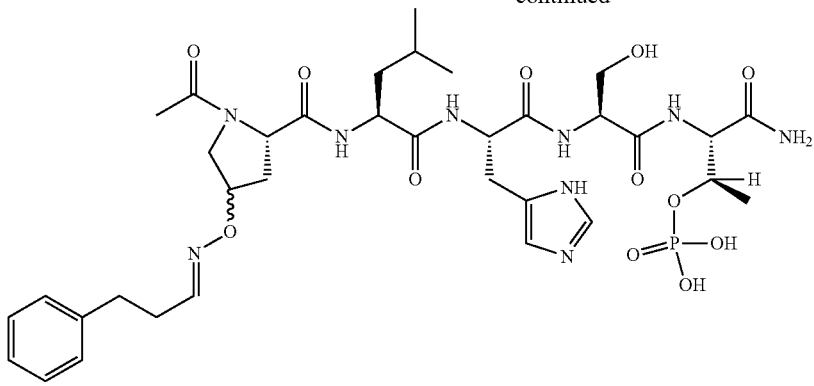
Trans-4-aminooxy-Pro:4-b
Cis-4-aminooxy-Pro:5-b
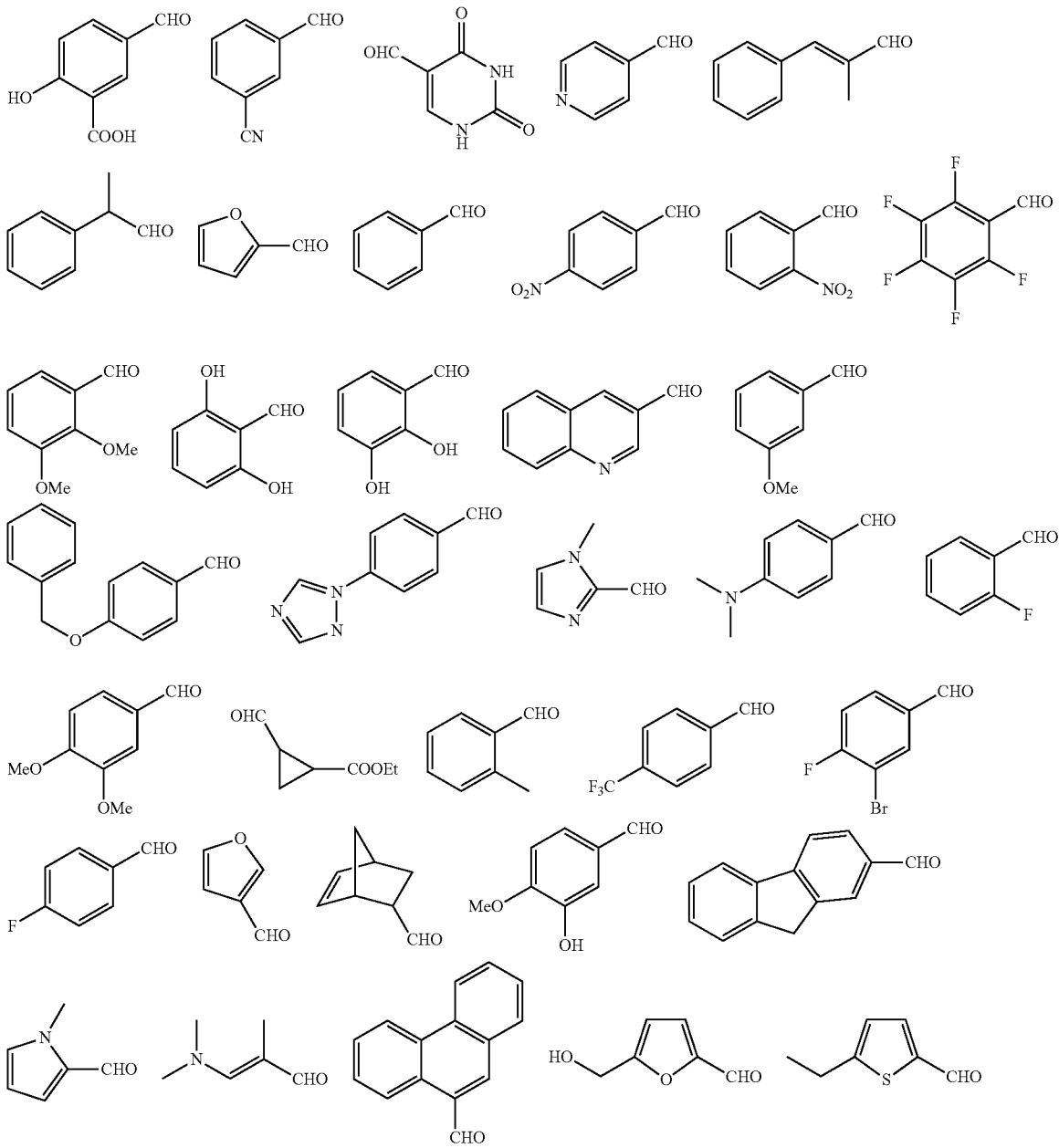

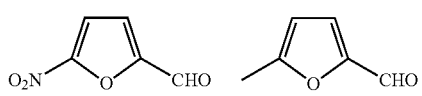 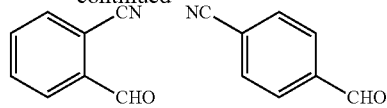

Application of Peptoid-Peptide Hybrid Libraries to Optimization of Polo Box Domain-Binding Peptides Structural studies are provided herein of the 5-mer PLHSpT peptide bound to PBD protein. In the PLHSpT•PBD complex, (29) the Ser and pThr residues provide important protein contacts. However, the N-terminal Pro residue provides further interactions with the protein by docking into a hydrophobic pocket formed by the two aromatic residues Trp414 and Phe535. Importantly, this Pro is crucial for the peptide's binding specificity for Plk1 as compared to Plk2 and Plk3. In the current EIR solid-phase synthesis of NSG-containing libraries was achieved by the "submonomer approach," (33) in which the N-terminal Leu residue of peptide 8 was first bromoacetylated to yield 9, and then reacted with various amines to yield the corresponding NSG containing peptoid-peptide hybrids (10, FIG. 4). Acetylation provided the final peptides [11].

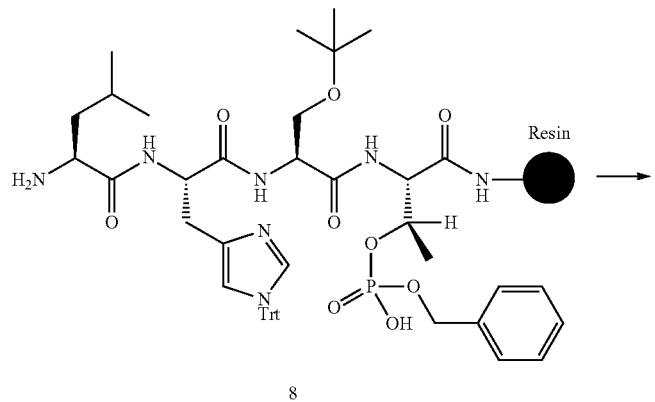

8

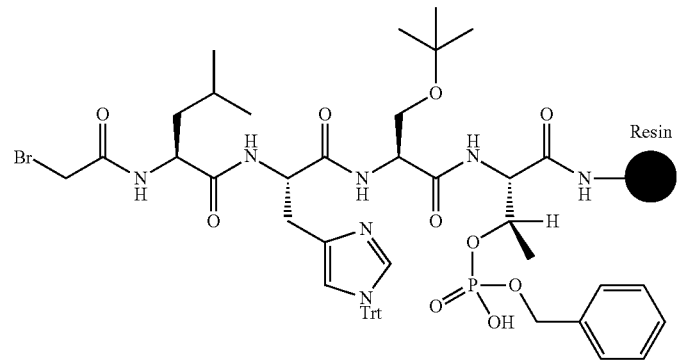

9

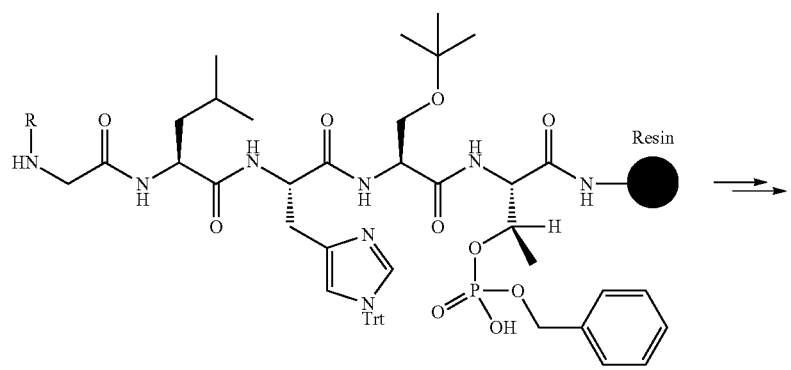

10

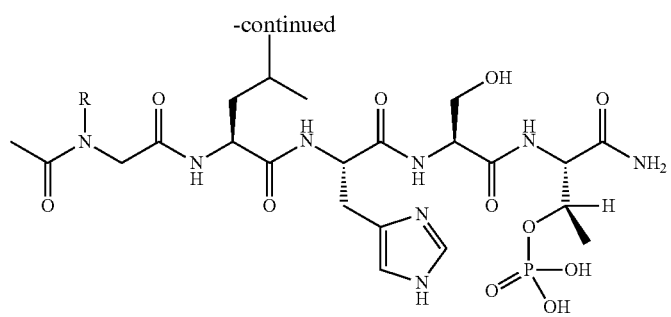

11

Preparation of peptide-peptoid hybrid using the "sub-monomer approach."

Hybrids 11D and 11E had dramatically diminished binding affinity, which indicated that both positive and negative charges are not tolerated at this position. As compared to the original 5-mer (37), hybrids 11A, 11C and 11J (substituents as indicated) showed slightly higher binding affinity, while 11F and 11I showed similar affinity and the remaining analogues were weaker binders. Work is in progress to examine additional NSG residues at the Pro site and to apply the methodology to examine NSG residue replacements of other critical residues.

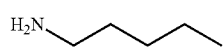 A

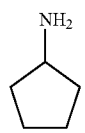 B

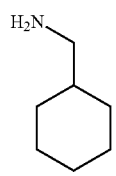 C

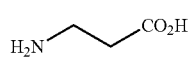 D

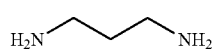 E

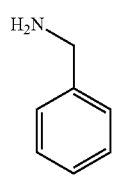 F

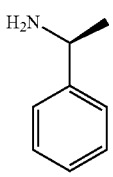 G

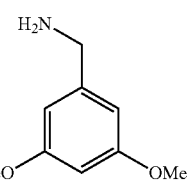 H

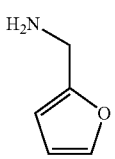 I

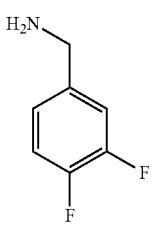 J

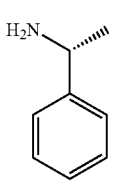 K

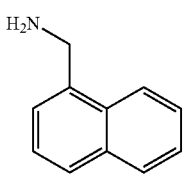 L

Structures of amines used to prepare peptide-peptoid hybrid 11.

TABLE 6

MALDI-TOF-MS for the peptoid-peptide hybrids 11.

R1 = H or acetyl

| | | Expected (M + H)+ | Observed (M + H)+ |
|---|---|---|---|
| 11A | Acetyl | 705.3 | 705.8 |
| 11B | H | 661.3 | 661.5 |
| 11C | Acetyl | 731.3 | 731.7 |
| 11D | Acetyl | 707.3 | 707.4 |
| 11E | Acetyl | 692.3 | 690.8 |
| 11F | Acetyl | 725.3 | 725.4 |
| 11-G | H | 697.3 | 697.6 |
| 11-H | Acetyl | 785.3 | 785.9 |
| 11-I | Acetyl | 715.3 | 715.9 |
| 11-G | Acetyl | 761.3 | 761.8 |
| 11-K | H | 697.3 | 698.0 |
| 11-L | H | 733.3 | 732.6 |

Example 9

Further Peptoid-Peptide Hybrids to Optimization of Polo Box Domain-Binding Peptides Further variants of the compounds in Example 8, particularly of compound 4b, were generated and tested for specific binding to Plk1.

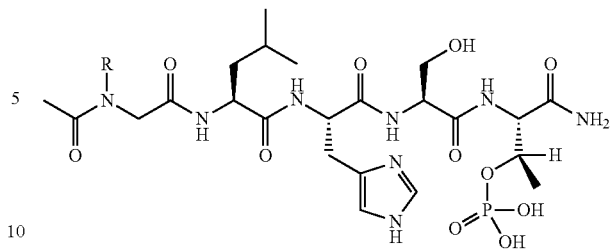

FA476: R = CH$_2$CH$_2$Ph
FA477: R = CH$_2$CH$_2$CH$_2$Ph
FA478: R = CH$_2$CH$_2$CH$_2$CH$_2$Ph
FA501: R = CH$_2$CH$_2$CH$_2$CH$_2$CH$_2$Ph
FA502: R = CH$_2$CH$_2$CH$_2$CH$_2$CH$_2$CH$_2$Ph
FA503: R = CH$_2$CH$_2$CH$_2$CH$_2$CH$_2$CH$_2$CH$_2$Ph

Compound FA502 appeared to be the best one among all the peptide and peptoids we have prepared. The K$_d$ value of FA420 (which is compound 4b) is 48 nM determined by calorimetric experiments. To quantitatively determine the efficiency of PBD-binding inhibition by the indicated peptides, an ELISA-based inhibition assay was carried out. The level of HA-EGFP-Plk1 bound to an immobilized biotinylated p-T78 peptide was quantified in the presence of various amounts of the competitor peptides. The results are shown in FIG. 14A. As shown, FA502 and FA503 most effectively competed for binding to the p-T78 peptide.

Example 10

Monocharged Phosphates and Cyclic Peptides

Monocharged phosphate peptoids and cyclic peptides were generated and tested for specific binding to Plk1. The structures of the compounds are shown below.

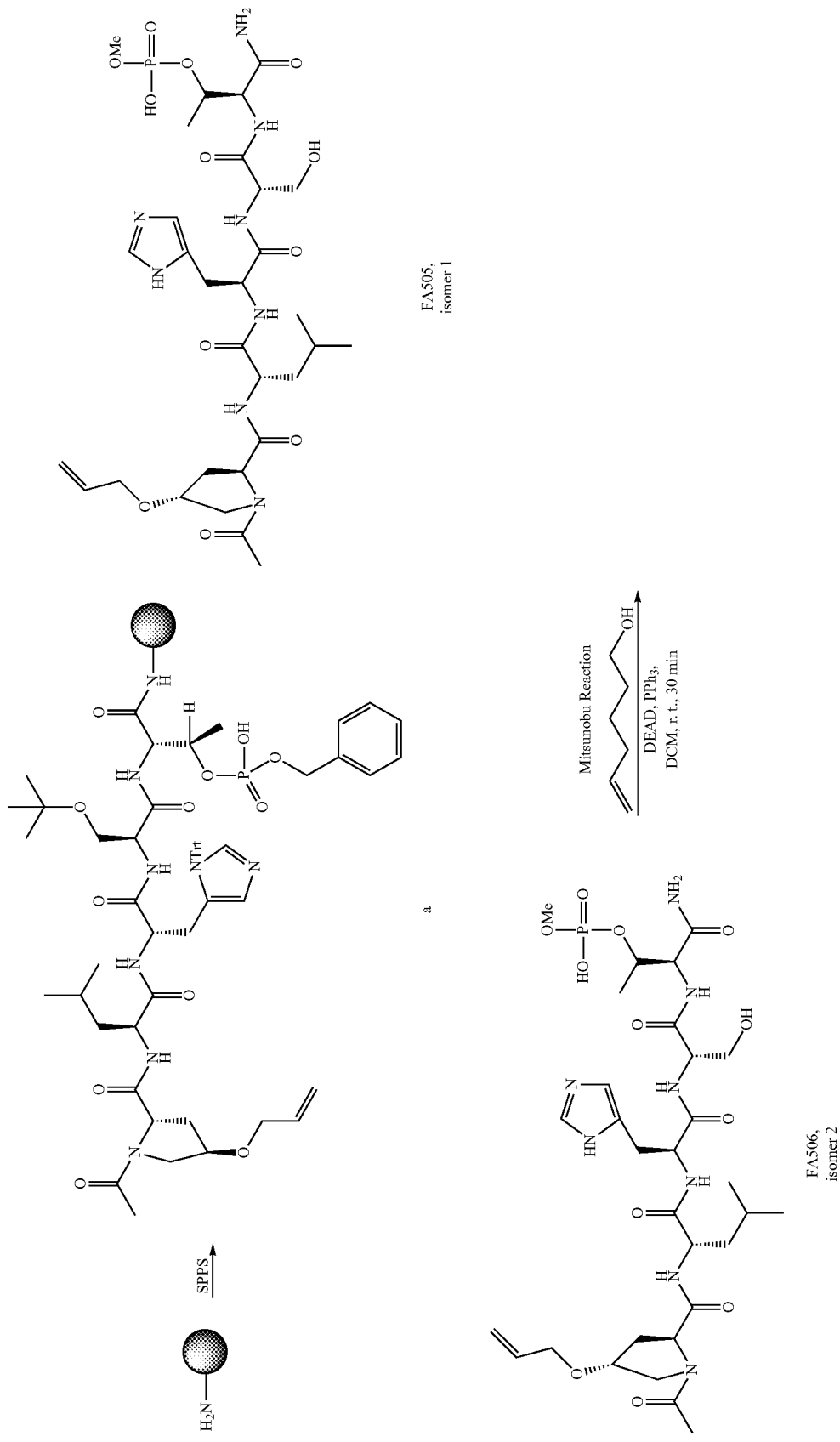

-continued
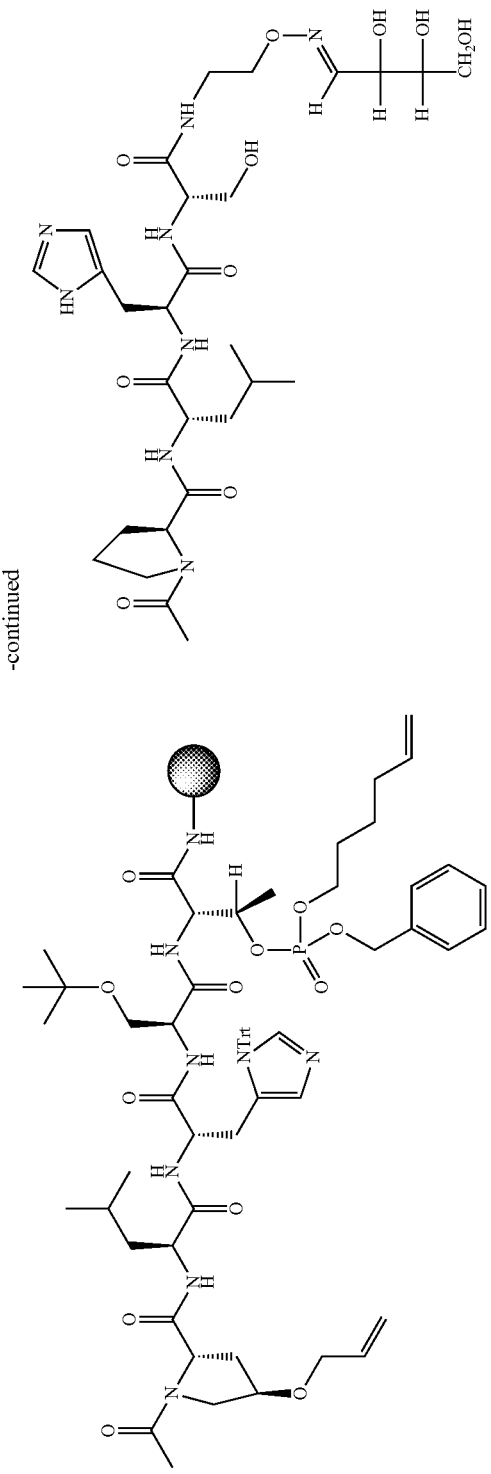
FA510
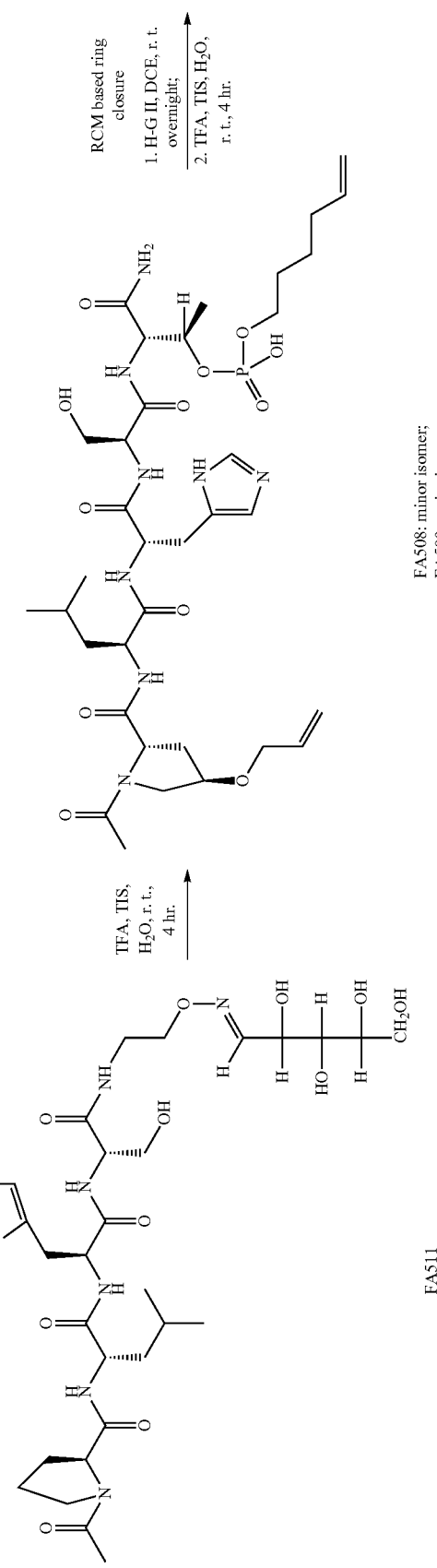
FA508: minor isomer;
FA509: major isomer;
FA511

-continued
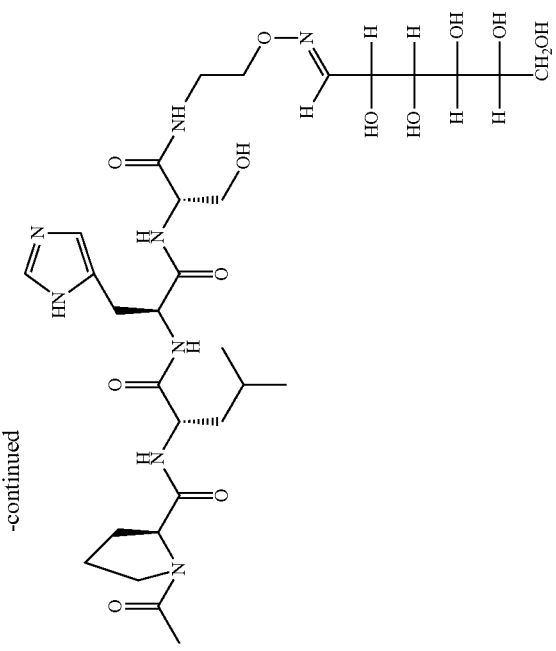
FA512
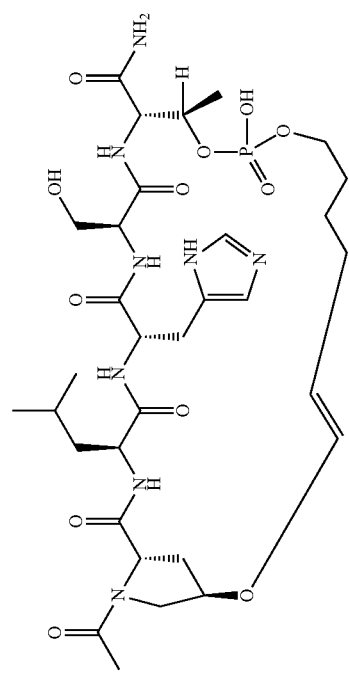
FA507

To quantitatively determine the efficiency of PBD-binding inhibition by the indicated peptides, an ELISA-based inhibition assay was carried out. The level of HA-EGFP-Plk1 bound to an immobilized biotinylated p-T78 peptide was quantified in the presence of various amounts of the competitor peptides. The results are shown in FIG. 14B. The minor isomer of monocharged phosphate FA508 had equivalent binding potency as WT 5-mer. The cyclic peptide FA507 bound better than FA509.

Preparation of peptide FA505-FA509. 1.Mitsunobu Reaction: Resin 0.10 mmol was mixed with DEAD (0.46 mL, 40% solution in toluene, 1.0 mmol), PPh3 (262 mg, 1.0 mmol) and alcohol (118 µL, 1.0 mmol) in DCM (2.50 mL), shaken gently at room temperature for 30 mins, then washed by DCM and DMF. 2. RCM based ring closure: Dried resin (0.05 mmol, 200 mg) was dissolved in DCE (3.0 mL), degassed by Argon for 3 mins, supplemented with Hoveyda-Grubbs generation II catalyst (10 mg), shaken gently overnight, and then washed by DCM.

Example 11

Preparation of Orthogonally Protected (2S,3R)-2-amino-3-methyl-4-phosphonobutyric acid (Pmab) as a Phosphatase—Stable Phosphothreonine Mimetic and its use in the Synthesis of Polo-Box Domain-Binding Peptides Stereoselective synthesis of (2S,3R)-4-[bis-(tert-butyloxy)phosphinyl]-2-[(9H-fluoren-9-ylmethoxy)carbonyl]amino-3-methylbutanoic acid [(N-Fmoc, O,O-(bis-(tert-butyl))-Pmab, 4] as a hydrolytically-stable phosphothreonine mimetic bearing orthogonal protection compatible with standard solid-phase protocols. The synthetic approach used employs Evans' oxazolidinone for chiral induction. Also presented is the application of 4 in the solid-phase synthesis of polo-like kinase 1 (Plk1) polo box domain (PBD)-binding peptides. These Pmab-containing peptides retain PBD binding efficacy similar to a parent pThr containing peptide. Reagent 4 should be a highly useful reagent for the preparation of signal transduction-directed peptides.

Phosphorylation of proteins facilitates critical protein-protein binding interactions that may result in signal propagation or modulation of enzyme activity. Changes in normal post-translational modification of proteins through phosphorylation of tyrosine, serine and threonine residues is a central paradigm in oncogenic transformation. In light of this, development of kinase-directed signal transduction inhibitors is a promising approach toward new anticancer therapeutics. Synthetic phosphopeptides based on shortened sequences derived from phosphoproteins, can retain significant binding affinities and they can serve as competitive antagonists of cognate protein-protein interactions. In this fashion they can provide initial starting points for the design of peptidomimetic-based therapeutics. Typically, a key component of the recognition provided by phosphoamino acids is derived from the phosphoryl group itself.[11] However the hydrolytic lability of phosphoryl esters to phosphatases limits the use of phosphopeptides in cellular contexts. Development of hydrolytically-stable mimetics, in which the labile phosphoryl ester oxygen has been replaced non-hydrolyzable methylene or difluoromethylene groups, offers one approach to circumvent this limitation. Peptides containing metabolically stable analogues have proven to be useful biological tools that may serve as potential leads for further therapeutic design.

Although a significant body of literature exists concerning the development and application of phosphotyrosyl (pTyr) mimetics, fewer examples can be found dealing with mimetics of phosphothreonine (pThr, 1,). Stereoselective synthesis of the pThr mimetic (2S,3R)-2-amino-3-methyl-4-phosphonobutanoic acid (Pmab, 2) has been reported using Schollkopf's bislactim ether. This has provided derivatized Pmab bearing O,O-(bis-allyl) protection of the phosphonic acid group along with N-Fmoc protection.[19] Synthesis of the corresponding 4,4-difluoro analogue (F₂Pmab, 3) bearing O,O-(bis-ethyl) phosphonic acid and N-Boc protection groups, has been approached using both (R)-isopropylideneglycerol as a chiral synthon and Oppolzer's sultam chiral auxiliary. To date, there have been no stereoselective syntheses reported of Pmab bearing orthogonal O,O-[bis-(tert-butyl)]phosphonic acid and N-Fmoc groups. This protection scheme would allow facile use in standard solid-phase protocols on acid-labile resins. Therefore, herein the first synthesis of (2S,3R)-4-[bis-(tert-butyloxy)phosphinyl]-2-[(9H-fluoren-9-ylmethoxy)carbonyl]amino-3-methylbutanoic acid [(N-Fmoc, O,O-(bis-(tert-butyl))-Pmab, 4] by a route using Evans' oxazolidinone for chiral induction is reported. Also presented herein is the application of this reagent in the solid-phase synthesis of a biologically active peptide.

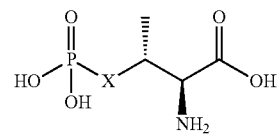

1 pThr: X = O
2 Pmab: X = CH₂
3 F₂Pmab: X = CF₂

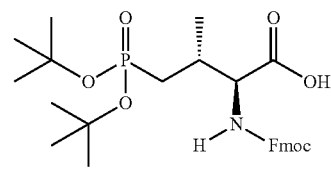

4

Chemistry.

Stereoselective synthesis of orthogonally-protected Pmab (4) began with the Swern oxidation of tert-butyldimethylsilyl (TBDMS) mono-protected (2E)-2-butene-1,4-diol 5 followed by sodium chlorite oxidation. This provided acid 6 with Z-double bond geometry (previously reported as the E-isomer[23]) (Scheme 1). Acid 6 was coupled with the Evan's chiral auxiliary, (4R)-4-phenyl-2-oxazolidinone and the Z-double bond geometry was isomerized by treatment with tri-n-butyl phosphine in THF to give the desired E-isomer (7). Both α and β stereogenic centers of 9 were constructed by a tandem sequence consisting of an asymmetric Cu(I)-catalyzed 1,4-Michael addition of methylmagnesium chloride followed by electrophilic α-bromination. The crude (2R)-bromide was then converted to the corresponding (2S)-azide by nuclephilic SN2 replacement using sodium azide. A single (2S,3R)-diastereomer (9) was obtained by column chromatographic purification and crystallization. Assignment of absolute stereochemistries was based on well-established literature precedence.[25-27] Removal of the TBDMS group by treatment with catalytic p-toluenesulfonic acid was followed by cyclization to release the Evan's auxiliary group and provide the 5-membered lactone. The azide was reduced by hydrogenation in a mixture of AcOH and MeOH and protected in situ to provide the lactone 10 as well as the ring-open alcohol 11 in a 1 to 4 ratio. Lactone 10 was further converted to 11 (Scheme 1).

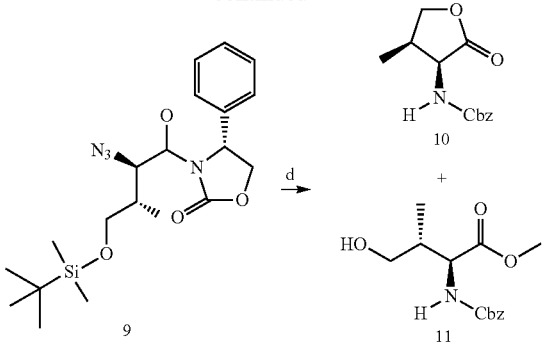

Reagents and conditions: (a) 1. Oxalyl chloride, DMSO, DCM, -78° C., 2 hrs; 2. NaClO$_2$, KH$_2$PO$_4$, 2-methyl-2-butene, tert-butanol and H$_2$O, rt, overnight, 97% for 2 steps. (b) 1. Trimethylacetyl chloride, triethylamine, THF, -78° C. - 0° C., 20 min; 2. (R)-(+)-Phenyl-2-oxazolidione lithium salt, THF, -78° C. - 0° C., overnight, 100%. (c) Tributylphosphine, THF, rt, 1 hr, 84%. (d) 1. Methylmagnesium chloride, copper(I) bromide•dimethyl sulfide, dimethyl sulfide/THF, -78° C. - -40° C., 2 hr; 2. NBS, -78° C., 1.5 hr; 3. NaN$_3$, DMF, 0° C., 2 hr, 79% for 2 steps. (e) p-Toluenesulfonic acid monohydrate, MeOH, rt, 6 hr; 2. 1 atm H$_2$, 10% Pd•C (10%), MeOH/AcOH, rt, overnight; 3. Benzyl chloroformate, NaHCO$_3$, THF/H$_2$O, 0° C., 4 hr, 49% for 11 over 3 steps.

Scheme 1. Reagents and conditions: (a) 1. Oxalyl chloride, DMSO, DCM, -78° C., 2 hrs; 2. NaClO, KH$_2$PO$_4$, 2-methyl-2-butene, tert-butanol and H$_2$O, rt, overnight, 97% for 2 steps. (b) 1. Trimethylacetyl chloride, triethylamine, THF, -78° C.-0° C., 20 min; 2. (R)-(+)-Phenyl-2-oxazolidione lithium salt, THF, -78° C.-0° C., overnight, 100%. (c) Tributylphosphine, rt, 1 hr, 84%. (d) 1. Methylmagnesium chloride, copper (I) bromide.dimethyl sulfide, dimethyl sulfide/THF, -78° C.--40° C., 2 hr; 2. NBS, -78° C., 1.5 hr; 3. NaN$_3$, DMF, 0° C., 2 hr, 79% for 2 steps. (e) 1. p-Toluenesulfonic acid monohydrate, MeOH, rt, 6 hr; 2. 1 atm H$_2$, 10% Pd.C (10%), MeOH/AcOH, rt, overnight; 3. Benzyl chloroformate, NaHCO$_3$, THF/H$_2$O, 0° C., 4 hr, 49% for 11 over 3 steps.

It is of note that alcohol 11 can also be prepared from L-aspartic acid through the known his-methyl ester 13. Selectively reduction of the γ-carboxyl of 13 using DIBAL provided the alcohol 14 (Scheme 2). Key to this reaction was the use of substrate concentrations less than 0.03 M. Similar to above, N-deprotection of 14 by hydrogenation in a mixture of AcOH and MeOH and subsequent Cbz protection gave the lactone 10 and the alcohol 11 in a 1 to 4 ratio.

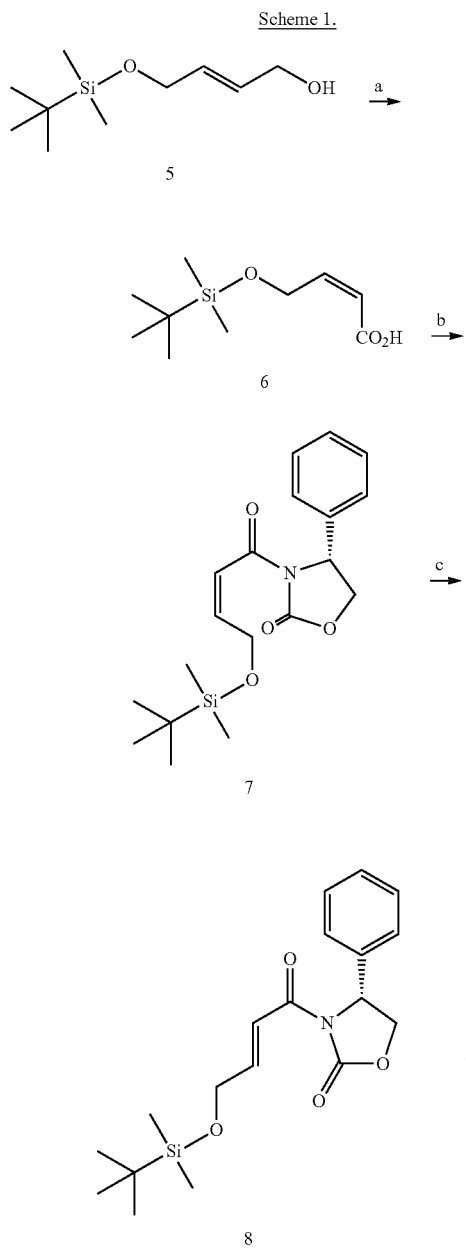

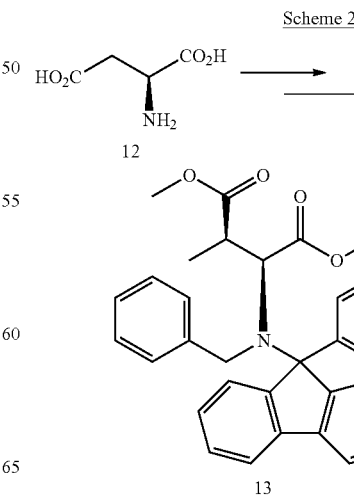

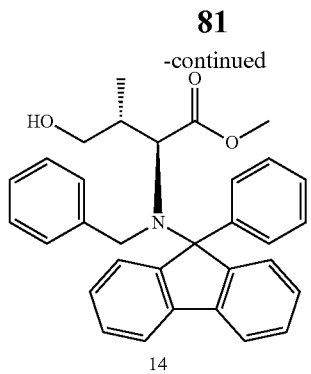

14

Reagents and conditions: (a) DIBAL, THF, −40° C. - 0° C., 4 hr, 61%. (b) 1. 1 atm H₂, 10% Pd•C (10%), MeOH/AcOH, rt, overnight; 2. Benzyl chloroformate, NaHCO3, THF/H2O, 0° C., 4 hr.

Scheme 2. Reagents and conditions: (a) DIBAL, THF, −40° C.-0° C., 4 hr, 61%. (b) 1. 1 atm H$_2$, 10% Pd.C (10%), MeOH/AcOH, rt, overnight; 2. Benzyl chloroformate, NaHCO3, THF/H2O, 0° C., 4 hr.

Swern oxidation of alcohol 11 gave the corresponding aldehyde (15). This aldehyde was subjected to a phospho-Mukaiyama aldol reaction with freshly-prepared di-tert-butyltrimethylsilyl phosphite (17) to yield the aldehyde 17 (Scheme 3). Subsequent treatment with citric acid gave the free alcohol (18), which was derivatized as the phenylthiocarbonate 19 and subjected to Barton-McCombie deoxygenation to yield 20. Hydrolysis of the methyl ester, then hydrogenation and re-protection using Fmoc-OSu provided the orthogonally protected Pmab derivative 4.

Scheme 3.

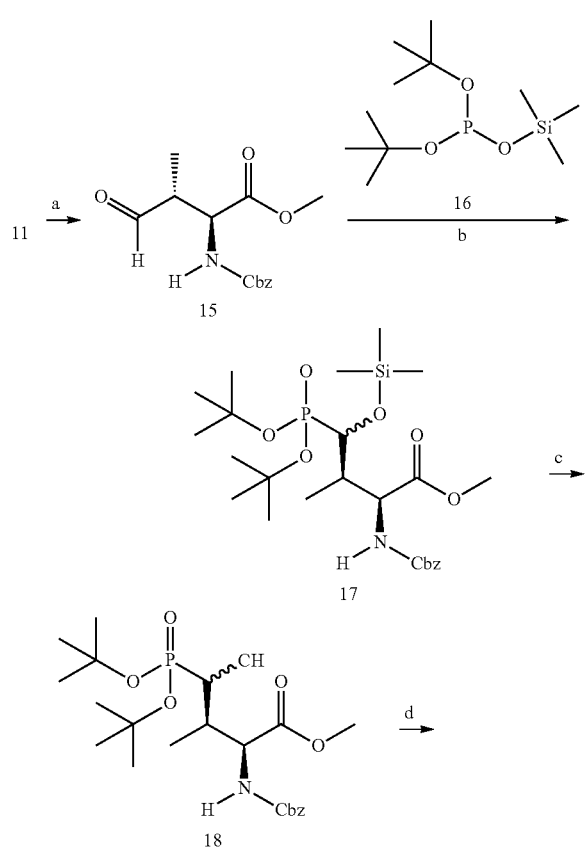

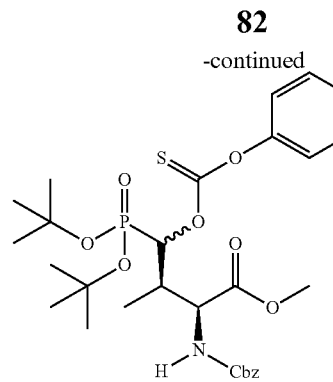

19

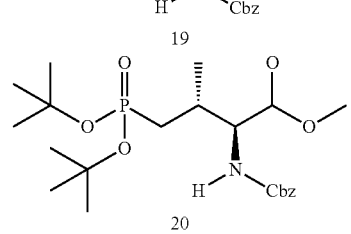

20

Reagents and conditions: (a) Oxalyl chloride, DMSO, DCM, -78° C., 2 hrs. (b) 16, DCM, rt, 3 hr. (c) citric acid, MeOH/H₂O, rt, overnight, 88% over 3 steps. (d) O-phenylchlorothionoformate, DMAP (cat.) and N, N-diisopropylethylamine, DCM, r. t., overnight. (e) Tributyltin hydride, AIBN, toluene, 100° C., 20 min, 58% over 2 steps. (f) 1. LiOH, THF/H₂O, rt, overnight; 2. 1 atm H₂, 10% Pd•C (10%),MeOH, rt, overnight; 3. FmocOSu, NaHCO₃, dioxane/H₂O, rt, overnight, 100% over 3 steps.

Scheme 3. Reagents and conditions: (a) Oxalyl chloride, DMSO, DCM, −78° C., 2 hrs. (b) 16, DCM, rt, 3 hr. (c) citric acid, MeOH/H$_2$O, rt, overnight, 88% over 3 steps. (d) O-phenylchlorothionoformate, DMAP (cat.) and N,N-diisopropylethylamine, DCM, r.t, overnight. (e) Tributyltin hydride, AIBN, toluene, 100° C., 20 min, 58% over 2 steps. (f) 1. LiOH, THF/H$_2$O, rt, overnight; 2. 1 atm H$_2$, 10% Pd.C (10%), MeOH, rt, overnight; 3. FmocOSu, NaHCO$_3$, dioxane/H$_2$O, rt, overnight, 100% over 3 steps.

Application of reagent 4 to the synthesis of Polo Box Domain—binding peptides. The polo-like kinase 1 (Plk1) functions as an important mitotic regulator that phosphorylates serine and threonine residues. Its over-expression in a number of cancers and its association with poor prognosis have made it a potential anticancer therapeutic target. A main focus of Plk1 inhibitor development has been directed at the kinase catalytic domain. However, Plk1 contains modular C-terminal PBDs that bind specific phosphoserine and phosphothreonine-containing sequences to provide critical localization of Plk1. Competitive PBD binding antagonists could serve as inhibitors of Plk1 function that are distinct from kinase-directed agents. A starting point for the development of PBD-binding antagonists is given by short pThr-containing peptides modeled on consensus binding sequences derived from the p-Thr78 region (p-T78) of the PBD-binding protein, PBIP1. By examining various PBD-binding phosphpeptides, it has recently been shown that a 5-mer phosphopeptide "PLHSpT" (21) specifically interacts with the Plk1PBD with high affinity (K$_d$=0.45 μM). In order to provide phosphatase-stable peptides for in vivo studies, F$_2$Pmab (3) was also incorporated into a 6-mer T78 peptide, "PLHSTA", to give the corresponding peptide 25. (Note: The 6-mer sequence "PLHS-F$_2$Pmab-A" (25) was synthesized due to inefficient synthesis of the 5-mer sequence, "PLHS-F$_2$Pmab"). It was found that 25 showed much weaker PBD-binding affinity than the respective p-T78 peptide, "PLH-SpTA", and it exhibited significant toxicity in cell-based experiments. The toxicity can potentially be attributed to the highly acidic CF$_2$PO$_3$H moiety. Therefore, using solid-phase techniques and standard Fmoc-based protocols, we employed reagent 4 to synthesize the Pmab-containing peptides 23 and 24.

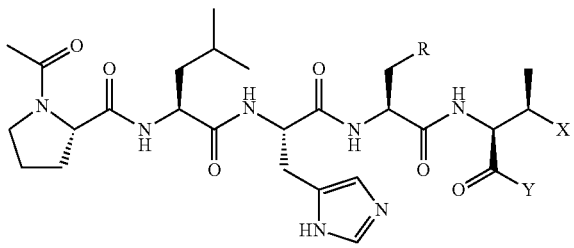

21 R = OH; Y = NH$_2$; X = OH
22 R = OH; Y = NH$_2$; X = O—PO(OH)$_2$
23 R = OH; Y = NH$_2$; X = CH$_2$—PO(OH)$_2$
24 R = H; Y = NH$_2$; X = CH$_2$—PO(OH)$_2$

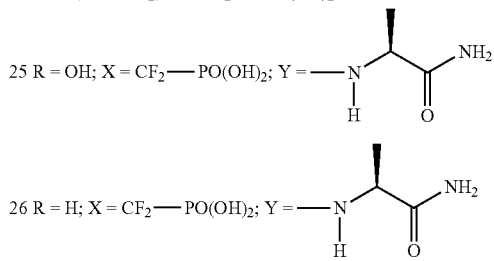

25 R = OH; X = CF$_2$—PO(OH)$_2$; Y =

26 R = H; X = CF$_2$—PO(OH)$_2$; Y =

Figure 16A:
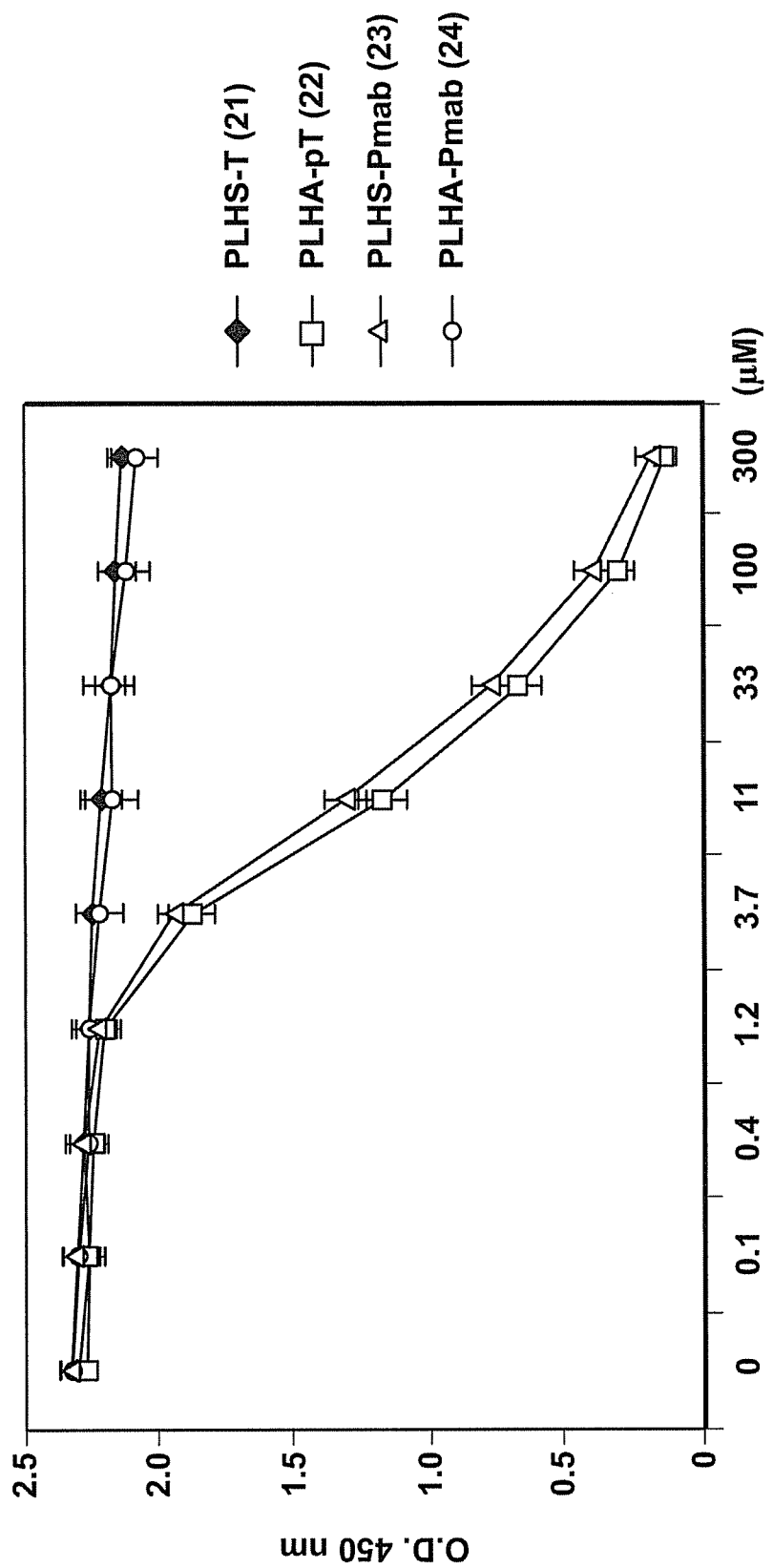
FIG. 16A-B. Measurement of the ability of synthetic peptides 21-24 to inhibit PBD-dependent interactions. (A) PBD-binding inhibition assays were carried out in the presence of different concentrations of the indicated inhibitory peptides. 49 The level of the remaining interaction between a biotinylated p-T78 peptide and full-length Plk1 was quantified by optical density (O.D.) at 450 nm (error bars represent standard deviation). (B) Representative images of green fluorescence in EGFP plasmid-containing HeLa cells following microinjection with PLHS-Pmab (23) or the PBD-binding defective peptides, PLHST (21) and PLHA-Pmab (24), are shown (procedure described in Example 1, Materials and Methods). Note induction of mitotically-arrested, rounded-up, morphologies associated with the PBD-binding competent PLHS-Pmab.

To examine the ability of Pmab- and F$_2$Pmab-containing peptides to inhibit PBD-dependent interactions, Plk1 PBD-binding inhibition assays were conducted in the presence of various concentrations of synthetic peptides. It was found that "PLHS-Pmab" (23) inhibits the interaction of the Plk1 PBD with a biotinylated 9-mer p-T78 peptide [Biotin-Cys-(CH$_2$)$_5$-CO-DPPLHSpTAI-NH$_2$] as effectively as the wild-type peptide, "PLHSpT" (22). In contrast, the peptide, "PLHS-F$_2$Pmab-A" (25, FIG. 2), inhibits the interaction at a somewhat reduced level. Replacement of the critical (pThr-1) Ser residue with an alanine (equivalent to S77A mutation) is known to significantly attenuate PBD binding affinity. The non-phosphorylated control peptide "PLHST" (21) and the S77A mutants of the Pmab- and the F$_2$Pmab-containing peptides (24 and 26, respectively), did not inhibit PBD binding even at 1000-fold higher molar concentrations (FIG. 16A). The ELISA-based PBD-binding inhibition assay was carried out using an immobilized biotinylated 9-mer p-T78 peptide [Biotin-Cys-(CH$_2$)$_5$—CO-DPPLHSpTAI-NH$_2$] and cellular lysates expressing HA-EGFP-Plk1.

Figure 16B:
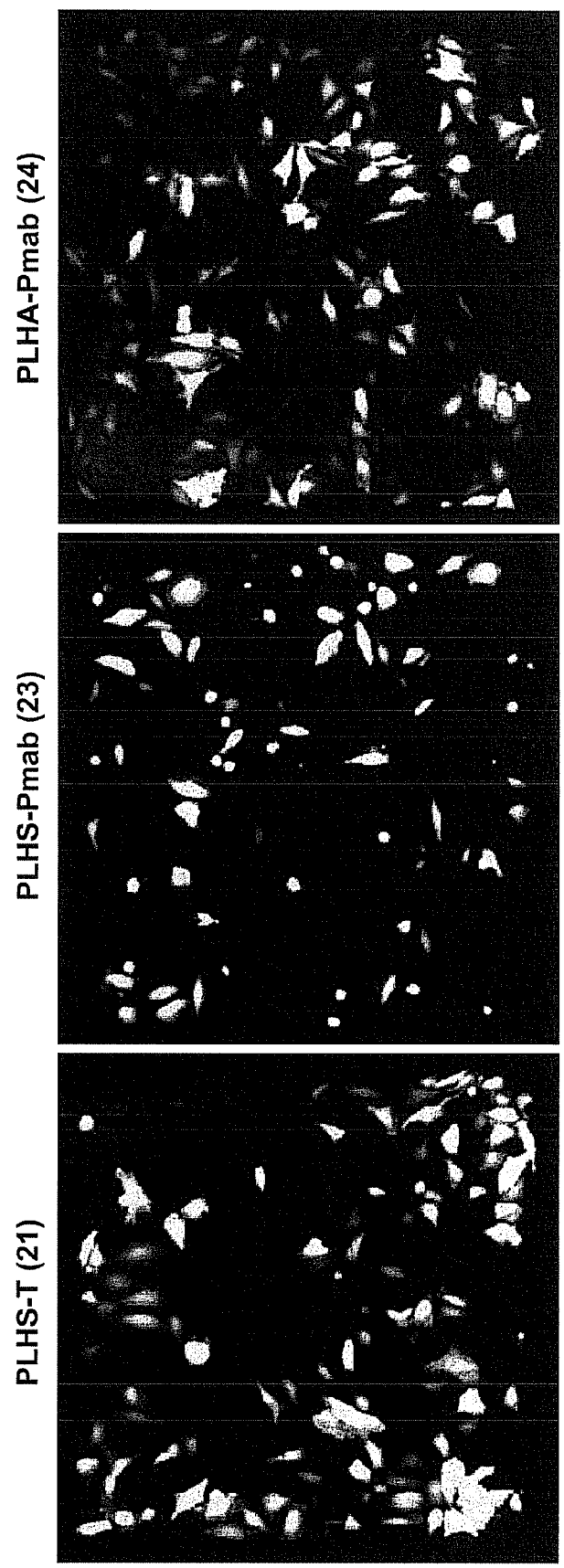
Figure 17A:
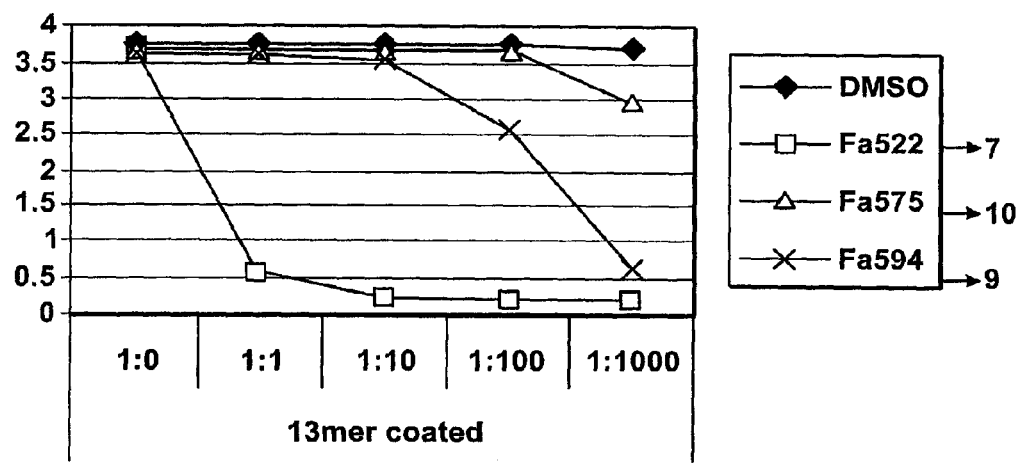
FIG. 17A-B ELISA PBD-1 binding data of (A) oxime Fa522 derivatives and (B) ether-containing Fa428 derivative peptides.
Figure 17B:
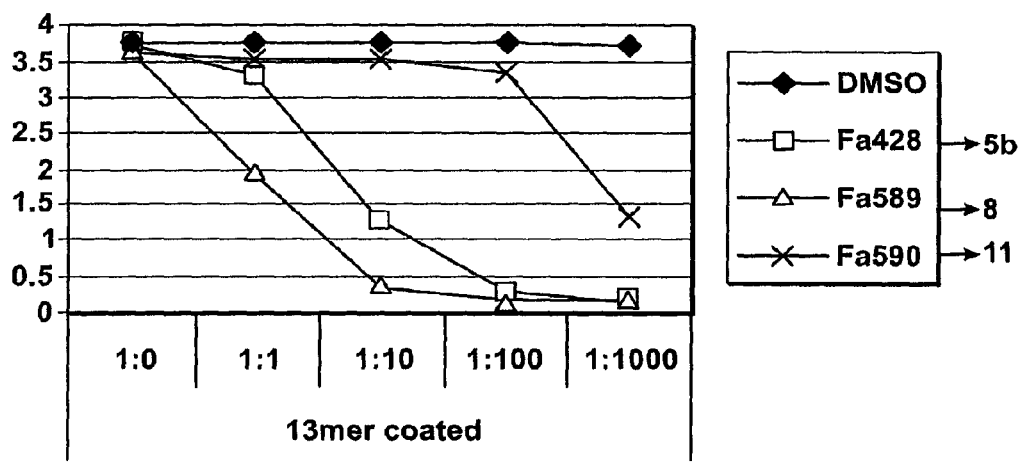
Figure 18:
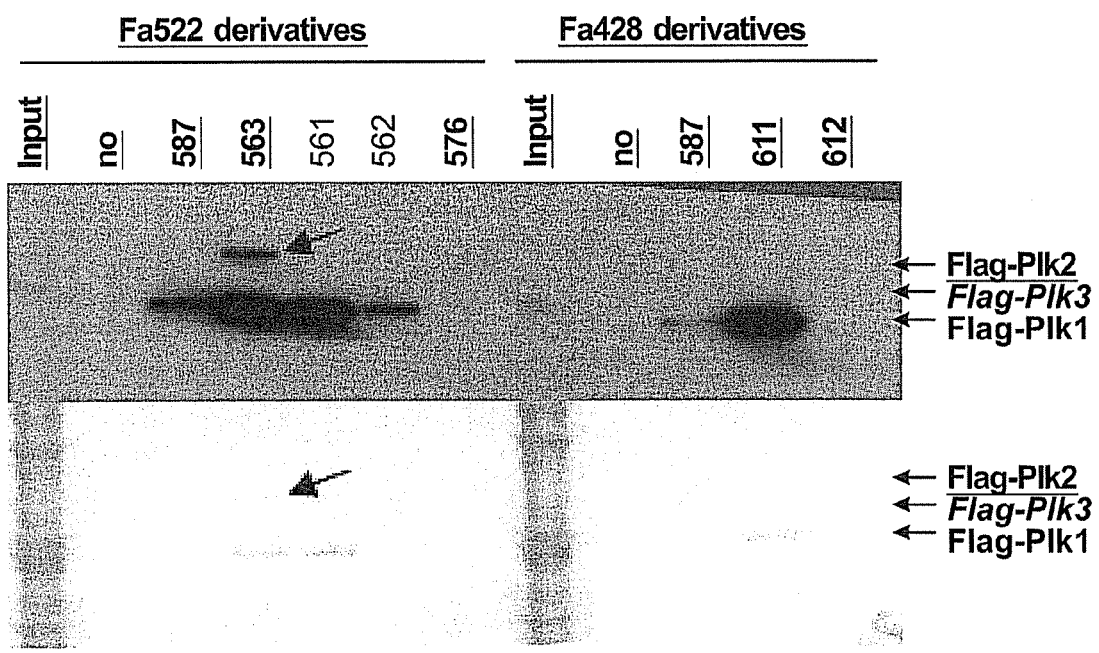
FIG. 18 Assay of specificity of interaction. Western blot (top) and coomassie stained gel (bottom) of Plk1,2,3 pull down assay using the indicated peptides.

Evidence suggests that the PBD plays critical roles in the proper sub-cellular localization and mitotic functions of Plk1. Disruption of PBD-dependent Plk1 functions by expressing a dominant-negative form of PBD results in a mitotic arrest that ultimately leads to apoptotic cell death.[50] To investigate the effects of inhibiting Plk1 PBD interactions peptides 21, 23 and 24 were introduced into HeLa cells. In order to overcome poor membrane permeability of the negatively charged Pmab-containing peptides, microinjection was employed. HeLa cells were arrested at the G1/S boundary by double thymidine treatment and released into fresh medium. Six hours after release, the cells were microinjected with a mixture of 3 mM of peptides 21, 23 or 24 and 30 ng/µL of pEGFP-C1 vector and the cells were then photographed 15 h after G1/S release. Co-injected EGFP plasmid provided a convenient marker to identify the microinjected cells. The Pmab-containing peptide (23), but not the non-phosphorylated peptide 21 or the respective S77A mutant (24), induced mitotically arrested, rounded-up, morphology in approximately 50% of the microinjected, green fluorescent protein (GFP)-positive population (FIG. 16B). These results demonstrate that inhibition of PBD function by the Pmab-containing p-T78 mimetic peptide is sufficient to interfere with the mitotic functions of Plk1.

Although a significant body of literature exists concerning the development and application of pTyr mimetics, fewer examples can be found dealing with mimetics of pThr. Presented herein is the first stereoselective synthesis of the hydrolytically-stable phosphothreonine mimetic Pmab (4), bearing (O,O)-bis-tert-butyl protection of the phosphonic acid group along with N-Fmoc derivatization. This orthogonal protection scheme allows facile use in standard solid-phase protocols on acid-labile resins, where side chain protecting groups can be removed during TFA-mediated resin cleavage. Our synthetic approach to Pmab utilizes Evans' oxazolidinone for chiral induction. Also presented herein is the application of 4 in the solid-phase synthesis of biologically active peptides directed against the Plk1 PBD. As show herein, Pmab-containing peptides retain PBD binding efficacy similar to a parent pThr-containing peptide, while retaining the ability to inhibit PBD-dependent interactions in whole cells. In summary, reagent 4 should be a highly useful reagent for the preparation of signal transduction-directed peptides.

(E)-4-[(Tert-butyldimethylsilyl)oxy]-2-buten-1-ol (5). To a solution of (2E)-2-butene-1,4-diol (8.22 mL, 0.10 mol) and imidazole (8.50 g, 0.125 mol) in DMF (50 mL) at 0° C., was added tert-butyldimethylsilyl chloride (7.50 g, 0.050 mol) in several portions over 10 minutes. The resulting mixture was warmed to room temperature and stirred (2 h), then poured into H$_2$O (200 mL) and extracted with EtOAc (2×150 mL). The organic layer was washed (brine), dried (Na$_2$SO$_4$) and purified by silica gel column chromatography (hexanes:EtOAc) to yield 5 as a colorless oil (9.0 g, 89% yield). $^1$H NMR (400 MHz, CDCl$_3$) δ 5.60-5.50 (m, 2H), 4.18 (m, 2H), 4.09 (m, 2H), 2.76 (br, 1H), 0.83 (s, 9H), 0.01 (s, 6H). $^{13}$C NMR (100 MHz, CDCl$_3$) δ 136.3, 135.4, 64.8, 63.8, 31.1, 23.6.

Z-4-[[(1,1-Dimethylethyl)dimethylsilyl]oxy]-2-butenoic acid (6). To a solution of oxalyl chloride (3.55 mL, 40.8 mmol) in CH$_2$Cl$_2$ (100 mL) at −78° C., was added a solution of DMSO (5.80 mL, 81.7 mmol) in CH$_2$Cl$_2$ (40 mL) and the mixture was stirred (15 minutes). Alcohol 5 (5.50 g, 27.2 mmol) in dry CH$_2$Cl$_2$ (40 mL) was added over 5 minutes, the mixture was stirred at −75° C. (2 h), then triethylamine (31 mL, 0.22 mol) was added. The mixture was warmed to room temperature, saturated NH$_4$Cl (50 mL) was added, and then the mixture was extracted with Et$_2$O (2×100 mL). The combined organic layers were washed (brine), dried (Na$_2$SO$_4$) and evaporated to yield the intermediate aldehyde as a pale yellow liquid. Without purification, a mixture of the aldehyde, potassium phosphate monobasic (5.55 g, 40.8 mmol) and 2-methyl-2-butene (14.4 mL, 136 mmol) in tert-butanol (150 mL) and H$_2$O (30 mL) at 0° C. was supplemented with sodium chlorite (9.23 g, 81.6 mmol, 80% technical grade) in several portions over 10 minutes. The mixture was warmed to room temperature slowly and stirred (night). After cooling to 0° C., a solution of sodium bisulfate (31.8 g, 0.30 mol) in H$_2$O (100 mL) was added slowly and the mixture was stirred (30 minutes) and extracted with EtOAc (2×150 mL). The combined organic layer was washed (brine), dried (Na$_2$SO$_4$) and purified by silica gel column chromatography (hexanes:EtOAc) to yield acid 6 as a colorless oil (5.70 g, 97% yield). $^1$H NMR (400 MHz, CDCl$_3$) δ 6.40 (dt, J=11.6, 4.6 Hz, 1H), 5.68 (dt, J=12.0, 2.6 Hz, 1H), 4.65 (dd, J=4.6, 2.4 Hz, 2H), 0.83 (s, 9H), 0.00 (s, 6H). $^{13}$C NMR (100 MHz, CDCl$_3$) δ 176.0, 159.7, 123.0, 67.1, 31.0, 23.0, 0.00. APCI (−VE) m/z: 215.2 (M−H)$^−$. HR-ESI MS cacld for C$_{10}$H$_{19}$O$_3$Si (M−H)$^−$: 215.1109. Found: 215.1103.

(4R)-3-[(2Z)-[4-[(1,1-Dimethylethyl)dimethylsilyl]oxy]-1-oxo-2-buten-1-yl]-4-phenyl-2-oxazolidinone (7). To a solution of acid 6 (6.0 g, 28.2 mmol) in THF (40 mL) at −78°

C., was added triethylamine (4.00 mL, 28.2 mmol) followed by trimethylacetyl chloride (3.46 mL, 28.2 mmol) drop-wise. The mixture was warmed to 0° C. over 20 minutes, then the anhydride mixture was cooled to −78° C. Separately, to a solution of (R)-(+)-phenyl-2-oxazolidinone (Aldrich) (4.60 g, 28.2 mmol) in THF (40 mL) at −78° C. was carefully added n-BuLi (2.50 M in THF, 11.3 mL, 28.2 mmol) and the mixture was stirred (30 minutes) then transferred to the anhydride solution at −78° C. The final reaction mixture was warmed to room temperature and stirred (over night). The mixture was diluted with EtOAc (200 mL), washed ($H_2O$ and brine), dried ($Na_2SO_4$), and purified by silica gel column chromatography (hexanes:EtOAc) to yield 7 as a colorless oil (10.2 g, 100% yield). $^1$H NMR (400 MHz, $CDCl_3$) δ 7.36-7.20 (m, 5H), 7.10 (dt, J=11.6, 2.6 Hz, 1H), 6.50 (dt, J=12.0, 4.6 Hz, 1H), 5.44 (dd, J=8.8, 4.0 Hz, 1H), 4.68-4.59 (m, 3H), 4.22 (dd, J=8.8, 4.0 Hz, 1H), 0.85 (s, 9H), 0.00 (s, 6H). $^{13}$C NMR (100 MHz, $CDCl_3$) δ 169.3, 160.6, 158.8, 144.3, 134.5, 134.0, 131.0, 122.0, 75.2, 67.9, 62.8, 31.1, 23.4, 0.00. ESI (+VE) m/z: 384.1 (M+HR-ESI cacld for $C_{19}H_{28}NO_4Si$ (M+Na)$^+$: 362.1782. Found: 362.1789.

(4R)-3-[(2E)-[4-[(1,1-Dimethylethyl)dimethylsilyl]oxy]-1-oxo-2-buten-1-yl]-4-phenyl-2-oxazolidinone (8). To a solution of 7 (5.00 g, 13.9 mmol) in anhydrous THF (70 mL) at room temperature was added tributylphosphine (0.34 mL, 1.39 mmol). The resulting solution was stirred at room temperature (60 minutes), then diluted with EtOAc (200 mL), washed ($H_2O$ and brine), dried ($Na_2SO_4$), and purified by silica gel column chromatography (hexanes:EtOAc) to yield 8 as a white solid (4.20 g, 84% yield). $[α]^{20}_D$-54.5 (c 1.40, $CHCl_3$). mp. 79-81° C. $^1$H NMR (400 MHz, $CDCl_3$) δ 7.48 (dt, J=15.2, 2.4 Hz, 1H), 7.30-7.21 (m, 5H), 7.02 (dt, J=15.2, 3.4 Hz, 1H), 5.39 (dd, J=8.6, 3.8 Hz, 1H), 4.60 (t, J=8.8 Hz, 1H), 4.28 (dd, J=3.4, 2.2 Hz, 2H), 4.17 (dd, J=8.8, 4.0 Hz, 1H), 0.85 (s, 9H), 0.00 (s, 6H). $^{13}$C NMR (100 MHz, $CDCl_3$) δ 170.0, 159.0, 155.4, 144.5, 134.6, 134.1, 131.4, 124.1, 75.3, 68.1, 63.2, 31.3, 23.8, 0.00. IR (KBr) $ν_{max}$ 2927, 2855, 1759, 1693, 1324, 1201, 1104, 951, 834, 715 cm$^-$. ESI (+VE) m/z: 384.1 (M+HR-ESI cacld for $C_{19}H_{28}NO_4Si$ (M+Na)$^+$: 362.1782. Found: 362.1790.

(4R)-3-[(2S,3R)-[2-Azido-4[(1,1-dimethylethyl)dimethylsilyl]oxy]-3-methyl-1-oxo-butyl)]-4-phenyl-2-oxazolidinone (9). To a solution of copper(I) bromide dimethyl sulfide complex (2.56 g, 12.45 mmol) in dimethyl sulfide (20 mL) and THF (30 mL) at −78° C. was added a solution of methylmagnesium chloride (3.0 M in THF, 5.50 mL, 16.4 mmol). The suspension was stirred at −78° C. (20 minutes), then warmed to 0° C. (20 minutes) and cooled to −78° C. The mixture was then transferred to a pre-cooled (−78° C.) solution of 8 (1.80 g, 4.98 mmol) in THF (16.0 mL) and $CH_2Cl_2$ (8.0 mL) using a cannula. The resulting mixture was kept at −78° C. (60 minutes) then warmed to −40° C. (60 minutes) and cooled again to −78° C. To the mixture was added a pre-cooled (−78° C.) solution of N-bromosuccinimide (4.45 g, 25.0 mmol) in THF (50 mL) and the mixture was stirred at −78° C. (90 minutes). The reaction was quenched by addition of saturated $NaHSO_3$ (50 mL), extracted with EtOAc (100 mL×2). The combined organic phase was washed ($H_2O$ and brine), dried ($Na_2SO_4$), and purified by silica gel column chromatography (hexanes:EtOAc) to yield the requisite α-bromo-containing intermediate as a white solid (1.93 g). To a solution of the α-bromo compound (1.93 g) in DMF (25 mL) at 0° C., was added sodium azide (1.00 g, 15.4 mmol) and the mixture was stirred (2 h). The mixture was diluted with EtOAc (150 mL), washed ($H_2O$ and brine), dried ($Na_2SO_4$), and purified by silica gel column chromatography (hexanes: EtOAc) then crystallized (EtOAc:petroleum ether) to yield azide 9 as a white solid (1.65 g, 79% yield). $[α]^{20}_D$73.0 (c 1.10, $CHCl_3$). mp. 80-82° C. $^1$H NMR (400 MHz, $CDCl_3$) δ 7.40-7.30 (m, 5H), 5.49 (dd, J=8.8, 4.0 Hz, 1H), 5.17 (d, J=8.8 Hz, 1H), 4.75 (t, J=9.0 Hz, 1H), 4.34 (dd, J=8.8, 4.0 Hz, 1H), 3.65 (dd, J=10.2, 5.4 Hz, 1H), 3.48 (dd, J=10.2, 3.4 Hz, 1H), 2.14 (m, 1H), 0.89 (s, 9H), 0.83 (d, J=6.8 Hz, 3H), 0.03 (s, 3H), 0.00 (s, 3H). $^{13}$C NMR (100 MHz, $CDCl_3$) δ 175.7, 158.7, 143.9, 134.8, 134.6, 131.9, 75.7, 69.3, 66.7, 63.4, 43.5, 31.4, 23.8, 19.4, 0.00. IR (KBr) $ν_{max}$ 2930, 2359, 2106, 1786, 1710, 1206, 1097, 833, 778 cm$^{-1}$. ESI (+VE) m/z: 441.1 (M+Na)$^+$. HR-ESI MS cacld for $C_{20}H_{31}N_4O_4Si$ (M+H)$^+$: 419.2109. Found: 419.2114.

[(3S,4R)-Tetrahydro-4-methyl-2-oxo-3-furanyl]-carbamic acid phenylmethyl ester (10) and (2S,3R)-4-hydroxy-N-(phenylmethoxycarbonyl)-L-valine methyl ester (11). To a solution of 9 (600 mg, 1.44 mmol) in MeOH (20 mL) at room temperature was added p-toluenesulfonic acid monohydrate (14 mg, 0.07 mmol). The solution was stirred at room temperature (6 h), then diluted with EtOAc (150 mL), washed ($H_2O$ and brine), dried ($Na_2SO_4$), and purified by silica gel column chromatography (hexanes:EtOAc) to yield the intermediate azide-containing lactone as a colorless liquid (270 mg, containing a small amount EtOAc). $^1$H NMR (400 MHz, $CDCl_3$) δ 4.36 (dd, J=8.8, 6.4 Hz, 1H), 4.26 (d, J=7.2 Hz, 1H), 4.02 (dd, J=9.2, 4.0 Hz, 1H), 2.75 (m, 1H), 1.13 (d, J=7.2 Hz, 3H). A suspension of the this lactone and Pd—C (10%, 60 mg) in MeOH (9.0 mL) and acetic acid (1.0 mL) was stirred under $H_2$ (1 atmosphere) at room temperature (overnight). The catalyst was removed by filtration though a celite pad under argon and the filtrate was concentrated. The residue was re-dissolved in THF (10.0 mL) containing $H_2O$ (10 mL) and then cooled to 0° C. To this was added benzyl chloroformate (0.32 mL, 2.25 mmol) and $NaHCO_3$ (840 mg, 10.0 mmol) and the mixture was stirred (4 h). The mixture was diluted with EtOAc (150 mL), washed ($H_2O$ and brine), dried ($Na_2SO_4$), and purified by silica gel column chromatography (hexanes:EtOAc) to yield 10 as a white crystalline solid (90 mg, 25% yield over 3 steps) and 11 as a viscous colorless oil (250 mg, 49% yield over 3 steps). For (10): mp. 125-127° C. $^1$H NMR (400 MHz, $CDCl_3$) δ 7.40-7.30 (m, 5H), 5.33 (m, 1H), 5.10 (s, 2H), 4.53 (t, J=6.8 Hz, 1H), 4.35 (dd, J=9.2, 5.2 Hz, 1H), 4.05 (d, J=9.2 Hz, 1H), 2.92 (m, 1H), 0.95 (d, J=7.2 Hz, 3H). $^{13}$C NMR (100 MHz, $CDCl_3$) δ 174.5, 156.1, 135.9, 128.5, 128.3, 128.1, 72.4, 67.3, 54.5, 34.1, 12.7. ESI (+VE) m/z: 272.1 (M+Na)$^+$. HR-ESI cacld for $C_{13}H_{16}NO_4$ (M+H)$^+$: 250.1074. Found: 250.1081. For (11): $^1$H NMR (400 MHz, $CDCl_3$) δ 7.29-7.28 (m, 5H), 5.98 (d, J=8.4 Hz, 1H), 5.04 (s, 2H), 4.34 (m, 1H), 3.65 (s, 3H), 3.54 (dd, J=11.2, 4.4 Hz, 1H), 3.44 (dd, J=11.2, 6.0 Hz, 1H), 2.92 (s, 1H), 2.14 (m, 1H), 0.92 (d, J=7.2 Hz, 3H). ESI (+VE) m/z: 304.2 (M+Na)$^+$. HR-ESI MS cacld for $C_{14}H_{20}NO_5$ (M+H)$^+$: 282.1336. Found: 282.1343.

(2S,3R)-4-hydroxy-N-(9-Phenylfluoren-9-yl)-N-benzyl-L-valine methyl ester (14). To a solution of 13 (4.00 g, 7.91 mmol) in anhydrous THF (260 mL) at −40° C., was added DIBAL (1.0 M in Hexanes, 19.8 mL, 19.8 mmol). The mixture was stirred for 4 hr (−40° C.-0° C.) before cooled down to −78° C., quenched by acetone (10 mL), warmed to r.t., stirred with 1 N $KH_2PO_4$ (500 mL) and sodium potassium tartrate (30.0 g) overnight, filtered through the celite. The filtrate was extracted with EtOAc, washed ($H_2O$ and brine), dried ($Na_2SO_4$), and purified by silica gel column chromatography (hexanes: EtOAc) to yield alcohol 14 as a white wax (2.30 g, 61% yield, quantitative yield based on recovered starting material) and recycled 13 as a white wax (1.60 g). $^1$H NMR (400 MHz, $CDCl_3$) δ 7.76-7.60 (m, 8H), 7.35-7.20 (m, 10H), 4.70 (AB, $J_{AB}$=13.6 Hz, 1H), 4.38 (AB, $J_{AB}$=13.6 Hz, 1H), 3.84 (dd, J=10.8, 3.6 Hz, 1H), 3.33 (dd, J=10.8, 6.4 Hz, 1H), 3.04 (d, J=8.4 Hz, 1H), 2.93 (s, 3H), 1.40 (m, 1H), 0.34 (d, J=6.8 Hz, 3H). $^{13}$C NMR (100 MHz, $CDCl_3$) δ 171.7, 148.3, 144.8, 144.0, 142.0, 141.3, 139.7, 129.7, 128.6, 128.4, 128.0, 127.7, 127.3, 127.2, 127.1, 127.0, 125.3, 120.2, 80.3, 65.5, 63.3, 50.6, 36.3, 14.2. ESI (+VE) m/z: 478.2 (M+H)+. HR-ESI MS cacld for $C_{32}H_{32}NO_3$ (M+H)+: 478.2377. Found: 478.2385.

(2S,3R)-4-[Di-(tert-butyl)-oxyphosphinyl]-4-hydroxy-N-phenylmethoxycarbonyl)-L-valine methyl ester (18). To a solution of oxalyl chloride (0.96 mL, 10.1 mmol) in $CH_2Cl_2$ (40 mL) at −78° C., was added a solution of DMSO (1.60 mL, 20.2 mmol) in $CH_2Cl_2$ (5 mL) and the mixture was stirred (15 minutes). To this was added alcohol 11 (0.63 g, 2.24 mmol) in dry $CH_2Cl_2$ (5 mL) over 5 minutes and the mixture was stirred at −75° C. (2 h). triethylamine (8.40 mL, 53.8 mmol) was added and the mixture was warmed to room temperature. To this was added saturated $NH_4Cl$ (50 mL) and the mixture was extracted with $Et_2O$ (100 mL×2) and the combined organic phase was washed (brine), dried ($Na_2SO_4$), and purified by silica gel column chromatography (hexanes:EtOAc). Aldehyde 15 was obtained as a viscous colorless oil (450 mg, 96% yield based on recovered starting material) along with starting alcohol 11 (160 mg). To a solution of di-tert-butyl phosphite (0.30 mL, 1.50 mmol) and triethylamine (0.21 mL, 1.50 mmol) in $CH_2Cl_2$ (5 mL) at 0° C., was added chlorotrimethylsilane (0.19 mL, 1.50 mmol) and the mixture was stirred (5 minutes) and then transfer to a solution of aldehyde 15 (300 mg, 1.08 mmol) in $CH_2Cl_2$ (5 mL) at room temperature and the mixture was stirred (3 h). The mixture was diluted with EtOAc (150 mL), washed (brine), dried ($Na_2SO_4$) and concentrated. The resulting crude silyl-protected 17 was re-dissolved in MeOH (10 mL), to this was added $H_2O$ (1.0 mL) and citric acid (200 mg) and the mixture was stirred at room temperature (over night). The mixture was diluted with EtOAc (200 mL), washed (saturated $NaHCO_3$ and brine), dried ($Na_2SO_4$) and purified by silica gel column chromatography (hexanes:EtOAc) to yield 18 as a white wax epimeric at the γ-carbon (450 mg, 88% yield). $^1$H NMR (400 MHz, $CDCl_3$) δ 7.30-7.29 (m, 5H), 6.30 (d, J=8.0 Hz, 0.7H), 5.30 (m, 0.3H), 5.10-5.05 (m, 2H), 4.30 (m, 0.7H), 4.09 (m, 0.3H), 3.75-3.55 (m, 4H), 2.51 (m, 0.7H), 1.51-1.40 (m, 18H), 1.15-1.00 (m, 3H). $^{13}$C NMR (100 MHz, $CDCl_3$) δ 172.3, 156.7, 136.4, 128.4, 128.0, 70.5, 68.8, 67.3, 66.8, 59.8, 53.9, 53.1, 52.2, 36.6, 35.4, 30.3, 24.1, 14.7, 11.5, 9.4. ESI (+VE) m/z: 496.2 (M+Na)+. HR-ESI MS cacld for $C_{22}H_{36}NO_8NaP$ (M+Na)+: 496.2071. Found: 496.2065.

(2S,3R)-4-[Di-(tert-butyl)-oxyphosphinyl]-Nhenylmethoxycarbonyl)-L-valine methyl ester (20). A solution of alcohol 18 (250 mg, 0.53 mmol), O-phenylchlorothionoformate (215 µL, 1.60 mmol), 4-(dimethylamino) pyridine (DMAP) (15 mg, 0.20 eq.) and N,N-diisopropylethylamine (363 µL, 2.10 mmol) in anhydrous $CH_2Cl_2$ (8.0 mL) was stirred at room temperature (overnight). The mixture was diluted with EtOAc (100 mL), washed (sat. $NaHCO_3$ and brine), dried ($Na_2SO_4$) and purified by silica gel column chromatography (hexanes:EtOAc) to give the intermediate thiocarbonate 19 as a pale brown wax (225 mg). Crude 19 was dissolved in toluene (10 mL) and to this was added tributyltin hydride (0.42 mL, 1.59 mmol) and azobisisobutyronitrile (AIBN) (one spatula tip). The mixture was maintained at 100° C. (20 minutes), then cooled to room temperature and concentrated under vacuum. The residue was purified by silica gel column chromatography (hexanes:EtOAc) to give 20 as viscous colorless oil (140 mg, 58% yield for 2 steps). $[\alpha]^{20}_D$+ 2.4 (c 0.85, $CHCl_3$). $^1$H NMR (400 MHz, $CDCl_3$) δ 7.27-7.20 (m, 5H), 5.80 (d, J=8.4 Hz, 1H), 5.07 (AB, $J_{AB}$=12.4 Hz, 1H), 5.02 (AB, $J_{AB}$=12.4 Hz, 1H), 4.23 (m, 1H), 3.67 (s, 3H), 2.33 (m, 1H), 1.69-1.10 (m, 20H), 1.05 (d, J=6.8 Hz, 3H). $^{13}$C NMR (100 MHz, $CDCl_3$) δ 172.1, 156.2, 136.3, 128.4, 128.1, 82.1, 66.9, 59.4, 52.2, 32.2, 30.3, 29.6, 27.8, 26.9, 17.5, 13.5. IR (KBr) $v_{max}$ 2976, 1720, 1535, 1322, 1252, 975 cm$^{-1}$. ESI (+VE) m/z: 480.3 (M+Na)+. HR-ESI MS cacld for $C_{22}H_{36}NO_7NaP$ (M+Na)+: 480.2122. Found: 480.2126.

(2S,3R)-4-[Di-(tert-butyl)-oxyphosphinyl]-N-[(9H-fluoren-9-ylmethoxy)carbonyl]-L-valine (4). To a solution of 20 (140 mg, 0.31 mmol) in THF (3.0 mL) and $H_2O$ (3.0 mL) at 0° C., was added $LiOH.H_2O$ (26 mg, 0.62 mmol) and the mixture was stirred room temperature (over night). The THF was removed by rotary evaporation and the residual aqueous phase was neutralized by addition of saturated aqueous $NH_4Cl$ (20 mL) and extracted with EtOAc (3×50 mL). The combined organic extract was washed with $H_2O$ (50 mL), brine (50 mL), dried ($Na_2SO_4$) and concentrated. The resulting residue was dissolved in MeOH (20 mL) and hydrogenated (1 atmosphere $H_2$) over 10% Pd—C (40 mg) at room temperature (over night). The catalyst was removed by filtration and the filtrate was concentrated. The resulting residue was dissolved in dioxane (5.0 mL) and $H_2O$ (5.0 mL) and 9-fluorenylmethyl-succinimidyl carbonate Fmoc-OSu (173 mg, 0.465 mmol) and $NaHCO_3$ (62 mg, 0.62 mmol) were added and the mixture was stirred at room temperature (over night). The reaction mixture was neutralized by addition of saturated $NH_4Cl$ (20 mL) and extracted with EtOAc (3×50 mL). The combined EtOAc layer was washed with $H_2O$ (50 mL), brine (50 mL), dried ($Na_2SO_4$) and purified by silica gel column chromatography ($CH_2Cl_2$: MeOH) to yield 4 as a white wax (166 mg, quantitative yield over 3 steps). $[\alpha]^{20}_D$+ 16.5 (c 0.65, $CHCl_3$). $^1$H NMR (400 MHz, DMS)-d6) δ 7.88 (d, J=7.6 Hz, 2H), 7.70 (d, J=7.2 Hz, 2H), 7.41 (t, J=7.4 Hz, 2H), 7.31 (t, J=7.6 Hz, 2H), 4.30-4.19 (m, 4H), 3.84 (m, 1H), 2.31 (m, 1H), 1.80-1.55 (m, 2H), 1.42 (s, 18H), 0.96 (d, J=6.4 Hz, 3H). $^{13}$C NMR (100 MHz, $CDCl_3$) δ 155.8, 143.9, 140.7, 127.6, 127.0, 125.1, 120.0, 80.7, 65.4, 60.5, 46.7, 31.5, 30.0, 16.9. ESI (+VE) m/z: 554.2 (M+Na)+. HR-ESI MS cacld for $C_{28}H_{38}NO_7NaP$ (M+Na)+: 554.2278. Found: 554.2277.

Peptide Synthesis 21-24. Fmoc-Thr(PO(OBzl)OH)—OH and other Fmoc protected amino acids were purchased from Novabiochem. Peptides were synthesize on NovaSyn® TGR resin (Novabiochem, cat. no. 01-64-0060) using standard Fmoc solid-phase protocols in N-Methyl-2-pyrrolidone (NMP). 1-O-Benzotriazole-N,N,N',N'-tetramethyl-uronium-hexafluoro-phosphate (HBTU) (5.0 eq.), hydroxybenzotriazole (HOBT) (5.0 eq.) and N,N-Diisopropylethylamine (DIPEA) (10.0 eq.) were used as coupling reagents. The N-terminal was acetylated by 1-Acetylimidazole. The final resin was washed with N,N-dimethylforamide (DMF), methanol, dichloromethane and ether then dried under vacuum (over night). Peptides were cleaved from resin (200 mg) by treatment with 5 mL of trifluoroacetic acid:triisbutyl-silane:$H_2O$ (90:5:5) (4 h). The resin was filtered off and the filtrate was concentrated under vacuum, then precipitated with ether and the precipitate washed with ether. The resulting solid was dissolved in 50% aqueous acetonitrile 5 mL) and purified by reverse phase preparative HPLC using a Phenomenex $C_{18}$ column (21 mm dia×250 mm, cat. no: 00G-4436-P0) with a linear gradient from 0% aqueous acetonitrile (0.1% trifluoroacetic acid) to 50% acetonitrile (0.1% trifluoroacetic acid) over 35 minutes at a flow rate of 10.0 mL/minute. Peptide 21: ESI (+VE) m/z: 595.3 (M+H)+. Peptide 22: ESI (+VE) m/z: 675.3 (M+H)+. Peptide 23: ESI (+VE) m/z: 673.3 (M+H)+. Peptide 24: ESI (+VE) m/z: 657.3 (M+H)+. Analytical HPLC [By using Phenomenex $C_{18}$ column (4.60 mm dia×250 mm, cat. no: 00G-4435-E0) with a linear gradient from 5% aqueous acetonitrile (0.1% trifluoroacetic acid) to 100% acetonitrile (0.1% trifluoroacetic acid) over 25 minutes at a flow rate of 1.0 mL/minute.] indicated the purity of peptide 21: 100%, peptide 22: 100%, peptide 23: 87%, peptide 24: 83%.

Example 12

Proline-Oxime and Proline-Ether Containing PDB-Binding Peptides

Figure 19:
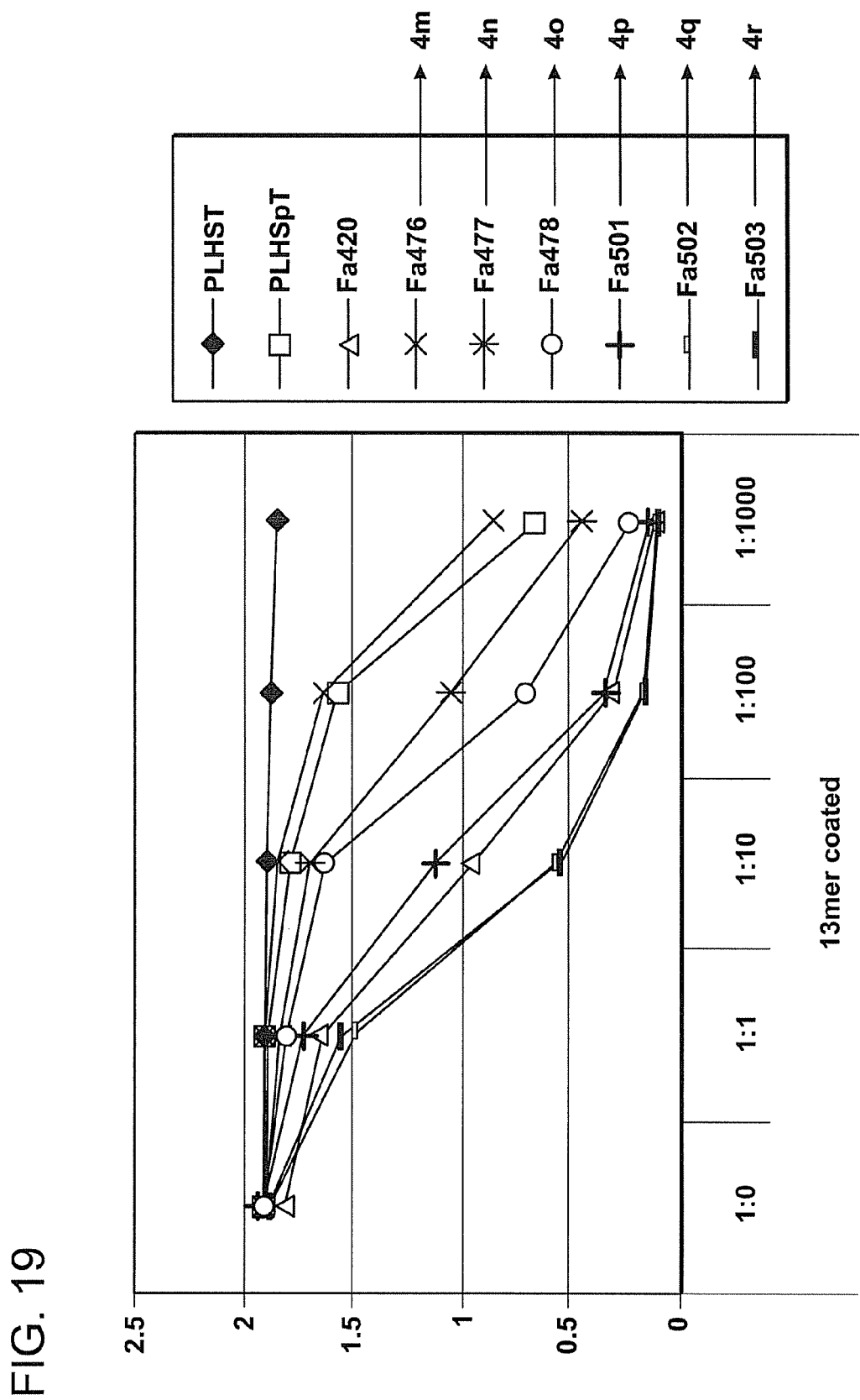
FIG. 19 ELISA screening of peptoid libraries. Results from the screening of the second round peptoid library by using ELISA assay.

Proline Oxime Derivatives. A focused oxime peptide library was conducted based on previously reported (Example 8) 4b (Example 8). These oximes were prepared from the aldehydes shown (below). Note that peptides 4i and 4j (resulting from aldehydes i and j) were previously included in Example 8. Of the series 4a-4p (4a-4j, being included in Example 8) peptides 4b, 4i and 4j gave the highest PBD-binding affinity. Peptide 4b (i.e., a carbon chain length of four units) represented the optimum linker length. To further optimize 4b, a "methyl scan" was performed (4k-4m), where methyl groups were substituted on the phenyl ring. Methyl groups at the ortho-, para-positions (4k and 4m, respectively) had little effect on binding affinity. However, a meta-methyl substitutent (4l) slightly increased the binding affinity. Three more meta-substituted analogues (4n-4p) were prepared, all gave similar binding potency as 4b; the 3-methoxy (4n) slightly increased the binding potency, and the 3-phenyl (4p) slightly decreased the binding potency (FIG. 19).

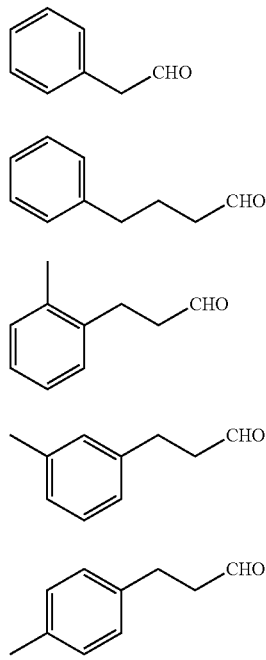

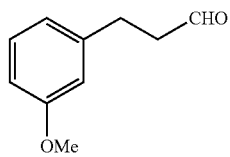

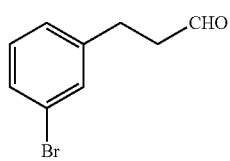

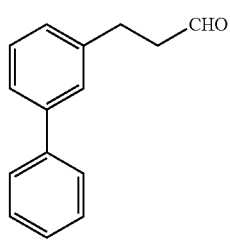

Aldehydes Used in the Second Round Focused Oxime Peptide Library

Proline Amidooxy and Ether Derivatives. To simplify further modification of 4b, the oxime bond was replaced with amidooxy or ether functionality. To prepare the amidooxy analogue 6, MTT was used as the aminooxy protective group instead of previous Boc. The MTT group can be cleaved by 1% TFA in DCM. Following amino deprotection amidation was achieved with hydrocinnamic acid. Unfortunately, the amide analogue 6 showed significantly decreased the binding affinity. The ether analogue 7 was also prepared using a pre-derivatized proline analogue. Surprisingly, the binding potency of 7 was enhanced compared to 4b. Therefore, 5b (Example 8) was converted to its ether format 8, which also gave higher binding affinity. The non-phosphate form of 7 (peptide 10), and S/A mutants of 7 and 8 (peptides 9 and 11) were also prepared, and these showed greater than 100 fold-loss of binding affinity or no affinity.

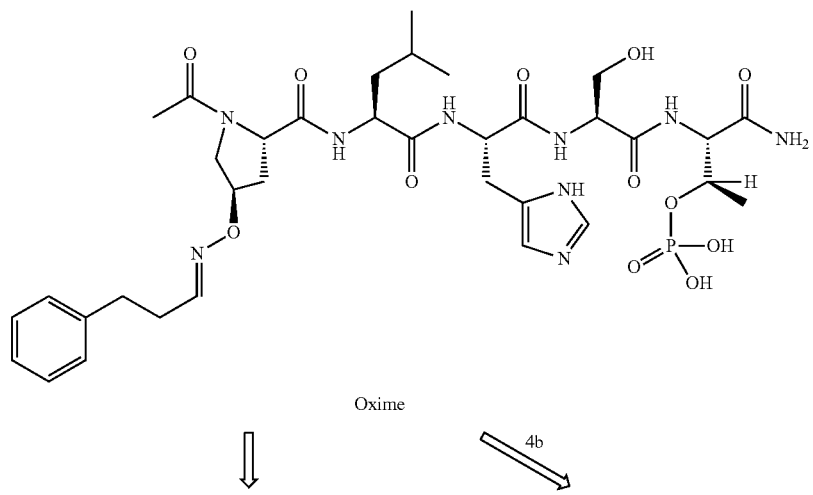

Oxime

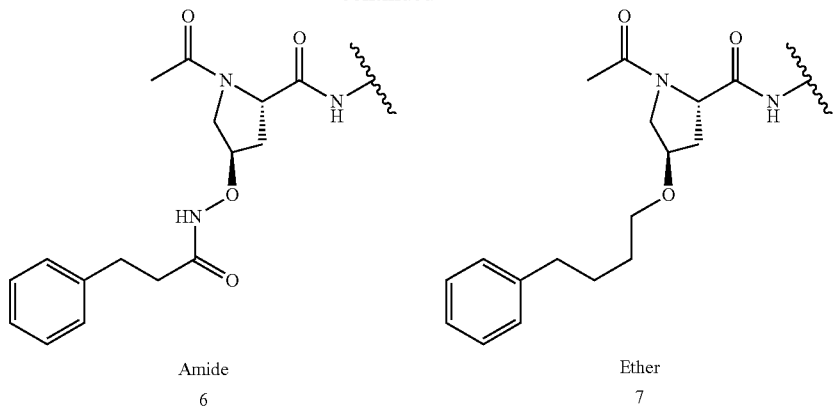
Amide 6
Ether 7
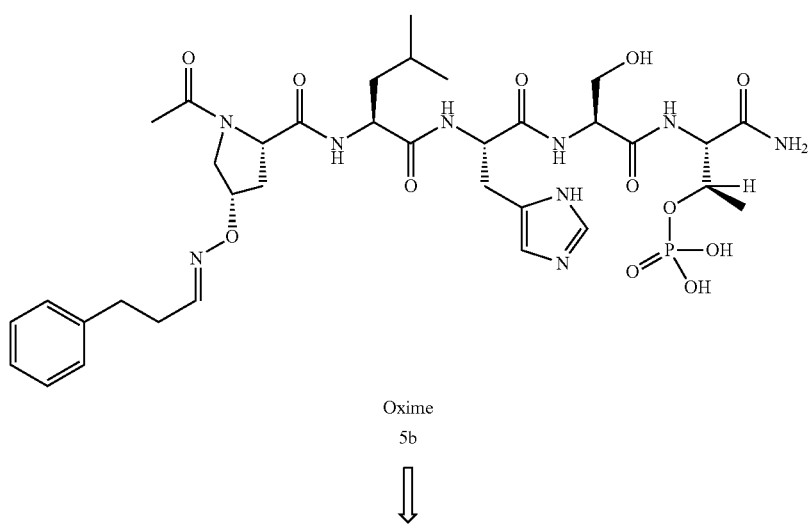
Oxime 5b
⇩
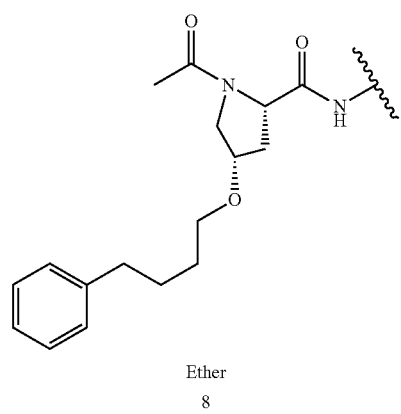
Ether 8

Oxime bond replacements.
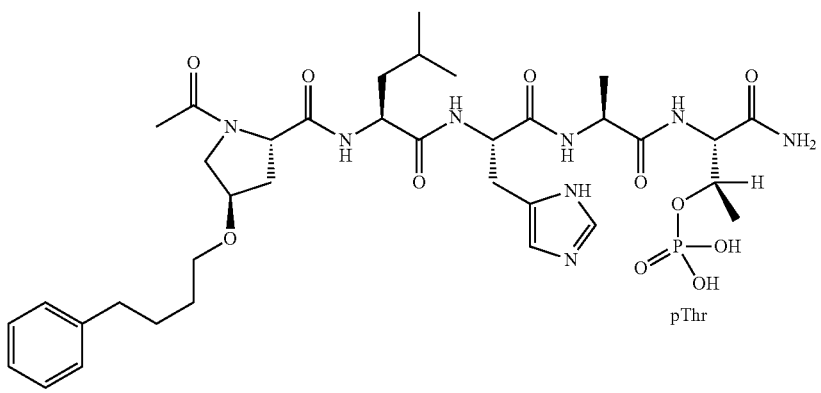
9
pThr
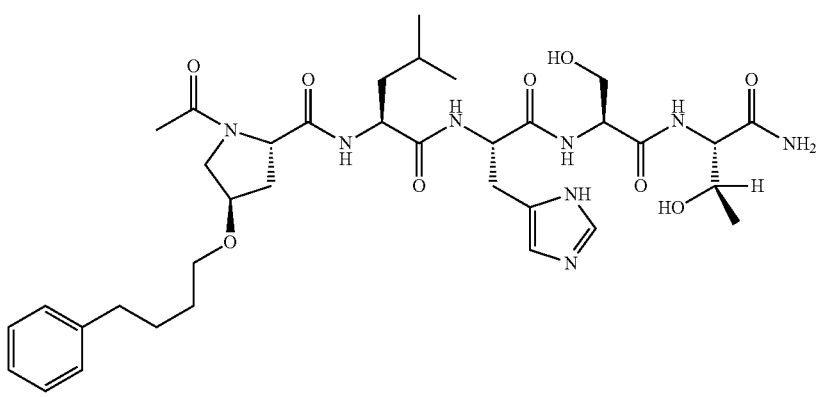
10
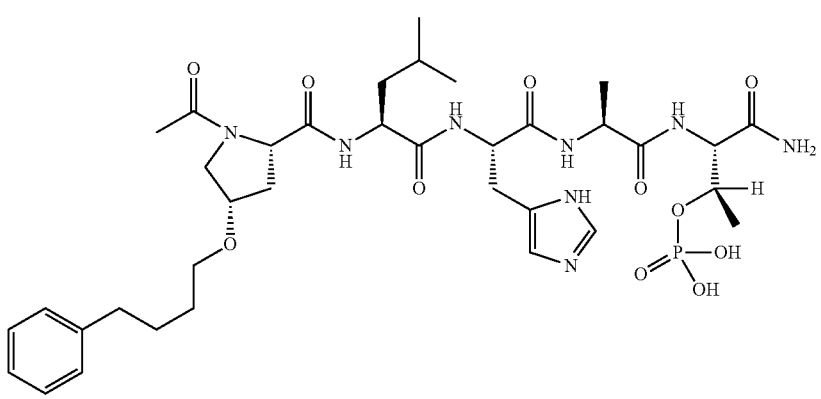
11

Non-Phosphate Peptide and S/A Mutants
Determination of Plk1 PBD Selectivity Relative to Plk2 and Plk3 PBDs
The following peptides were prepared for pull-down experiments intended to measure relative affinities to PBDs of Plk1, Plk2 and Plk3.
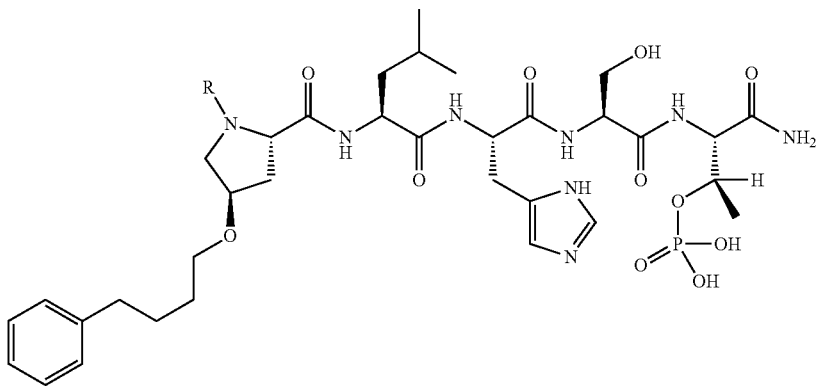
11
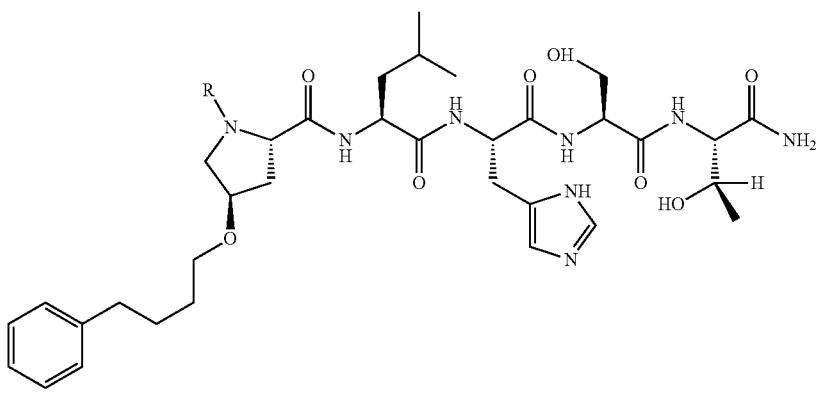
12
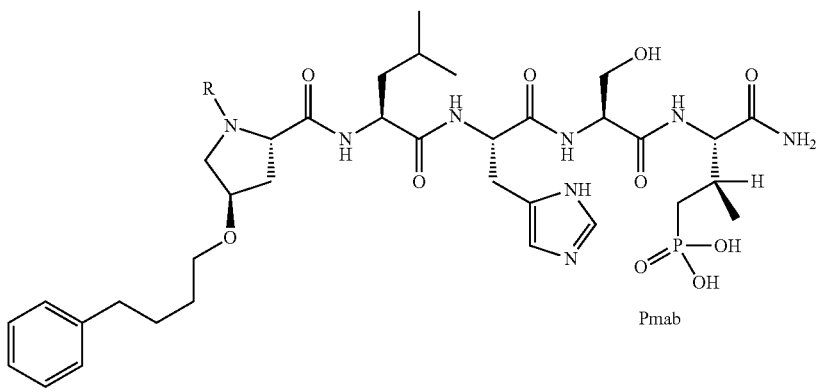
13
Pmab

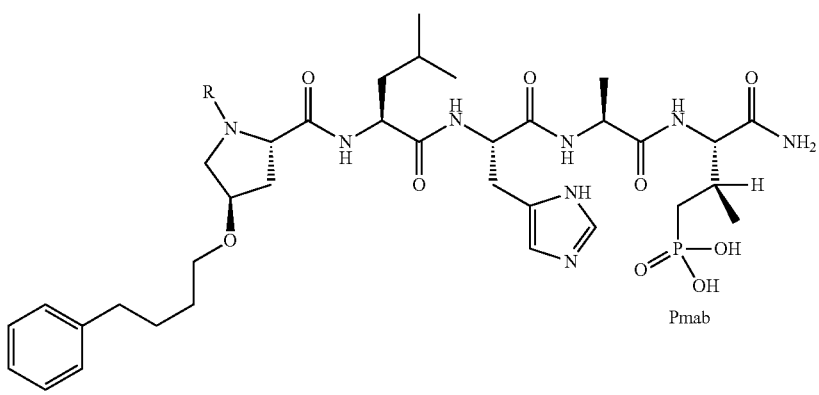

Pmab — 14

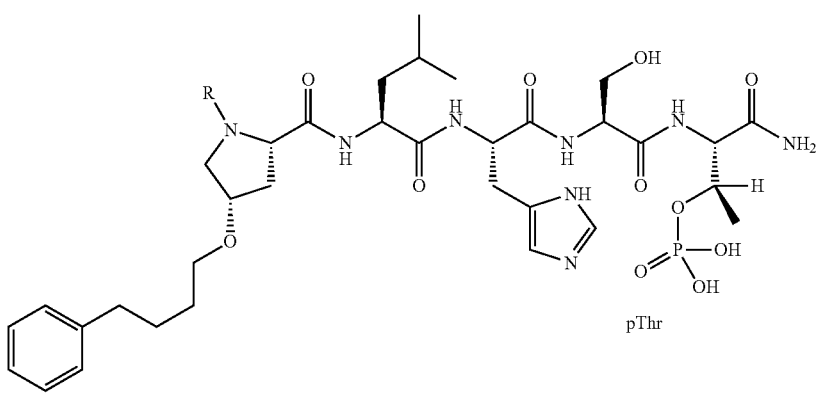

pThr — 15

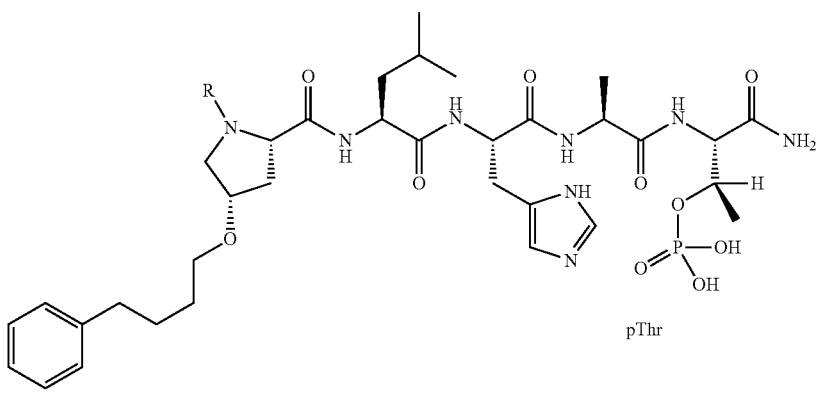

pThr — 16

R = Cys-Ahx

Cys-Ahx-Linker Containing Peptides for Plk Specifity Test

Peptide synthesis procedures, preparation of 3-5. Protected aminooxy proline 1 and 2 were prepared as reported, Fmoc-Thr(PO(OBzl)OH)—OH and other Fmoc protected amino acids were purchased from Novabiochem. Peptides were synthesize on NovaSyn®TGR resin (Novabiochem, cat. no. 01-64-0060) using standard Fmoc solid-phase protocols in N-Methyl-2-pyrrolidone (NMP). 1-O-Benzotriazole-N,N,N',N'-tetramethyl-uronium-hexafluoro-phosphate (HBTU) (5.0 eq.), hydroxybenzotriazole (HOBT) (5.0 eq.) and N,N-Diisopropylethylamine (DIPEA) (10.0 eq.) were used as coupling reagents. The N-terminal was acetylated by 1-Acetylimidazole. The final resin was washed with N,N-dimethylforamide (DMF), methanol, dichloromethane and ether then dried under vacuum (over night). Peptides were cleaved from resin (200 mg) by treatment with 5 mL of trifluoroacetic acid:triisbutylsilane:$H_2O$ (90:5:5) (4 h). The resin was filtered off and the filtrate was concentrated under vacuum, then precipitated with ether and the precipitate washed with ether. The resulting solid was dissolved in 50% aqueous acetonitrile 5 mL) and purified by reverse phase preparative HPLC using a Phenomenex $C_{18}$ column (21 mm dia×250 mm, cat. no: 00G-4436-P0) with a linear gradient from 0% aqueous acetonitrile (0.1% trifluoroacetic acid) to 100% acetonitrile (0.1% trifluoroacetic acid) over 30 minutes at a flow rate of 10.0 mL/minute. Lyophilization gave the products as white powders.

Post Solid-Phase Diversification, preparation of 4a-4p, 5a-5j. A mixture of HPLC-purified aminooxy-proline containing peptide (4, 5) (15 mM in DMSO, 10 μL), aldehdye (a-p) (15 mM in DMSO, 10 μL) and acetic acid (70 mM in DMSO, 10 μL) was gently agitated at room temperature (over night). Crude reaction mixtures were used directly for biological evaluation.

TABLE 7

Low resolution ESI-Mass Spec.

| | Expected (M + H)+ | Observed (M + H)+ | Expected (M − H)− | Observed (M − H)− |
|---|---|---|---|---|
| 3 | | | 675.3 | 675.3 |
| 4 | | | 706.3 | 706.6 |
| 5 | | | 706.3 | 706.6 |

Chemical Formula: $C_{26}H_{44}N_9O_{12}P$
Exact Mass: 705.2847
Molecular Weight: 705.6544

| | Expected (M + H)⁺ | Observed (M + H)⁺ | Expected (M − H)⁻ | Observed (M − H)⁻ |
|---|---|---|---|---|
| 4b | | | 822.3 | 822.3 |
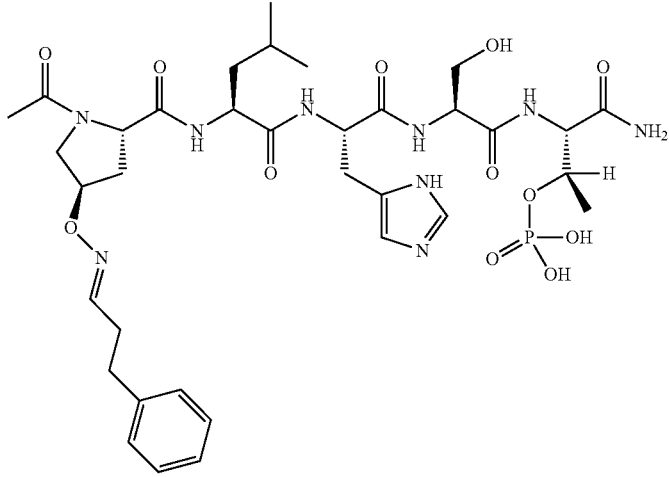
Chemical Formula: C$_{35}$H$_{52}$N$_9$O$_{12}$P
Exact Mass: 821.3473
Molecular Weight: 821.8142
| | | | | |
|---|---|---|---|---|
| 5b | | | 822.3 | 822.3 |
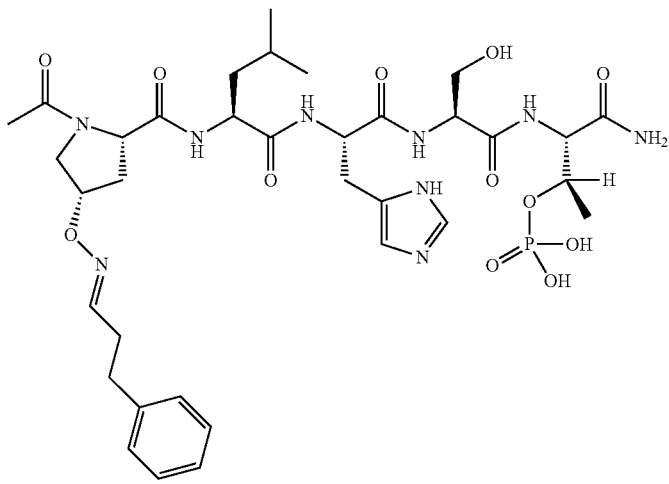
Chemical Formula: C$_{35}$H$_{52}$N$_9$O$_{12}$P
Exact Mass: 821.3473
Molecular Weight: 821.8142

TABLE 7-continued
Low resolution ESI-Mass Spec.
| | Expected (M + H)⁺ | Observed (M + H)⁺ | Expected (M − H)⁻ | Observed (M − H)⁻ |
|---|---|---|---|---|
| 6 | 838.3 | 838.3 | | |
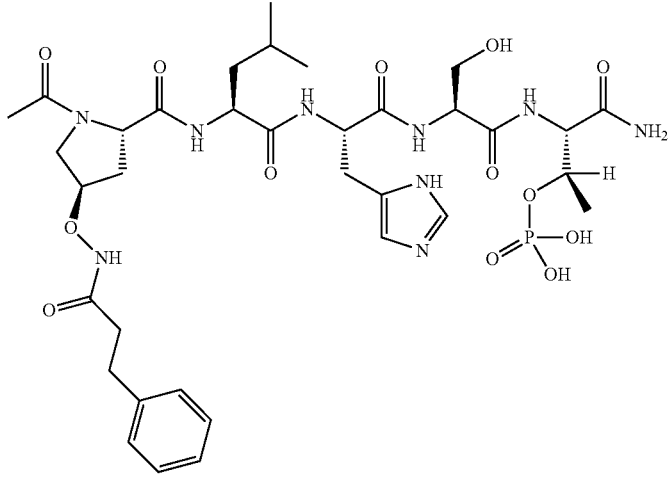
Chemical Formula: $C_{35}H_{52}N_9O_{13}P$
Exact Mass: 837.3422
Molecular Weight: 837.8136
| | | | | |
|---|---|---|---|---|
| 7 | 823.4 | 823.3 | | |
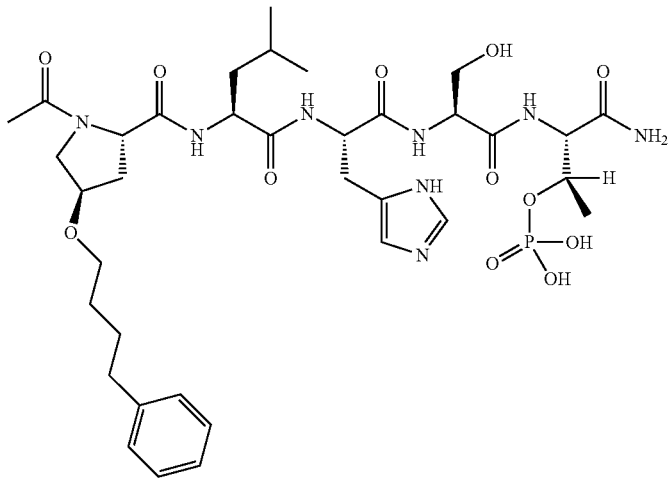
Chemical Formula: $C_{36}H_{55}N_8O_{12}P$
Exact Mass: 822.3677
Molecular Weight: 822.8421

TABLE 7-continued

Low resolution ESI-Mass Spec.

| | Expected (M + H)⁺ | Observed (M + H)⁺ | Expected (M − H)⁻ | Observed (M − H)⁻ |
|---|---|---|---|---|
| 8 | 823.4 | 823.5 | 821.4 | 821.4 |

Chemical Formula: $C_{36}H_{55}N_8O_{12}P$
Exact Mass: 822.3677
Molecular Weight: 822.8421

| | | | | |
|---|---|---|---|---|
| 11 | 997.5 | 997.3 | 995.5 | 994.6 |

Chemical Formula: $C_{43}H_{69}N_{10}O_{13}PS$
Exact Mass: 996.4504
Molecular Weight: 997.1059

| | | | | |
|---|---|---|---|---|
| 12 | 917.5 | 917.4 | | |

Chemical Formula: $C_{43}H_{68}N_{10}O_{10}S$
Exact Mass: 916.4841
Molecular Weight: 917.1260

TABLE 7-continued
Low resolution ESI-Mass Spec.
| | Expected (M + H)$^+$ | Observed (M + H)$^+$ | Expected (M − H)$^-$ | Observed (M − H)$^-$ |
|---|---|---|---|---|
| 9 | 807.4 | 807.4 | 805.4 | 805.4 |
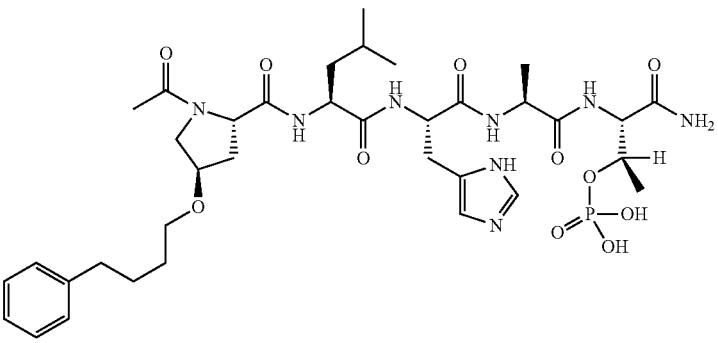
Chemical Formula: $C_{36}H_{55}N_8O_{11}P$
Exact Mass: 806.3728
Molecular Weight: 806.8427
| | | | | |
|---|---|---|---|---|
| 10 | 743.4 | 743.2 | | |
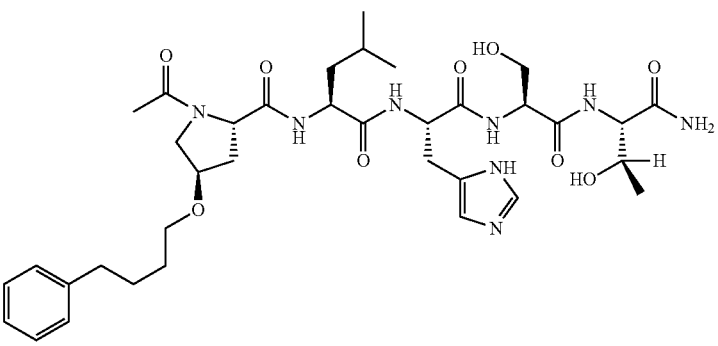
Chemical Formula: $C_{36}H_{54}N_8O_9$
Exact Mass: 742.4014
Molecular Weight: 742.8622
| | | | | |
|---|---|---|---|---|
| 17 | 821.4 | 821.4 | 819.4 | 819.3 |
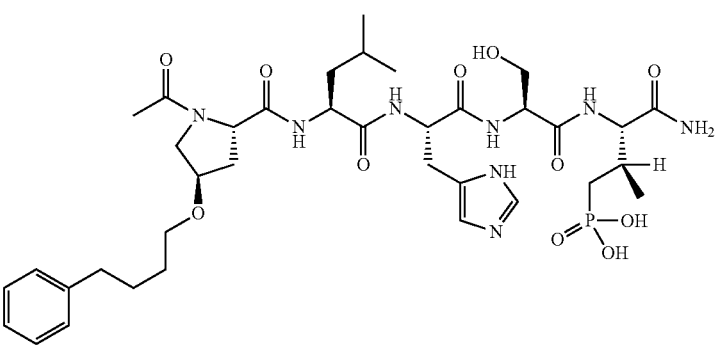
Chemical Formula: $C_{37}H_{57}N_8O_{11}P$
Exact Mass: 820.3884
Molecular Weight: 820.8692

TABLE 7-continued
| | | Expected (M + H)⁺ | Observed (M + H)⁺ | Expected (M − H)⁻ | Observed (M − H)⁻ |
|---|---|---|---|---|---|
| 13 | 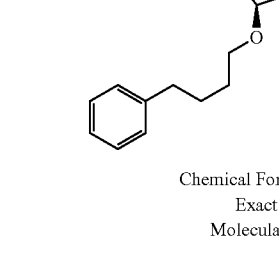 Chemical Formula: C$_{44}$H$_{71}$N$_{10}$O$_{12}$PS<br>Exact Mass: 994.4711<br>Molecular Weight: 995.1331 | 995.4 | 995.2 | 993.5 | 992.7 |
| 18 | 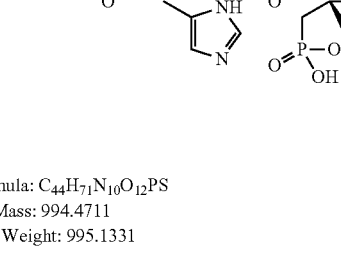 Chemical Formula: C$_{37}$H$_{57}$N$_8$O$_{10}$P<br>Exact Mass: 804.3935<br>Molecular Weight: 804.8698 | 805.4 | 805.3 | 803.4 | 803.4 |
| 14 | 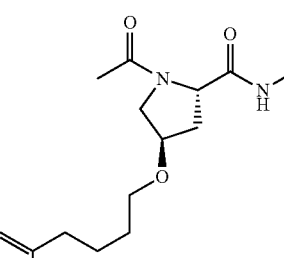 Chemical Formula: C$_{44}$H$_{71}$N$_{10}$O$_{11}$PS<br>Exact Mass: 978.4762<br>Molecular Weight: 979.1337 | 979.5 | 979.3 | 977.5 | 976.6 |

TABLE 7-continued
Low resolution ESI-Mass Spec.
| | Expected (M + H)+ | Observed (M + H)+ | Expected (M − H)− | Observed (M − H)− |
|---|---|---|---|---|
| 15 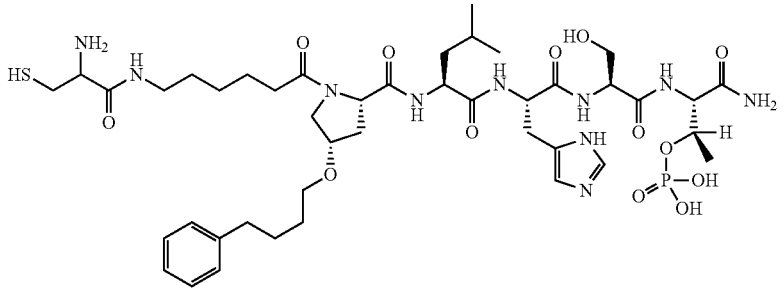 Chemical Formula: $C_{43}H_{69}N_{10}O_{13}PS$<br>Exact Mass: 996.4504<br>Molecular Weight: 997.1059 | 997.5 | 997.5 | 995.5 | 995.4 |
| 11 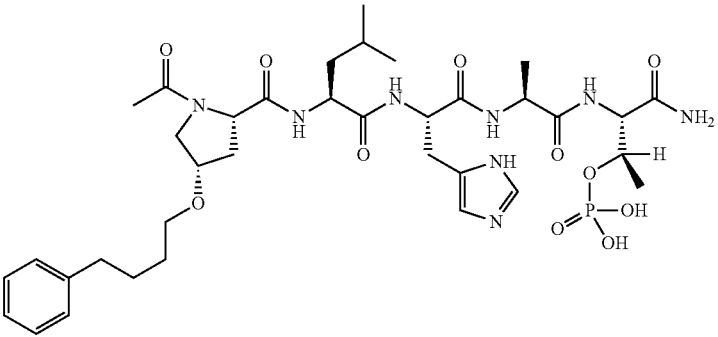 Chemical Formula: $C_{36}H_{55}N_8O_{11}P$<br>Exact Mass: 806.3728<br>Molecular Weight: 806.8427 | 807.4 | 807.4 | 805.4 | 805.3 |
| 16 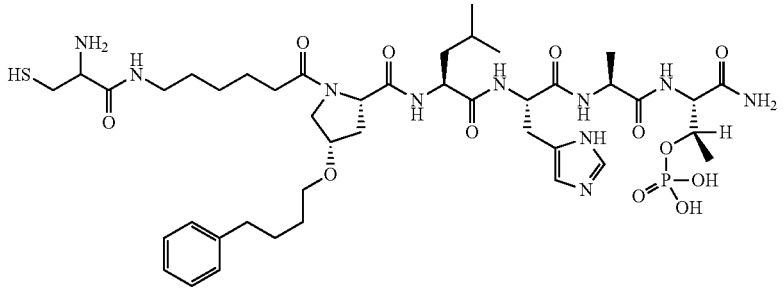 Chemical Formula: $C_{43}H_{69}N_{10}O_{12}PS$<br>Exact Mass: 980.4555<br>Molecular Weight: 981.1065 | 981.5 | 981.4 | 979.5 | 979.5 |

TABLE 8

HRMS of selected peptides.

| | Expected (M + H)⁺ | Observed (M + H)⁺ | Expected (M − H)⁻ | Observed (M − H)⁻ |
|---|---|---|---|---|
| 4 (structure) Chemical Formula omitted | | | C26H43N9O12P | 704.2745 |
| | | | 704.2774 | |
| 5 (structure) Chemical Formula: $C_{26}H_{44}N_9O_{12}P$; Exact Mass: 705.2847; Molecular Weight: 705.6544 | | | C26H43N9O12P 704.2774 | 704.2787 |
| 4b (structure) Chemical Formula: $C_{35}H_{52}N_9O_{12}P$; Exact Mass: 821.3473; Molecular Weight: 821.8142 | C35H53N9O12P 822.3546 | 822.3551 | | |
| 5b (structure) Chemical Formula: $C_{35}H_{52}N_9O_{12}P$; Exact Mass: 821.3473; Molecular Weight: 821.8142 | | | C35H51N9O12P 820.3400 | 820.3357 |

TABLE 8-continued
HRMS of selected peptides.
| | | Expected (M + H)+ | Observed (M + H)+ | Expected (M − H)− | Observed (M − H)− |
|---|---|---|---|---|---|
| 7 | 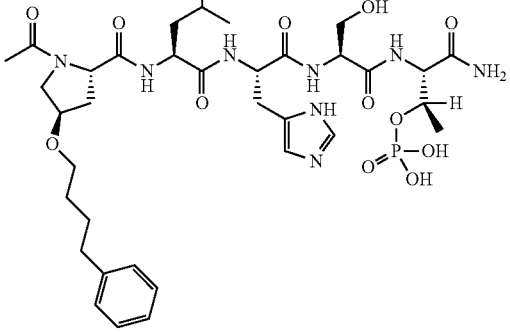 Chemical Formula: $C_{36}H_{55}N_8O_{12}P$<br>Exact Mass: 822.3677<br>Molecular Weight: 822.8421 | | | $C_{36}H_{54}N_8O_{12}P$<br>821.3604 | 821.3590 |
| 8 | 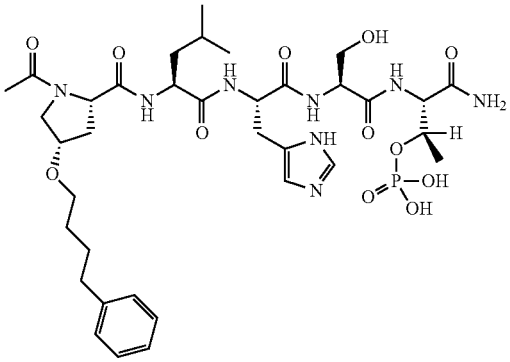 Chemical Formula: $C_{36}H_{55}N_8O_{12}P$<br>Exact Mass: 822.3677<br>Molecular Weight: 822.8421 | | | $C_{36}H_{54}N_8O_{12}P$<br>821.3604 | 821.3585 |
| 17 | 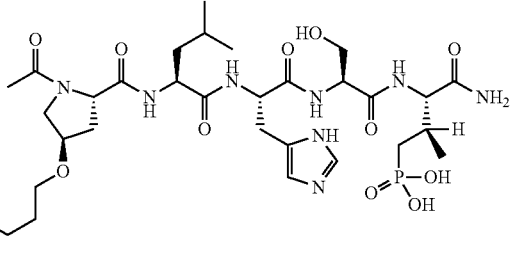 Chemical Formula: $C_{37}H_{57}N_8O_{11}P$<br>Exact Mass: 820.3884<br>Molecular Weight: 820.8692 | | | $C_{37}H_{58}N_8O_{11}P$<br>821.3957 | 821.3977 |

TABLE 8-continued

HRMS of selected peptides.

| | | Expected (M + H)+ | Observed (M + H)+ | Expected (M − H)− | Observed (M − H)− |
|---|---|---|---|---|---|
| 18 | 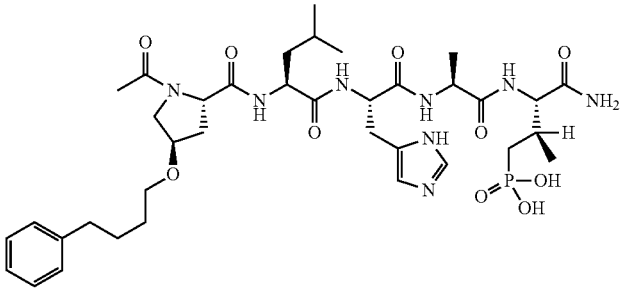 Chemical Formula: $C_{37}H_{57}N_8O_{10}P$<br>Exact Mass: 804.3935<br>Molecular Weight: 804.8698 | C37H58N8O10P<br>805.4008 | 805.4033 | | |

Preparation of Proline Analogues 22 and 24

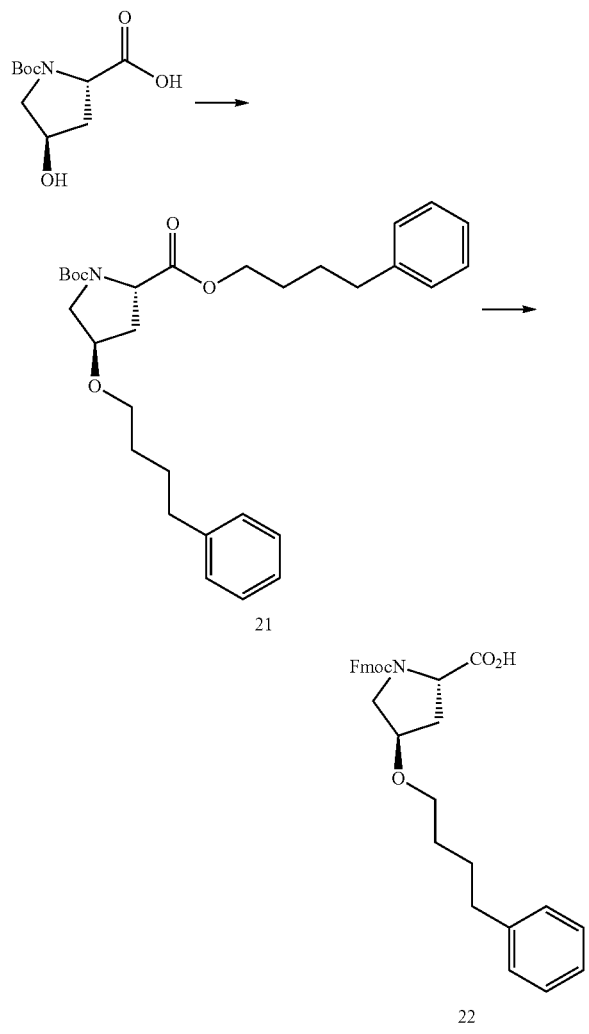

4-Phenyl-1-iodobutane was prepared from 4-phenyl-1-butanol

To a suspension of sodium hydride (60% in mineral oil, 1.90 g, 47.5 mmol) in DMF (30 mL) at 0° C., was added a solution of Boc-L-hydroxyproline (5.0 g, 21.6 mmol) in DMF (30 mL) dropwisely during 5 min. The mixture was kept at 0° C. for another 15 min before the addition of 4-phenyl-1-iodobutane (16.9 g, 64.8 mmol), then stirred overnight from 0° C. to r.t. The reaction was quenched by sat. NH$_4$Cl (50 mL), extracted with EtOAc (300 mL). The organic layer was washed, dried and purified by and column chromatography (hexanes:EtOAc) to yield 21 as a colorless oil (5.1 g, 48% yield). $^1$H NMR (400 MHz, CDCl$_3$) δ 7.26-7.23 (m, 5H), 7.16-7.13 (m, 5H), 4.34 (dd, J=8.0, 6.4 Hz, 0.3H), 4.27 (t, J=7.6 Hz, 0.7H), 4.14-4.08 (m, 2H), 3.98 (m, 1H), 3.60-3.55 (m, 2H), 3.42-3.33 (m, 2H), 2.65-2.58 (m, 4H), 2.25 (m, 1H), 1.98 (m, 1H), 1.70-1.60 (m, 8H), 1.41 (s, 3.5H), 1.36 (s, 5.5H).

A mixture of 21 (5.00 g, 10.1 mmol) and LiOH monohydrate (848 mg, 20.2 mmol) in THF (30 mL), MeOH (10 mL) and H$_2$O (15 mL) was stirred at r.t. for 3 hr. The organic solvent was removed by rotary evaporator; the aqueous phase was washed with ether (50 mL×2), then acidified to pH 3-4 by 1N HCl, extracted with EtOAc (150 mL). The EtOAc layer was washed, dried (NaSO$_4$) and evaporated to a colorless oil, which was treated by a mixture of TFA (30 mL) and dichloromethane (30 mL) for 2 hr at r.t. The solvent was removed, and the left residue was dried under oil pump for 2 hr. This residue was dissolved in dioxane (30 mL) and H$_2$O (30 mL), followed by the addition of NaHCO$_3$ (4.20 g, 50.0 mmol) and FmocOSu (3.71 g, 11.0 mmol), and stirred at r.t. overnight. Dioxane was removed by rotary evaporator, the left aqueous was washed by ether (50 mL×20), acidified to pH 3-4 by 1 N HCl, extracted by EtOAc (200 mL). The EtOAc layer was washed (brine), dried (NaSO$_4$) and evaporated to give analytical pure 22 as a thick oil (5.1 g, 100% yield). $^1$H NMR (400 MHz, CDCl$_3$) δ 10.36 (brs, 1H), 7.74 (d, J=7.6 Hz, 1H), 7.68 (d, J=7.6 Hz, 1H), 7.57-7.46 (m, 2H), 7.40-7.22 (m, 7H), 7.18-7.12 (m, 2H), 4.49 (t, J=7.6 Hz, 0.5H), 4.45-4.32 (m, 2.5H), 4.24 (t, J=7.2 Hz, 0.5 Hz), 4.15-4.00 (m, 1.5H), 3.70 (m, 0.40H), 3.60-3.55 (m, 1.6H), 3.44-3.34 (m, 2H), 2.64-2.57 (m, 2H), 2.35 (m, 1H), 0.86 (m, 1H), 1.70-1.55 (m, 4H). $^{13}$C NMR (100 MHz, CDCl$_3$) δ 177.7, 176.5, 171.8, 159.1, 158.6, 155.9, 154.9, 143.7, 142.2, 141.3, 128.4, 128.3, 127.1, 119.9, 76.8, 76.2, 69.2, 68.0, 60.7, 58.1, 57.5, 52.0, 51.7, 47.1, 36.8, 35.6, 35.0, 29.3, 27.9, 21.0, 14.1.

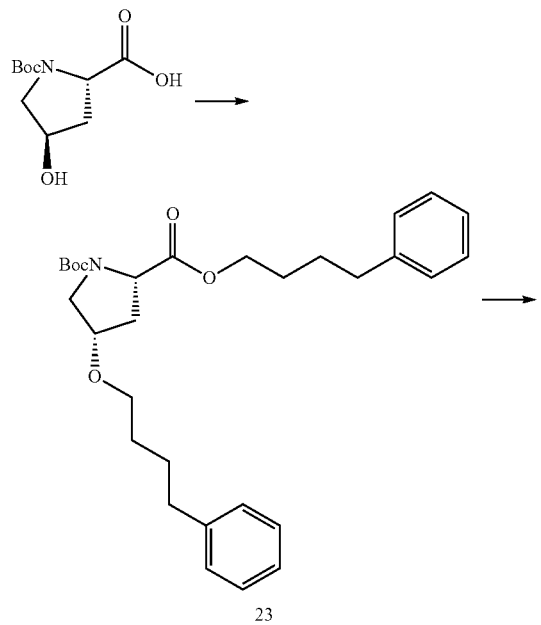

23 was prepared from N-Boc-cis-4-hydroxy-L-proline in 29% yield by using the same method described above for the preparation of 21. $^1$H NMR (400 MHz, CDCl$_3$) δ 7.28-7.22 (m, 5H), 7.18-7.12 (m, 5H), 4.39 (dd, J=8.4, 3.6 Hz, 0.4H), 4.27 (dd, J=8.4, 4.0 Hz, 0.6H), 4.15-3.98 (m, 2H), 3.93 (m, 1H), 3.63 (m, 0.60H), 3.55 (dd, J=11.2, 5.2 Hz, 0.4H), 3.43 (ddd, J=18.4, 11.6, 3.2 Hz, 1H), 3.36-3.28 (m, 2H), 2.65-2.55 (m, 4H), 2.30-2.15 (m, 2H), 1.70-1.55 (m, 6H), 1.55-1.46 (m, 2H), 1.45 (s, 3.5H), 1.40 (s, 5.5H). $^{13}$C NMR (100 MHz, CDCl$_3$) δ 172.3, 172.0, 154.2, 153.8, 142.3, 142.1, 141.9, 128.3, 125.8, 79.9, 79.8, 77.4, 76.3, 68.9, 64.8, 57.8, 57.4, 52.0, 51.4, 36.2, 35.7, 35.4, 35.0, 29.4, 28.4, 28.3, 28.1, 27.9, 27.6.

24 was prepared from 23 in 30% yield by using the same method described above for the preparation of 22. $^1$H NMR (400 MHz, CDCl$_3$) δ 8.70 (brs, 1H), 7.73 (d, J=7.6 Hz, 1H), 7.69 (d, J=7.2 Hz, 1H), 7.60-7.50 (m, 2H), 7.40-7.25 (m, 7H), 7.17-7.10 (m, 2H), 4.50-4.43 (m, 1.6H), 4.40-4.30 (m, 1.4H), 4.23 (m, 0.60H), 4.17 (m, 0.40H), 4.00 (m, 1H), 3.63-3.53 (m, 2H), 3.45 (m, 0.5H), 3.40-3.30 (m, 1.5H), 2.60-2.53 (m, 2H), 2.42 (m, 0.5H), 2.30 (m, 1H), 2.20 (m, 0.5H), 1.70-1.50 (m, 4H). $^{13}$C NMR (100 MHz, CDCl$_3$) δ 175.8, 174.5, 155.7, 143.9, 143.6, 142.3, 141.3, 128.3, 127.8, 127.0, 125.7, 125.0, 120.0, 76.3, 68.8, 67.8, 60.4, 58.1, 57.6, 52.2, 47.1, 36.0, 35.5, 34.1, 31.6, 29.1, 27.8, 25.4, 22.6, 21.0, 14.4.

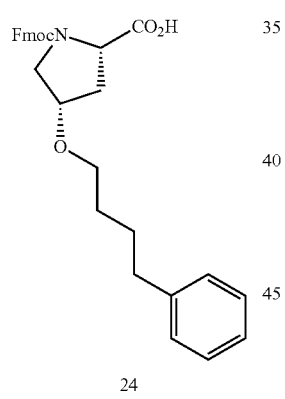

Example 13

Design, Synthesis and Biological Evaluation of Further Peptoid-Peptide Hybrids

Synthesis of NSG-containing libraries was achieved by the "submonomer approach," in which the N-terminal Leu residue of peptide 1 on the resin was firstly bromoacetylated to yield resin 2, and then treated with various amines to yield the corresponding NSG containing peptoid-peptide hybrids 3 on the resin. Acetylation and acidic cleavage provided the final peptoid-peptide hybrids 4. (Figure below)

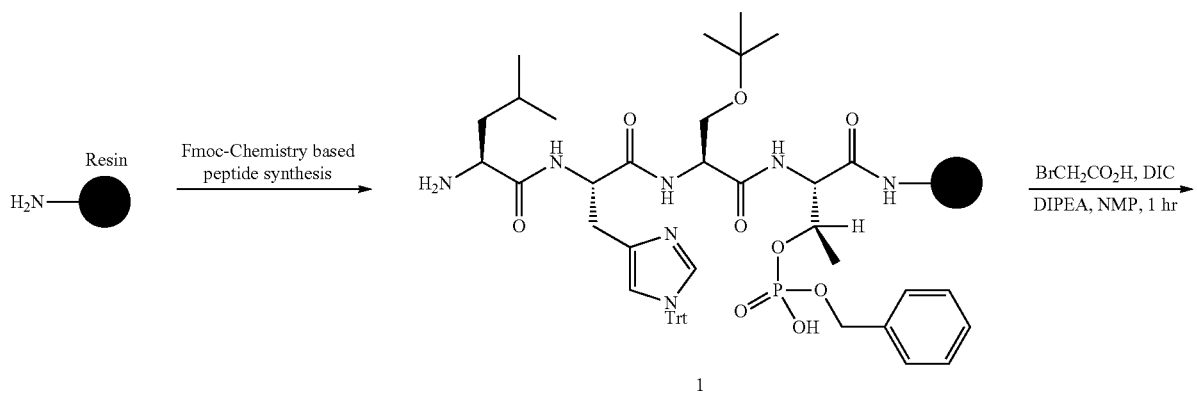

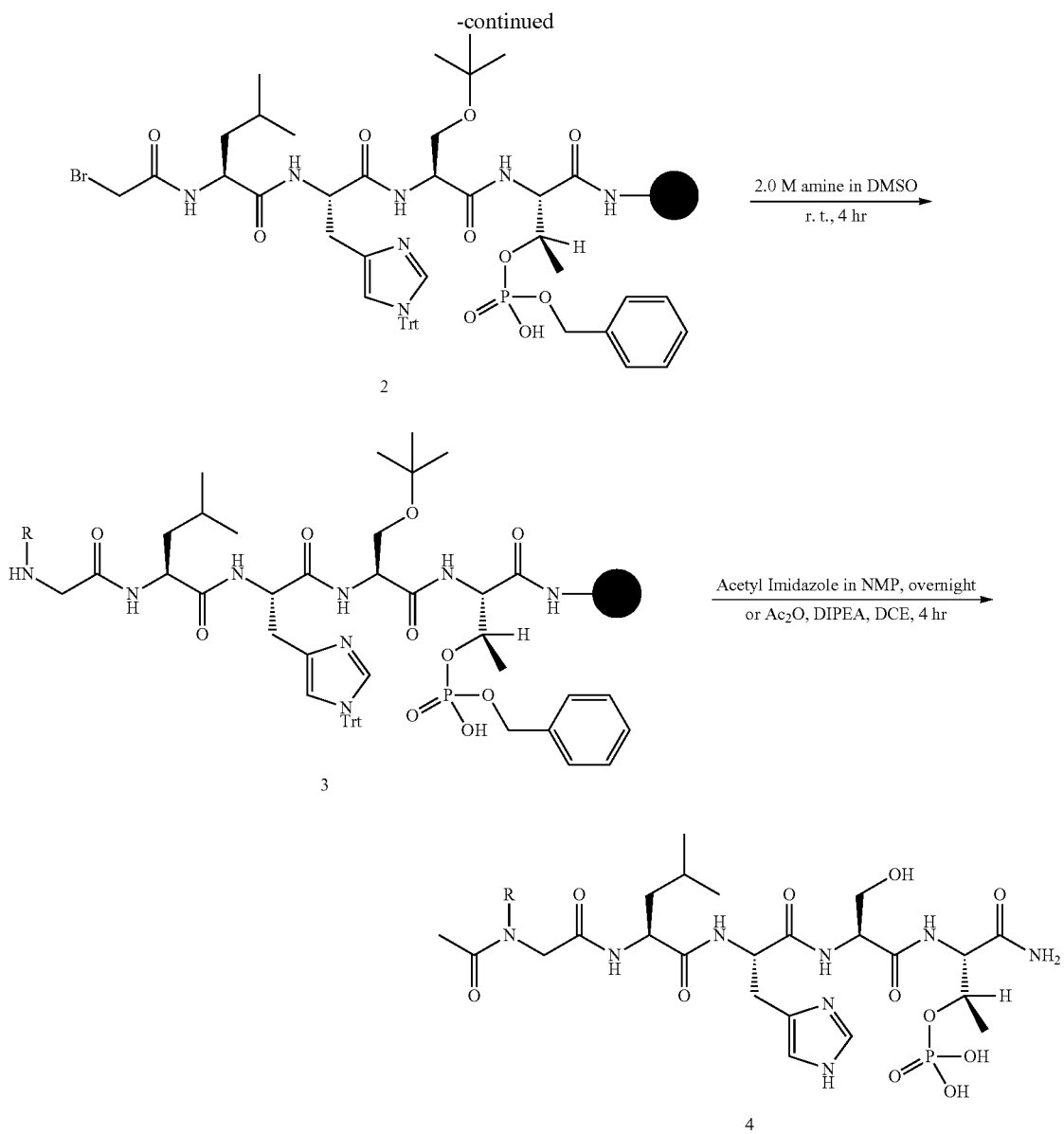

Preparation of Peptide-Peptoid Hybrid Using the "Submonomer Approach"

ELISA based Plk1 PBD-binding inhibition assays were conducted in the presence of 5 different concentrations of these peptoid-peptide hybrids (see Example 8). Hybrids 4d and 4e had dramatically diminished binding affinity, which indicated that both positive and negative charges are not tolerated at this position. As compared to the WT 5-mer (Ac-PLHSpT-NH$_2$), hybrids 4a, 4c and 4j (substituents as indicated in the Figure below) showed slightly higher binding affinity, while 11f and 11i showed similar affinity and the remaining analogues were weaker binders.

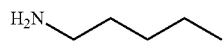

a

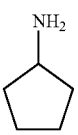

b

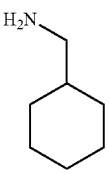

c d 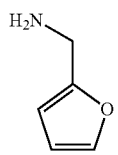

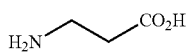

e 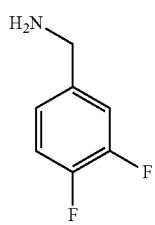

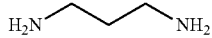

f 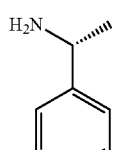

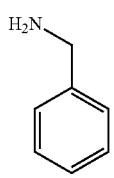

g 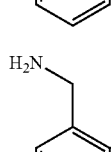

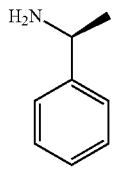

Structures of Amines Used to Prepare
Peptide-Peptoid Hybrid 4

Based on the above results that non-charged hydrophobic group is preferred, while too bulky group compromised the binding affinity, we further explored the phenyl group linked by a serious of linkers with gradually increased length. Surprisingly, the binding potency of this serious of peptoid-peptide hybrids (4f and 4m-4r) increased along with the linker length, 4q and 4r gave the highest potency according to the ELISA assay results (FIG. 19). Peptide 5, Ser to Ala mutant of 4q, is not active.

h $NH_2—(CH_2)_2$-Ph, m  $NH_2—(CH_2)_5$-Ph, p
$NH_2—(CH_2)_3$-Ph, n  $NH_2—(CH_2)_6$-Ph, q
$NH_2—(CH_2)_4$-Ph, o  $NH_2—(CH_2)_7$-Ph, r

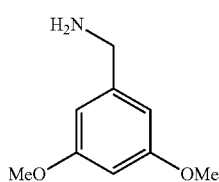

Structures of Amines Used to Further Explore
Peptide-Peptoid Hybrid 4

5

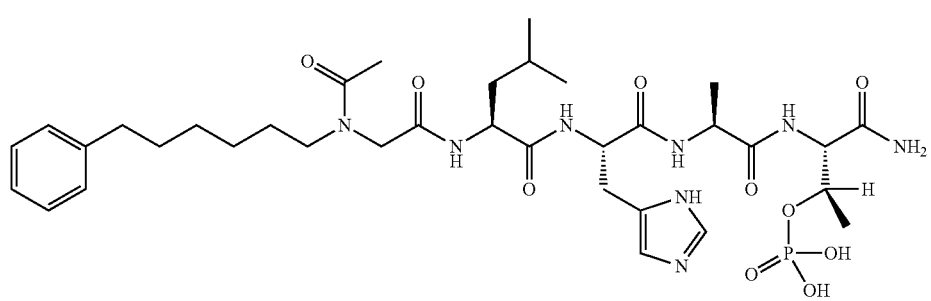

Ser to Ala Mutant of 4q

A tetra-peptide 6 with the same linker length as 4q was prepared and gave same binding potency as 4q. Click chemistry was attempted to partially restrict the flexibility of the long linker in 6. Alkyne containing peptide 7 was prepared on the resin, the following Cu(I) catalyzed 1,4-Huisgen cyclization with azides followed by resin cleavage gave 8 and 9. Conventional heat (100° C. in DMF, 2 days) condition gave a mixture of 1,4 and 1,5-triazole product, therefore provided analogue 10 and 11. But all of these peptides (8-11) gave diminished binding potency (see below).

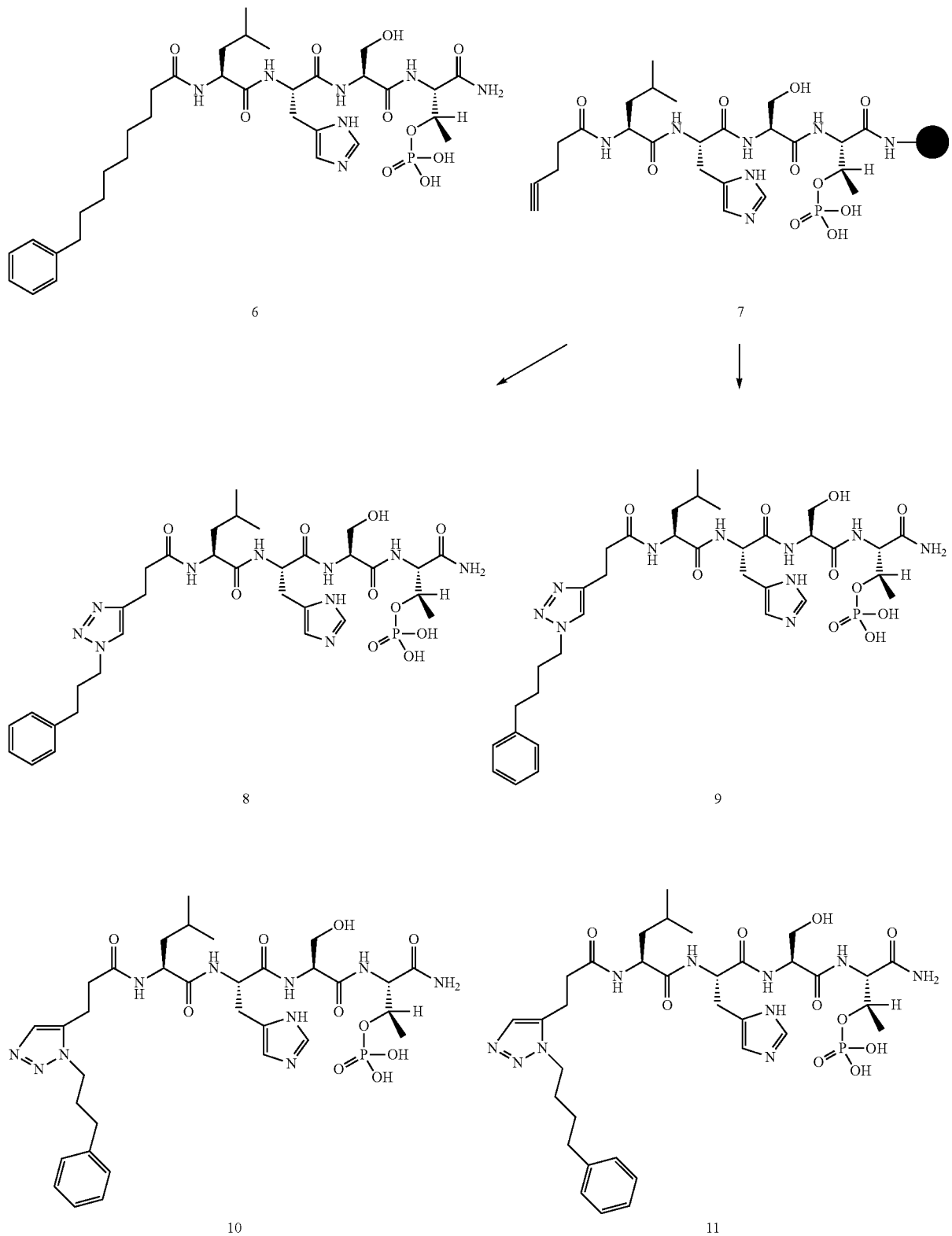

Modification by Using Click Chemistry

Plk1 Specificity Test.

Peptides 12-15 have been prepared for further biological evaluations.

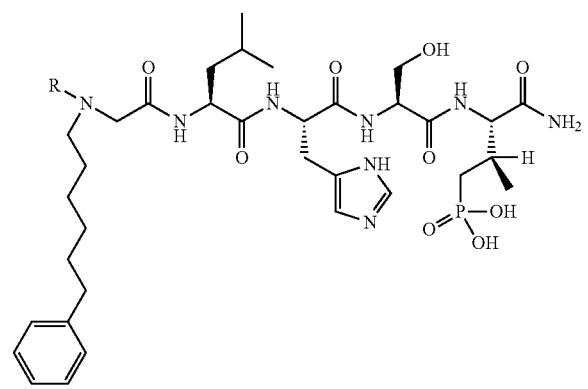

Pmab
12: R = Acetyl
13: R = Cys-Ahx-

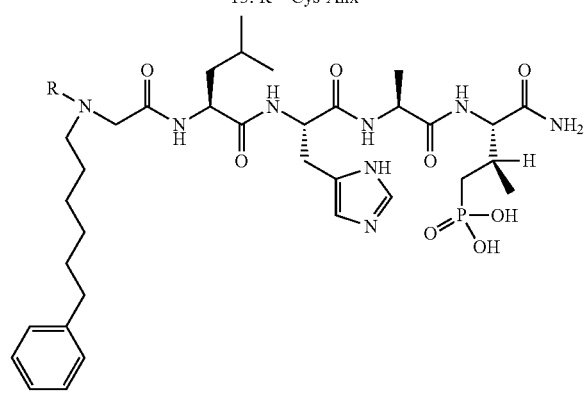

Pmab
14: R = Acetyl
15: R = Cys-Ahx-

Further conversion of peptoid-peptide hybrids into peptoid inhibitors was undertaken to generate. a whole peptoid ligand. A systematical peptide library by using natural amino acids has been constructed and evaluated in the literature, which gave the information that preferred side chains at the other 4 residues. Keeping the best NSG (4q) at the Pro position, we firstly tried to further explore the Leu position. Although all of them gave decreased binding potency compared to 4q, interestingly, the hybrid with a NSG of Leu mimetic (16s) is the best compound.

16

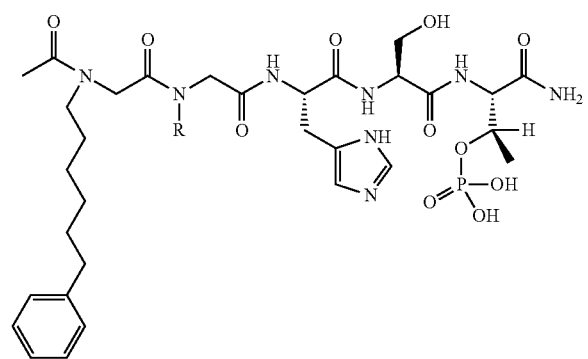

R—NH2:

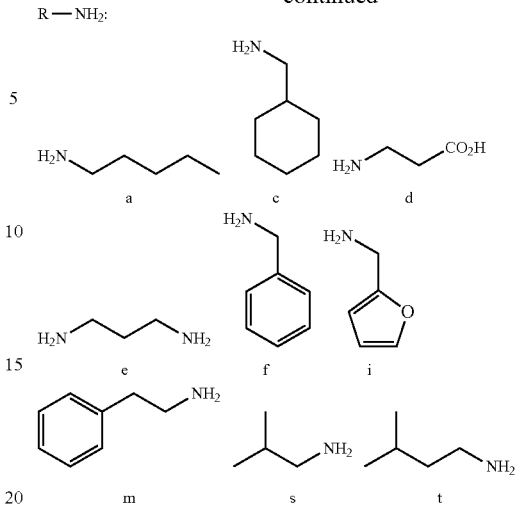

Peptoid-Peptide Hybrid Library with Variations at Leu Position

We further developed peptoid-peptide hybrid ligand based on 16s, three hybrids were prepared, but all of them (17f-fu) showed further decreased binding. Considering the Ser is the only recognized the amino acid at the −1 position, and the same importance of the pThr residue, we stopped working the Ser and pThr residue.

17

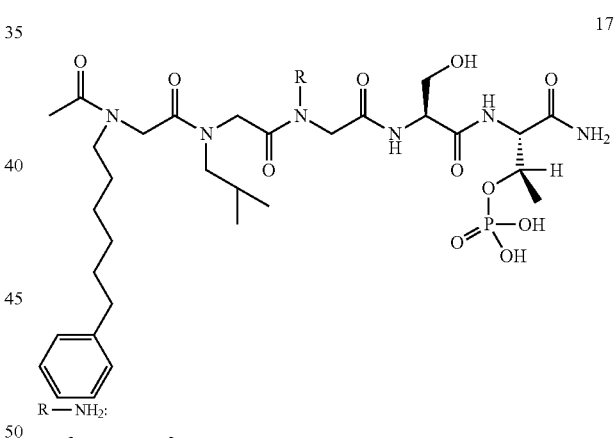

R—NH2:

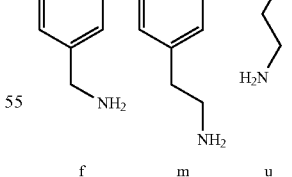

Peptoid-Peptide Hybrids Library at His Position

Peptoid-peptide hybrid synthesis procedures. Fmoc-Thr (PO(OBzl)OH)—OH and other Fmoc protected amino acids were purchased from Novabiochem. Peptides were synthesize on NovaSyn® TGR resin (Novabiochem, cat. no. 01-64-0060) using standard Fmoc solid-phase protocols in N-Methyl-2-pyrrolidone (NMP). 1-O-Benzotriazole-N,N,N',N'-tetramethyl-uronium-hexafluoro-phosphate (HBTU) (5.0 eq.), hydroxybenzotriazole (HOBT) (5.0 eq.) and N,N-Diisopropylethylamine (DIPEA) (10.0 eq.) were used as coupling reagents. After Leu was coupled and its amine group was freed, the resin was treated with bromoacetic acid (10.0 eq.), DIC (10.0 eq.) and DIPEA (20.0 eq.) in NMP for 30 mins. This resin was washed and treated with ~2.5 M individual amine in DMSO over night. The amine terminal was acetylated by acetylimidazole overnight, or by acetic anhydride (10.0 eq.), DIPEA (20.0 eq) in 1,2-dichloroethane 4 hr at rt. The final resin was washed with N,N-dimethylforamide (DMF), methanol, dichloromethane and ether then dried under vacuum (overnight). Peptides were cleaved from resin (200 mg) by treatment with 5 mL of trifluoroacetic acid:triisbutylsilane:$H_2O$ (90:5:5) (4 h). The resin was filtered off and the filtrate was concentrated under vacuum, then precipitated with ether and the precipitate washed with ether. The resulting solid was dissolved in 50% aqueous acetonitrile (5 mL) and purified by reverse phase preparative HPLC using a Phenomenex $C_{18}$ column (21 mm dia×250 mm, cat. no: 00G-4436-P0) with a linear gradient from 0% aqueous acetonitrile (0.1% trifluoroacetic acid) to 100% acetonitrile (0.1% trifluoroacetic acid) over 30 minutes at a flow rate of 10.0 mL/minute.

Post-modification of the peptides by Click chemistry. Azides were obtained by treatment of the corresponding alcohols with methanesulfonyl chloride followed by sodium azide. Copper catalyzed cyclization: Dried resin 7 (100 mg) was suspended in acetonitrile (4.0 mL) and DMSO (1.0 mL) in a plastic tube, de-gassed by argon for 5 mins, and supplemented with DIPEA (10 µL), CuI (19 mg) and azide (10.0 eq.). The tube was sealed and shaked at room temperature overnight. The resin was washed with DMF, H2O, MeOH and ether, dried under high vacuum for 4 hr before cleavage. Heat driven cyclization: Dried resin 7 (100 mg) and azide (10.0 eq.) were mixed in DMF (2.0 mL) in a flask and heated to 100° C. for 2 days. The resulting resin was washed with DMF, methanol, dichloromethane and ether, and dried under high vacuum before cleavage. The products of copper catalyzed reaction were assigned as the 1,4-triazole products, the 1,5-triazole products were identified by comparing the HPLC retention times of the heat driven cyclization products with the 1,4-triazole product for copper catalyzed cyclization.

TABLE 9

Low resolution ESI-Mass Spec.

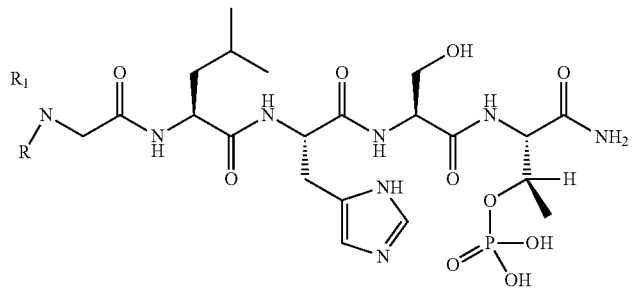

R1 = H or acetyl

|  |  | Expected (M + H)+ | Observed (M + H)+ | Expected (M − H)− | Observed (M − H)− |
| --- | --- | --- | --- | --- | --- |
| 4a | Acetyl | 705.3 | 705.8 |  |  |
| 4b | H | 661.3 | 661.5 |  |  |
| 4c | Acetyl | 731.3 | 731.7 |  |  |
| 4d | Acetyl | 707.3 | 707.4 |  |  |
| 4e | Acetyl | 692.3 | 690.8 |  |  |
| 4f | Acetyl | 725.3 | 725.4 |  |  |
| 4g | H | 697.3 | 697.6 |  |  |
| 4h | Acetyl | 785.3 | 785.9 |  |  |
| 4i | Acetyl | 715.3 | 715.9 |  |  |
| 4g | Acetyl | 761.3 | 761.8 |  |  |
| 4k | H | 697.3 | 698.0 |  |  |
| 4l | H | 733.3 | 732.6 |  |  |
| 4m | Acetyl | 739.3 | 739.2 |  |  |
| 4n | Acetyl | 753.3 | 753.3 |  |  |
| 4o | Acetyl | 767.3 | 767.2 |  |  |
| 4p | Acetyl | 781.4 | 781.3 |  |  |
| 4q | Acetyl | 795.4 | 795.3 |  |  |
| 4r | Acetyl | 809.4 | 809.4 |  |  |

| Compound number | Expected (M + H)+ | Observed (M + H)+ | Expected (M − H)− | Observed (M − H)− |
| --- | --- | --- | --- | --- |
| 5 | 779.4 | 779.4 | 777.4 | 777.4 |
| 6 | 752.4 | 752.4 | 750.4 | 750.3 |
| 8 | 777.3 | 777.3 |  |  |
| 9 | 791.4 | 791.2 |  |  |
| 10 | 777.3 | 777.4 | 775.3 | 775.4 |
| 11 | 791.4 | 791.2 |  |  |
| 12 | 793.4 | 793.5 | 791.4 | 791.4 |

TABLE 9-continued
Low resolution ESI-Mass Spec.
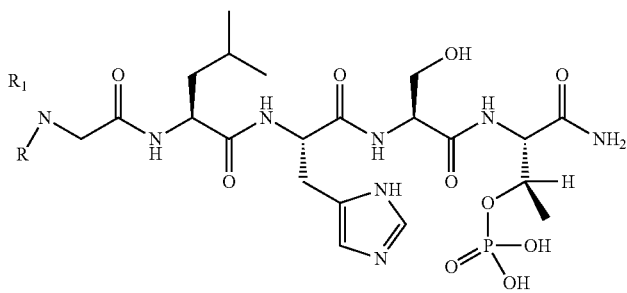
R1 = H or acetyl
| 13 | 967.5 | 967.5 | 965.5 | 965.5 |
| 14 | 777.4 | 777.4 | 775.4 | 775.4 |
| 15 | 951.5 | 951.6 | | |
TABLE 10
High resolution ESI-MS of selected peptoid-peptide hybrids.
| | Structure | Expected | Observed |
|---|---|---|---|
| 4a | 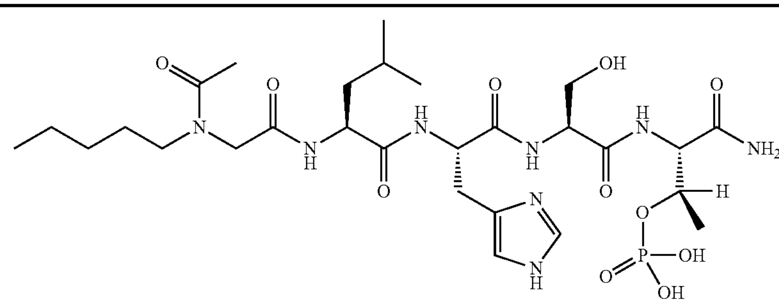 | $(M-H)^-$ C28H48N8O11P 703.3186 | $(M-H)^-$ 703.3166 |
| 4f | 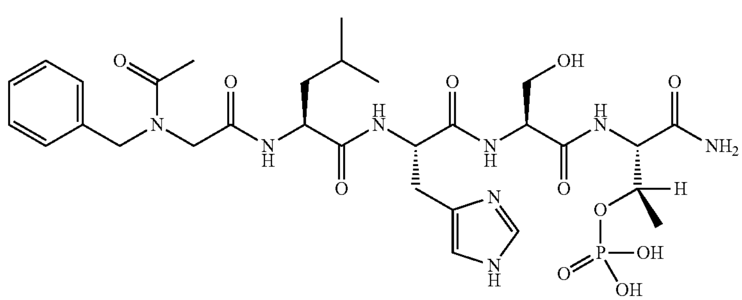 [SMILES: CC(=O)N(CC(=O)N[C@@H](CC(C)C)C(=O)N[C@@H](Cc1c[nH]cn1)C(=O)N[C@@H](CO)C(=O)N[C@H](C(N)=O)[C@@H](C)OP(=O)(O)O)Cc1ccccc1] | $(M-H)^-$ C30H44N8O11P 723.2873 | 723.2846 |
| 4o | 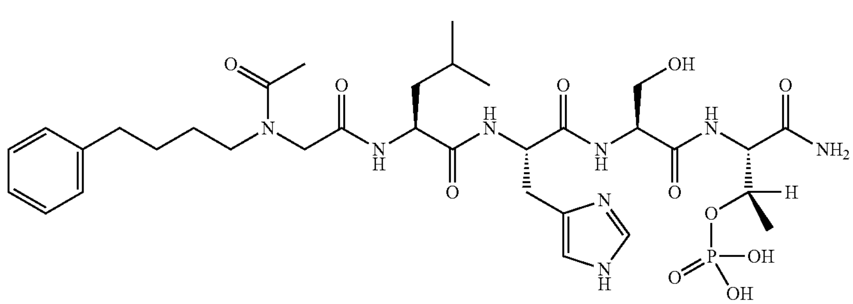 [SMILES: CC(=O)N(CCCCc1ccccc1)CC(=O)N[C@@H](CC(C)C)C(=O)N[C@@H](Cc1c[nH]cn1)C(=O)N[C@@H](CO)C(=O)N[C@H](C(N)=O)[C@@H](C)OP(=O)(O)O] | $(M-H)^-$ C33H50N8O11P 765.3342 | 765.3328 |

TABLE 10-continued

High resolution ESI-MS of selected peptoid-peptide hybrids.

| | Structure | Expected | Observed |
|---|---|---|---|
| 4r | 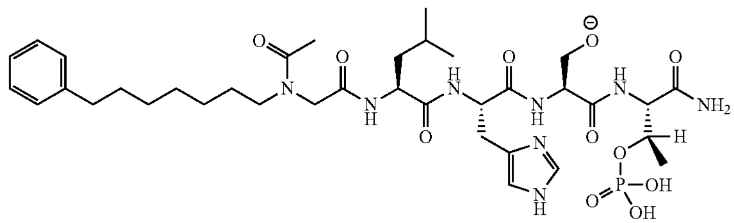 [SMILES: CC(=O)N(CCCCCCCc1ccccc1)CC(=O)N[C@@H](CC(C)C)C(=O)N[C@@H](Cc1c[nH]cn1)C(=O)N[C@@H](C[O-])C(=O)N[C@H](C(N)=O)[C@@H](C)OP(=O)(O)O] | $(M - H)^-$ C36H56N8O11P 807.3812 | 807.3799 |
| 6 | 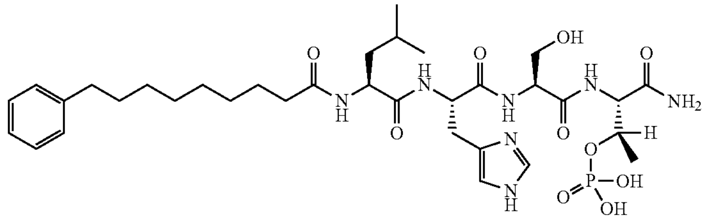 [SMILES: CC(C)C[C@H](NC(=O)CCCCCCCCc1ccccc1)C(=O)N[C@@H](Cc1c[nH]cn1)C(=O)N[C@@H](CO)C(=O)N[C@H](C(N)=O)[C@@H](C)OP(=O)(O)O] | $(M - H)^-$ C34H53N7O10P 750.3597 | 750.3583 |
| 12 | 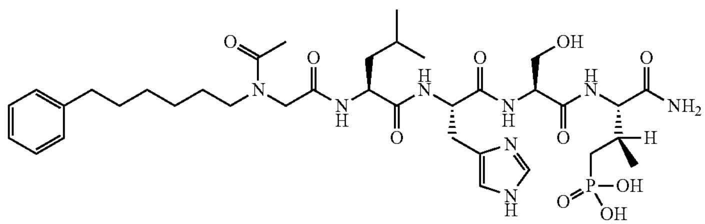 [SMILES: CC(=O)N(CCCCCCc1ccccc1)CC(=O)N[C@@H](CC(C)C)C(=O)N[C@@H](Cc1c[nH]cn1)C(=O)N[C@@H](CO)C(=O)N[C@H](C(N)=O)[C@@H](C)CP(=O)(O)O] | $(M + H)^+$ C36H58N8O10P 793.4008 | 793.4021 |
| 14 | 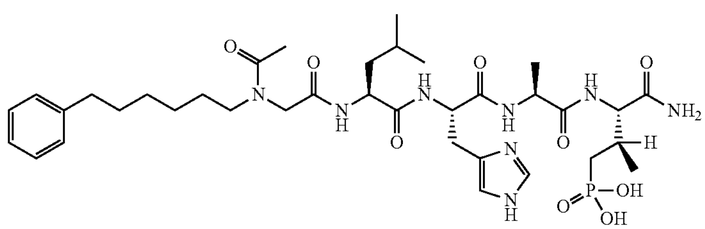 [SMILES: CC(=O)N(CCCCCCc1ccccc1)CC(=O)N[C@@H](CC(C)C)C(=O)N[C@@H](Cc1c[nH]cn1)C(=O)N[C@@H](C)C(=O)N[C@H](C(N)=O)[C@@H](C)CP(=O)(O)O] | $(M + H)^+$ C36H58N8O9P 777.4059 | 777.4079 |

Example 15

Peptides Containing Phosphate Monoesters and Arylalkyl-Histine-Containing PBD-Binding Peptides We used a structure-based rational design method based on the Mitsunobu reaction to make di-ester. The approach provides numerous advantages including, but not limited to, highly efficient library construction, resistance to phosphatase, and increased cell permeability.

Post-modification of the peptide on the resin gave two products 3 and 4 with the same molecular weight as about 1 to 4 ratio, the minor product 3 consistently gave higher potency than the major product 4.

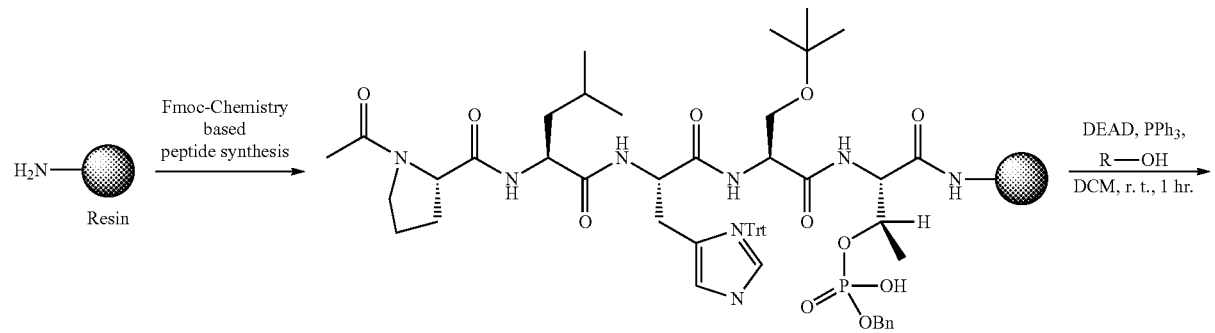

-continued

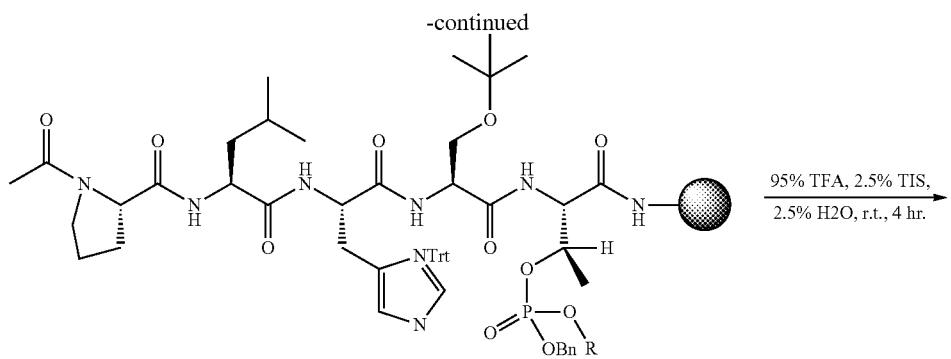

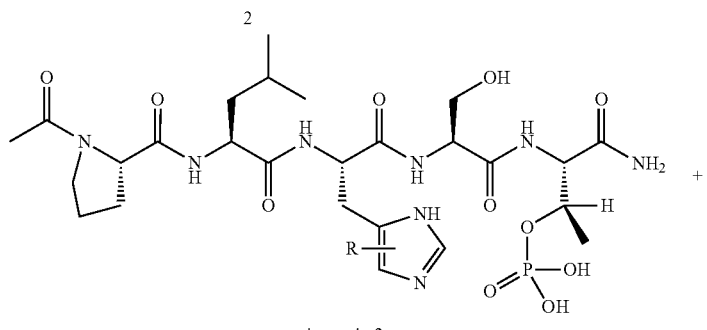
minor pdt, 3

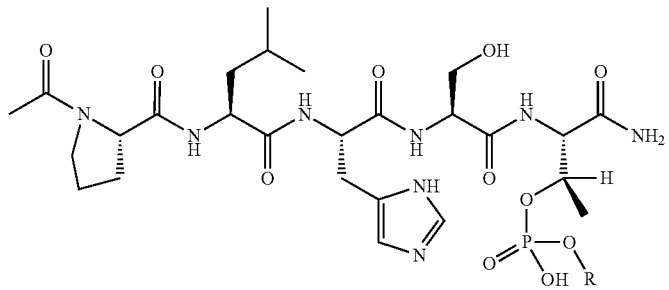
minor pdt, 4

Post-Modification on the Solid Phase by Using Mitsunobu Reaction

Figure 20A:
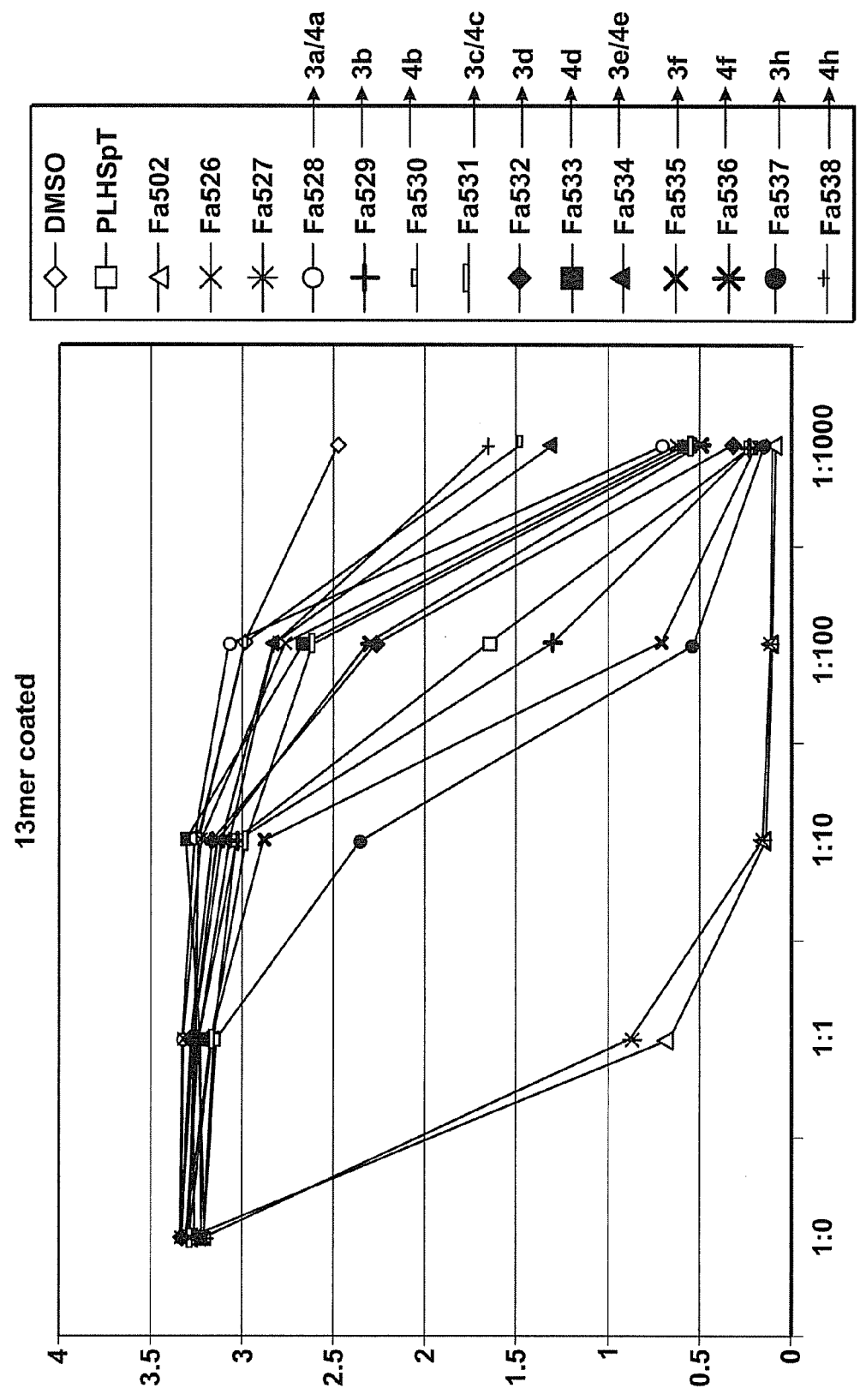
FIG. 20A through C ELISA screening of alcohol libraries. Results from the screening of the alcohol libraries using the indicated peptides.
Figure 20B:
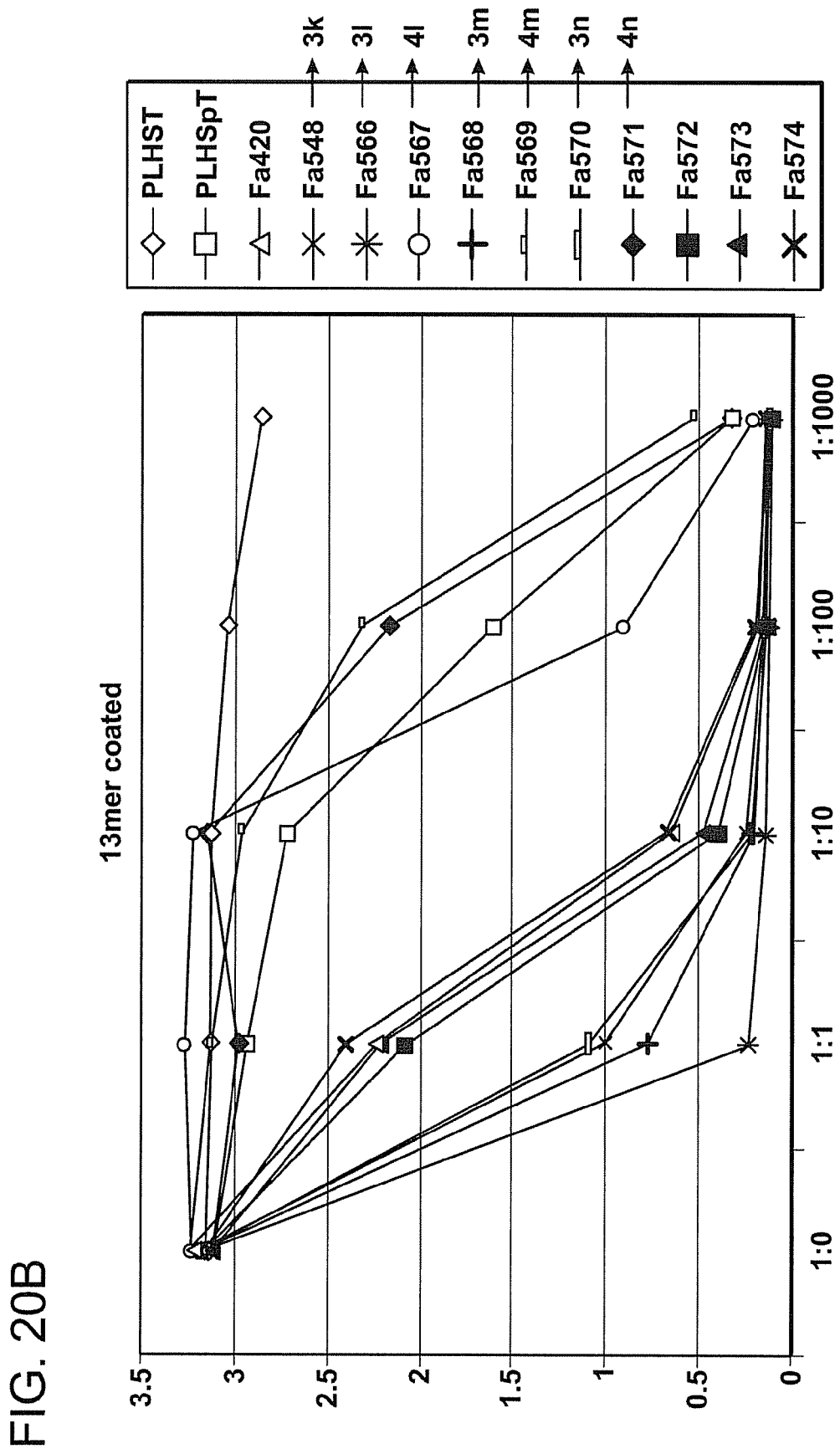
Figure 20C:
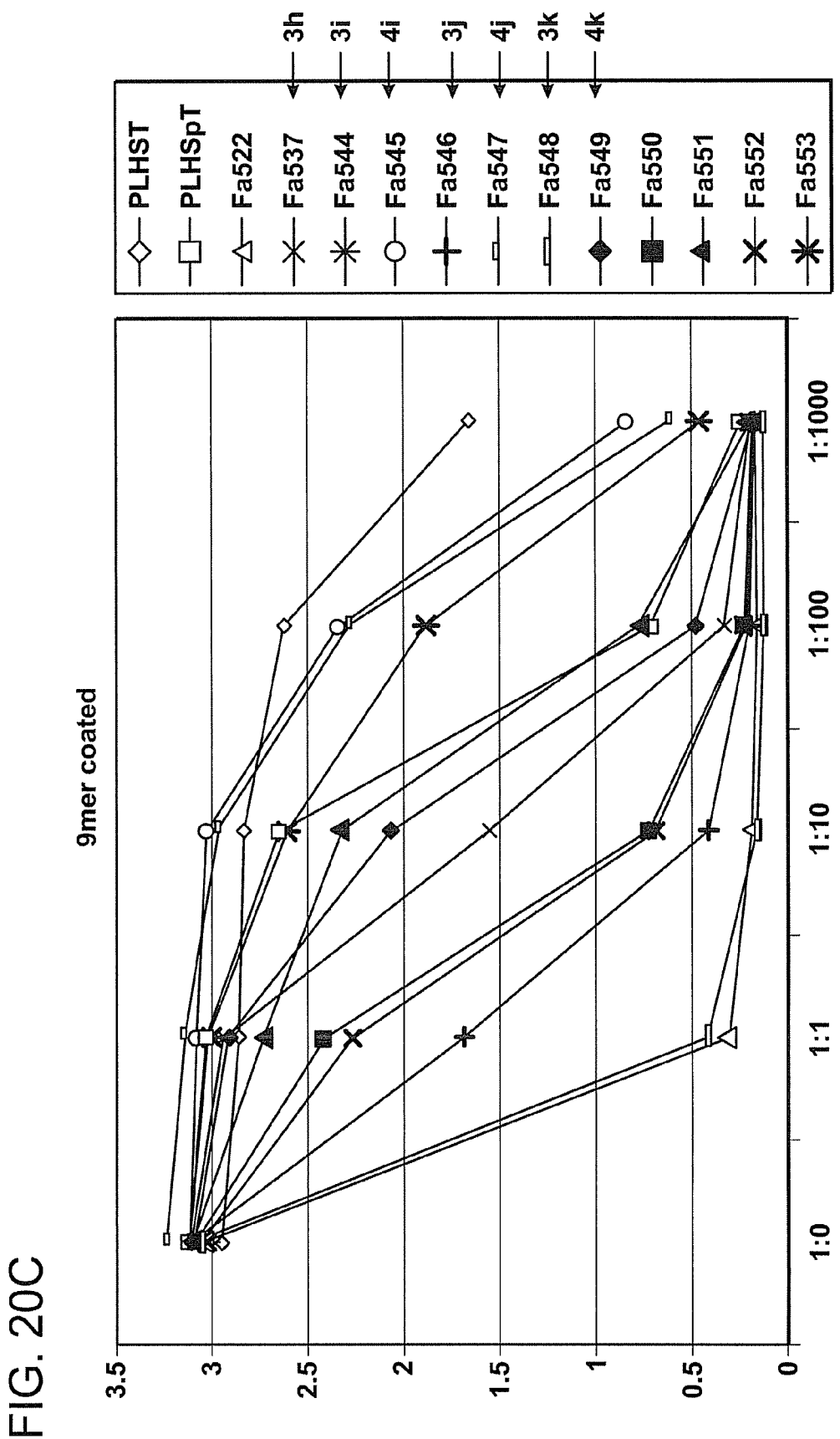

In the first round alcohol library, a variety of functional groups including di-ol, carbon chains, carboxylic acid, amine, and hetero ring were examined. It was determined that the hydrophobic group Ph-(CH$_2$)$_4$— gave the highest binding affinity for minor product 3. 4h was much less active than 3h, also less active than the WT (FIG. 20).

MeOH  a

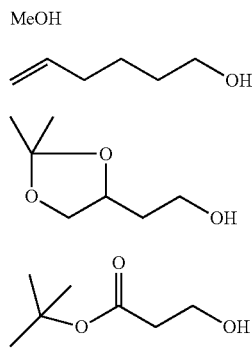
b c d

-continued

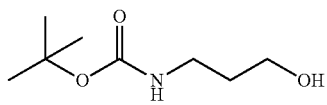
e

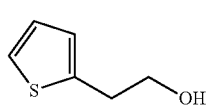
f

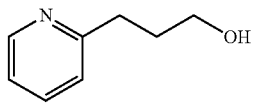
g

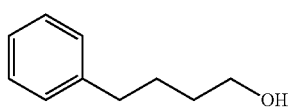
h

Initial Alcohol Library Used Prepare Peptide 3 and 4

Figure 21A:
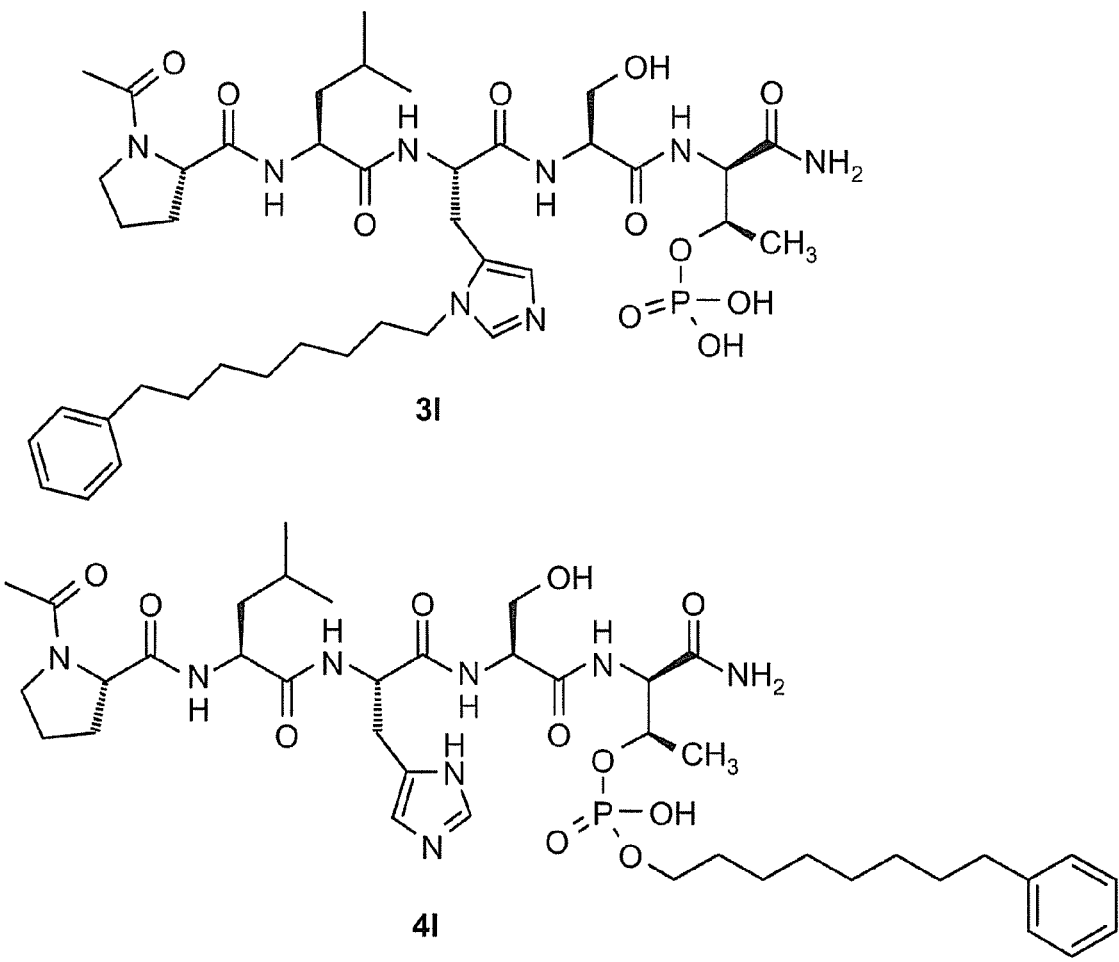
FIGS. 21A and B Structures of the 31 and 41 peptides (A) the structures of 31 and 41; and (B) X-ray crystal structure of 31 (FA566) bound to PBD-1 protein showing site of N-alkylaryl attachment.
Figure 21B:
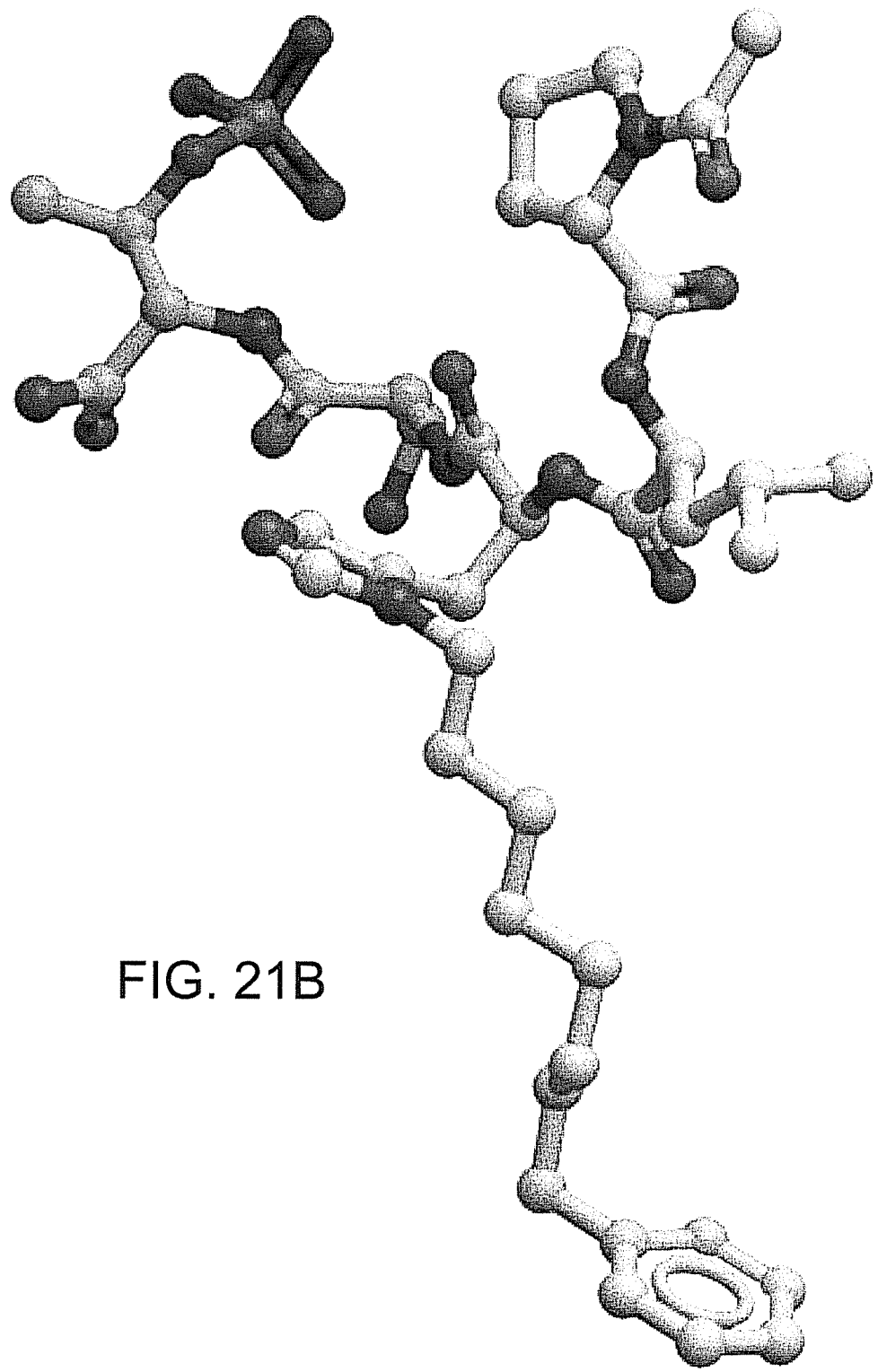
Figure 22:
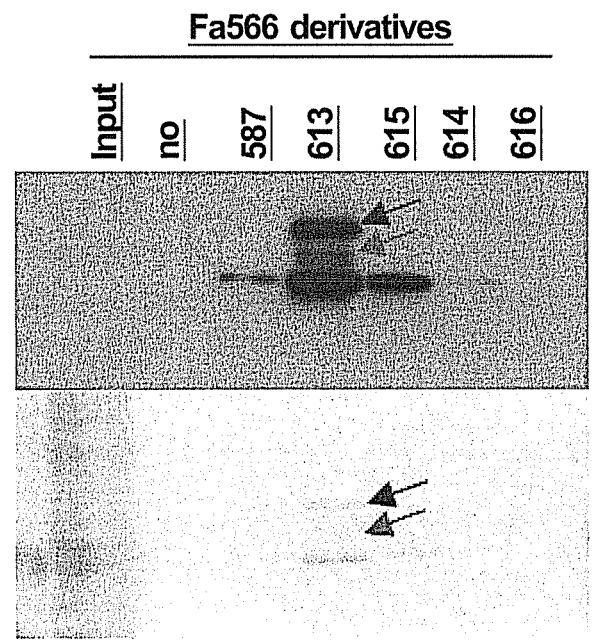
FIG. 22 Assay of specificity of interaction. Western blot (top) and coomassie stained gel (bottom) of Plk1,2,3 pull down assay using the indicated peptides.

In the second round focused alcohol library, the linker length was systematically examined, and alcohol 1 found to be the best hit according to the ELISA assay results (FIGS. 21A to C).

Ph-(CH$_2$)$_5$—OH, i
Ph-(CH$_2$)$_6$—OH, j
Ph-(CH$_2$)$_7$—OH, k
Ph-(CH$_2$)$_8$—OH, l
Ph-(CH$_2$)$_9$—OH, m
Ph-(CH$_2$)$_{10}$—OH, n

Focused Alcohol Library to Prepare Peptide 3 and 4

The S/A mutants of peptide 3l and 4l were also prepared and determined by ELISA. 5 gave 100-fold decreased binding compared to 3l, and 6 didn't show any activity.

5

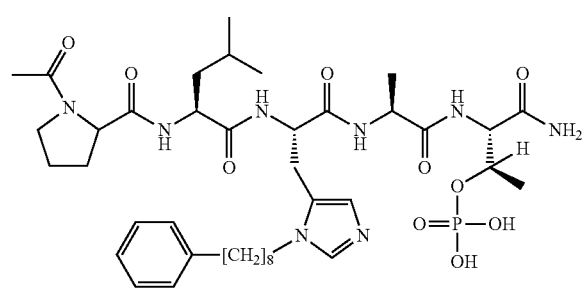

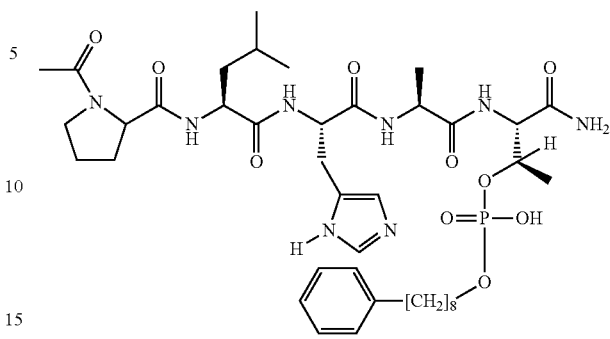

S/A mutants of peptide 3l and 4l, respectively. (The X-ray crystal structure of 3l bound PBD protein has been solved, the bound conformation of 3l is provided in FIG. 21B. This structural information provide valuable information for ligand design.)

Plk1, 2 and 3 Specificity Test

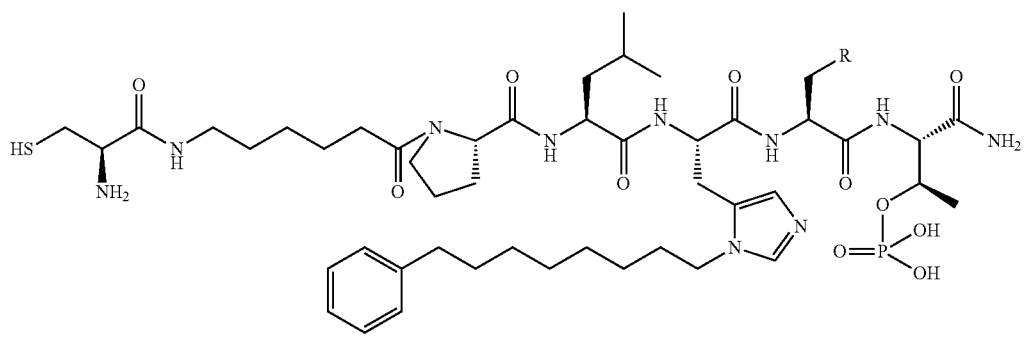

7: R = OH
8: R = H

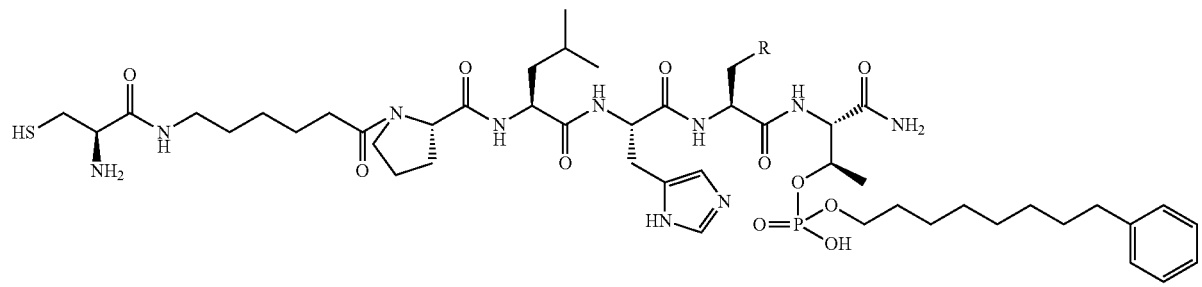

9: R = OH
10: R = H

Peptide synthesis procedures. Fmoc-Thr(PO(OBzl)OH)—OH and other Fmoc protected amino acids were purchased from Novabiochem. Peptides were synthesize on NovaSyn® TGR resin (Novabiochem, cat. no. 01-64-0060) using standard Fmoc solid-phase protocols in N-Methyl-2-pyrrolidone (NMP). 1-O-Benzotriazole-N,N,N',N'-tetramethyl-uronium-hexafluoro-phosphate (HBTU) (5.0 eq.), hydroxybenzotriazole (HOBT) (5.0 eq.) and N,N-Diisopropylethylamine (DIPEA) (10.0 eq.) were used as coupling reagents. The N-terminal was acetylated by 1-Acetylimidazole, then the resin was washed with DMF, methanol, dichloromethane and ether then dried under vacuum (overnight).

Post-modification of the peptide by Mitsunobu reaction. The above resin (200 mg, 0.04 mmol) was swelled in dichloromethane for 15 mins, treated by triphenylphosphine (262 mg, 1.0 mmol), DEAD (0.46 mL, 40% solution in toluene, 0.10 mol) and alcohol a-n (0.10 mmol) in dry dichloromethane for 2 hr at room temperature, washed by dichloromethane, dried under vacuum for 2 hr before cleavage.

Peptide cleavage and purification. Peptides were cleaved from resin (200 mg) by treatment with 5 mL of trifluoroacetic acid:triisbutylsilane:$H_2O$ (90:5:5) (4 h). The resin was filtered off and the filtrate was concentrated under vacuum, then precipitated with ether and the precipitate washed with ether. The resulting solid was dissolved in 50% aqueous acetonitrile (5 mL) and purified by reverse phase preparative HPLC using a Phenomenex $C_{18}$ column (21 mm dia×250 mm, cat. no: 00G-4436-P0) with a linear gradient from 0% aqueous acetonitrile (0.1% trifluoroacetic acid) to 100% acetonitrile (0.1% trifluoroacetic acid) over 30 minutes at a flow rate of 10.0 mL/minute. Lyophilization gave the product as white powders.

TABLE 11

Mass Spec. Data Low Resolution ESI-Mass Spec.

| | Peptide Structure | Expected (M + H)+ | Observed (M + H)+ | Expected (M − H)− | Observed (M − H)− |
|---|---|---|---|---|---|
| 3a | | 689.3 | 689.3 | 687.3 | 687.3 |
| 4a | | 689.3 | 689.3 | 687.3 | 687.3 |
| 3b | | 757.4 | 757.3 | | |

TABLE 11-continued
Mass Spec. Data Low Resolution ESI-Mass Spec.
| | Peptide Structure | Expected (M + H)+ | Observed (M + H)+ | Expected (M − H)− | Observed (M − H)− |
|---|---|---|---|---|---|
| 4b | 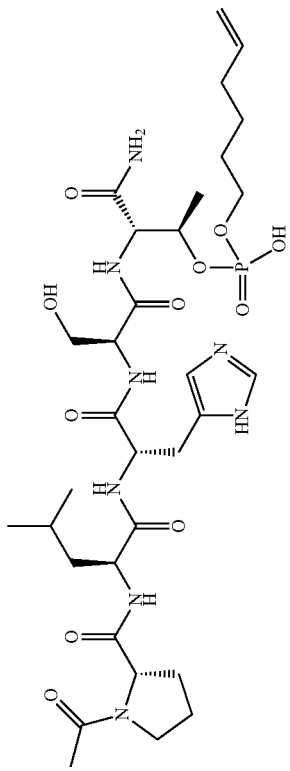 | 757.4 | 757.4 | | |
| 3c/4c* | 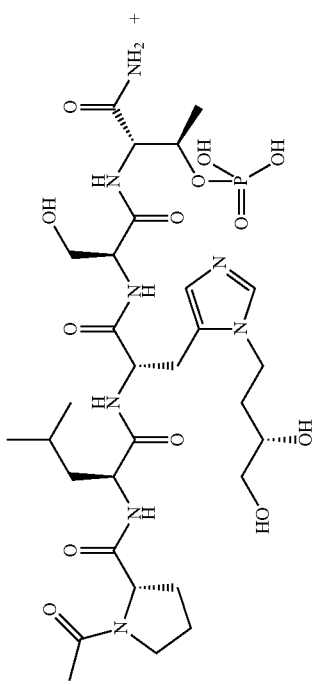  3c | 763.3 | 763.3 | | |

TABLE 11-continued
Mass Spec. Data Low Resolution ESI-Mass Spec.
| Peptide Structure | Expected (M + H)+ | Observed (M + H)+ | Expected (M − H)− | Observed (M − H)− |
|---|---|---|---|---|
| 4c | 747.3 | 747.3 | | |
| 3d | | | | |
| 4d | 747.3 | 747.3 | | |
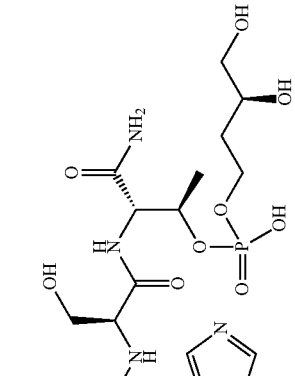
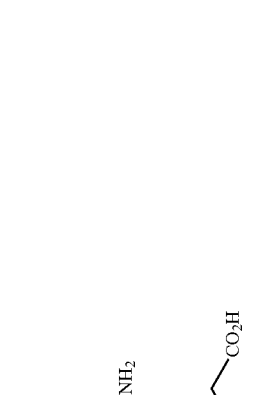

TABLE 11-continued
Mass Spec. Data Low Resolution ESI-Mass Spec.
| Peptide Structure | Expected (M + H)+ | Observed (M + H)+ | Expected (M − H)− | Observed (M − H)− |
|---|---|---|---|---|
| 3e/4e* | 732.3 | 732.3 | | |
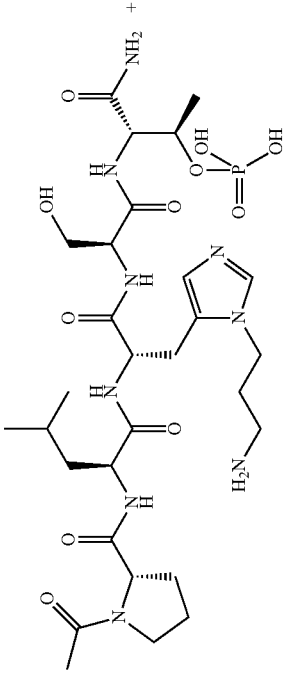

TABLE 11-continued
Mass Spec. Data Low Resolution ESI-Mass Spec.
| | Peptide Structure | Expected (M + H)+ | Observed (M + H)+ | Expected (M − H)− | Observed (M − H)− |
|---|---|---|---|---|---|
| 3f | 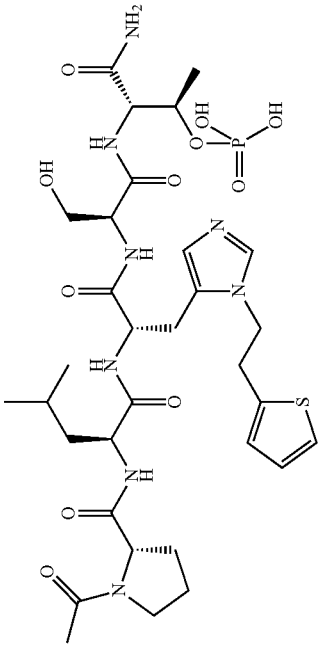 | 785.2 | 785.2 | | |
| 4f | 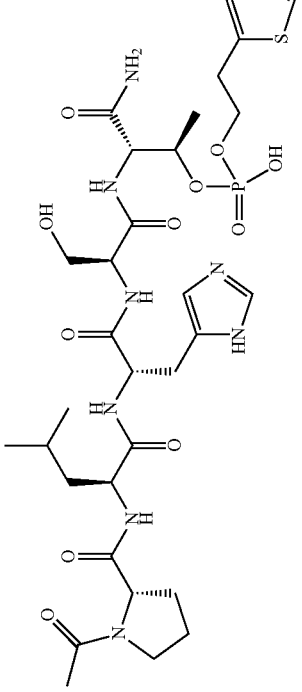 | 785.2 | 785.2 | | |
| 3g/4g** | 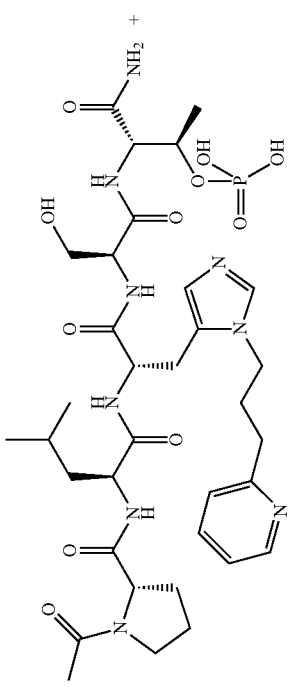 | | | | |

TABLE 11-continued
Mass Spec. Data Low Resolution ESI-Mass Spec.
| Peptide Structure | Expected (M+H)+ | Observed (M+H)+ | Expected (M−H)− | Observed (M−H)− |
|---|---|---|---|---|
| 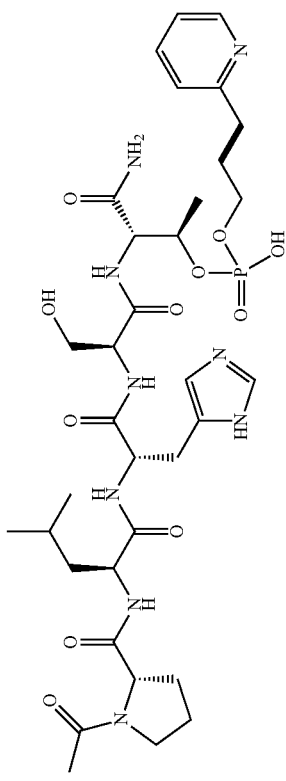 4g | 807.4 | 807.4 | | |
| 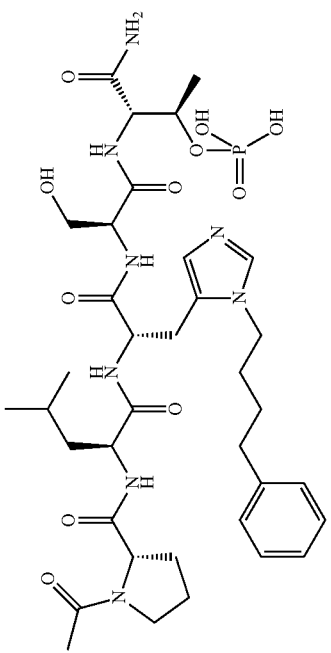 3h | | | | |

TABLE 11-continued

Mass Spec. Data Low Resolution ESI-Mass Spec.

| | Peptide Structure | Expected (M + H)+ | Observed (M + H)+ | Expected (M − H)− | Observed (M − H)− |
|---|---|---|---|---|---|
| 4h | | 807.4 | 807.3 | | |
| 3i | | 821.4 | 821.2 | 819.4 | 818.8 |
| 4i | | 821.4 | 821.2 | 819.4 | 818.8 |

TABLE 11-continued

Mass Spec. Data Low Resolution ESI-Mass Spec.

| | Peptide Structure | Expected (M + H)+ | Observed (M + H)+ | Expected (M − H)− | Observed (M − H)− |
|---|---|---|---|---|---|
| 3j | | 835.4 | 835.2 | 833.4 | 832.8 |
| 4j | | 835.4 | 835.2 | 833.4 | 932.8 |
| 3k | | 849.4 | 849.3 | 847.4 | 846.7 |

TABLE 11-continued
Mass Spec. Data Low Resolution ESI-Mass Spec.
| | Peptide Structure | Expected (M + H)⁺ | Observed (M + H)⁺ | Expected (M − H)⁻ | Observed (M − H)⁻ |
|---|---|---|---|---|---|
| 4k | 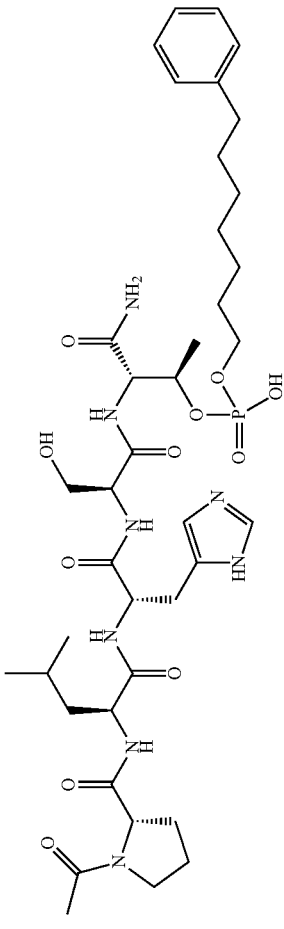 | 849.4 | 849.3 | 847.4 | 846.7 |
| 3l | 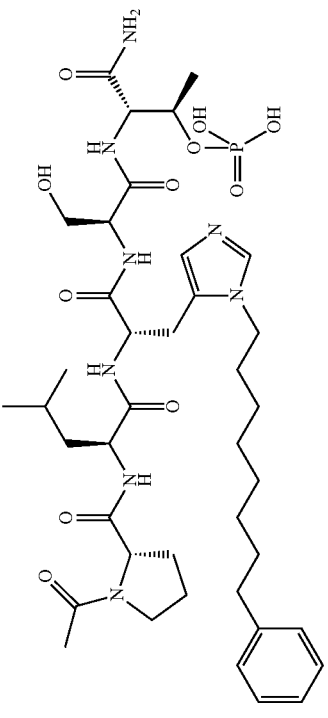 | 863.4 | 863.5 | 861.4 | 861.4 |
| 4l | 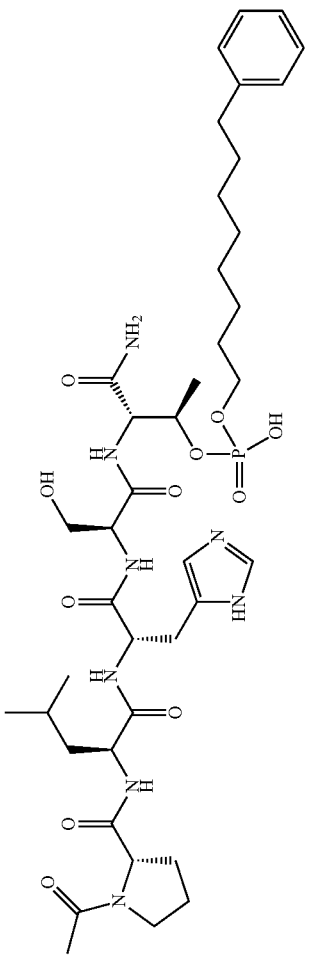 | 863.4 | 863.5 | 861.4 | 861.4 |

TABLE 11-continued

Mass Spec. Data Low Resolution ESI-Mass Spec.

| | Peptide Structure | Expected (M + H)+ | Observed (M + H)+ | Expected (M − H)− | Observed (M − H)− |
|---|---|---|---|---|---|
| 3m | | 877.5 | 877.3 | 875.5 | 874.8 |
| 4m | | 877.5 | 877.3 | 875.5 | 874.8 |
| 3n | | 891.5 | 891.3 | 889.5 | |

TABLE 11-continued

Mass Spec. Data Low Resolution ESI-Mass Spec.

| | Peptide Structure | Expected (M + H)+ | Observed (M + H)+ | Expected (M − H)− | Observed (M − H)− |
|---|---|---|---|---|---|
| 4n | | 891.5 | 891.3 | 889.5 | 888.9 |
| 5 | | 847.4 | 847.5 | | |
| 6 | | 847.4 | 847.5 | | |

TABLE 11-continued

Mass Spec. Data Low Resolution ESI-Mass Spec.

| | Peptide Structure | Expected (M + H)+ | Observed (M + H)+ | Expected (M − H)− | Observed (M − H)− |
|---|---|---|---|---|---|
| 7 | | 1037.5 | 1037.5 | | |
| 8 | | 1021.5 | 1021.5 | | |

TABLE 11-continued
Mass Spec. Data Low Resolution ESI-Mass Spec.
| | Peptide Structure | Expected (M + H)+ | Observed (M + H)+ | Expected (M − H)− | Observed (M − H)− |
|---|---|---|---|---|---|
| 9 | 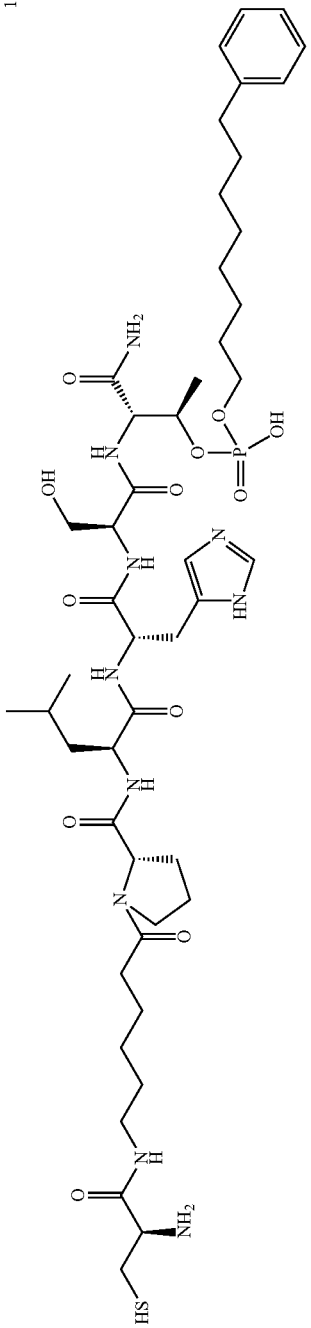 | 1037.5 | 1037.5 | | |
| 10 | 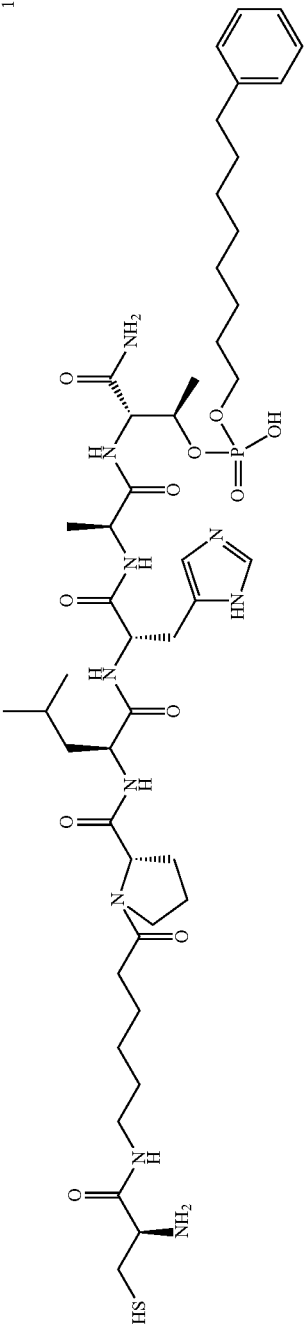 | 1021.5 | 1021.5 | | |
*These two products are not separable on preparative HPLC.
**No expected products were isolated.

TABLE 12

HRMS of selected peptides.

| Peptide Structure | Expected (M + H)+ | Observed (M + H)+ |
|---|---|---|
| 3h | 807.3801 | 807.3797 |
| 4h | 807.3801 | 807.3812 |
| 3l | 863.4427 | 863.4446 |
| 4l | 863.4427 | 863.4439 |

TABLE 12-continued
HRMS of selected peptides.
| Peptide Structure | Expected (M + H)+ | Observed (M + H)+ |
|---|---|---|
| 5 [structure] | 847.4478 | 847.4466 |
| 6 [structure] | 847.4478 | 847.4463 |
The modifications on the Pro discovered by oxime library approach and the modifications on His or pThr discovered by the above described Mitsunobu reaction were combined together to provide compounds FA550-FA553.
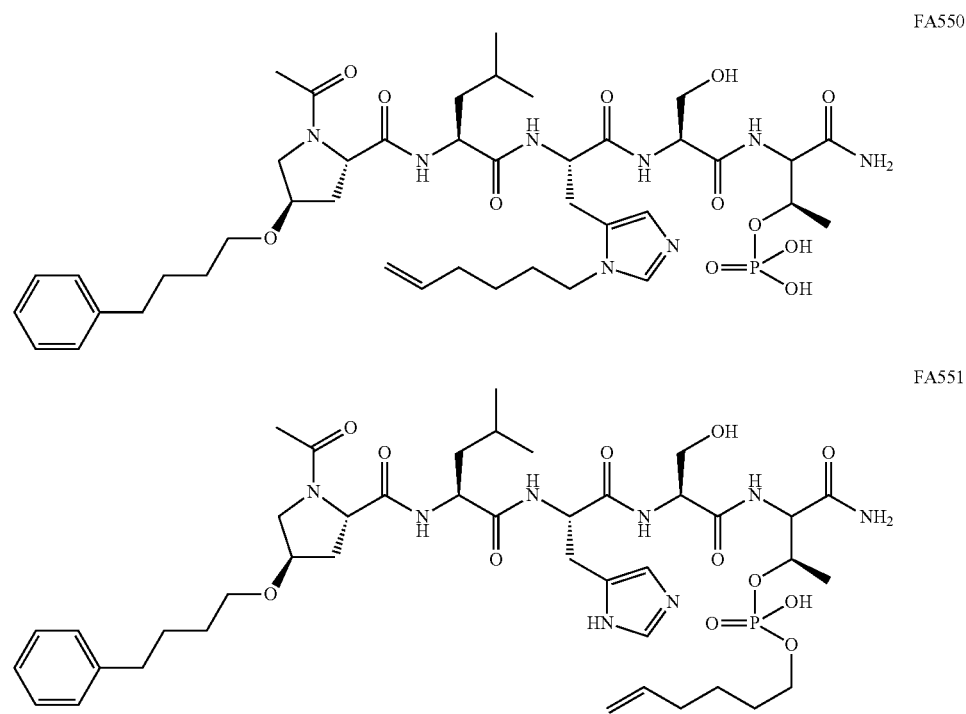
FA550
FA551

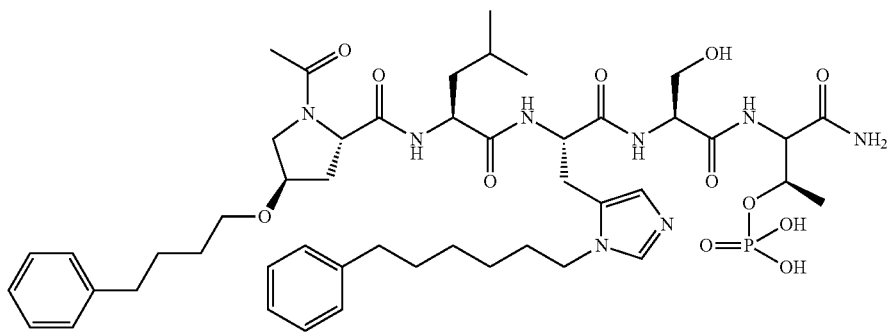
FA552
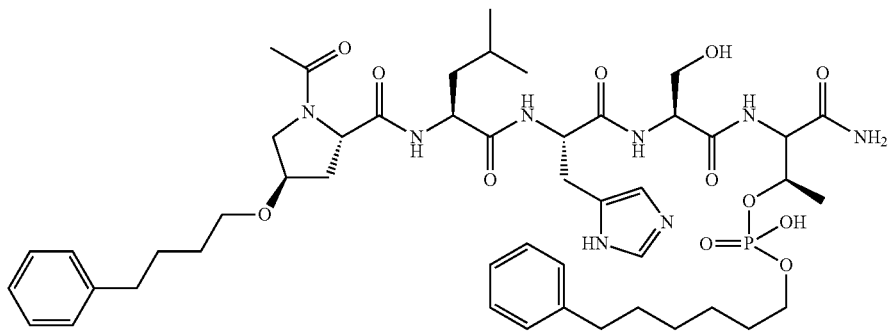
FA553
Example 16
Design and Synthesis of Pmab pThr Mimetics in Prodrug Form for Incorporation into Bioavailable PBD-Binding Peptides
Pmab Analogue Synthesis.
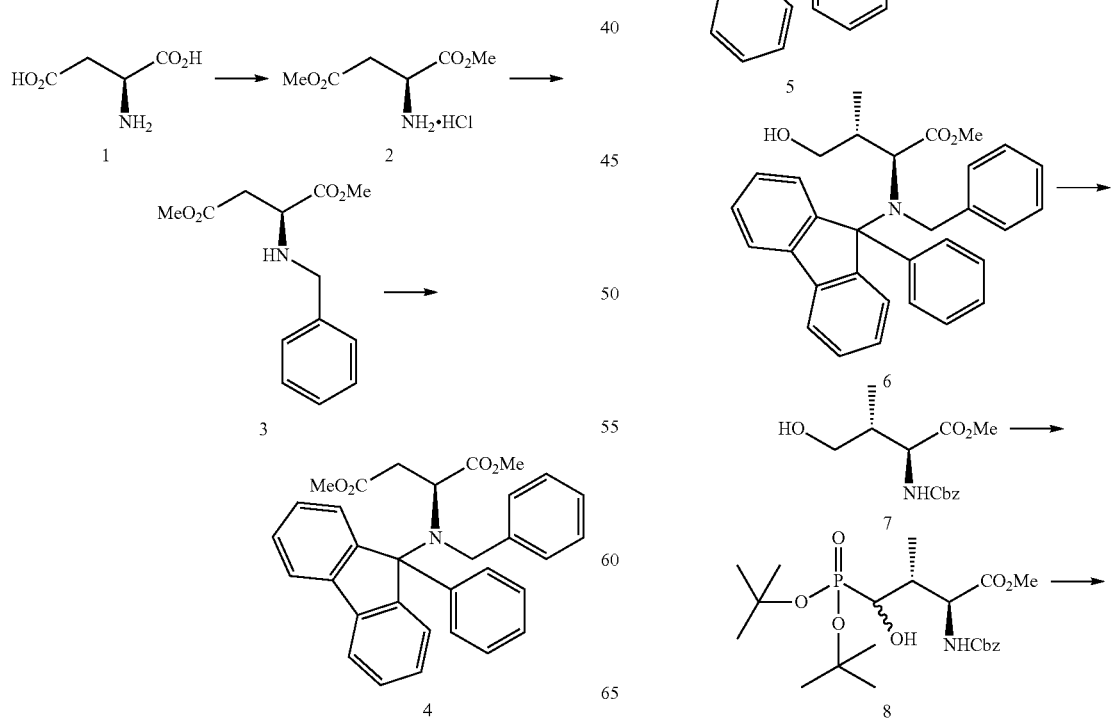

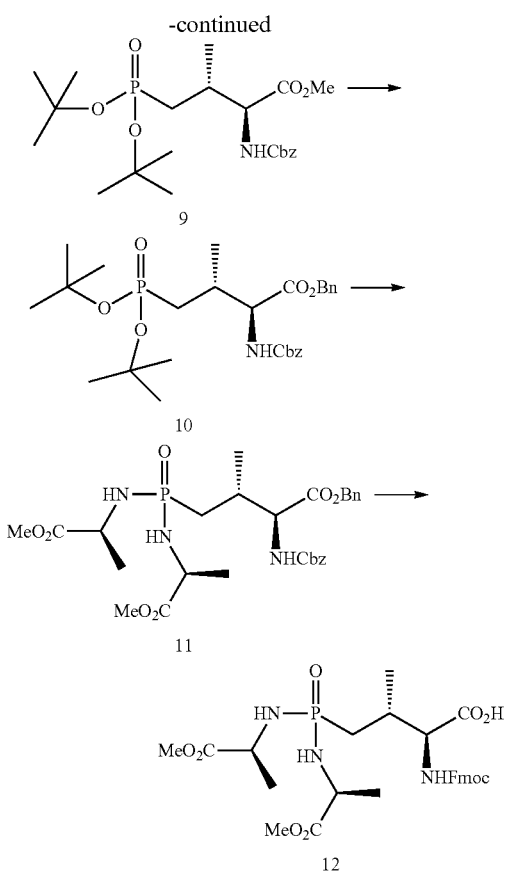

The preparation of compound 5 from L-Aspatic acid was conducted according to the literature (Humphrey, J. M.; Bridges, R. J.; Hart, J. A.; Chamberlin, A. R. *J. Org. Chem.* 1994, 59, 2467), these reactions are very re-producible in over 10 gram scale. The conversion of 5 to 9 thought multiple steps have been reported in our Tetrahedron paper (accepted). The preparation of Pmab analogue 12 from compound 9 are described below.

Preparation of compound 10. A mixture of 9 (180 mg, 0.39 mmol) and LiOH.H$_2$O (34 mg, 0.81 mg) in a mixture solvent of THF (3.0 mL) and H$_2$O (3.0 mL) was stirred at 0° C. to room temperature overnight, quenched by sat. NH$_4$Cl (50 mL), and extracted by EtOAc (150 mL). The EtOAc layer was washed (brine), dried (Na$_2$SO$_4$), and concentrated by rotary evaporator to an oil, which was dissolved in DMF (5.0 mL). NaHCO$_3$ (168 mg, 2.0 mmol), benzylbromide (120 µL, 1.0 mmol), and NaI (5 mg) were added to the above DMF solution. The resultant mixture was stirred at room temperature overnight, diluted by EtOAc (150 mL), washed (brine), dried (Na$_2$SO$_4$) and purified by silica gel column chromatography (hexanes:EtOAc) to gave 10 as a colorless oil (134 mg, 65% yield for 2 steps). $^1$H NMR (400 MHz, CDCl$_3$) δ 7.40-7.25 (m, 10H), 5.86 (d, J=8.4 Hz, 1H), 5.13-5.04 (m, 4H), 4.30 (dd, J=8.0, 6.4 Hz, 1H), 2.37 (m, 1H), 1.73 (m, 1H), 1.50-1.35 (m, 19H), 1.05 (d, J=6.8 Hz, 3H). $^{13}$C NMR (100 MHz, CDCl$_3$) δ 171.4, 156.2, 142.3, 136.3, 135.1, 128.6, 128.5, 128.3, 128.1, 128.0, 110.4, 82.1, 67.3, 66.9, 59.6, 34.4, 33.8, 32.3, 31.9, 30.3, 24.1, 17.4. ESI (+VE) m/z: 556.3 (M+Na)$^+$.

Preparation of compound 11. Compound 10 (140 mg, 0.262 mmol) was treated by a solution of TFA (5.0 mL) in dichloromethane (5.0 mL) at room temperature for 2 hr. The solvent was removed by rotary evaporator, and the left residue was dissolved in toluene (10 mL) and concentrated again. The obtained residue was dried under high vacuum (oil pump) for 2 hr, then dissolved in dichloromethane (5.0 mL), and cooled to 0° C. Oxalyl chloride (0.20 mL, 2.30 mmol) was added to the above solution, followed by one drop of DMF. The mixture was stirred at room temperature for 2 hr, then concentrated by using rotary evaporator. In another flask, L-Alanine methyl ester hydrochloride (200 mg, 1.43 mmol) and DIPEA (0.80 mL) were dissolved in dichloromethane (4.0 mL) and cooled to 0° C., followed by the slow addition of the above-prepared phosphorus oxychloride solution in dichloromethane (2.0 mL). The resulted mixture was stirred at room temperature overnight, diluted by EtOAc (150 mL), washed (brine), dried (Na$_2$SO$_4$) and purified by silica gel column chromatography (hexanes:EtOAc) to gave 11 as a colorless oil (40 mg, 26% yield for 3 steps). $^1$H NMR (400 MHz, CDCl$_3$) δ 7.32-7.25 (m, 10H), 6.01 (d, J=7.6 Hz, 1H), 5.16 (s, 2H), 5.06 (s, 2H), 4.56 (dd, J=7.6, 4.8 Hz, 1H), 4.05-3.95 (m, 2H), 3.65 (s, 3H), 3.63 (s, 3H), 3.45 (brs, 1H), 3.20 (m, 1H), 2.45 (m, 1H), 1.85 (m, 1H), 1.65 (m, 1H), 1.33-1.28 (m, 6H), 0.97 (d, J=6.8 Hz, 3H). $^{13}$C NMR (100 MHz, CDCl$_3$) δ 175.1, 175.0, 171.0, 156.0, 136.2, 134.9, 128.7, 128.5, 128.1, 67.4, 67.0, 57.9, 52.2, 49.1, 48.2, 33.5, 32.2, 29.6, 21.2, 20.9, 17.6. ESI (+VE) m/z: 614.2 (M+Na)$^+$.

Preparation of compound 12. A mixture of compound 11 (60 mg, 0.102 mmol) and Pd/C (10%, 10 mg) in methanol was stirred under 1 atm hydrogen at room temperature for 5 hr. Pd/C was filtered off, the filtrate was concentrated and the left residue was dissolved in a mixture solvent of dioxane (3.0 mL) and H$_2$O (3.0 mL), followed by the addition of NaHCO$_3$ (42 mg, 0.51 mmol) and FmocOSu (76 mg, 0.204 mmol). The resulted mixture was stirred at room temperature overnight. Dioxane was removed by rotary evaporator, the left aqueous phase was washed by ether (50 mL×2), acidified to pH 3-4 by 1 N HCl, and extracted by EtOAc (100 mL). The EtOAc layer was washed (brine), dried (NaSO4) and evaporated to give analytical pure 12 as a white wax (50 mg, 83% yield for 2 steps), which was used directly for solid phase peptide synthesis without further purification. $^1$H NMR (400 MHz, CDCl$_3$) δ 7.71 (d, J=7.6 Hz, 2H), 7.55 (d, J=7.2 Hz, 2H), 7.37-7.33 (m, 2H), 7.28-7.23 (m, 2H), 5.96 (d, J=6.4 Hz, 1H), 4.71 (m, 1H), 4.34-4.31 (m, 2H), 4.18 (m, 1H), 4.10-3.95 (m, 2H), 3.66 (s, 6H), 2.50 (m, 1H), 2.00-1.85 (m, 2H), 1.45 (d, J=6.8 Hz, 3H), 1.35 (d, J=6.8 Hz, 3H), 1.01 (d, J=6.8 Hz, 3H). $^{13}$C NMR (100 MHz, CDCl$_3$) δ 174.7, 171.8, 155.8, 143.8, 141.2, 127.7, 127.0, 125.1, 120.0, 67.0, 60.4, 52.4, 49.1, 48.3, 47.1, 31.5, 29.7, 20.7, 14.1. ESI β-VE) m/z: 418.1 (M*–H)$^-$. ESI (+VE) m/z: 420.1 (M*+H)$^+$, 442.2 (M*+Na)$^+$.

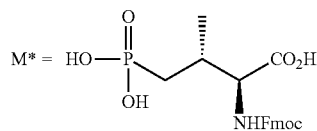

Chemical Formula: C$_{20}$H$_{22}$NO$_7$P
Exact Mass: 419.1134
Molecular Weight: 419.3649

Di-amide pro-drug peptide synthesis. Peptides were synthesize on NovaSyn® TGR resin (Novabiochem, cat. no. 01-64-0060) using standard Fmoc solid-phase protocols in N-Methyl-2-pyrrolidone (NMP). Fmoc-Pro-OH, Fmoc-Leu-OH, Fmoc-His(Trt)-OH and Fmoc-Ser(tBu)-OH were purchased from Novabiochem and used. Pmab analogue 12 was coupled to the resin by using 12 (1.0 eq), HATU (1.0 eq.), HOBT (1.0 eq.) and DIPEA (2.0 eq.) in NMP, r.t., overnight. The following residue are coupled by using Fmoc protected amino acid (5.0 eq.), 1-O-Benzotriazole-N,N,N',N'-tetramethyl-uronium-hexafluoro-phosphate (HBTU) (5.0 eq.), hydroxybenzotriazole (HOBT) (5.0 eq.) and N,N-Diisopropylethylamine (DIPEA) (5.0 eq.) in NMP, r.t, 2 hr. The N-terminal was acetylated by 1-Acetylimidazole. The final resin was washed with N,N-dimethylforamide (DMF), methanol, dichloromethane and ether then dried under vacuum (over night). Peptides were cleaved from resin (200 mg) by treatment with 5 mL of trifluoroacetic acid:triisbutylsilane:$H_2O$ (90:5:5) (4 h). The resin was filtered off and the filtrate was concentrated under vacuum, then precipitated with ether and the precipitate washed with ether. The resulting solid was dissolved in 50% aqueous acetonitrile (5 mL) and purified by reverse phase preparative HPLC using a Phenomenex $C_{18}$ column (21 mm dia×250 mm, cat. no: 00G-4436-P0) with a linear gradient from 0% aqueous acetonitrile (0.1% trifluoroacetic acid) to 100% acetonitrile (0.1% trifluoroacetic acid) over 25 minutes at a flow rate of 10.0 mL/minute.

13

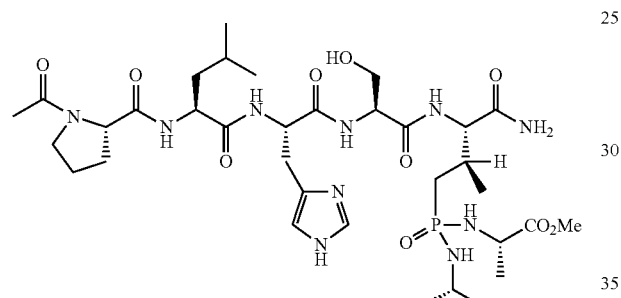

14

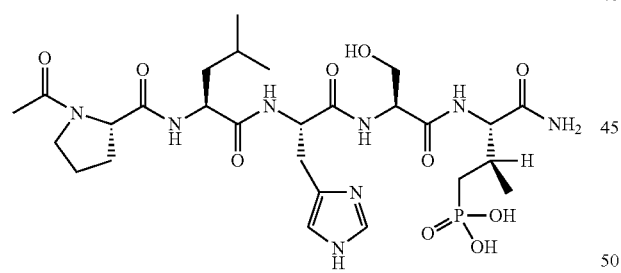

It turned out the 5% $H_2O$ in the final cleavage conditions totally hydrolyzed the methyl ester, therefore released the L-alanine to give the free phosphate peptide 14.

TABLE A

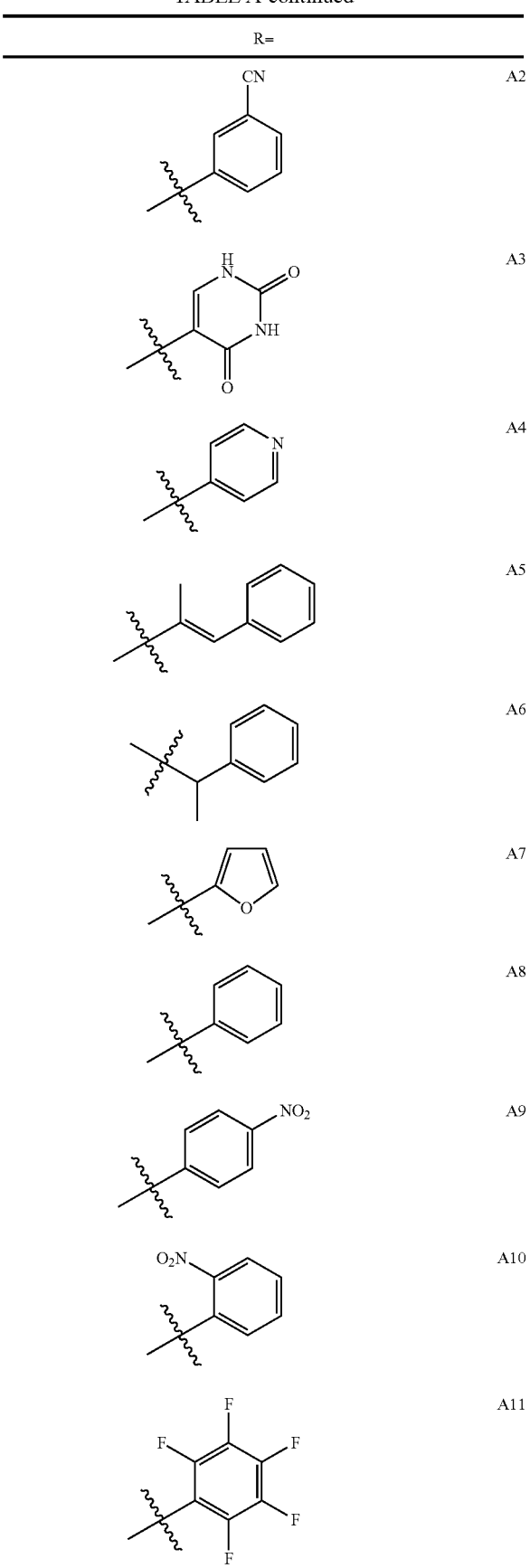

TABLE A-continued

R=

| | |
|---|---|
| (2,3-dimethoxyphenyl) | A12 |
| (2,6-dihydroxyphenyl) | A13 |
| (2,3-dihydroxyphenyl) | A14 |
| (quinolin-3-yl) | A15 |
| (3-methoxyphenyl) | A16 |
| (4-benzyloxyphenyl) | A17 |
| (4-(1H-1,2,4-triazol-1-yl)phenyl) | A18 |
| (1-methyl-1H-imidazol-2-yl) | A19 |
| (4-(dimethylamino)phenyl) | A20 |
| (3,4-dimethoxyphenyl) | A21 |
| (2-(ethoxycarbonyl)cyclopropyl) | A22 |
| (3-bromo-4-fluorophenyl) | A23 |
| (9H-fluoren-2-yl) | A24 |
| (3-(dimethylamino)-2-methylprop-1-en-1-yl) | A25 |
| (phenanthren-9-yl) | A26 |
| (5-ethylfuran-2-yl) | A27 |
| (2-cyanophenyl) | A28 |

TABLE A-continued

| R= | |
|---|---|
| 4-cyanophenyl | A29 |
| 4-trifluoromethylphenyl | A30 |
| 2-fluorophenyl | A31 |
| 4-fluorophenyl | A32 |
| 3-furyl | A33 |
| norbornenyl | A34 |
| 3-hydroxy-4-methoxyphenyl | A35 |
| 1-methylpyrrol-2-yl | A36 |
| 5-(hydroxymethyl)furan-2-yl | A37 |
| 5-ethylthiophen-2-yl | A38 |
| 5-nitrofuran-2-yl | A39 |
| 5-methylfuran-2-yl | A40 |
| 3-methylphenyl | A41 |

Those skilled in the art will recognize, or be able to ascertain using no more than routine experimentation, many equivalents to the specific embodiments of the invention described herein. Such equivalents are intended to be encompassed by the following claims.

REFERENCES

All references, patents, patent publications, and sequence reference numbers cited herein are incorporated herein by reference as if they were each incorporated individually.

1. Barr, F. A., Sillje, H. H. & Nigg, E. A. Polo-like kinases and the orchestration of cell division. Nat. Rev. Mol. Cell Biol. 5, 429-440. (2004).
2. van de Weerdt, B. C. & Medema, R. H. Polo-like kinases: a team in control of the division. Cell Cycle 5, 853-864. (2006).
3. Lowery, D. M., Lim, D. & Yaffe, M. B. Structure and function of polo-like kinases. Oncogene 24, 248-259. (2005).
4. Eckerdt, F., Yuan, J. & Strebhardt, K. Polo-like kinases and oncogenesis. Oncogene 24, 267-276. (2005).
5. Strebhardt, K. & Ullrich, A. Targeting polo-like kinase 1 for cancer therapy. Nat. Rev. Cancer 6, 321-330. (2006).
6. Burns, T. F., Fei, P., Scata, K. A., Dicker, D. T. & El-Deiry, W. S. Silencing of the novel p53 target gene Snk/Plk2 leads to mitotic catastrophe in paclitaxel (taxol)-exposed cells. Mol. Cell Biol. 23, 5556-5571. (2003).
7. Xie, S., Xie, B., Lee, M. Y. & Dai, W. Regulation of cell cycle checkpoints by polo-like kinases. Oncogene 24, 277-286. (2005).
8. Jang, Y. J., Lin, C. Y., Ma, S. & Erikson, R. L. Functional studies on the role of the C-terminal domain of mammalian polo-like kinase. Proc. Natl. Acad. Sci. USA. 99, 1984-1989. (2002).
9. Lee, K. S., Grenfell, T. Z., Yarm, F. R. & Erikson, R. L. Mutation of the polo-box disrupts localization and mitotic functions of the mammalian polo kinase Plk. Proc. Natl. Acad. Sci. USA 95, 9301-9306. (1998).
10. Seong, Y. S. et al. A spindle checkpoint arrest and a cytokinesis failure by the dominant-negative polo-box domain of Plk1 in U-2 OS cells. J. Biol. Chem. 277, 32282-32293. (2002).
11. Elia, A. E., Cantley, L. C. & Yaffe, M. B. Proteomic screen finds pSer/pThr-binding domain localizing Plk1 to mitotic substrates. Science 299, 1228-1231. (2003). (incorporated herein by reference)

12. Cheng, K. Y., Lowe, E. D., Sinclair, J., Nigg, E. A. & Johnson, L. N. The crystal structure of the human polo-like kinase-1 polo box domain and its phospho-peptide complex. EMBO J. 22, 5757-5768. (2003).
13. Elia, A. E. et al. The molecular basis for phospho-dependent substrate targeting and regulation of Plks by the polo-box domain. Cell 115, 83-95. (2003). (incorporated herein by reference)
14. Leung, G. C. et al. The Sak polo-box comprises a structural domain sufficient for mitotic subcellular localization. Nat. Struct. Biol. 9, 719-724. (2002).
15. Kang, Y. H. et al. Self-regulation of Plk1 recruitment to the kinetochores is critical for chromosome congression and spindle checkpoint signaling. Mol. Cell 24, 409-422 (2006).
16. Minoshima, Y. et al. The constitutive centromere component CENP-50 is required for recovery from spindle damage. Mol. Cell. Biol. 25, 10315-10328. (2005).
17. Foltz, D. R. et al. The human CENP-A centromeric nucleosome-associated complex. Nat. Cell Biol. 8, 458-469. (2006).
18. Okada, M. et al. The CENP-H-I complex is required for the efficient incorporation of newly synthesized CENP-A into centromeres. Nat. Cell Biol. 8, 446-457. (2006).
19. Hanisch, A., Wehner, A., Nigg, E. A. & Sillje, H. H. Different Plk1 functions show distinct dependencies on Polo-Box domain-mediated targeting. Mol. Biol. Cell 17, 448-459. (2006).
20. Otwinowski, Z. & Minor, W. Processing of X-ray diffraction data collected in oscillation mode. Methods Enzymol. 276, 307-326. (1997).
21. Murshudov, G. N., Vagin, A. A. & Dodson, E. J. Refinement of macromolecular structures by the maximum-likelihood method. Acta Crystallogr. D Biol. Crystallogr. 53, 240-255. (1997).
22. Brünger, A. T. et al. Crystallography & NMR system: A new software suite for macromolecular structure determination. Acta Crystallogr. D Biol. Crystallogr. 54, 905-921. (1998).
23. Emsley, P. & Cowtan, K. Coot: model-building tools for molecular graphics. Acta Crystallogr. D Biol. Crystallogr. 60, 2126-2132. (2004).
24. McRee, D. E. XtalView/Xfit—A versatile program for manipulating atomic coordinates and electron density. J. Struct. Biol. 125, 156-165. (1999).
25. Navaza, J. AMoRe: an automated package for molecular replacement. Acta Cryst. A50, 157-163. (1994).
26. Brunger, A. T. Version 1.2 of the Crystallography and NMR system. Nat. Protoc. 2, 2728-2733. (2007).
27. Adams, P. D. et al. PHENIX: building new software for automated crystallographic structure determination. Acta Crystallogr. D. Biol. Crystallogr. 58, 1948-1954. (2002).
1a. Otaka, A., Mitsuyama, E., Kinoshita, T., Tamamura, H. & Fujii, N. Stereoselective synthesis of CF(2)-substituted phosphothreonine mimetics and their incorporation into peptides using newly developed deprotection procedures. J. Org. Chem. 65, 4888-4899. (2000).
2a. Simizu, S. & Osada, H. Mutations in the Plk gene lead to instability of Plk protein in human tumour cell lines. Nat. Cell Biol. 2, 852-854. (2000).
3a. Ma, S., Liu, M. A., Yuan, Y.-L. & Erikson, R. L. The serum-inducible protein kinase Snk is a G1 phase polo-like kinase that is inhibited by the calcium- and integrin-binding protein CIB. Mol. Cancer Res. 1, 376-384. (2003).
4a. Elia, A. E. et al. The molecular basis for phospho-dependent substrate targeting and regulation of Plks by the polo-box domain. Cell 115, 83-95. (2003).
5a. Seong, Y. S. et al. A spindle checkpoint arrest and a cytokinesis failure by the dominant-negative polo-box domain of Plk1 in U-2 OS cells. J. Biol. Chem. 277, 32282-32293. (2002).
6a. Brünger, A. T. Free R value: a novel statistical quantity for assessing the accuracy of crystal structures. Nature 355, 472-475. (1992).
7a. Seong, Y. S. et al. Characterization of a novel cyclin-dependent kinase 1 inhibitor, BMI-1026. Cancer Res. 63, 7384-7391. (2003).
1b. Strebhardt, K. and A. Ullrich, Targeting polo-like kinase 1 for cancer therapy. Nat. Rev. Cancer 2006, 6, 321-330.
2b. Kyung S. Lee et al., manuscipt in review.
3b. Liu, F.; Stephen A. G.; Waheed A. A.; Aman, M. J.; Freed E. O.; Fisher R. J.; Burke T. R., Jr. SAR by oxime-containing peptide libraries: application to Tsg101 ligand optimization. Chembiochem 2008, 9, 2000-2004.
4b. Liu, F.; Stephen, A. G.; Fisher, R. J.; Burke, T. R., Jr. Protected aminooxyprolines for expedited library synthesis: Application to Tsg101-directed proline-oxime containing peptides. Bioorg. Med. Chem. Lett. 2008, 18, 1096-1101.
5b. Nguyen, J. T.; Turck, C. W.; Cohen Fred, E.; Zuckermann Ronald, N.; Lim, W. A. Exploiting the basis of proline recognition by SH3 and WW domains: design of N-substituted inhibitors. Science 1998, 282, 2088-2092.
6b. Zuckermann, R. N.; Kerr, J. M.; Kent, S. B.; Moos, W. H. Efficient method for the preparation of peptoids [oligo(N-substituted glycines)] by submonomer solid-phase synthesis. J. Am. Chem. Soc. 1992, 114, 10646-7.
7b. Ojea, V.; Ruiz, M.; Shapiro, G.; Pombo-Villar, E. Enantiospecific synthesis of 2-amino-3-methyl-4-phosphonobutanoic acids via 1,4-addition of lithiated Schoellkopf anion to prop-2-enylphosphonates. Tetrahedron Lett. 1994, 35, 3273-3276.
8b. Ojea, V.; Ruiz, M.; Shapiro, G.; Pombo-Villar, E. Conjugate additions of 1-propenylphosphonates to metalated Schoellkopf's bis-lactim ether: Stereocontrolled access to 2-amino-3-methyl-4-phosphonobutanoic acids. J. Org. Chem. 2000, 65, 1984-1995.
9b. Ruiz, M.; Ojea, V.; Quintela, J. M.; Guillin, J. J. Stereoselective synthesis of (E±-monofluorinated phosphonate mimetics of naturally occurring phosphoserine and phosphothreonine, via electrophilic fluorination of lithiated bis-lactim ethers. Chem. Commun. (Cambridge, U. K.) 2002, 1600-1601.
10b. Ruiz, M.; Ojea, V.; Shapiro, G.; Weber, H.-P.; Pombo-Villar, E. Asymmetric synthesis of a protected phosphonate isostere of phosphothreonine for solid-phase peptide synthesis. Tetrahedron Lett. 1994, 35, 4551-4554.

We claim:
1. A compound comprising the structure:
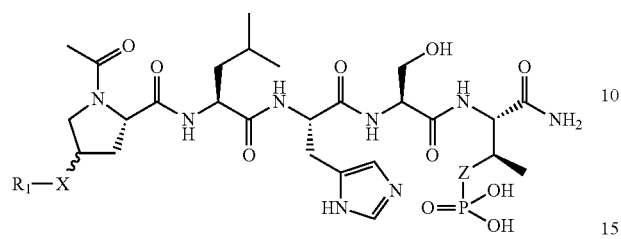
(1)
wherein
Z is selected from the group consisting of: O, CH$_2$, and CF$_2$;
R$_1$X is selected from the group consisting of: R$_1$—CH=N—O—; R$_1$—CH$_2$—CH$_2$—O—; R$_1$—C(O)—NH—O—; R$_1$—CH$_2$—CH$_2$—CH$_2$—; and R$_1$—CH$_2$—CH$_2$—S—;
R$_1$ is selected from the group consisting of:
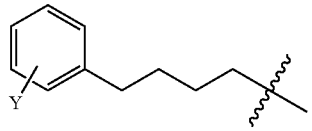
a-1
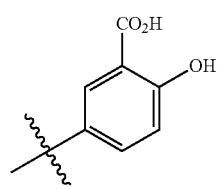 [SMILES: *c1ccc(O)c(C(=O)O)c1]
a-2
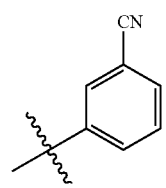 [SMILES: *c1cccc(C#N)c1]
a-3
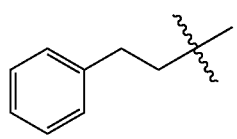
a-4
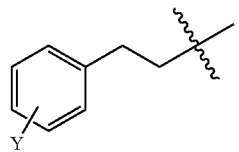
a-5
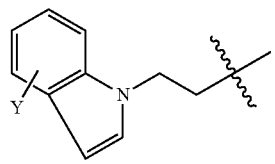
a-6
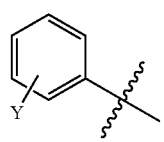
a-7
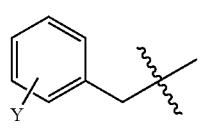
A1
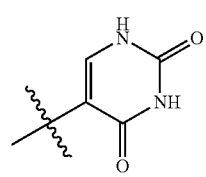 [SMILES: *c1c[nH]c(=O)[nH]c1=O]
A2
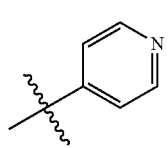
A3
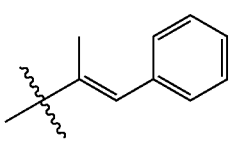
A4
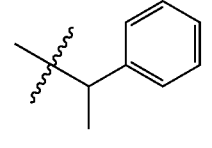 [SMILES: *C(C)c1ccccc1]
A5
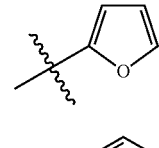
A6
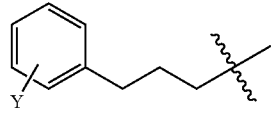
A7
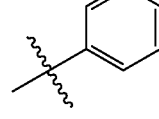
A8

| | |
|---|---|
| A9 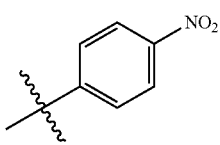 | A18 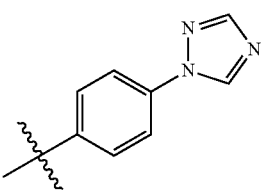 |
| A10 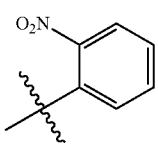 [SMILES: *c1ccccc1[N+](=O)[O-]] | A19 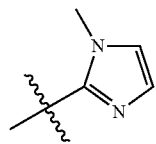 |
| A11 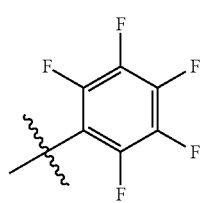 [SMILES: *c1c(F)c(F)c(F)c(F)c1F] | A20 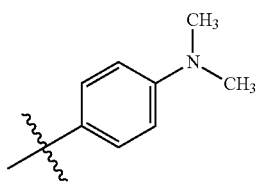 |
| A12 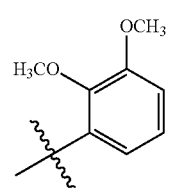 | A21 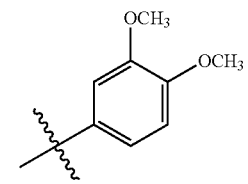 |
| A13 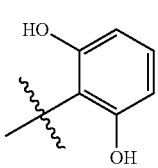 [SMILES: *c1c(O)cccc1O] | A22 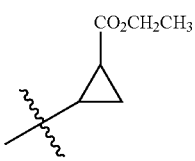 |
| A14 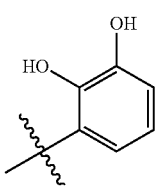 [SMILES: *c1cccc(O)c1O] | A23 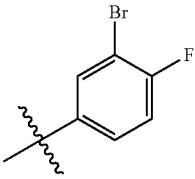 |
| A15 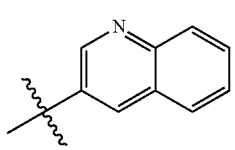 [SMILES: *c1cnc2ccccc2c1] | A24 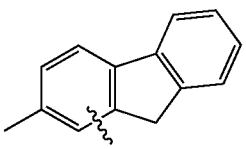 |
| A16 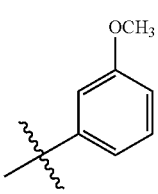 [SMILES: *c1cccc(OC)c1] | A25 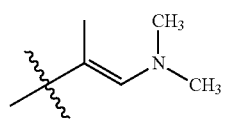 |
| A17 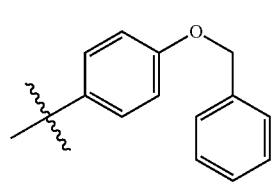 | A26 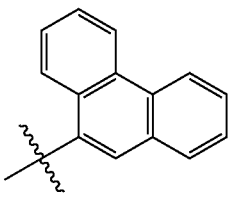 |

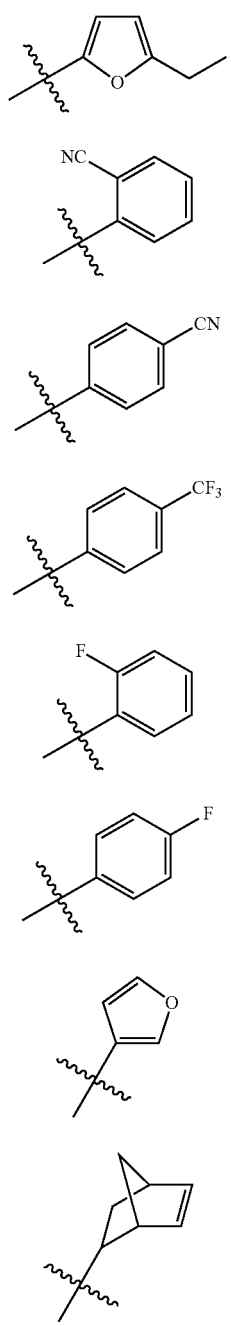
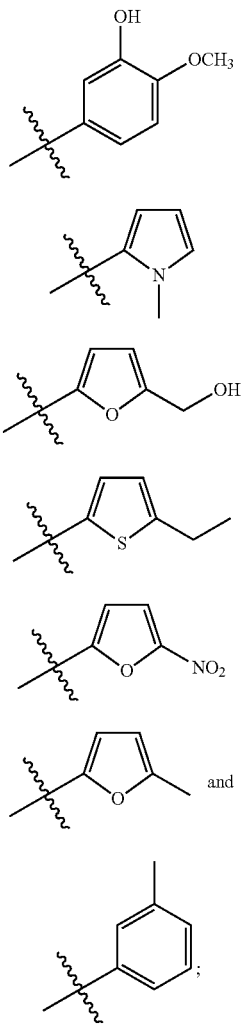

Y is a group selected from the group consisting of: aryl, heteroaryl, lower alkyl, higher alkyl, lower alkene, higher alkene, halogen, amine, amide, carboxyl, olefin, and carbonyl;

or any pharmaceutically acceptable salt thereof.

2. The compound of claim 1, wherein
 Z is O; and
 $R_1$ is selected from the group consisting of a-1, a-2, a-3, a-4, a-5, a-6, and a-7;
 or any pharmaceutically acceptable salt thereof.

3. The compound of claim 1, wherein the compound is selected from the group consisting of (2)

and any pharmaceutically acceptable salt thereof.

4. A compound comprising the structure:

(4)

wherein:
   Z is selected from the group consisting of: O, CH₂, and CF₂;
   R₁X is selected from the group consisting of: R₁—CH₂—CH₂—CH₂—; R₁—CH₂—CH₂—CH₂—CH₂—; R₁—CH₂—CH₂—S—; R₁—CH=N—O—; R₁—CH₂—CH₂—O—; and R₁—C(O)—NH—O—;
   R₁ is selected from the group consisting of:

| | |
|---|---|
| 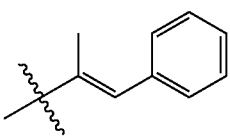 A5 | 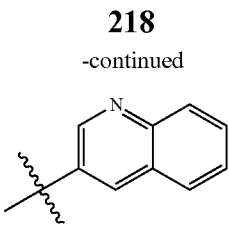 A15 |
| 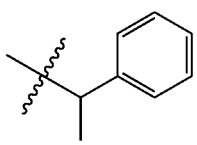 A6 | 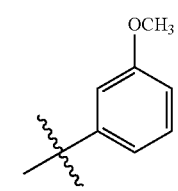 A16 |
| 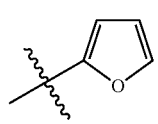 A7 | 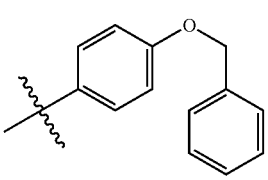 [SMILES: *c1ccc(OCc2ccccc2)cc1] A17 |
| 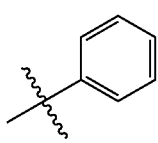 A8 | 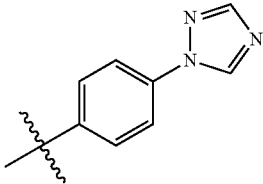 A18 |
| 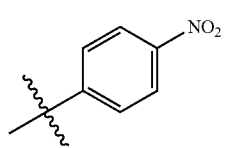 A9 | 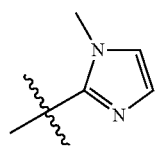 A19 |
| 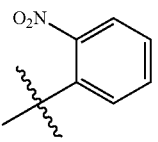 A10 | 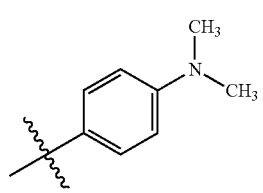 [SMILES: *c1ccc(N(C)C)cc1] A20 |
| 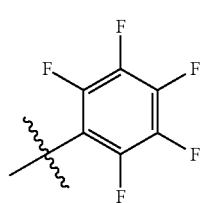 A11 | 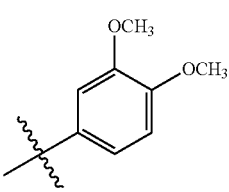 A21 |
| 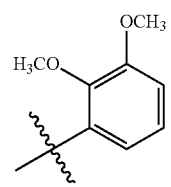 A12 | 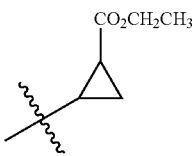 A22 |
| 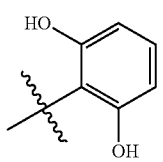 A13 | 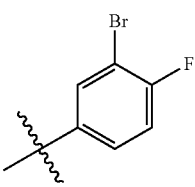 [SMILES: *c1ccc(F)c(Br)c1] A23 |
| 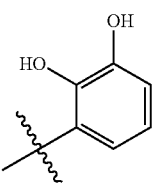 A14 | |

| A24 | 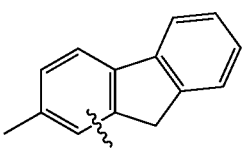 | A34 | 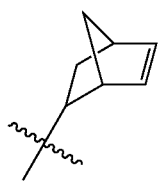 |
| A25 | 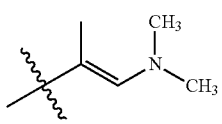 | A35 | 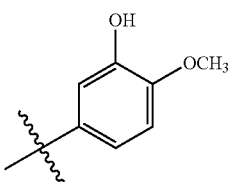 |
| A26 | 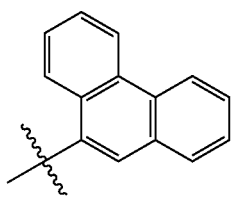 [SMILES: *c1cc2ccccc2c2ccccc12] | A36 | 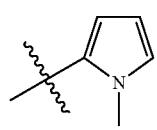 |
| A27 | 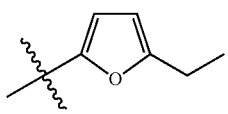 | A37 | 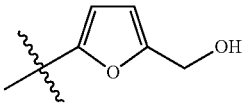 |
| A28 | 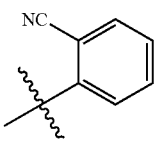 | A38 | 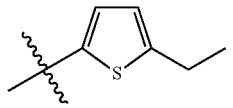 [SMILES: *c1ccc(CC)o1] |
| A29 | 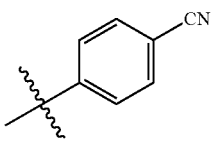 [SMILES: *c1ccc(C#N)cc1] | A39 | 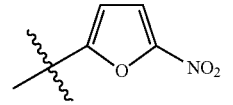 |
| A30 | 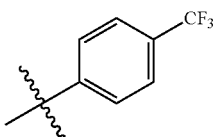 [SMILES: *c1ccc(C(F)(F)F)cc1] | A40 | 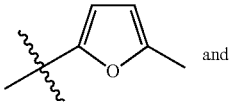 and |
| A31 | 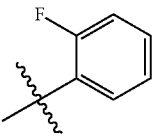 | A41 | 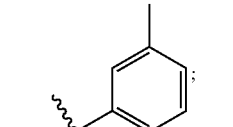 ; |
| A32 | 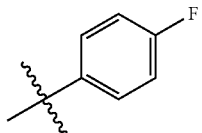 [SMILES: *c1ccc(F)cc1] | | |
| A33 | 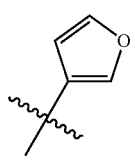 | | |

Y is a group selected from the group consisting of: aryl, heteroaryl, lower alkyl, higher alkyl, lower alkene, higher alkene, halogen, amine, amide, carboxyl, olefin, and carbonyl;

or any pharmaceutically acceptable salt thereof.

5. The compound of claim 4, wherein

Z is O; and $R_1$ is selected from the group consisting of a-1, a-2, a-3, a-4, a-5, a-6, and a-7;

or any pharmaceutically acceptable salt thereof.

6. The compound of claim 4, wherein:

Z is O;

$R_1X$ is selected from the group consisting of $R_1$—$CH_2$—$CH_2$—$CH_2$— or $R_1$—$CH_2$—$CH_2$—$CH_2$—$CH_2$—;

and $R_1$ is a-1, wherein the compound has the structure of

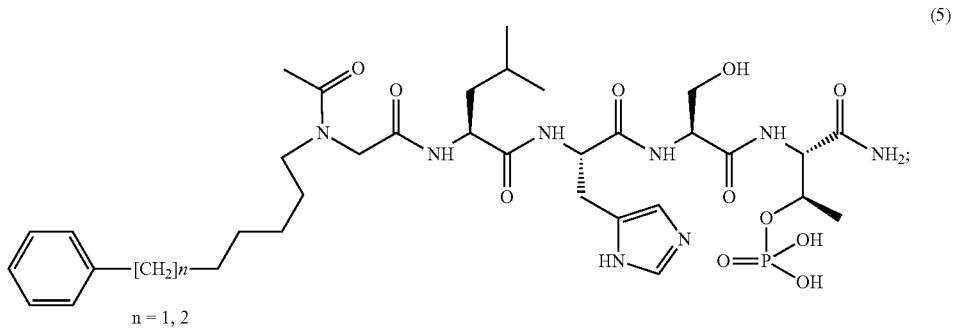

(5)

n = 1, 2 or any pharmaceutically acceptable salt thereof.

7. A compound comprising the structure:

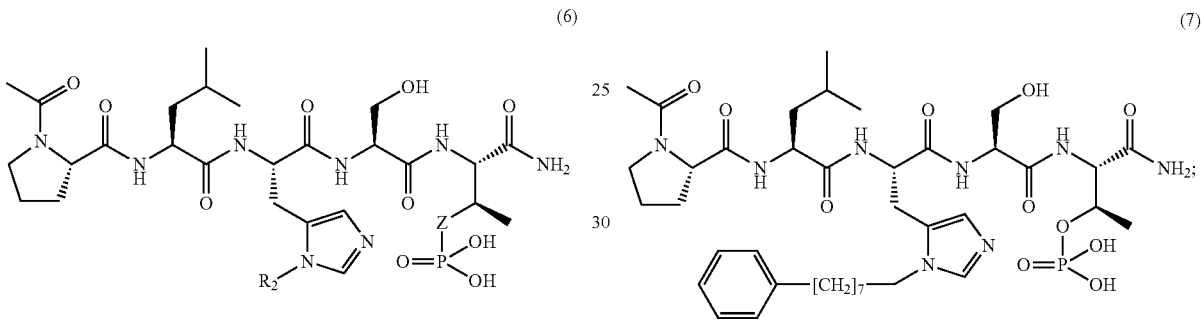

(6)

wherein Z is selected from the group consisting of O, $CH_2$, and $CF_2$;
$R_2$ is a group selected from the group consisting of:

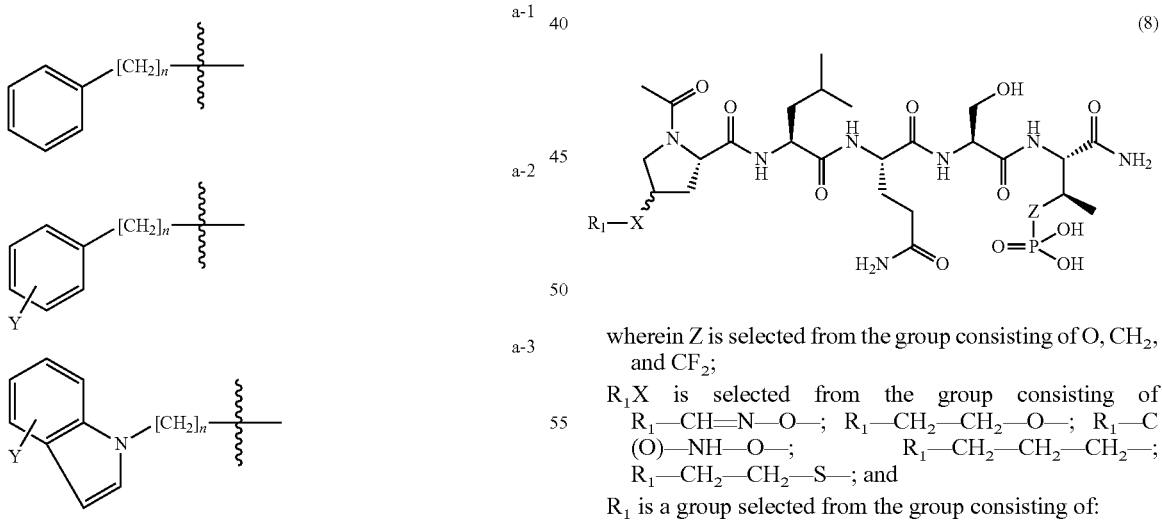

a-1 a-2 a-3 wherein n=8, 1, 2, 3, 4, 5, 6, 7, 9, or 10; and
Y is a group selected from the group consisting of: aryl, heteroaryl, lower alkyl, higher alkyl, lower alkene, higher alkene, halogen, amine, amide, carboxyl, olefin, and carbonyl;
or any pharmaceutically acceptable salt thereof.

8. The compound of claim 7, wherein Z is O; or any pharmaceutically acceptable salt thereof.

9. The compound of claim 7, wherein Z is O, $R_2$ is a-1, and n=8, wherein the compound has the structure of (7)

or any pharmaceutically acceptable salt thereof.

10. A compound comprising the structure:

(8)

wherein Z is selected from the group consisting of O, $CH_2$, and $CF_2$;
$R_1X$ is selected from the group consisting of
$R_1$—CH=N—O—; $R_1$—$CH_2$—$CH_2$—O—; $R_1$—C(O)—NH—O—; $R_1$—$CH_2$—$CH_2$—$CH_2$—; $R_1$—$CH_2$—$CH_2$—S—; and
$R_1$ is a group selected from the group consisting of:

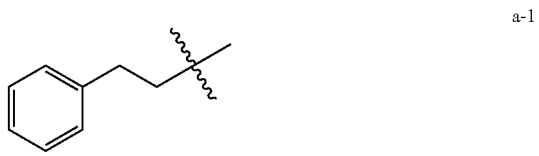

a-1

-continued

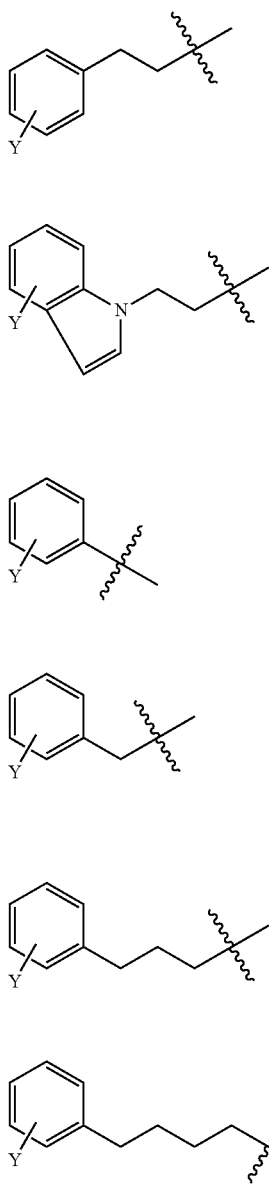

and any compound A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-31, A-33, A-34, A-35, A-36, A-37, A-38, A-39, A-40, and A-41 from Table A; and Y is a group selected from the group consisting of: aryl, heteroaryl, lower alkyl, higher alkyl, lower alkene, higher alkene, halogen, amine, amide, carboxyl, olefin, and carbonyl;

or any pharmaceutically acceptable salt thereof.

11. The compound of claim 10, wherein Z is O; and $R_1$ is a group selected from the group consisting of a-1, a-2, a-3, a-4, a-5, a-6, and a-7;

or any pharmaceutically acceptable salt thereof.

12. A compound comprising the structure

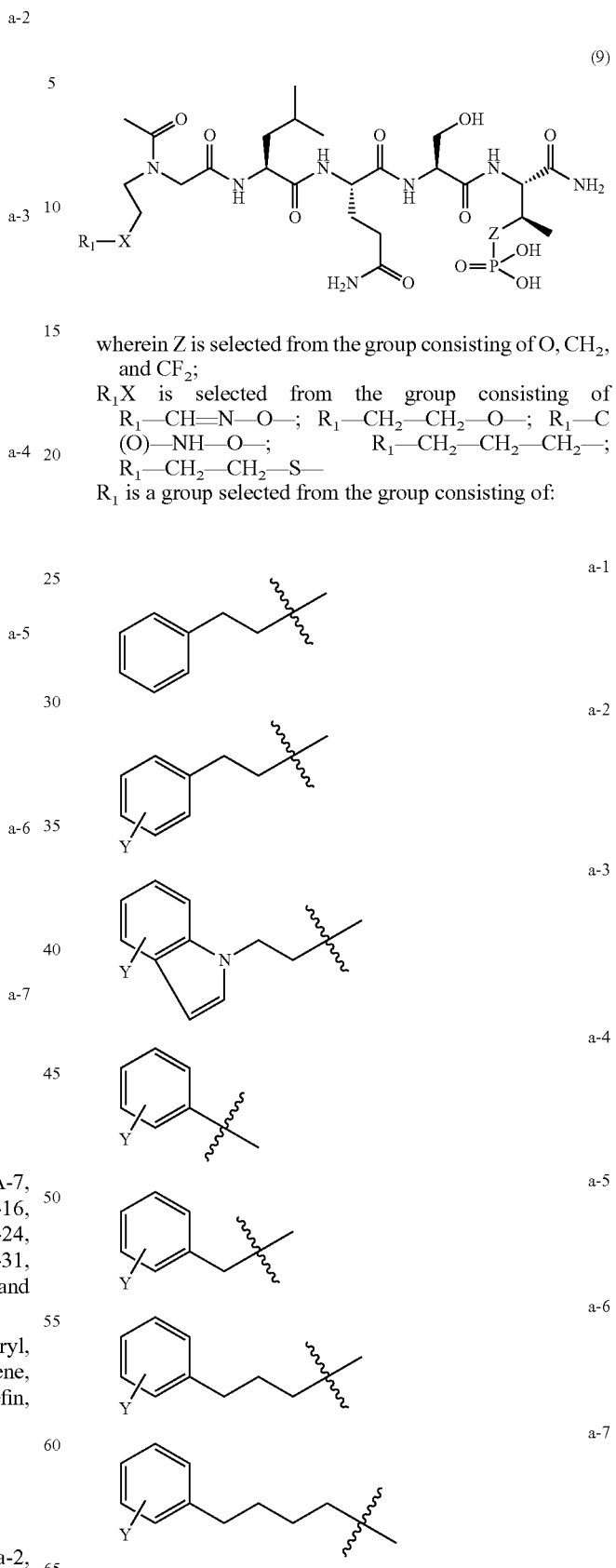

(9)

wherein Z is selected from the group consisting of O, $CH_2$, and $CF_2$;

$R_1X$ is selected from the group consisting of $R_1$—CH=N—O—; $R_1$—$CH_2$—$CH_2$—O—; $R_1$—C(O)—NH—O—; $R_1$—$CH_2$—$CH_2$—$CH_2$—; $R_1$—$CH_2$—$CH_2$—S—

$R_1$ is a group selected from the group consisting of:

and any compound A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-31, A-33, A-34, A-35, A-36, A-37, A-38, A-39, A-40, and A-41 from Table A; and Y is a group selected from the group consisting of: aryl, heteroaryl, lower alkyl, higher alkyl, lower alkene, higher alkene, halogen, amine, amide, carboxyl, olefin, and carbonyl;

or any pharmaceutically acceptable salt thereof.

13. The compound of claim 12,
wherein Z is O; and
$R_1$ is a group selected from the group consisting of a-1, a-2, a-3, a-4, a-5, a-6, and a-7;
or any pharmaceutically acceptable salt thereof.

14. A compound comprising the structure:

(10)

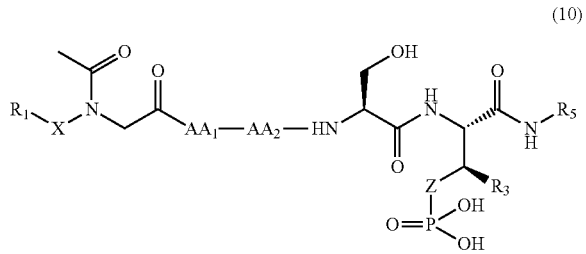

wherein $R_1$ is selected from the group consisting of a-1

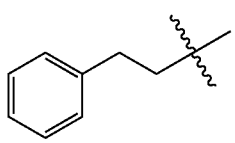

a-2

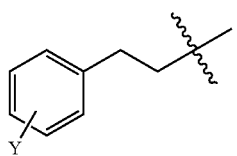

a-3

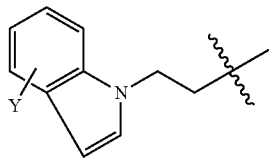

a-4

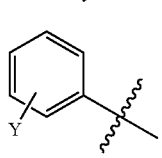

a-5

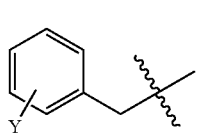

a-6

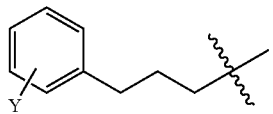

a-7

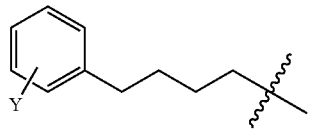

and any compound A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-31, A-33, A-34, A-35, A-36, A-37, A-38, A-39, A-40, and A-41;

Y is a group selected from the group consisting of: aryl, heteroaryl, lower alkyl, higher alkyl, lower alkene, higher alkene, halogen, amine, amide, carboxyl, olefin, and carbonyl;

$R_1$—X is selected from the group consisting of $R_1$—CH=N—O—; $R_1$—CH$_2$—CH$_2$—O—; $R_1$—C(O)—NH—O—; $R_1$—CH$_2$—CH$_2$—CH$_2$—; $R_1$—CH$_2$—CH$_2$—S—; $R_1$-lower alkyl chain; $R_1$-higher alkyl chain; and $R_1$-lower heteroalkyl or $R_1$-higher heteroalkyl wherein said heteroalkyl comprises a group selected from the group consisting of: alkenyl, aryl, heteroaryl, cycloalkyl, heterocycloalkyl, amide, ester, oxime, ether or thioether;

$AA_1$ is an amino acid selected from the group consisting of Cys, Asp, Glu, Phe, Gly, His, Ile, Lys, Leu, Met, Asn, Pro, Gln, Arg, Ser, Thr, Val, Trp, and Tyr;

$AA_2$ is an amino acid selected from the group consisting of His, Gln, Ala, Cys, Glu, Phe, Ile, Met, Asn, Ser, Thr, Val, and Tyr;

Z is selected from the group consisting of O, CH$_2$, and CF$_2$;

$R_3$ is selected from the group consisting of —CH$_3$ and —H; and $R_5$ is selected from the group consisting of —H or Gly;

or any pharmaceutically acceptable salt thereof.

15. A compound comprising the structure:

(11)

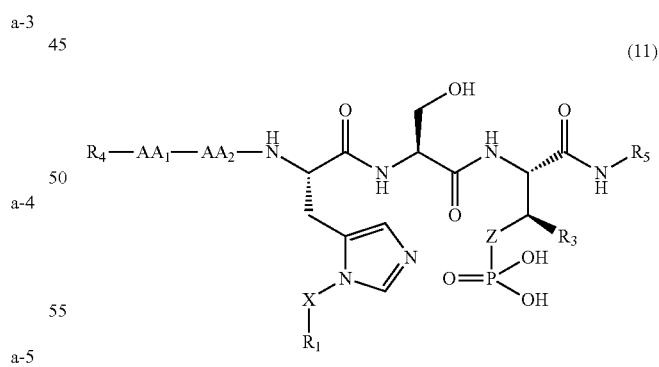

$R_1$—X is selected from the group consisting of $R_1$—CH=N—O—; $R_1$—CH$_2$—CH$_2$—O—; $R_1$—C(O)—NH—O—; $R_1$—CH$_2$—CH$_2$—CH$_2$—; $R_1$—CH$_2$—CH$_2$—S—; $R_1$-lower alkyl chain; $R_1$-higher alkyl chain; and $R_1$-lower heteroalkyl or $R_1$-higher heteroalkyl wherein said heteroalkyl comprises a group selected from the group consisting of: alkenyl, aryl, heteroaryl, cycloalkyl, heterocycloalkyl, amide, ester, oxime, ether or thioether;

R₁ is selected from the group consisting of

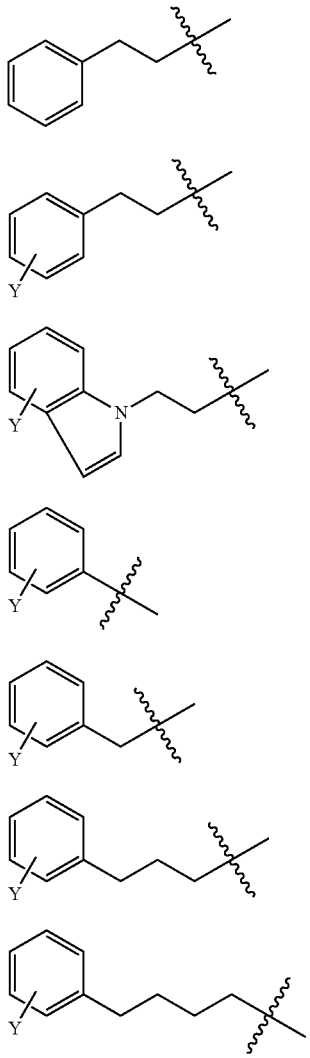

and any compound A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-31, A-33, A-34, A-35, A-36, A-37, A-38, A-39, A-40, and A-41;

Y is a group selected from the group consisting of: aryl, heteroaryl, lower alkyl, higher alkyl, lower alkene, higher alkene, halogen, amine, amide, carboxyl, olefin, and carbonyl;

R₃ is H or any acyl group;

Z is O, CH₂, and CF₂;

AA₁ is a natural amino acid selected from the group consisting of Cys, Asp, Glu, Phe, Gly, His, Ile, Lys, Leu, Met, Asn, Pro, Gln, Arg, Ser, Thr, Val, Trp, and Tyr; and any non-natural amino acid except alanine analogs;

AA₂ is an amino acid selected from the group consisting of His, Gln, Ala, Cys, Glu, Phe, Ile, Met, Asn, Ser, Thr, Val, and Tyr; and R₅ is selected from the group consisting of —H or Gly;

or any pharmaceutically acceptable salt thereof.

16. A compound comprising the structure:

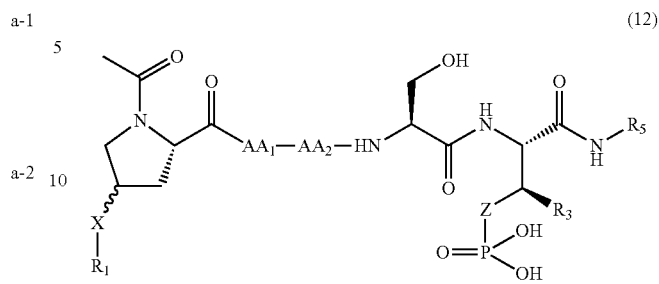

(12)

wherein R₁—X is selected from the group consisting of R₁—CH=N—O—; R₁—CH₂—CH₂—O—; R₁—C(O)—NH—O—; R₁—CH₂—CH₂—CH₂—; R₁—CH₂—CH₂—S—; R₁-lower alkyl chain; R₁-higher alkyl chain; and R₁-lower heteroalkyl or R₁-higher heteroalkyl wherein said heteroalkyl comprises a group selected from the group consisting of: alkenyl, aryl, heteroaryl, cycloalkyl, heterocycloalkyl, amide, ester, oxime, ether or thioether;

R₁ is selected from the group consisting of:

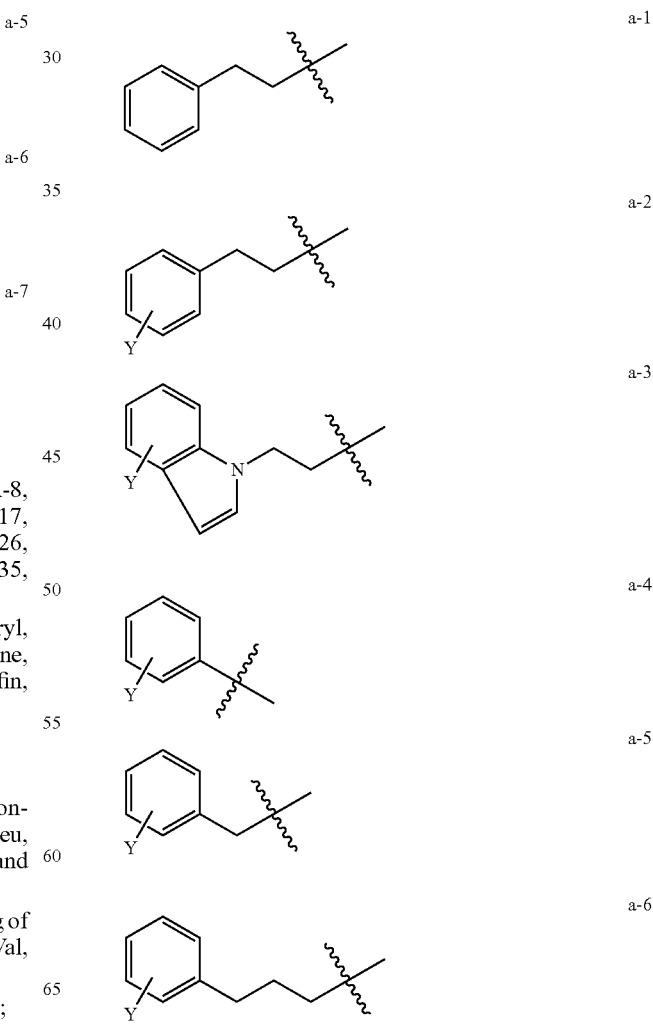

-continued

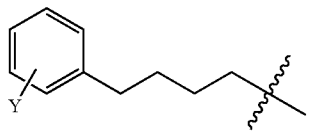
a-7 and any compound A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-31, A-33, A-34, A-35, A-36, A-37, A-38, A-39, A-40, and A-41;

Y is a group selected from the group consisting of: aryl, heteroaryl, lower alkyl, higher alkyl, lower alkene, higher alkene, halogen, amine, amide, carboxyl, olefin, and carbonyl Z is selected from the group consisting of O, $CH_2$, and $CF_2$;

$AA_1$ is a natural amino acid selected from the group consisting of Cys, Asp, Glu, Phe, Gly, His, Ile, Lys, Leu, Met, Asn, Pro, Gln, Arg, Ser, Thr, Val, Trp, and Tyr; and any non-natural amino acid except alanine analogs;

$AA_2$ is an amino acid selected from the group consisting of His, Gln, Ala, Cys, Glu, Phe, Ile, Met, Asn, Ser, Thr, Val, and Tyr;

$R_3$ is selected from the group consisting of —H and $CH_3$; and $R_5$ is H or glycine;

or any pharmaceutically acceptable salt thereof.

17. A compound selected from the group consisting of:

Z is selected from the group consisting of O, $CH_2$, and $CF_2$; or a pharmaceutically acceptable salt thereof, or A compound comprising (17)

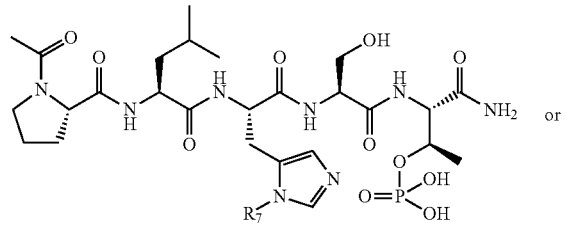

or (18)

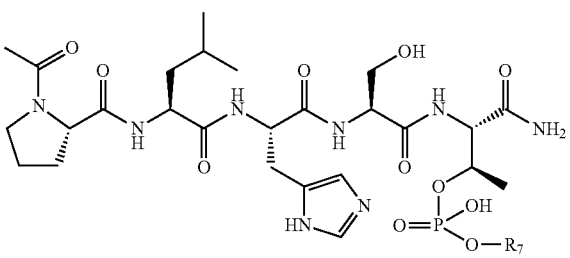

wherein $R_7$ is selected from the group consisting of:

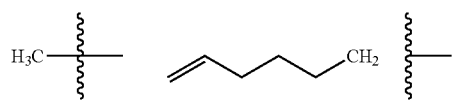

(13)

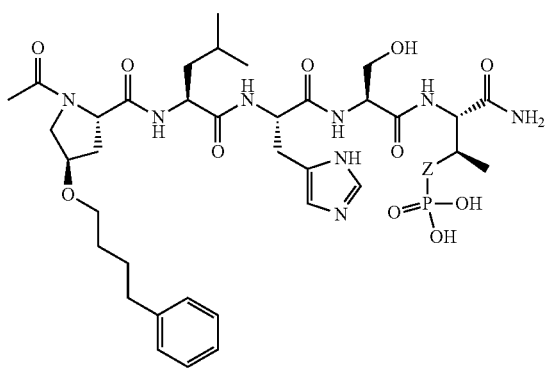

(14)

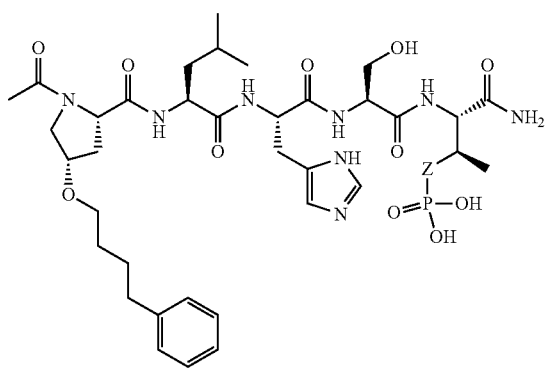

(15)

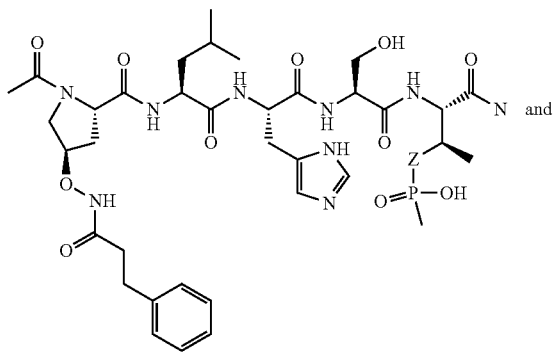

and (16)

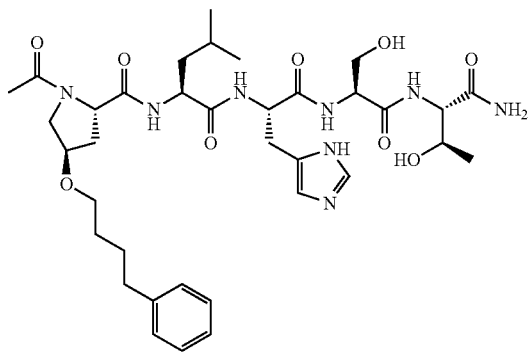

or a pharmaceutically acceptable salt thereof, or
A compound comprising a compound selected from the group consisting of:
(19)
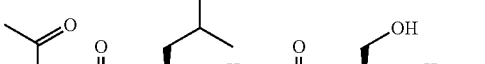
(20)
n is 7 or 8;
Z is selected from the group consisting of O, CH$_2$, and CF$_2$;
or a pharmaceutically acceptable salt thereof, or
A compound comprising a compound selected from the group consisting of:
(21)
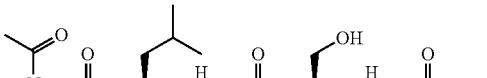
or -continued
(22)
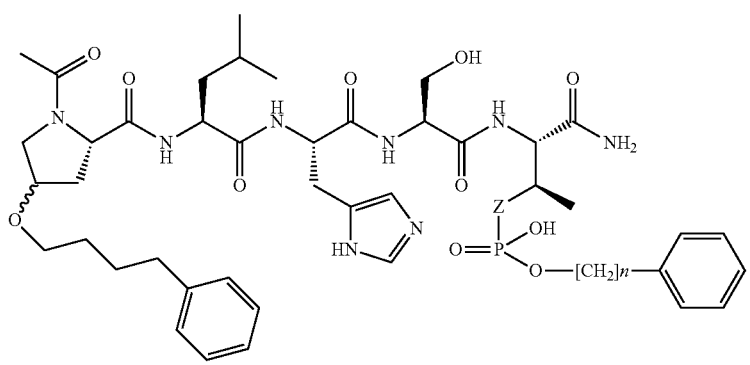
n is 2-10;
Z is selected from the group consisting of O, CH$_2$, and CF$_2$;
or a pharmaceutically acceptable salt thereof, or
A compound comprising the structure:
(23)
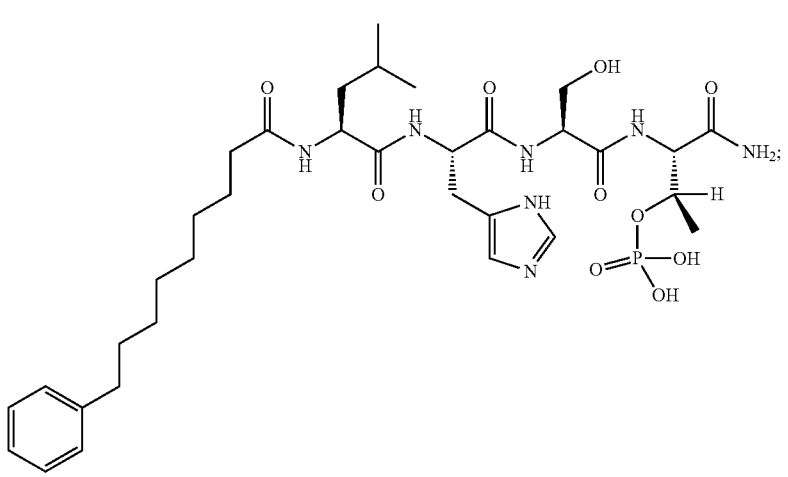
or a pharmaceutically acceptable salt thereof, or
A compound comprising the structure:
(24)
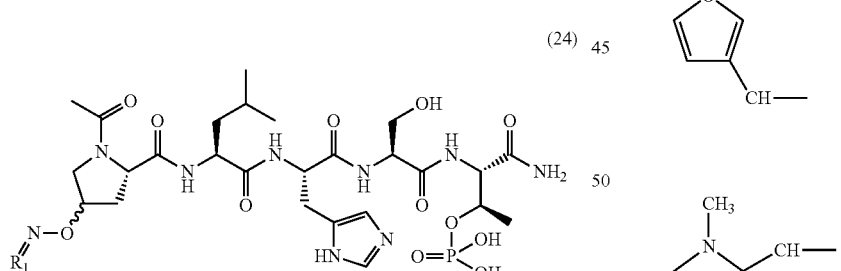
wherein R$_1$ is selected from the group consisting of:
aa
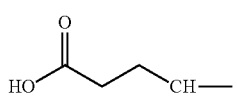
ab
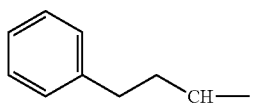
ac
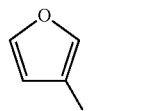
ad
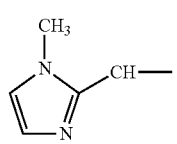
ae
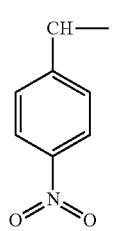

-continued
af 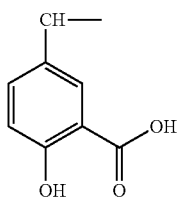
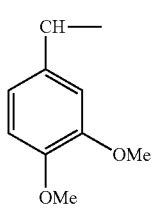
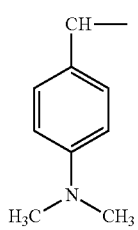
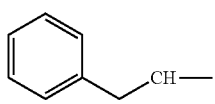
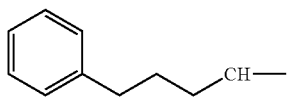
ak 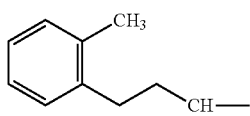
al 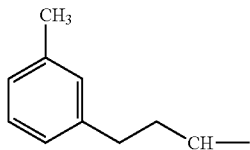
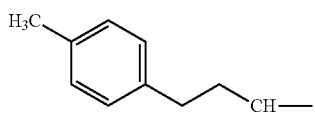
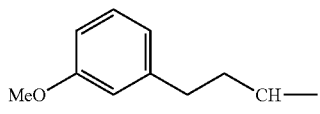
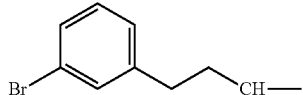
-continued
ap 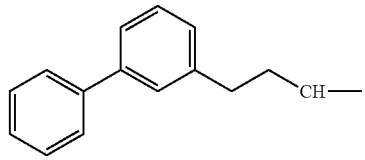
and an $R_1$ group derived from any aldehyde provided herein;
or any pharmaceutically acceptable salt thereof, or
A compound comprising structure:
(25)
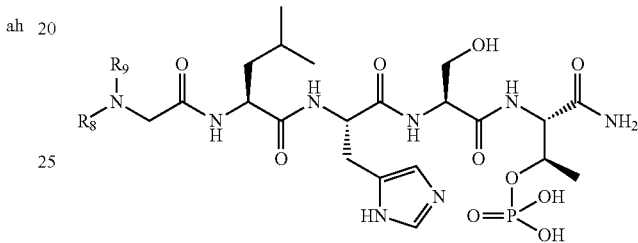
$R_9$ is H or acetyl;
and $R_8$ is selected from the group consisting of:
a 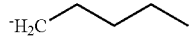
b 
c 
d 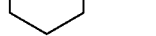
e 
f 
g 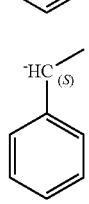

-continued
h 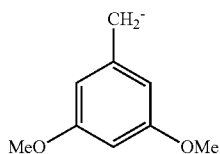
i 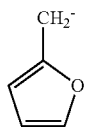
j 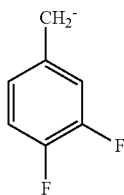
k 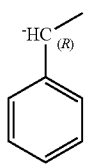
l 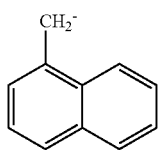
m 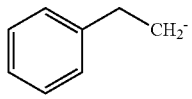
n 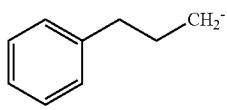
o 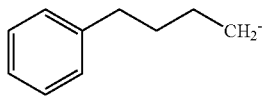
p 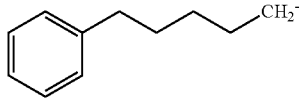
q 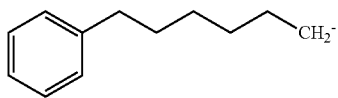
r 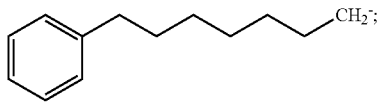
or any pharmaceutically acceptable salt thereof, or
A compound selected from the group consisting of:
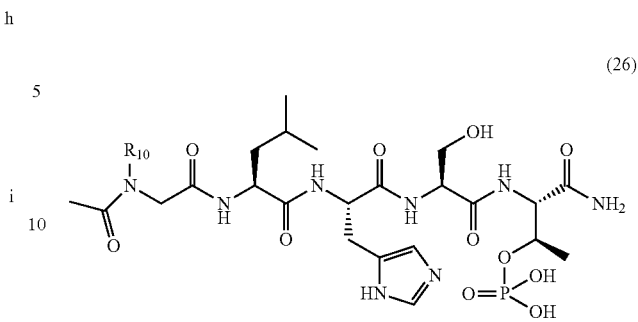
(26)
wherein $R_{10}$ comprises —$(CH_2)_n$-Ph wherein n=2, 3, 4, 5, 6, or 7; or any pharmaceutically acceptable salt thereof, or
A compound selected from the group consisting of:
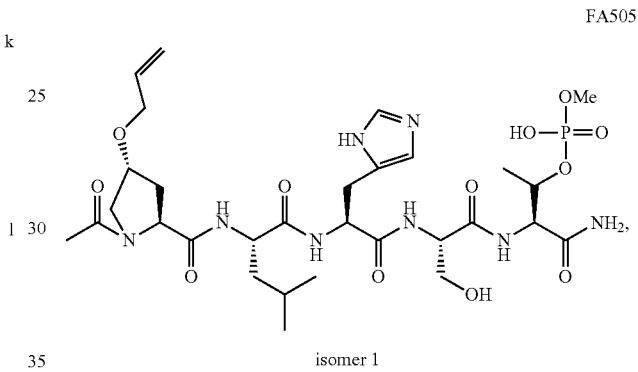
FA505
isomer 1
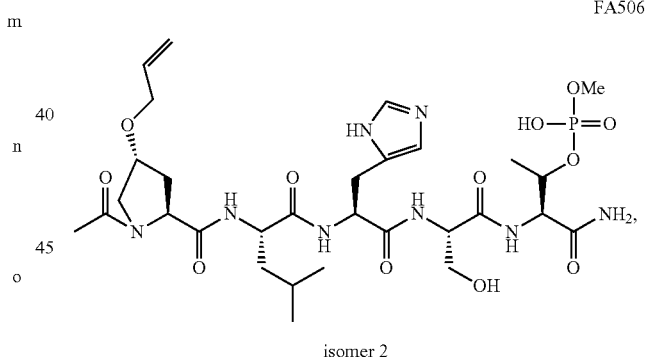
FA506
isomer 2
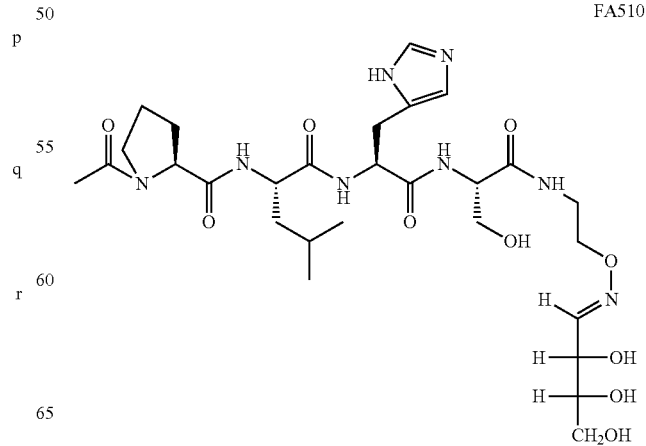
FA510

239
-continued
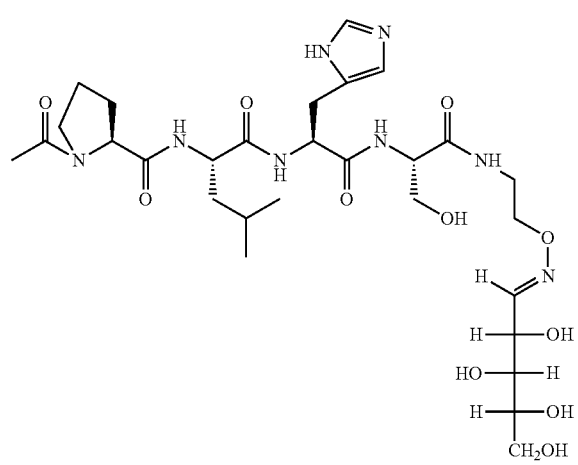
FA511
240
-continued
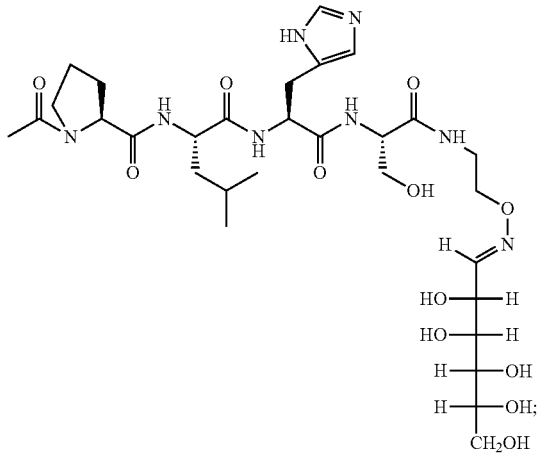
FA512
or any pharmaceutically acceptable salt thereof, or
A compound comprising a structure of any of the compounds in a table selected from the group consisting of
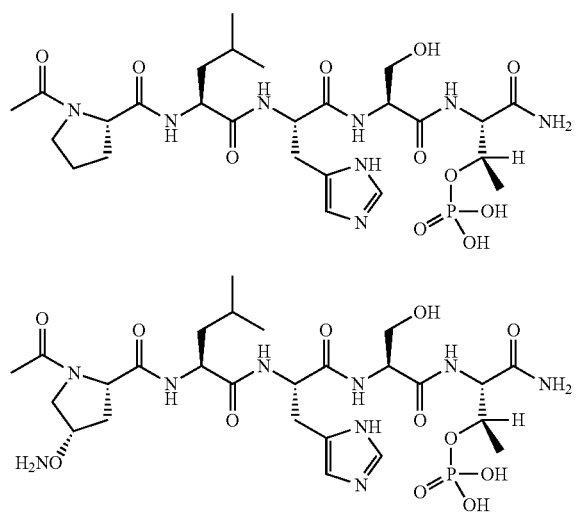
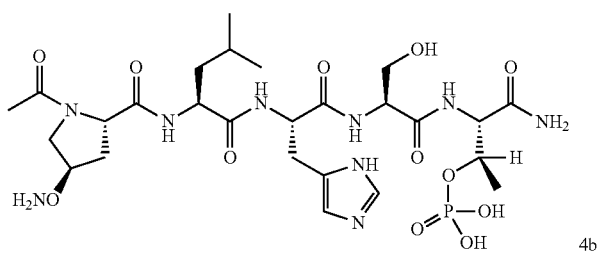
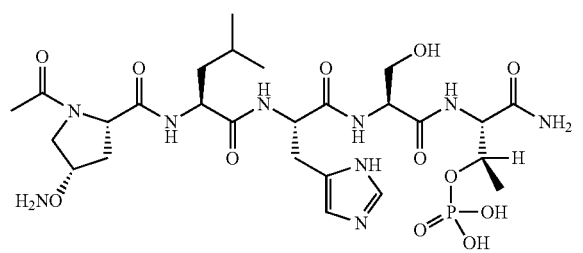
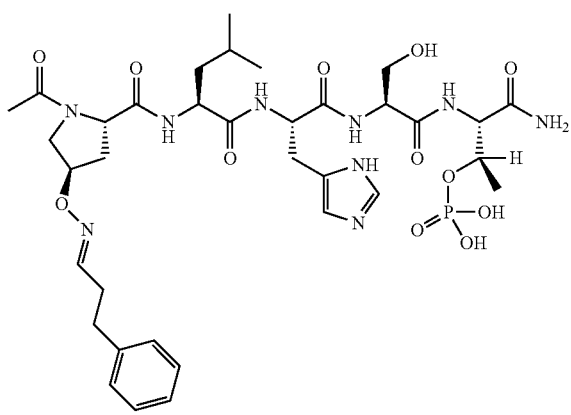
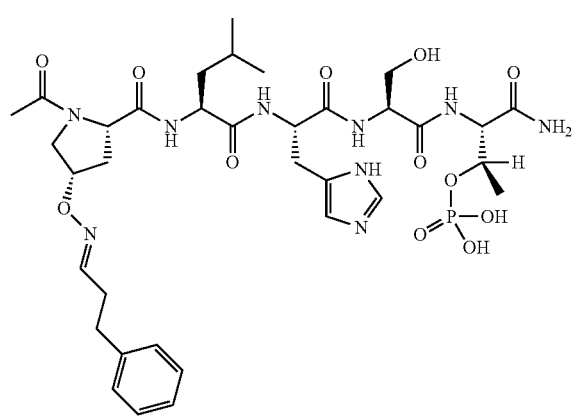
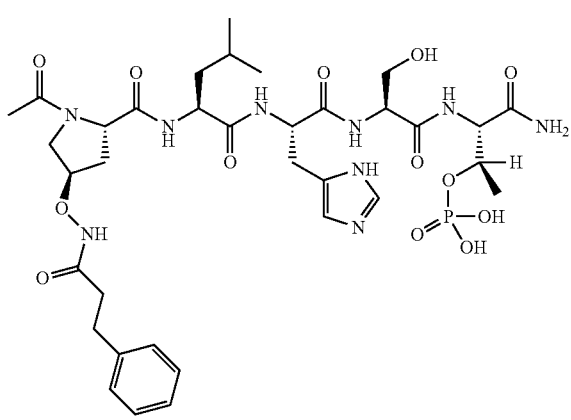

-continued
7
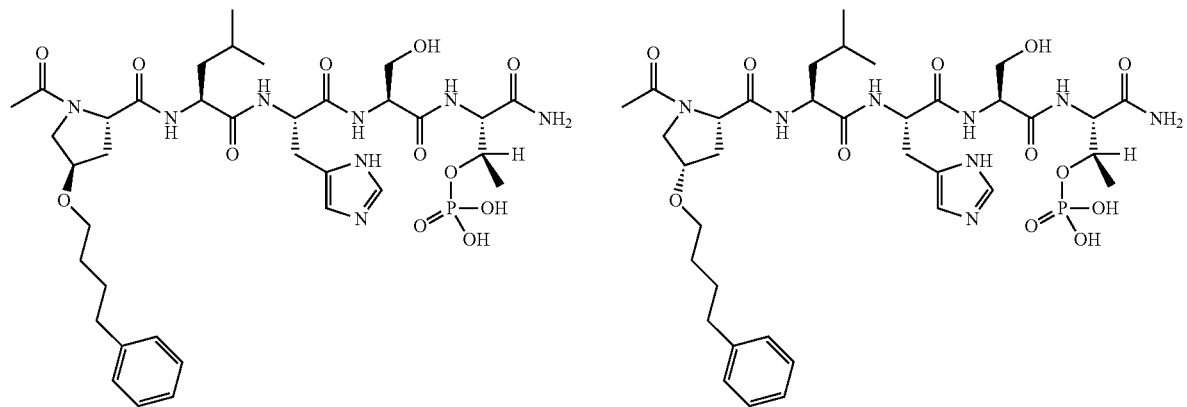
8
11
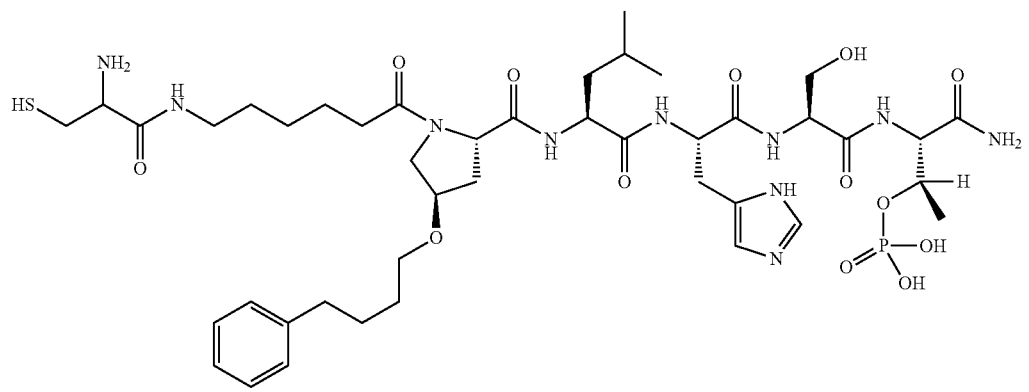
12
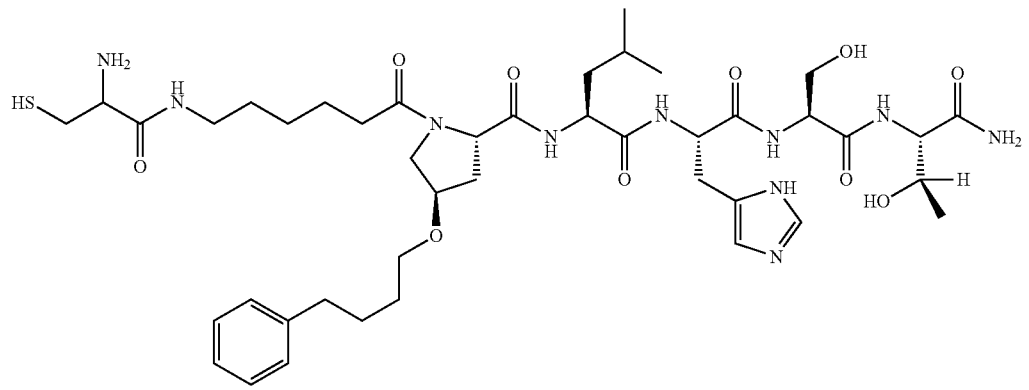
9
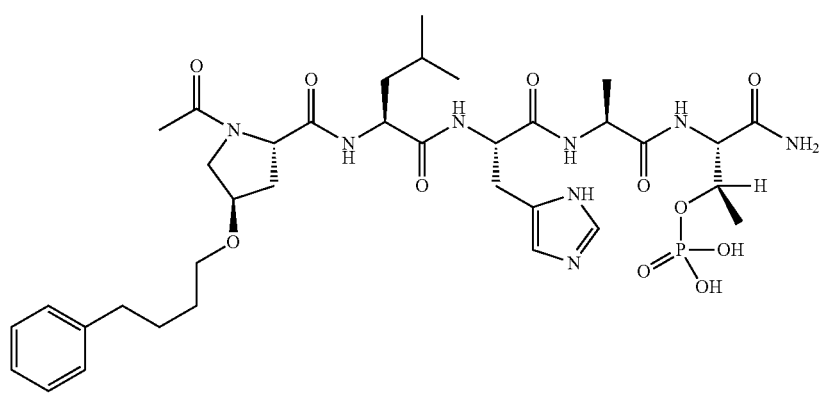

-continued
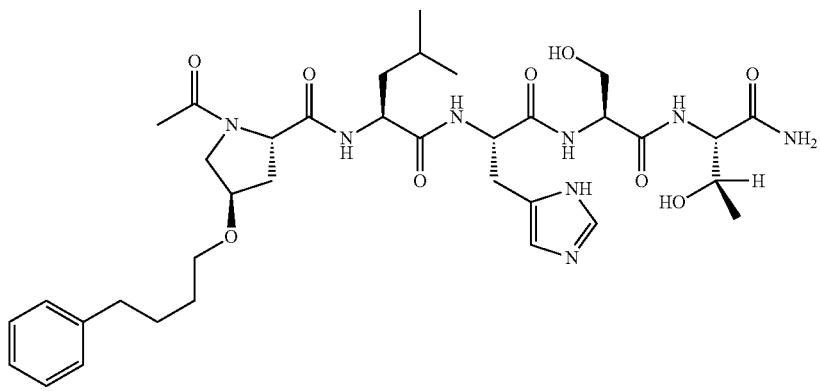
10
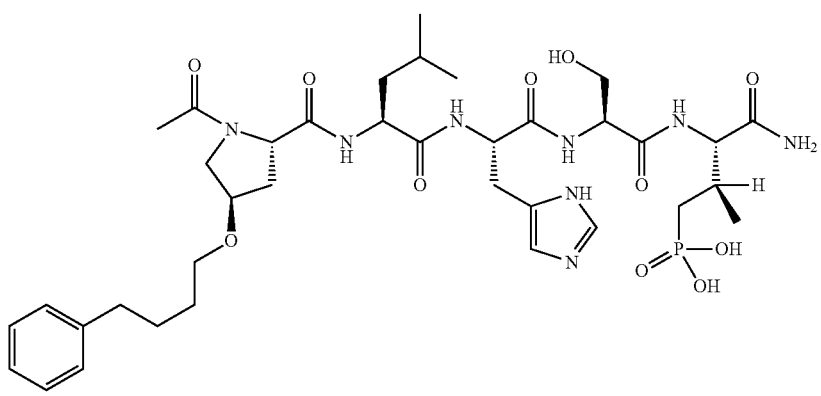
17
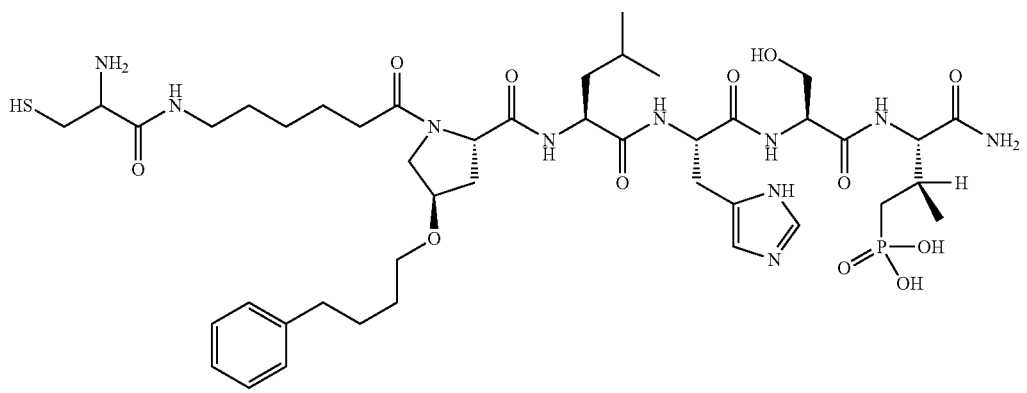
13
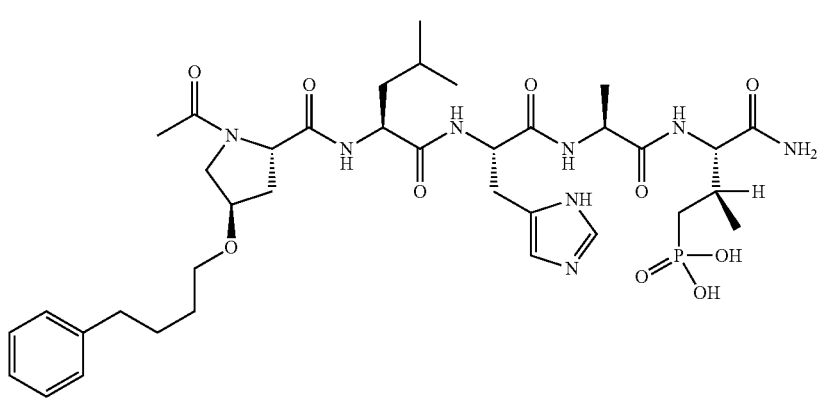
18

-continued
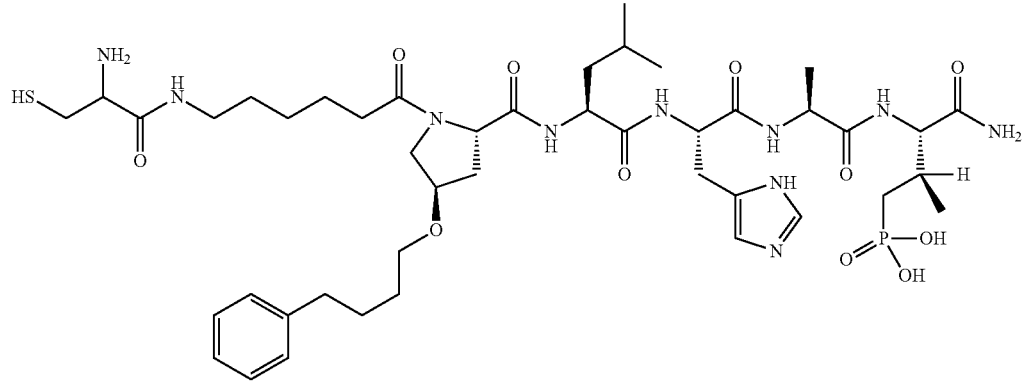
14
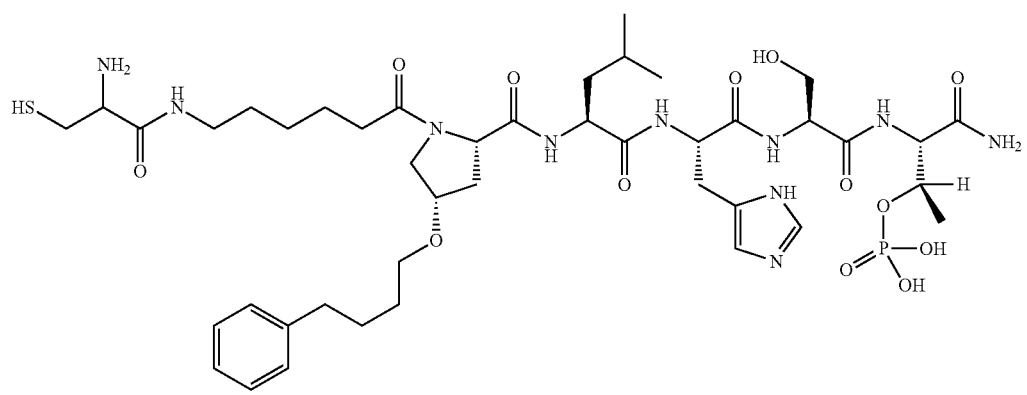
15
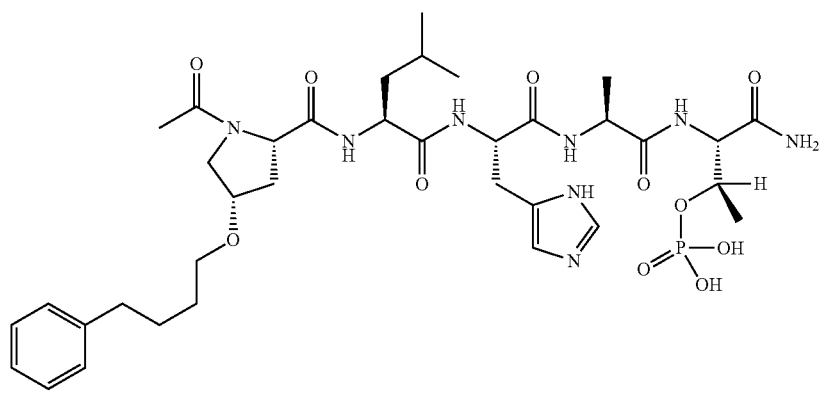
11
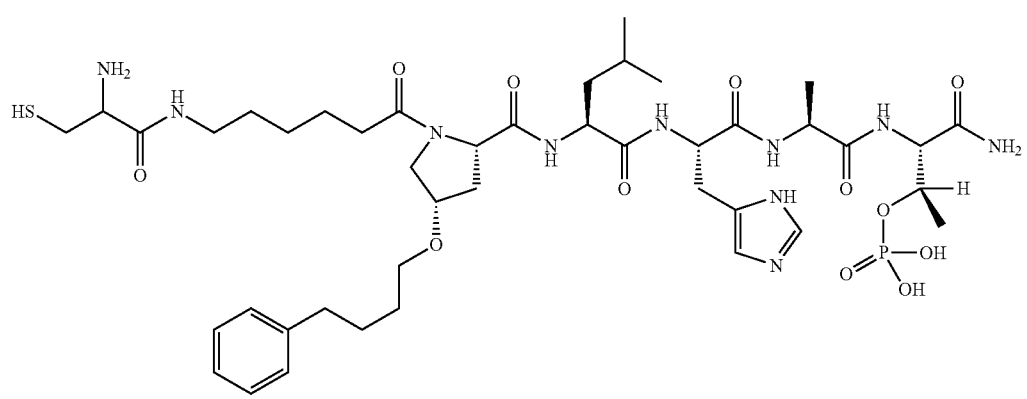
16

247
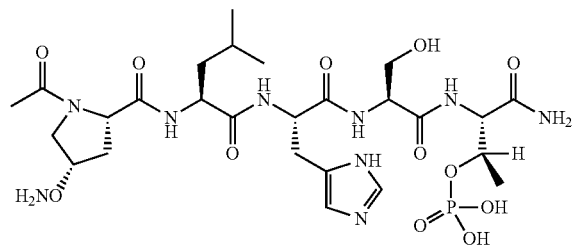
248
-continued
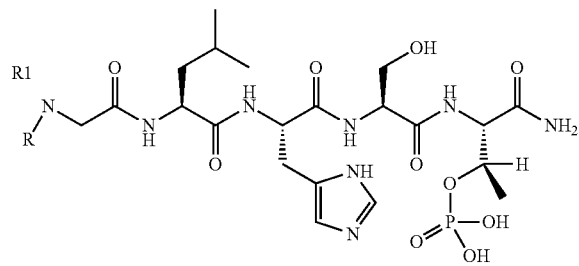
R1 = H or acetyl
5
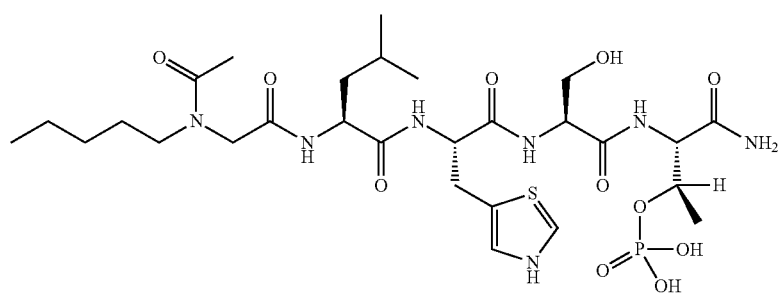
4a
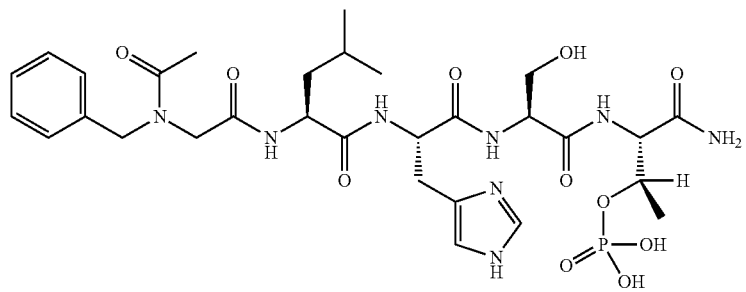
4f
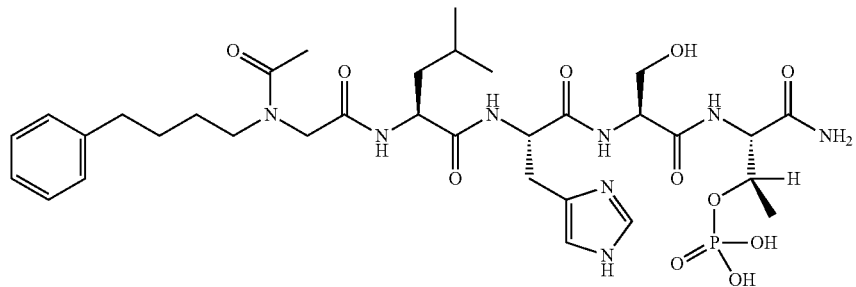
4o
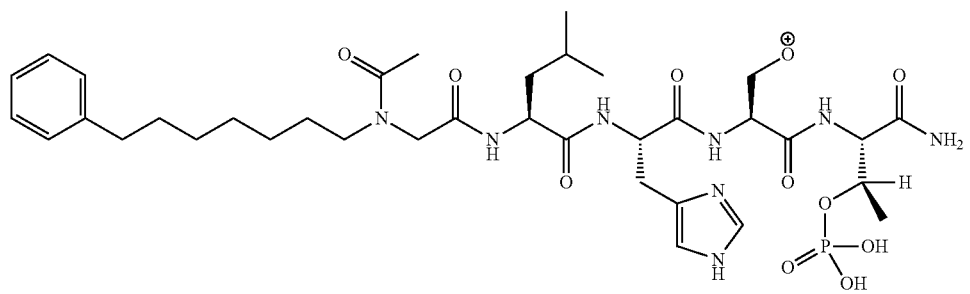
4r -continued
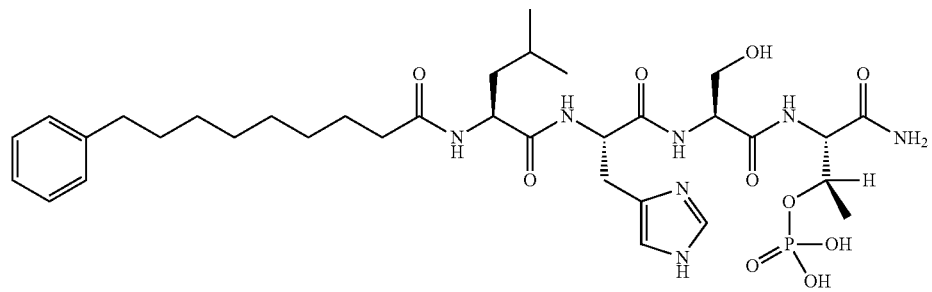
6
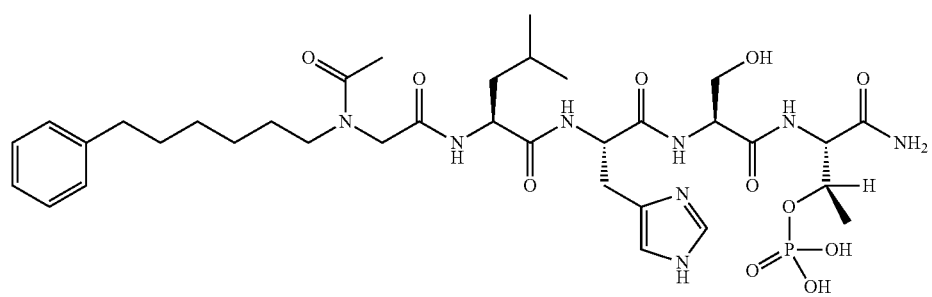
12
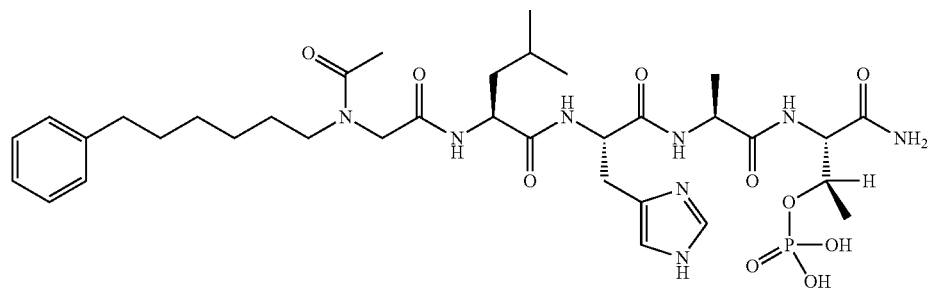
14
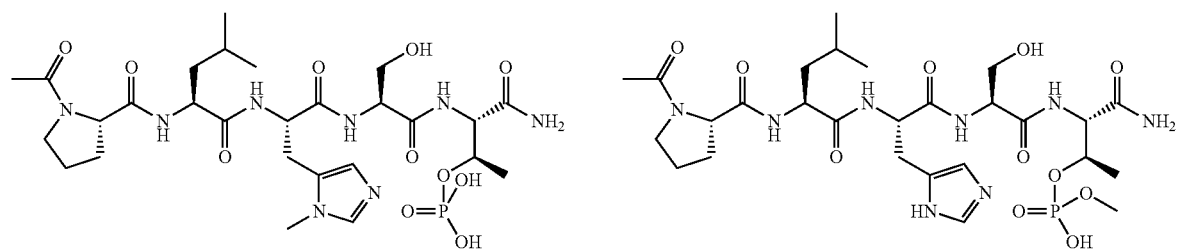
3a    4a
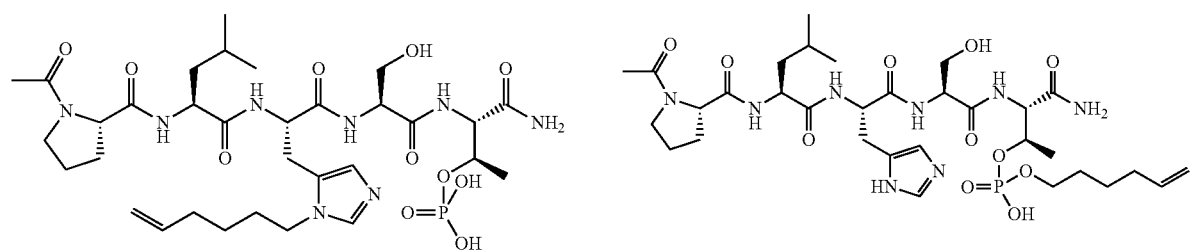
3b    4b -continued
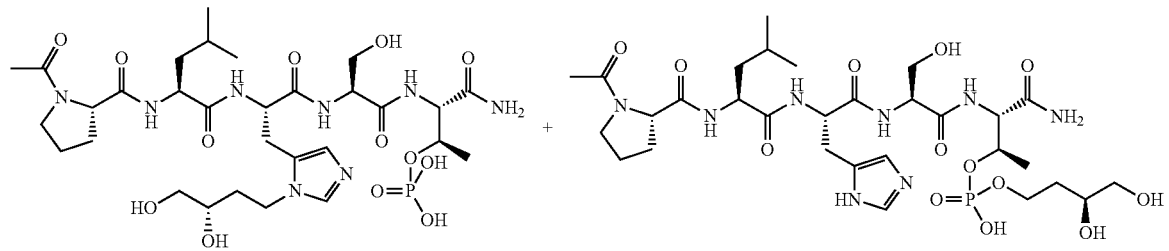
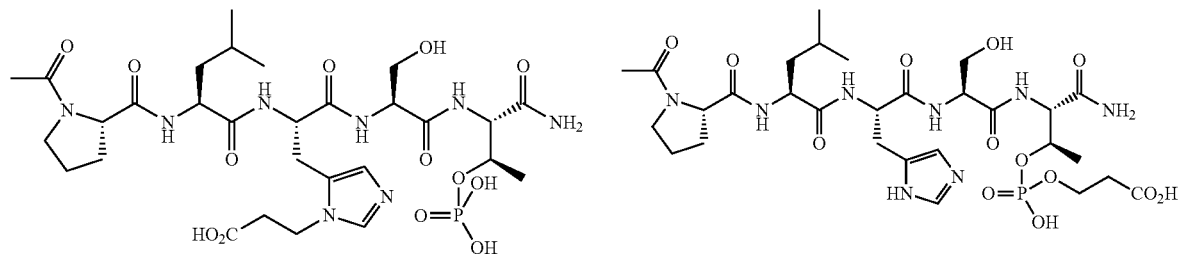
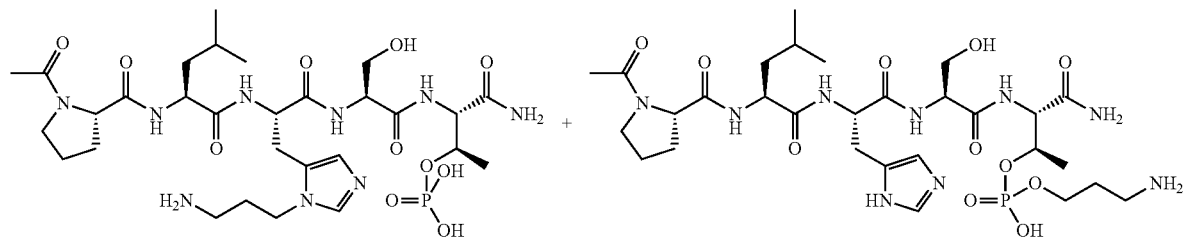
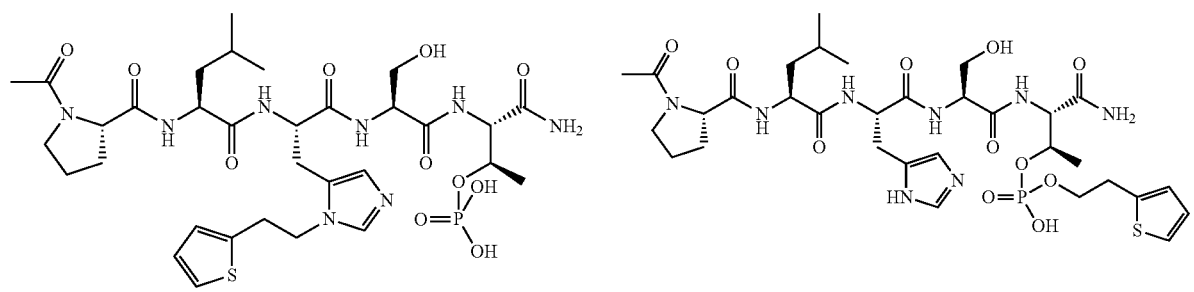
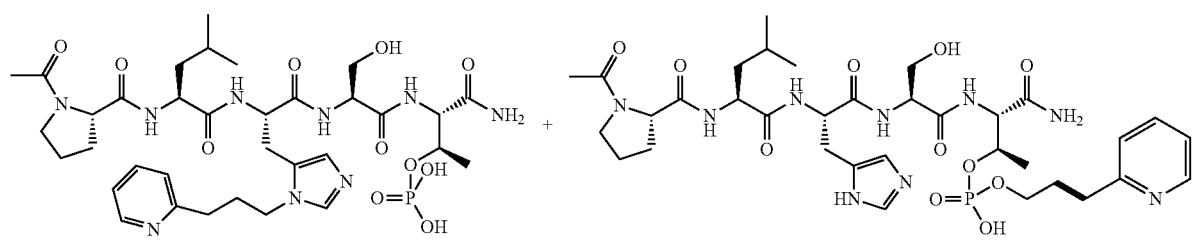

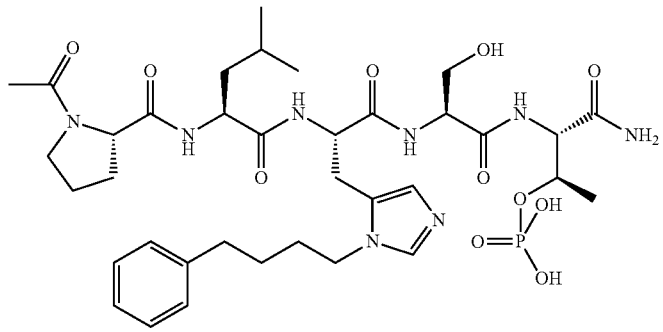
3h
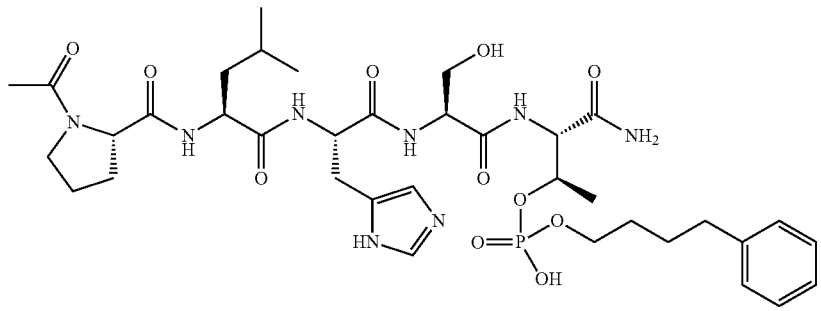
4h
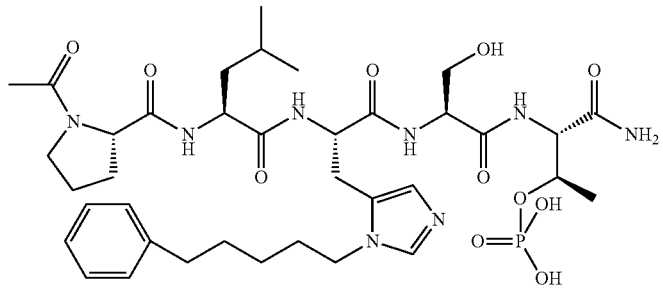
3i
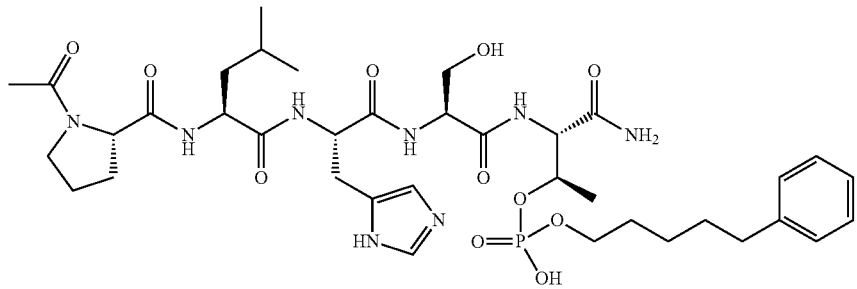
4i
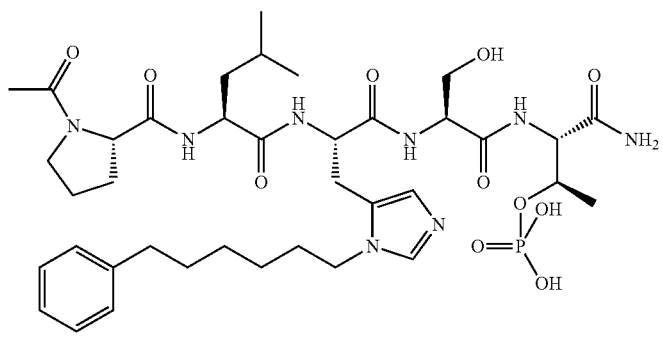
3j

-continued
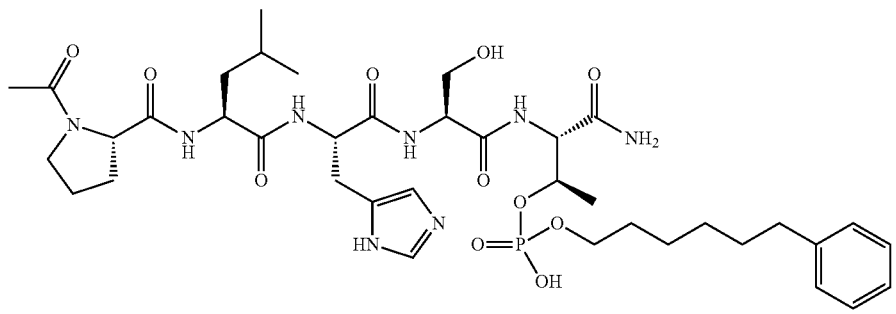
4j
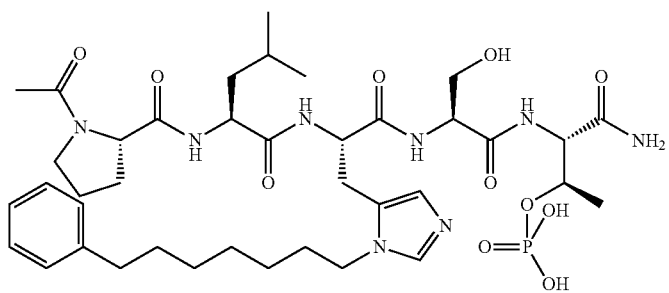
3k
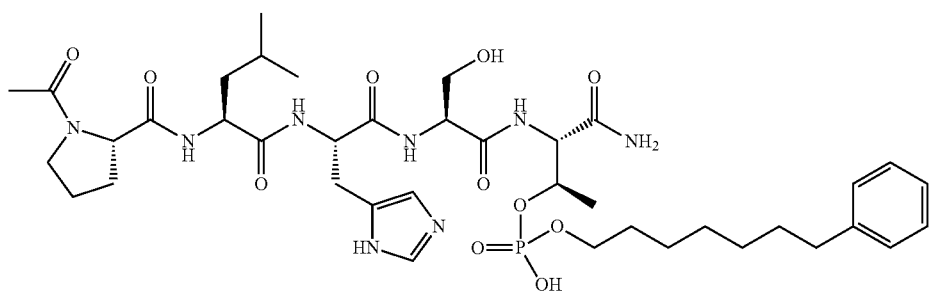
4k
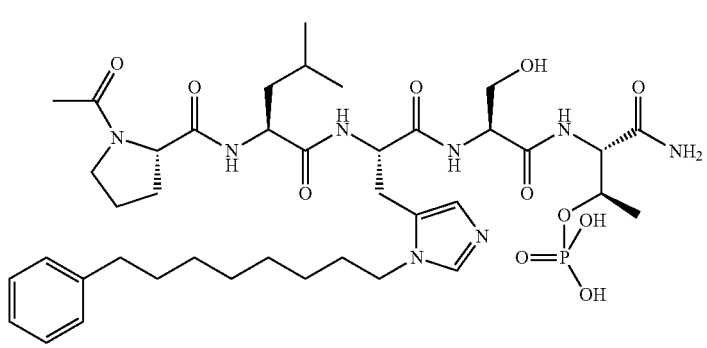
3l
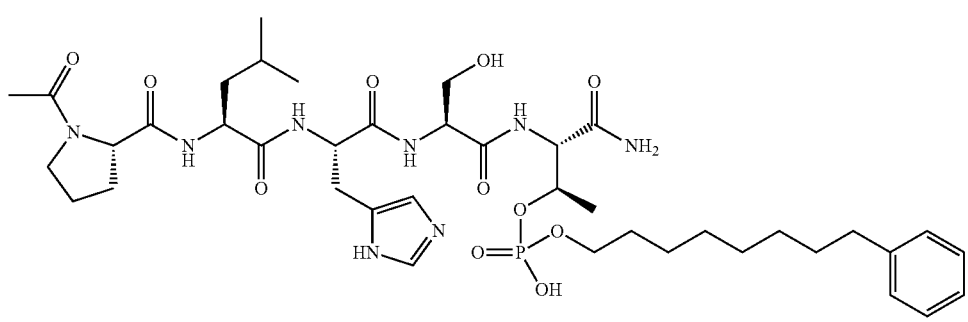
4l 3m
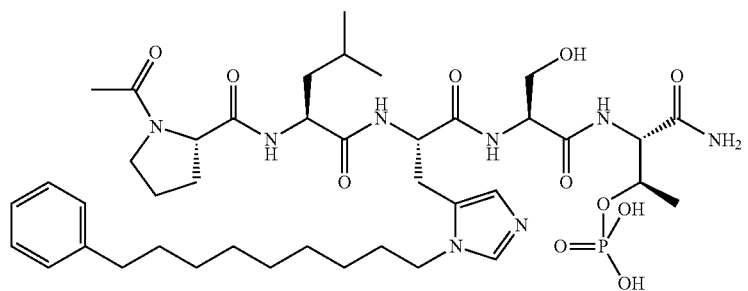
4m
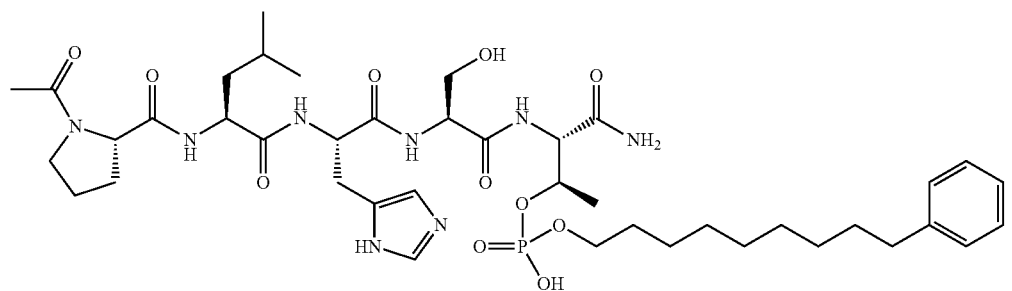
3n
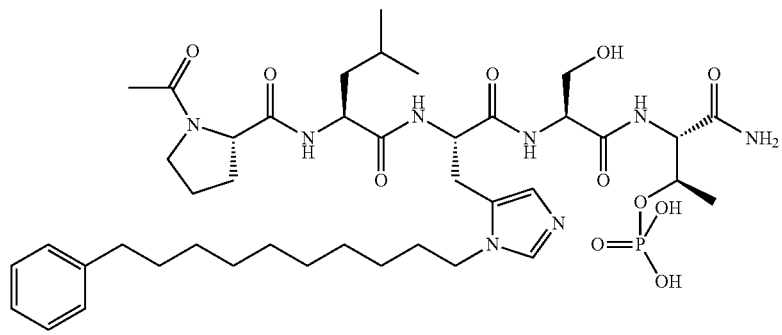
4n
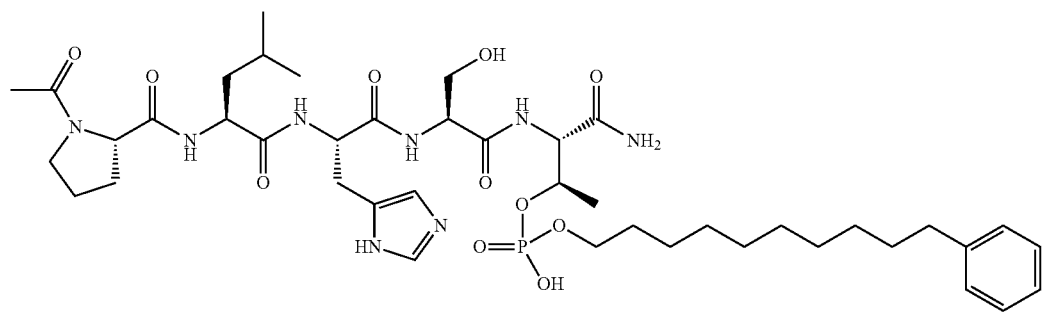
5
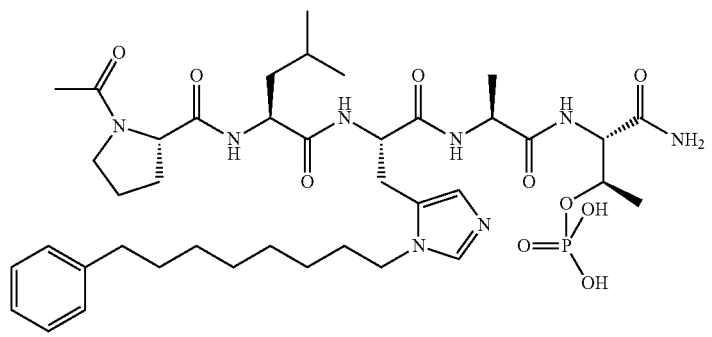

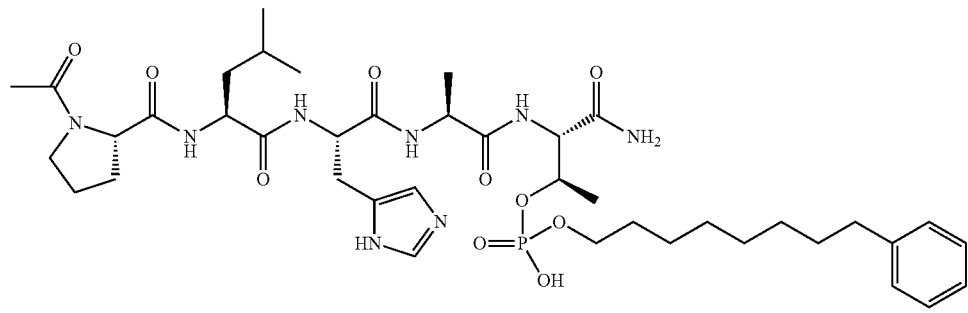
6
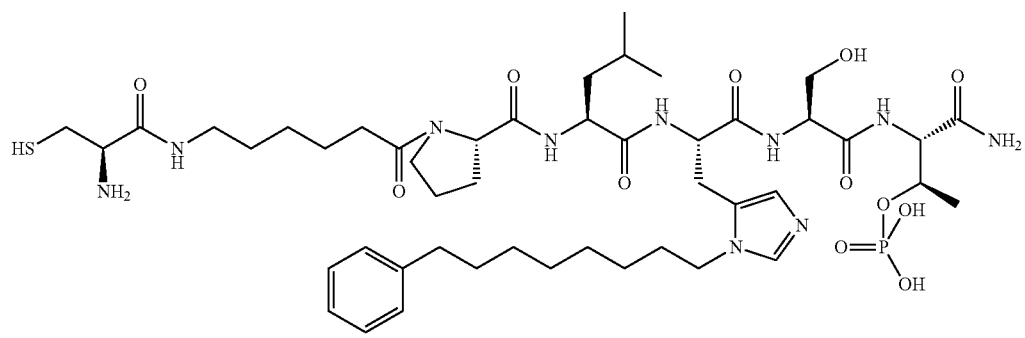
7
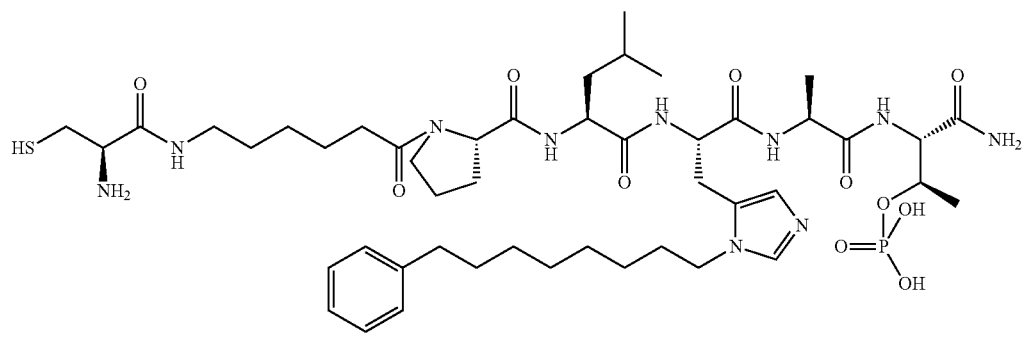
8
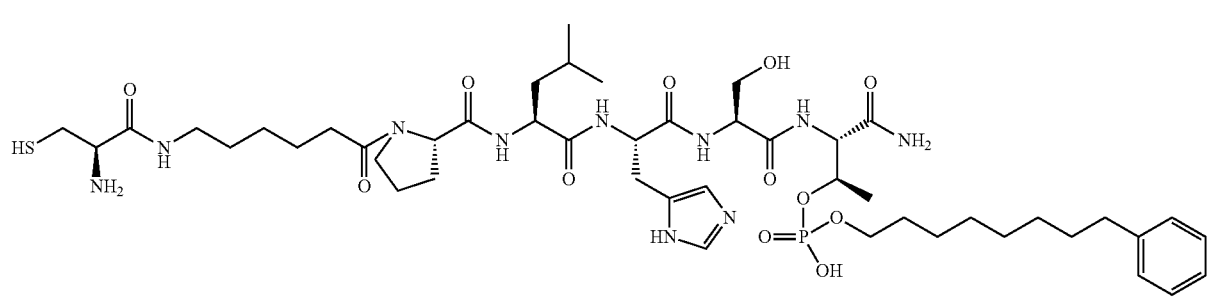
9
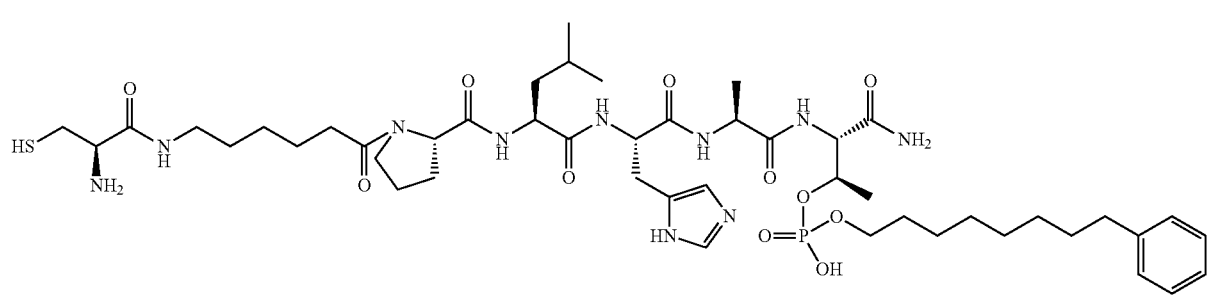
10

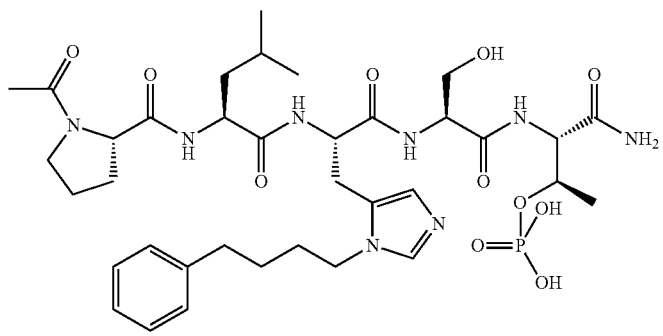
3h
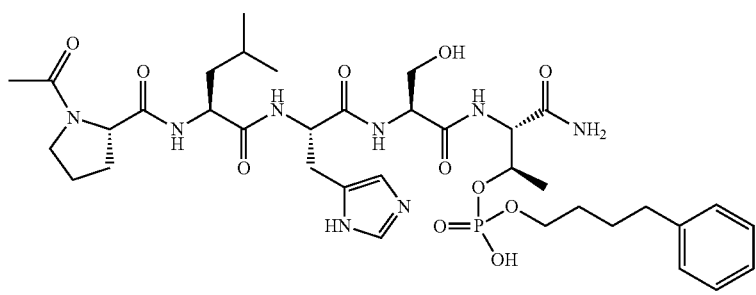
4h
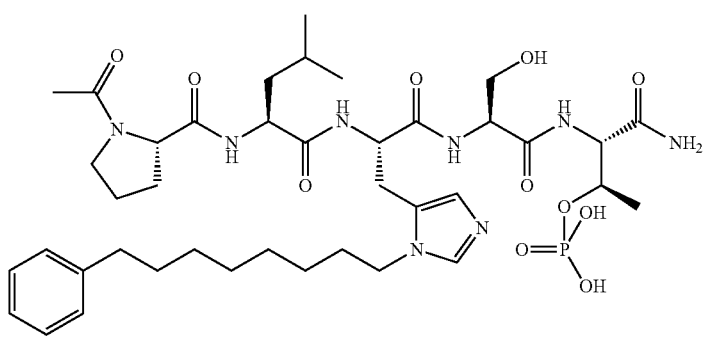
3l
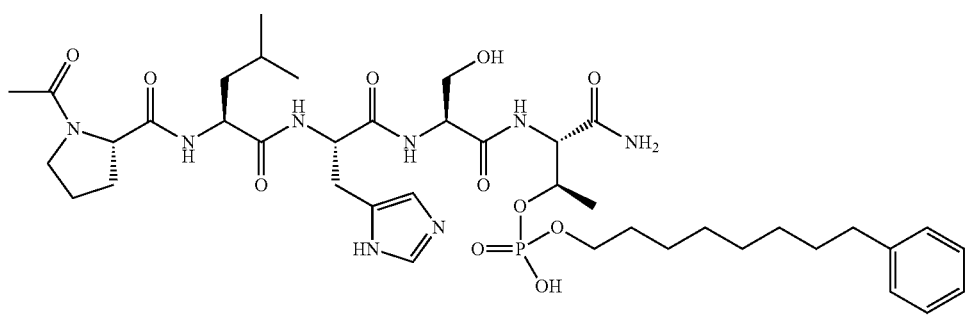
4l
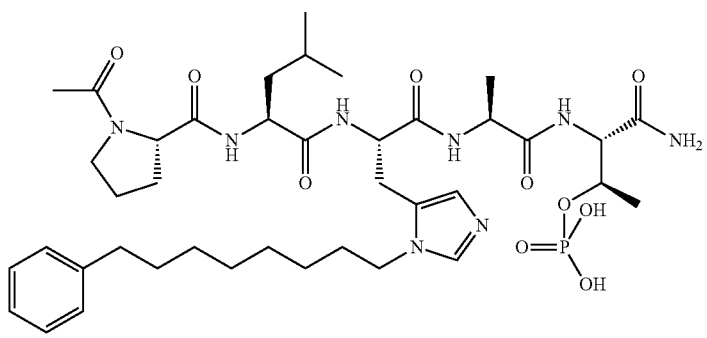
5

-continued
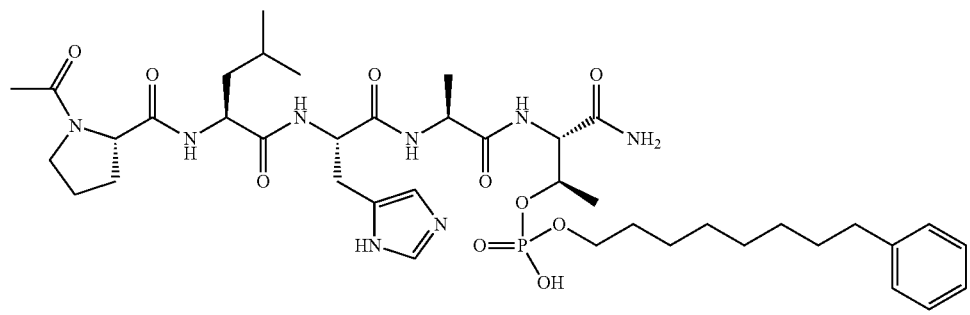
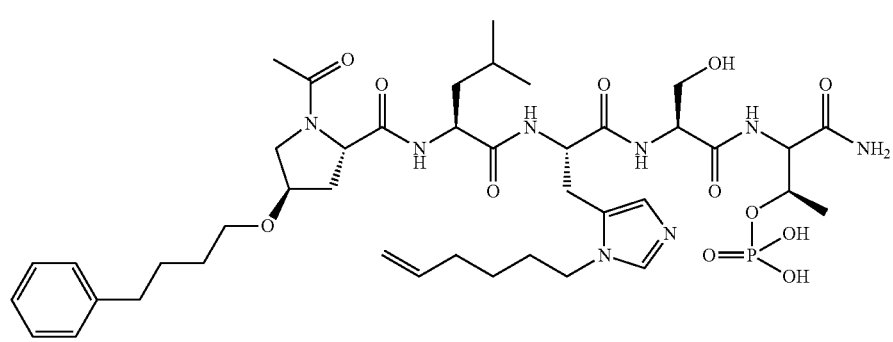
FA550
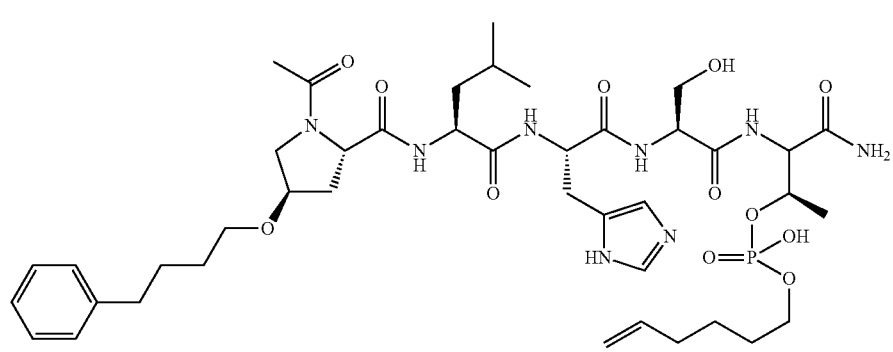
FA551
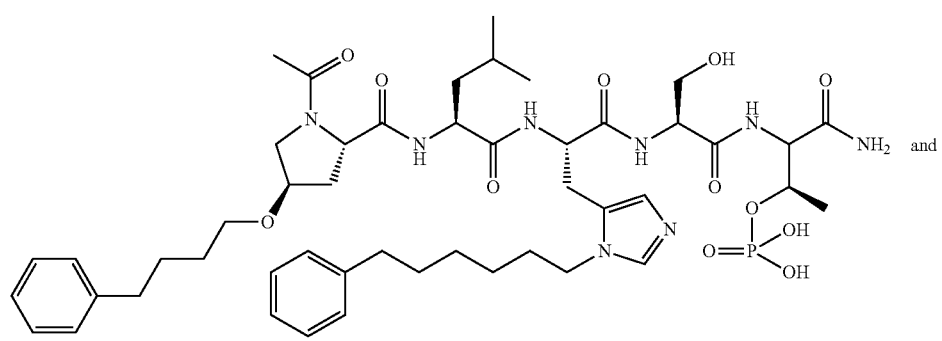
FA552
and

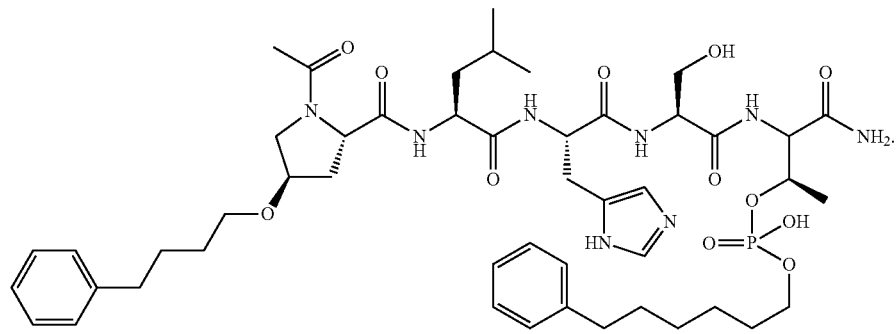
FA553
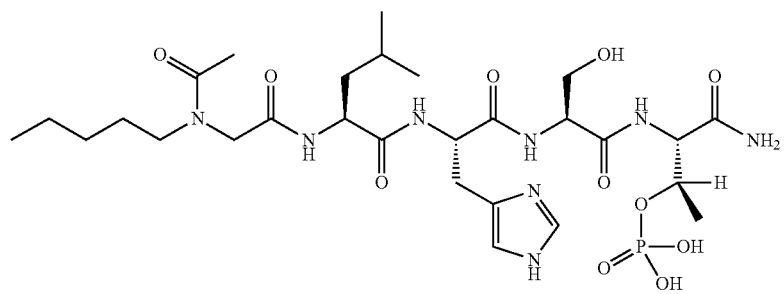
4a
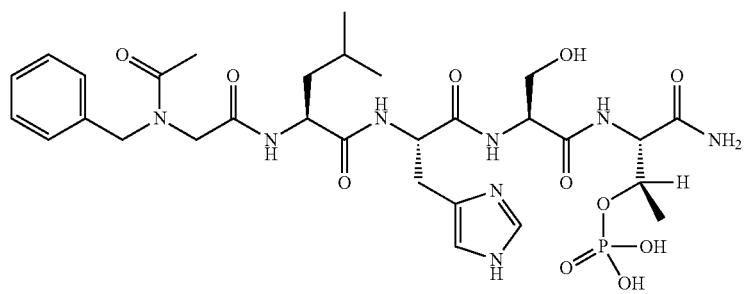
4f
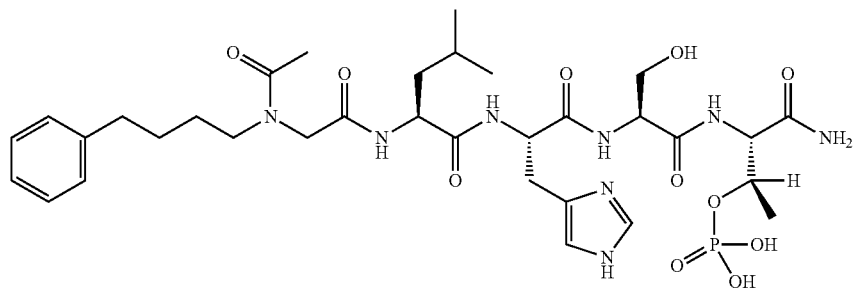
4o
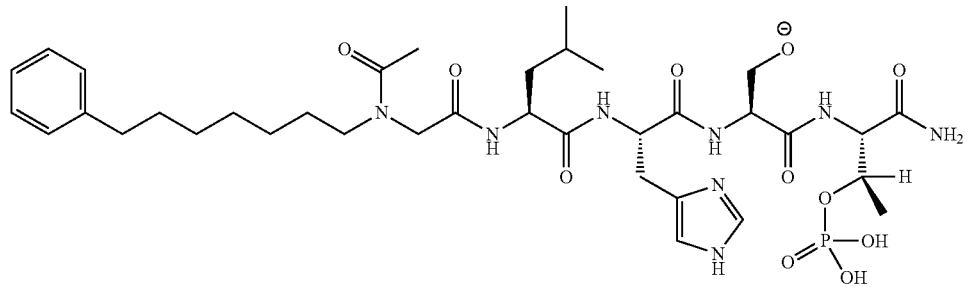
4r

-continued
6
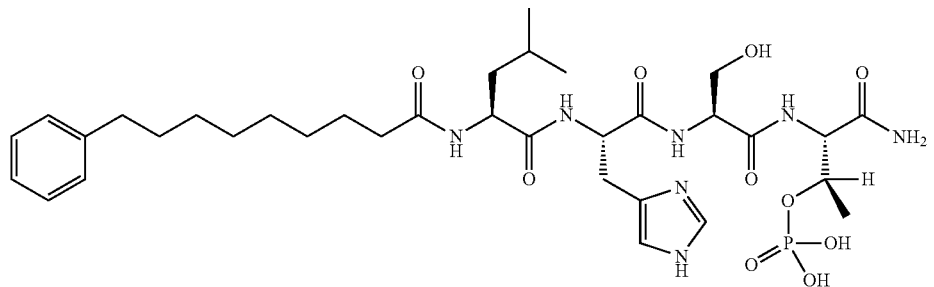
12
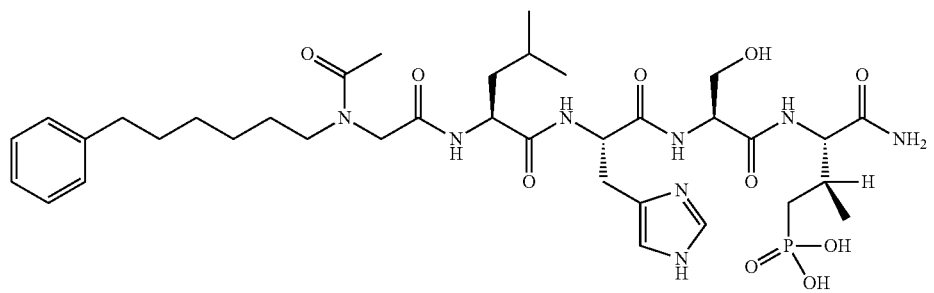
14
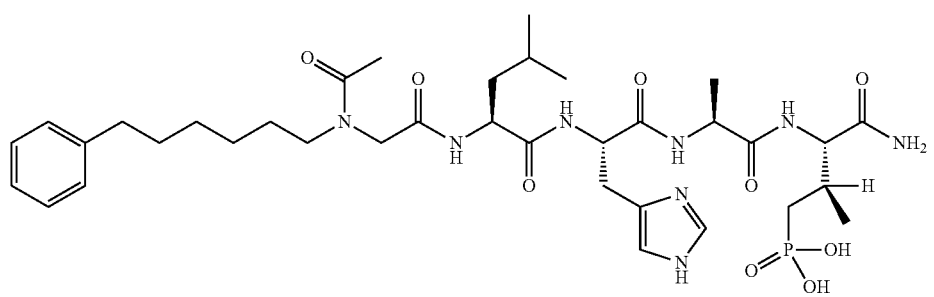
3a 4a
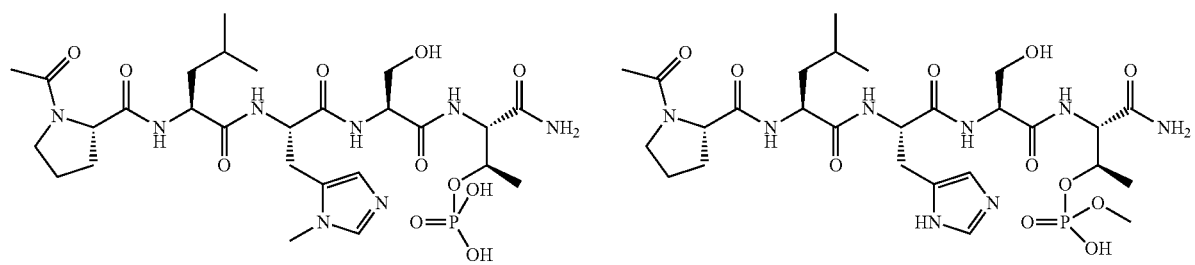
3b 4b
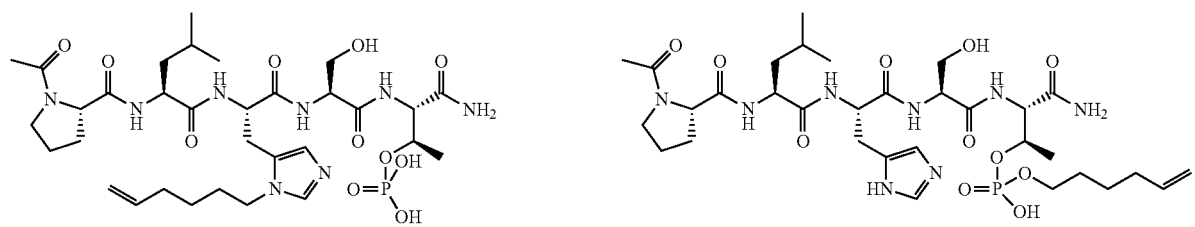

269                                                            270
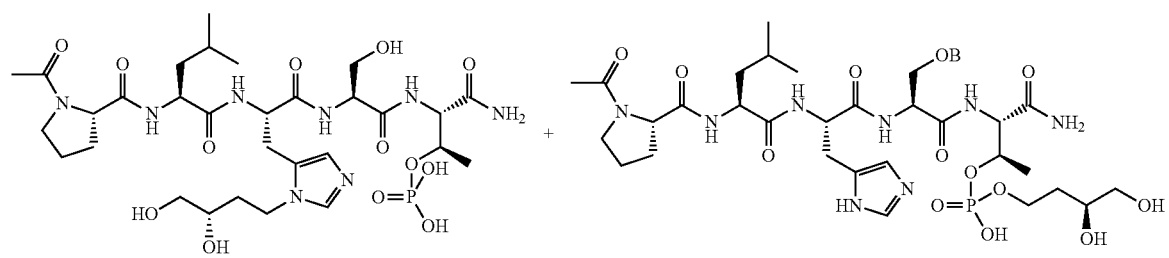
3c + 4c
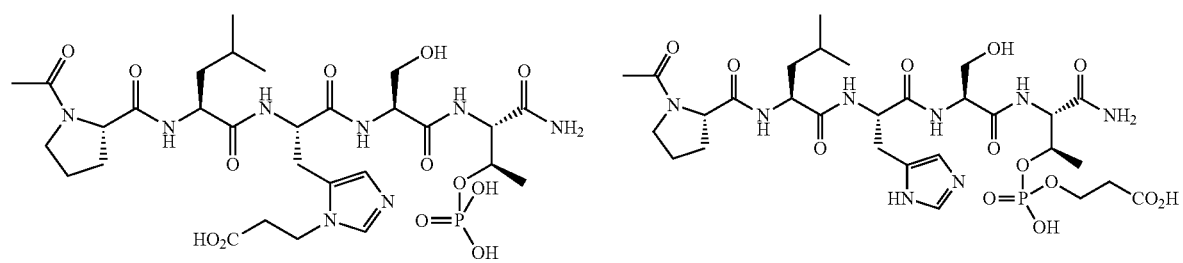
3d                                                                   4d
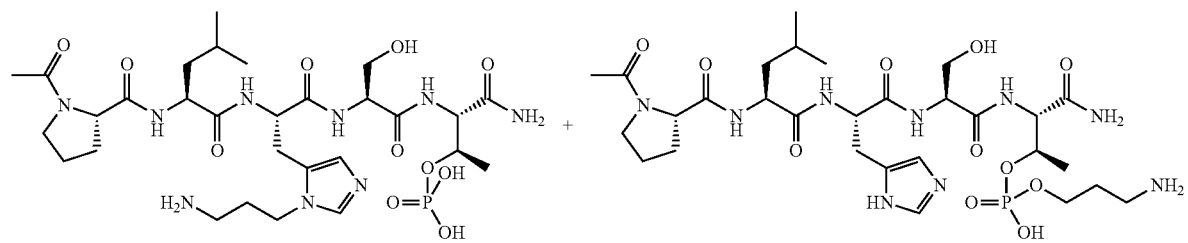
3e + 4e
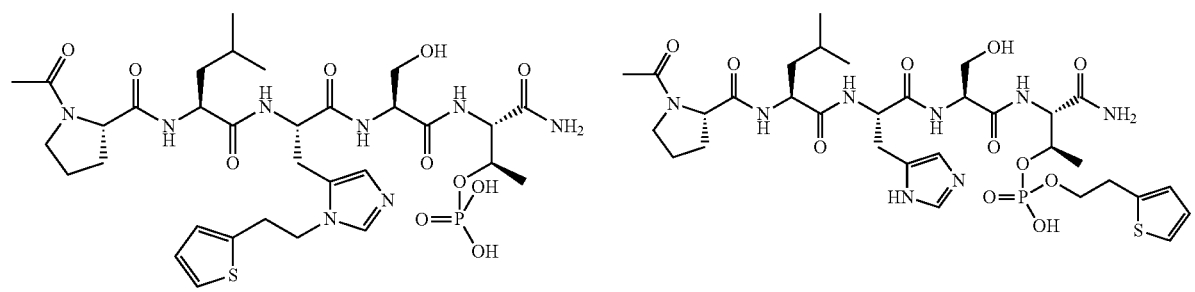
3f                                                                   4f
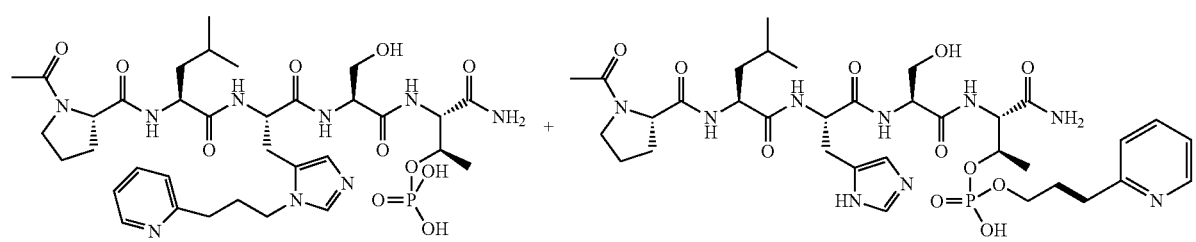
3g + 4g 3h
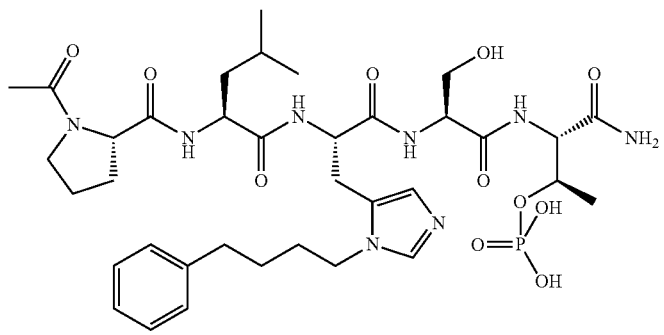
4h
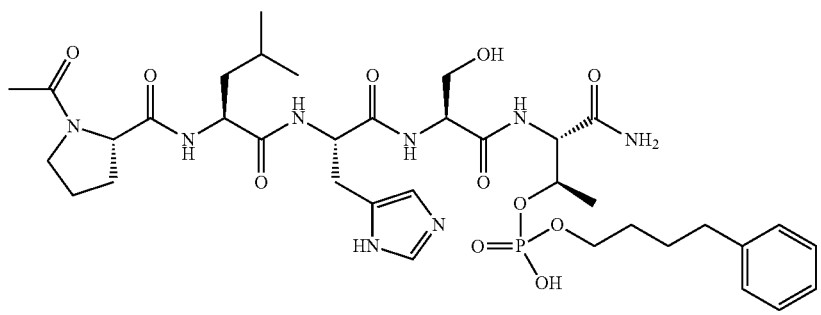
3i
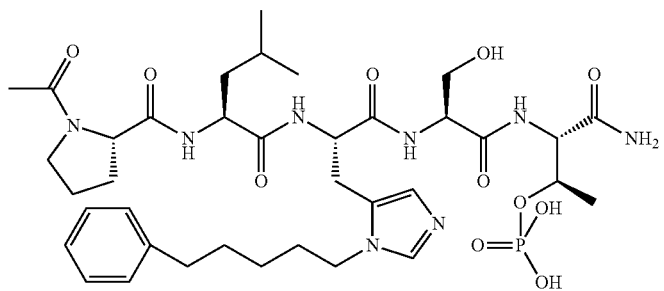
4i
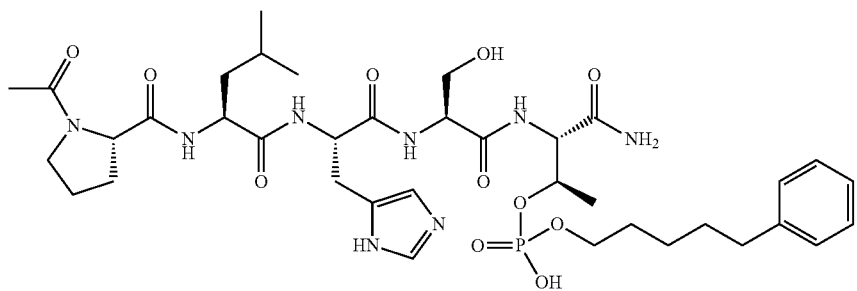
3j
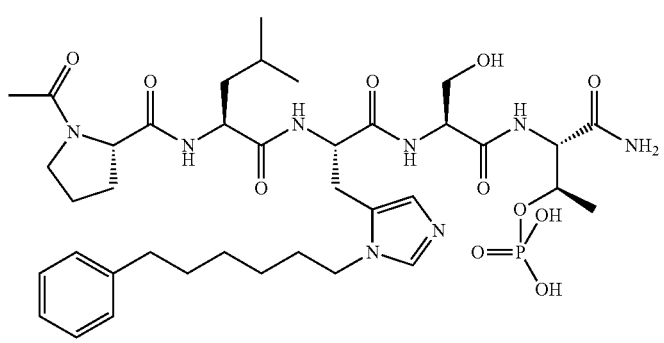

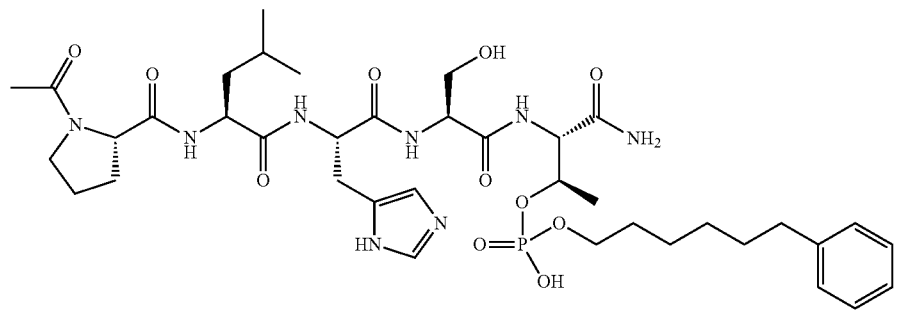
4j
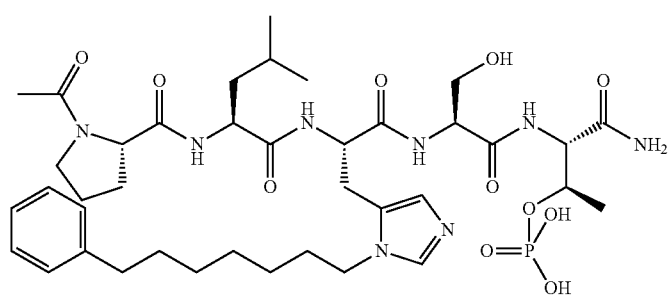
3k
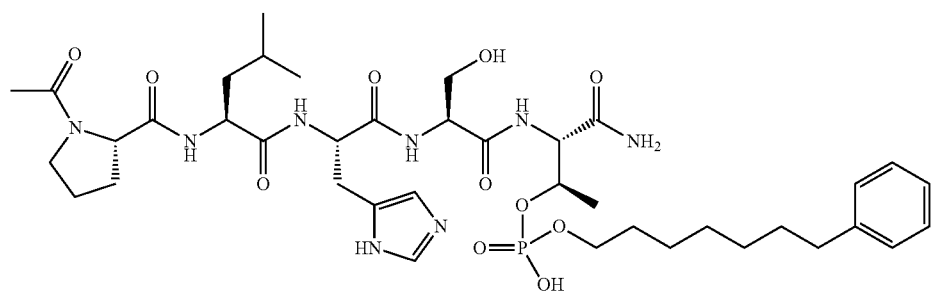
4k
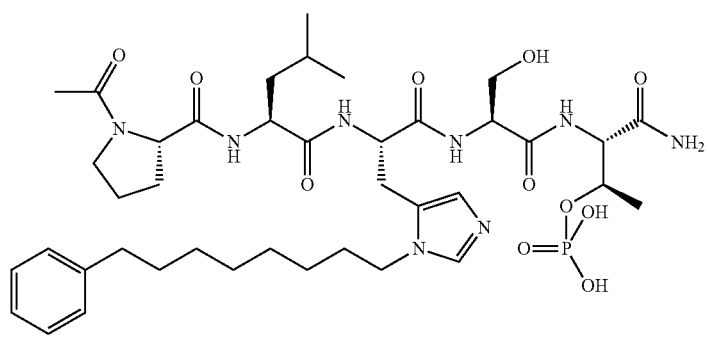
3l
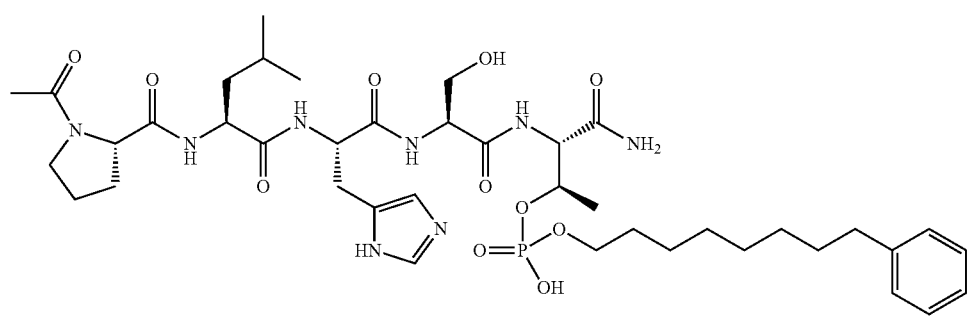
4l

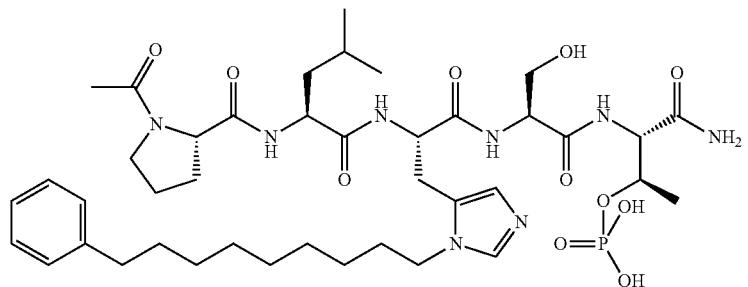
3m
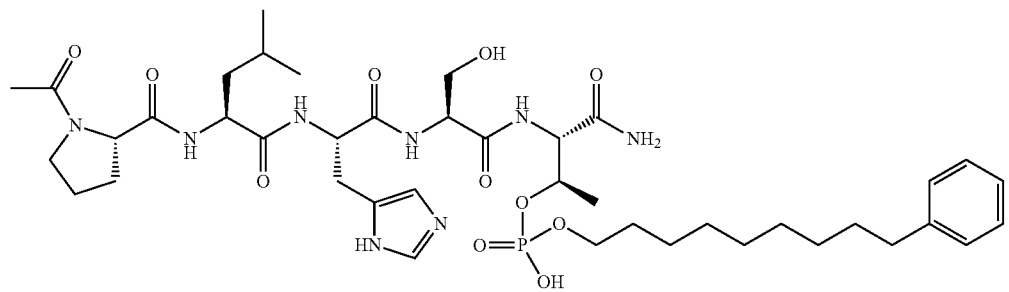
4m
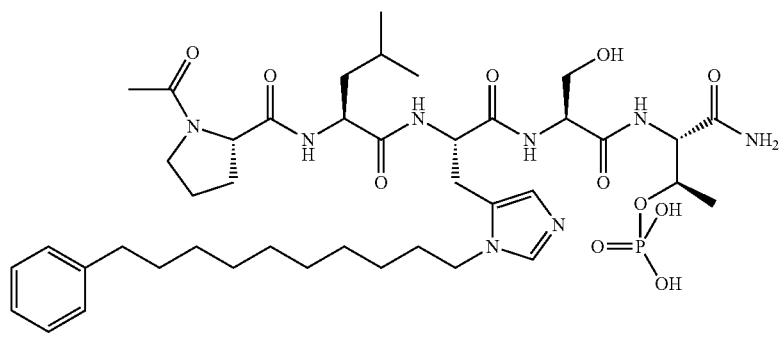
3n
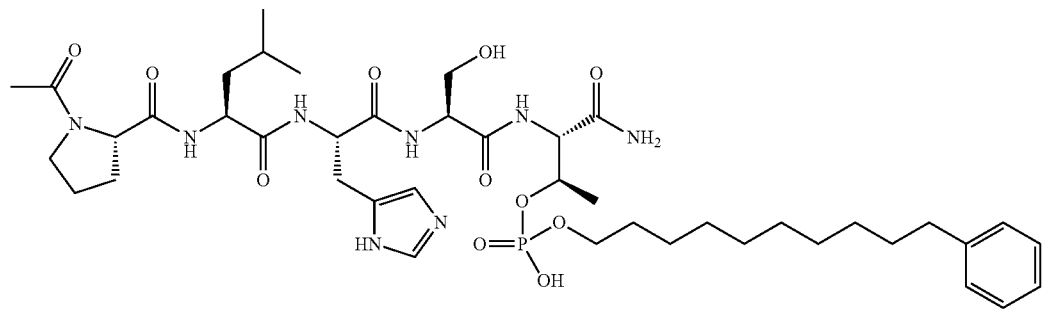
4n
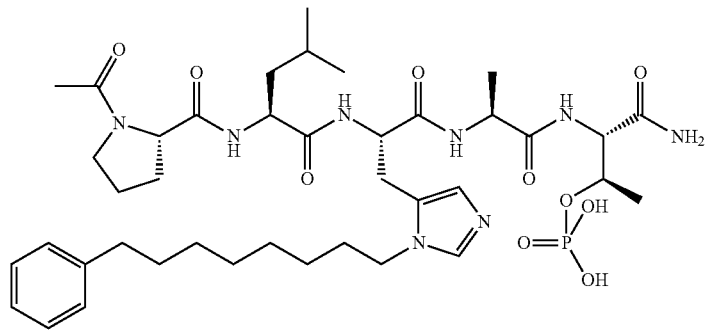
5

6
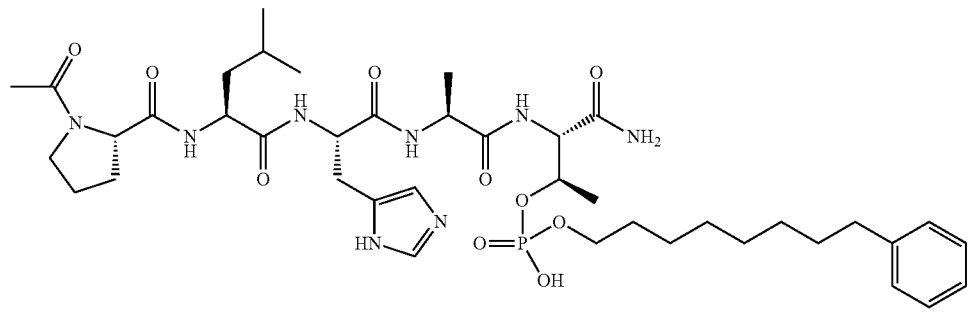
7
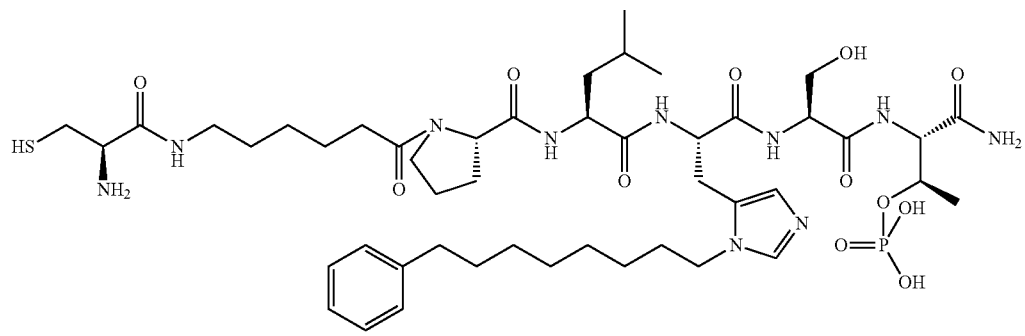
8
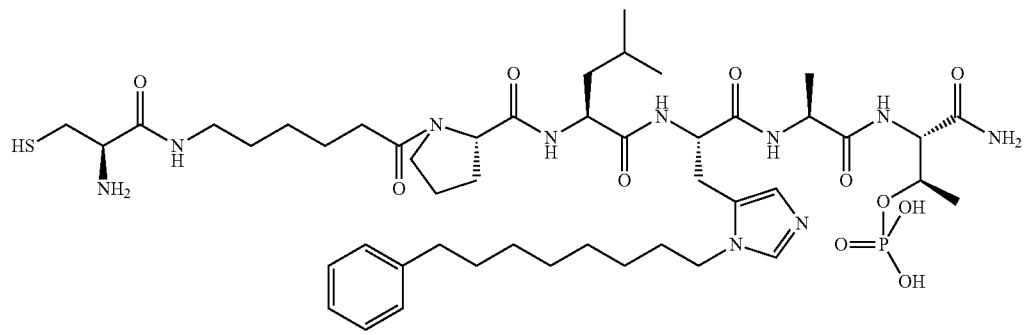
9
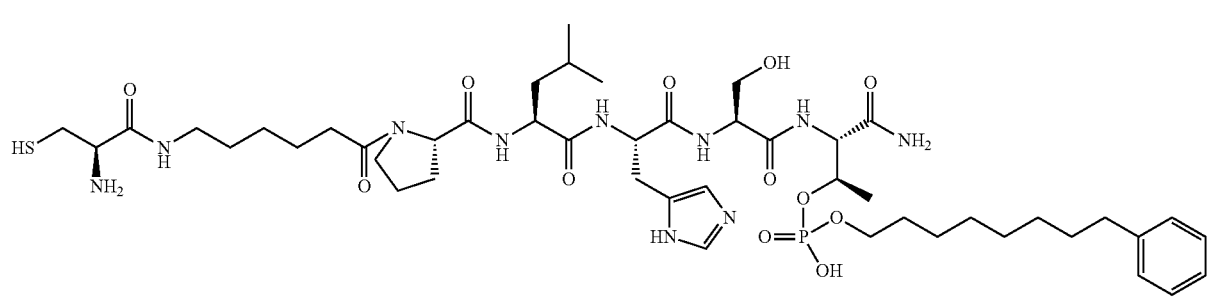
10
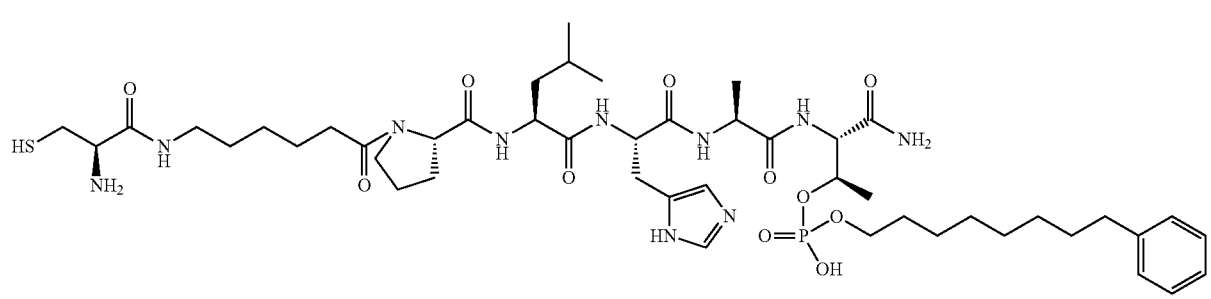

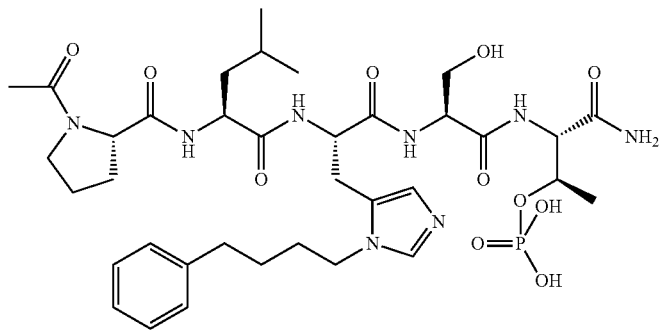
3h
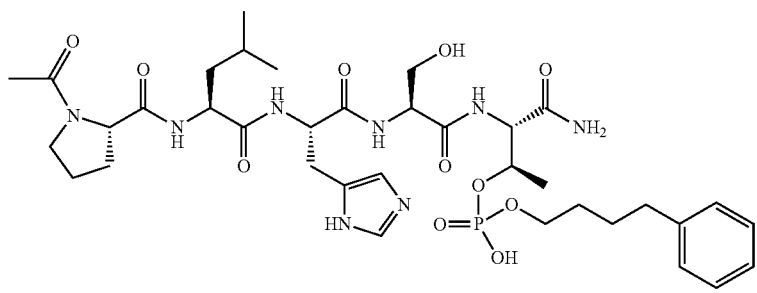
4h
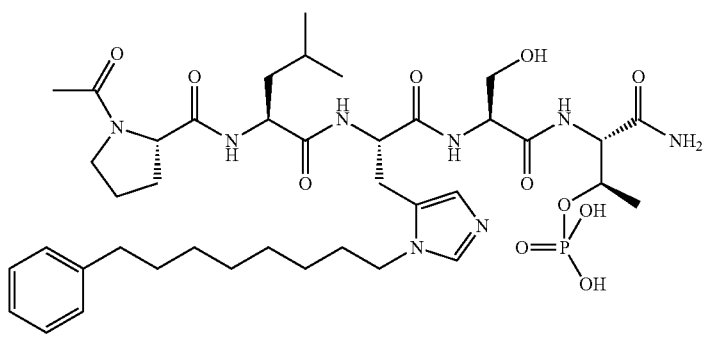
3l
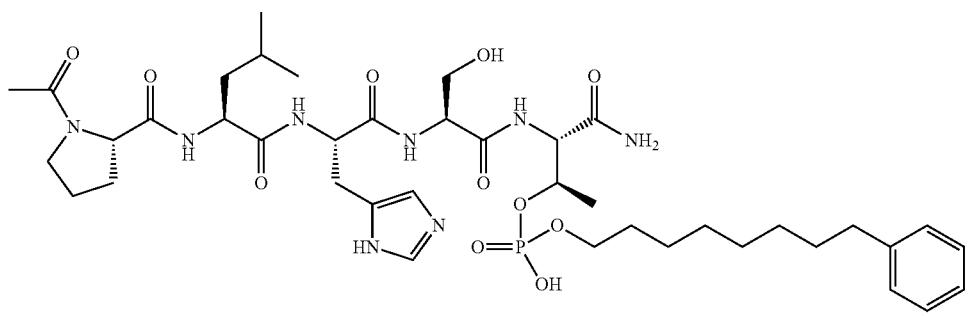
4l
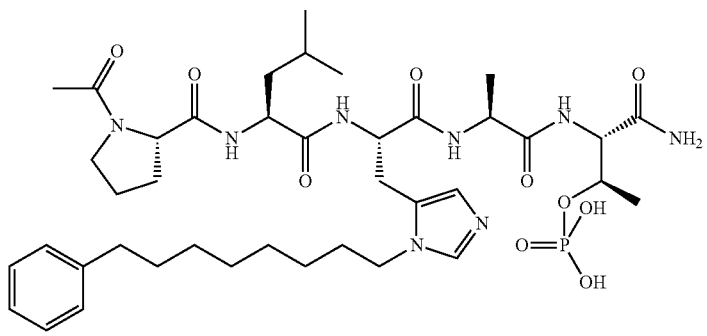
5

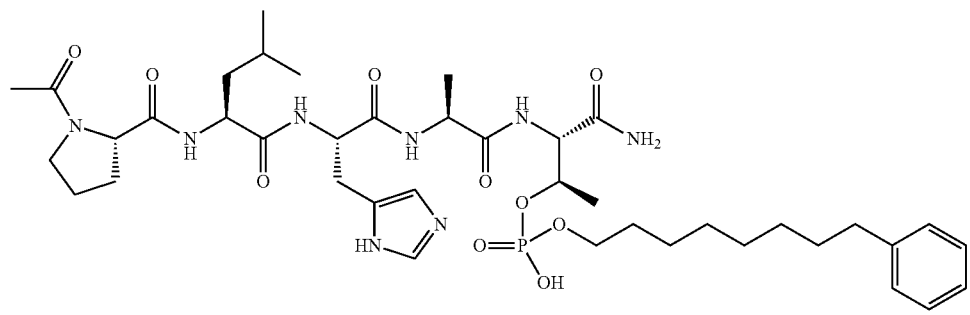
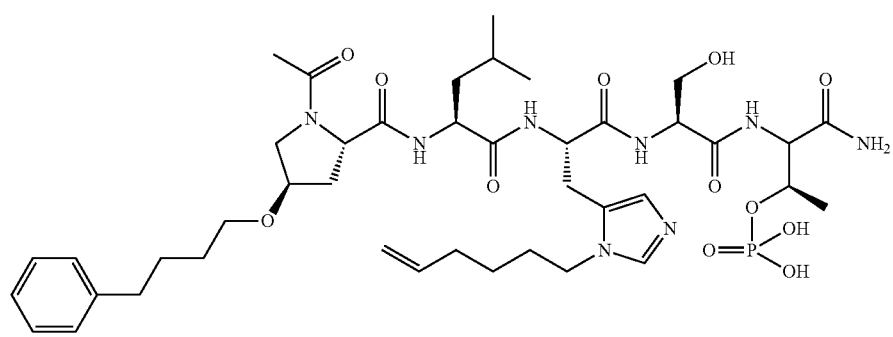
FA550
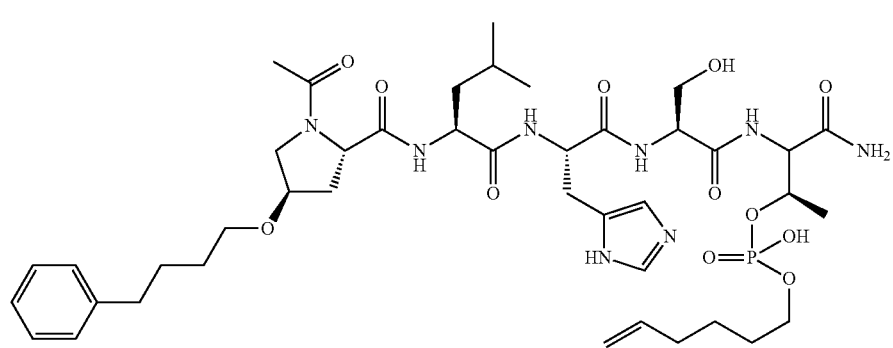
FA551
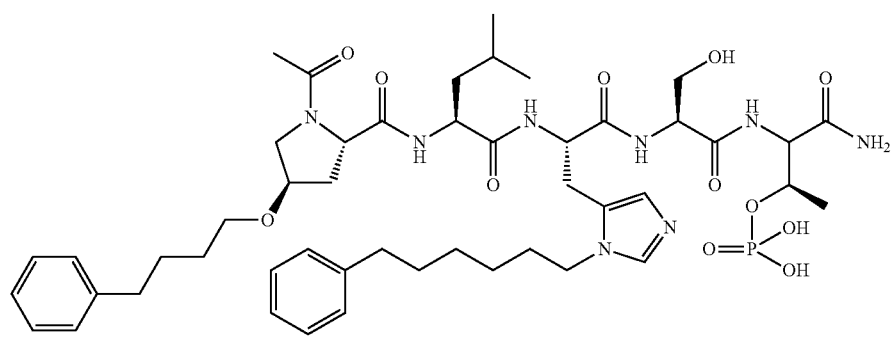
FA552

-continued

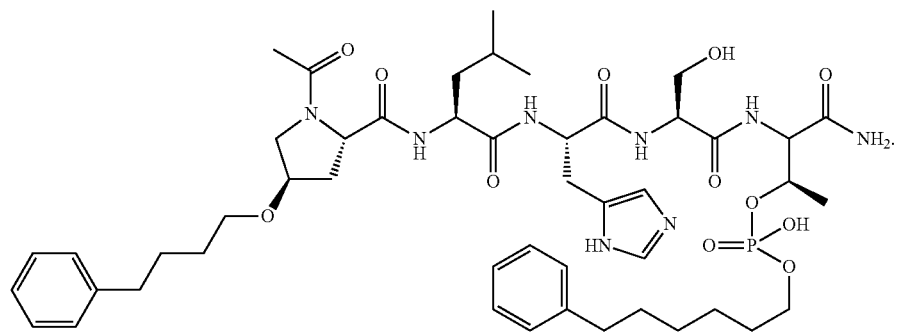

FA553

18. A composition comprising a compound of claim 1 in a pharmaceutically acceptable carrier.

19. A method for inhibiting Plk1 polo-box domain function in a cell comprising contacting the cell with a composition comprising any of the compounds of claim 1.

20. A kit comprising at least one compound of claim 1 and instructions for use.

21. A chemical library including two or more compounds of claim 1.

* * * * *

SEQUENCE LISTING

<160> NUMBER OF SEQ ID NOS: 50

<210> SEQ ID NO 1
<211> LENGTH: 6
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: phospho-Thr

<400> SEQUENCE: 1

Met Gln Ser Thr Pro Leu
1               5

<210> SEQ ID NO 2
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: phospho-Thr

<400> SEQUENCE: 2

Pro Leu His Ser Thr Ala
1               5

<210> SEQ ID NO 3
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: phospho-Thr

<400> SEQUENCE: 3

Leu His Ser Thr Ala Ile
1               5

<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: phospho-Thr

<400> SEQUENCE: 4

Leu His Ser Thr Ala
1               5

<210> SEQ ID NO 5
<211> LENGTH: 5
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: phospho-Thr

<400> SEQUENCE: 5

Pro Leu His Ser Thr
1               5

<210> SEQ ID NO 6
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: phospho-Thr

<400> SEQUENCE: 6

Leu His Ser Thr
1

<210> SEQ ID NO 7
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: phospho-Thr

<400> SEQUENCE: 7

His Ser Thr Ala
1

<210> SEQ ID NO 8
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Leu His Ser Thr Ala Ile
1               5

<210> SEQ ID NO 9
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: MOD_RES
<222> LOCATION: (7)..(7)
<223> OTHER INFORMATION: phospho-Thr

<400> SEQUENCE: 9

Asp Pro Pro Leu His Ser Thr Ala Ile Tyr Ala Asp Glu Glu
1               5                   10

<210> SEQ ID NO 10
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: phospho-Thr

<400> SEQUENCE: 10

Pro Leu His Ser Thr Ala Ile Tyr Ala Asp
1               5                   10

<210> SEQ ID NO 11
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: phospho-Thr

<400> SEQUENCE: 11

Pro Leu His Ser Thr Ala Ile Tyr Ala
1               5

<210> SEQ ID NO 12
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: phospho-Thr

<400> SEQUENCE: 12

Pro Leu His Ser Thr Ala Ile Tyr
1               5

<210> SEQ ID NO 13
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: MOD_RES
<222> LOCATION: (5)..(5)
<223> OTHER INFORMATION: phospho-Thr

<400> SEQUENCE: 13

Pro Leu His Ser Thr Ala Ile
1               5

<210> SEQ ID NO 14
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: phospho-Thr

<400> SEQUENCE: 14

His Ser Thr Ala Ile
1               5

<210> SEQ ID NO 15
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: phospho-Thr

<400> SEQUENCE: 15

Ser Thr Ala Ile
1

<210> SEQ ID NO 16
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: phospho-Thr

<400> SEQUENCE: 16

Pro Ala His Ser Thr
1               5

<210> SEQ ID NO 17
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: MOD_RES
<222> LOCATION: (5)..(5)
<223> OTHER INFORMATION: phospho-Thr

<400> SEQUENCE: 17

Pro Pro His Ser Thr
1               5

<210> SEQ ID NO 18
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: phospho-Thr

<400> SEQUENCE: 18

Pro Gln His Ser Thr
1               5

<210> SEQ ID NO 19
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: phospho-Thr

<400> SEQUENCE: 19

Pro Leu Gln Ser Thr
1               5

<210> SEQ ID NO 20
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: phospho-Thr

<400> SEQUENCE: 20

Pro Gln Gln Ser Thr
1               5

<210> SEQ ID NO 21
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: MOD_RES
<222> LOCATION: (5)..(5)
<223> OTHER INFORMATION: phospho-Thr

<400> SEQUENCE: 21

Met Leu His Ser Thr
1               5

<210> SEQ ID NO 22
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: phospho-Thr

<400> SEQUENCE: 22

Asp Pro Pro Leu His Ser Thr Ala Ile
1               5

<210> SEQ ID NO 23
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Asp Pro Pro Leu His Ser Thr Ala Ile Tyr Ala Asp Glu Glu
1               5                   10

<210> SEQ ID NO 24
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Pro Leu His Ser Thr Ala Ile Tyr Ala Asp
1               5                   10

<210> SEQ ID NO 25
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Pro Leu His Ser Thr Ala
1               5

<210> SEQ ID NO 26
<211> LENGTH: 5
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic peptide"

<400> SEQUENCE: 26

Pro Leu His Ser Thr
1               5

<210> SEQ ID NO 27
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Pmab

<400> SEQUENCE: 27

Pro Leu His Ser Xaa
1               5

<210> SEQ ID NO 28
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Pmab

<400> SEQUENCE: 28

Pro Leu His Ala Xaa
1               5

<210> SEQ ID NO 29
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: F2-Pmab

<400> SEQUENCE: 29

Pro Leu His Ser Xaa Ala
1               5

<210> SEQ ID NO 30
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: MOD_RES
<222> LOCATION: (5)..(5)
<223> OTHER INFORMATION: F2-Pmab

<400> SEQUENCE: 30

Pro Leu His Ala Xaa Ala
1               5

<210> SEQ ID NO 31
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Leu His Ser Thr Ala
1               5

<210> SEQ ID NO 32
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: phospho-Thr

<400> SEQUENCE: 32

Pro Met Gln Ser Thr Pro Leu
1               5

<210> SEQ ID NO 33
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: F2-Pmab

<400> SEQUENCE: 33

Pro Leu His Ser Xaa
1               5

<210> SEQ ID NO 34
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: phospho-Thr
```

```
<400> SEQUENCE: 34

Cys Glu Thr Phe Asp Pro Pro Leu His Ser Thr Ala Ile
1               5                   10

<210> SEQ ID NO 35
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 35

His His His His His His
1               5

<210> SEQ ID NO 36
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Asp Glu Glu Thr Tyr Glu Thr Phe Asp Pro Pro Leu His Ser Thr Ala
1               5                   10                  15

Ile Tyr Ala Asp Glu Glu Glu Phe Ser Lys His
            20                  25

<210> SEQ ID NO 37
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Pro Leu His Ser Thr Ala Ile Tyr Ala
1               5

<210> SEQ ID NO 38
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Pro Leu His Ser Thr Ala Ile Tyr
1               5

<210> SEQ ID NO 39
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 39

Pro Leu His Ser Thr Ala Ile
1               5

<210> SEQ ID NO 40
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Leu His Ser Thr
1

<210> SEQ ID NO 41
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

His Ser Thr Ala
1

<210> SEQ ID NO 42
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

His Ser Thr Ala Ile
1               5

<210> SEQ ID NO 43
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ser Thr Ala Ile
1

<210> SEQ ID NO 44
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Met Gln Ser Thr Pro Leu
1               5
```

<210> SEQ ID NO 45
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Pro Met Gln Ser Thr Pro Leu
1               5

<210> SEQ ID NO 46
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Asp Cys His Leu Ser Asp Met Leu Gln Gln Leu His Ser Val Asn Ala
1               5                   10                  15

Ser Lys Pro Ser Glu Arg Gly Leu Val Arg Gln Glu Glu Ala Glu Asp
                20                  25                  30

Pro Ala Cys Ile Pro Ile Phe Trp Val Ser Lys Trp Val Asp Tyr Ser
            35                  40                  45

Asp Lys Tyr Gly Leu Gly Tyr Gln Leu Cys Asp Asn Ser Val Gly Val
        50                  55                  60

Leu Phe Asn Asp Ser Thr Arg Leu Ile Leu Tyr Asn Asp Gly Asp Ser
65                  70                  75                  80

Leu Gln Tyr Ile Glu Arg Asp Gly Thr Glu Ser Tyr Leu Thr Val Ser
                85                  90                  95

Ser His Pro Asn Ser Leu Met Lys Lys Ile Thr Leu Leu Lys Tyr Phe
            100                 105                 110

Arg Asn Tyr Met Ser Glu His Leu Leu Lys Ala Gly Ala Asn Ile Thr
        115                 120                 125

Pro Arg Glu Gly Asp Glu Leu Ala Arg Leu Pro Tyr Leu Arg Thr Trp
    130                 135                 140

Phe Arg Thr Arg Ser Ala Ile Ile Leu His Leu Ser Asn Gly Ser Val
145                 150                 155                 160

Gln Ile Asn Phe Phe Gln Asp His Thr Lys Leu Ile Leu Cys Pro Leu
                165                 170                 175

Met Ala Ala Val Thr Tyr Ile Asp Glu Lys Arg Asp Phe Arg Thr Tyr
            180                 185                 190

Arg Leu Ser Leu Leu Glu Glu Tyr Gly Cys Cys Lys Glu Leu Ala Ser
        195                 200                 205

Arg Leu Arg Tyr Ala Arg Thr Met Val Asp Lys Leu Leu Ser Ser Arg
    210                 215                 220

<210> SEQ ID NO 47
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

```
Ser Cys Ser Ser Ser Glu Cys Leu Glu Asp Ser Thr Met Gly Ser
1               5                   10                  15

Val Ala Asp Thr Val Ala Arg Val Leu Arg Gly Cys Leu Glu Asn Met
            20                  25                  30

Pro Glu Ala Asp Cys Ile Pro Lys Glu Gln Leu Ser Thr Ser Phe Gln
            35                  40                  45

Trp Val Thr Lys Trp Val Asp Tyr Ser Asn Lys Tyr Gly Phe Gly Tyr
        50                  55                  60

Gln Leu Ser Asp His Thr Val Gly Val Leu Phe Asn Asn Gly Ala His
65                  70                  75                  80

Met Ser Leu Leu Pro Asp Lys Lys Thr Val His Tyr Tyr Ala Glu Leu
                85                  90                  95

Gly Gln Cys Ser Val Phe Pro Ala Thr Asp Ala Pro Glu Gln Phe Ile
            100                 105                 110

Ser Gln Val Thr Val Leu Lys Tyr Phe Ser His Tyr Met Glu Glu Asn
            115                 120                 125

Leu Met Asp Gly Gly Asp Leu Pro Ser Val Thr Asp Ile Arg Arg Pro
130                 135                 140

Arg Leu Tyr Leu Leu Gln Trp Leu Lys Ser Asp Lys Ala Leu Met Met
145                 150                 155                 160

Leu Phe Asn Asp Gly Thr Phe Gln Val Asn Phe Tyr His Asp His Thr
                165                 170                 175

Lys Ile Ile Ile Cys Ser Gln Asn Glu Glu Tyr Leu Leu Thr Tyr Ile
            180                 185                 190

Asn Glu Asp Arg Ile Ser Thr Thr Phe Arg Leu Thr Thr Leu Leu Met
            195                 200                 205

Ser Gly Cys Ser Ser Glu Leu Lys Asn Arg Met Glu Tyr Ala Leu Asn
            210                 215                 220

Met Leu Leu Gln Arg Cys Asn
225                 230
```

<210> SEQ ID NO 48
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

```
Gly Asp Gly Phe Glu Glu Gly Leu Thr Val Ala Thr Val Val Glu Ser
1               5                   10                  15

Ala Leu Cys Ala Leu Arg Asn Cys Ile Ala Phe Met Pro Pro Ala Glu
            20                  25                  30

Gln Asn Pro Ala Pro Leu Ala Gln Pro Glu Pro Leu Val Trp Val Ser
        35                  40                  45

Lys Trp Val Asp Tyr Ser Asn Lys Phe Gly Phe Gly Tyr Gln Leu Ser
    50                  55                  60

Ser Arg Arg Val Ala Val Leu Phe Asn Asp Gly Thr His Met Ala Leu
65                  70                  75                  80

Ser Ala Asn Arg Lys Thr Val His Tyr Asn Pro Thr Ser Thr Lys His
                85                  90                  95
```

```
Phe Ser Phe Ser Val Gly Ala Val Pro Arg Ala Leu Gln Pro Gln Leu
            100                 105                 110

Gly Ile Leu Arg Tyr Phe Ala Ser Tyr Met Glu Gln His Leu Met Lys
            115                 120                 125

Gly Gly Asp Leu Pro Ser Val Glu Glu Val Glu Val Pro Ala Pro Pro
        130                 135                 140

Leu Leu Leu Gln Trp Val Lys Thr Asp Gln Ala Leu Leu Met Leu Phe
145                 150                 155                 160

Ser Asp Gly Thr Val Gln Val Asn Phe Tyr Gly Asp His Thr Lys Leu
                165                 170                 175

Ile Leu Ser Gly Trp Glu Pro Leu Leu Val Thr Phe Val Ala Arg Asn
            180                 185                 190

Arg Ser Ala Cys Thr Tyr Leu Ala Ser His Leu Arg Gln Leu Gly Cys
            195                 200                 205

Ser Pro Asp Leu Arg Gln Arg Leu Arg Tyr Ala Leu Arg Leu Leu Arg
        210                 215                 220

Asp Arg Ser Pro Ala
225

<210> SEQ ID NO 49
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Ahx

<400> SEQUENCE: 49

Cys Xaa Pro Leu His Ser Thr
1               5

<210> SEQ ID NO 50
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Ahx
<220> FEATURE:
<221> NAME/KEY: MOD_RES
<222> LOCATION: (7)..(7)
<223> OTHER INFORMATION: phospho-Thr

<400> SEQUENCE: 50

Cys Xaa Pro Leu His Ser Thr
1               5
```